US011236361B2

(12) United States Patent
Uil et al.

(10) Patent No.: US 11,236,361 B2
(45) Date of Patent: Feb. 1, 2022

(54) ADENOVIRUS AND USES THEREOF

(71) Applicant: JANSSEN VACCINES & PREVENTION B.V., Leiden (NL)

(72) Inventors: Taco Gilles Uil, Amsterdam (NL); Soumitra Roy, Townsend, DE (US); Selina Khan, Leiden (NL); Jerôme H. H. V. Custers, Alphen aan den Rijn (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 16/760,518

(22) PCT Filed: Oct. 30, 2018

(86) PCT No.: PCT/EP2018/079713
§ 371 (c)(1),
(2) Date: Apr. 30, 2020

(87) PCT Pub. No.: WO2019/086456
PCT Pub. Date: May 9, 2019

(65) Prior Publication Data

US 2021/0198690 A1 Jul. 1, 2021

(30) Foreign Application Priority Data

Oct. 31, 2017 (EP) .................................... 17199348

(51) Int. Cl.

| | |
|---|---|
| ***C07H 21/04*** | (2006.01) |
| ***A61K 48/00*** | (2006.01) |
| ***C12N 15/85*** | (2006.01) |
| ***A61K 38/00*** | (2006.01) |
| ***C07K 14/435*** | (2006.01) |
| ***C12N 15/86*** | (2006.01) |
| ***A61P 31/20*** | (2006.01) |
| ***A61K 39/135*** | (2006.01) |
| ***C07K 14/005*** | (2006.01) |
| *A61K 39/00* | (2006.01) |

(52) U.S. Cl.
CPC ............ *C12N 15/86* (2013.01); *A61K 39/135* (2013.01); *A61P 31/20* (2018.01); *C07K 14/005* (2013.01); *A61K 2039/5256* (2013.01); *C12N 2710/10322* (2013.01); *C12N 2710/10334* (2013.01); *C12N 2710/10343* (2013.01); *C12N 2710/10371* (2013.01)

(58) Field of Classification Search
CPC ........ A61K 48/00; A61K 38/00; C12N 15/86; A61P 35/00; A61P 9/00
See application file for complete search history.

(56) References Cited

U.S. PATENT DOCUMENTS

| | | | |
|---|---|---|---|
| 5,559,099 | A | 9/1996 | Wickham et al. |
| 5,837,511 | A | 11/1998 | Falck-Pedersen et al. |
| 5,846,782 | A | 12/1998 | Wickham et al. |
| 5,851,806 | A | 12/1998 | Kovesdi et al. |
| 5,891,690 | A | 4/1999 | Massie |
| 5,965,541 | A | 10/1999 | Wickham et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 6,020,191 | A | 2/2000 | Scaria et al. |
| 6,040,174 | A | 3/2000 | Imler et al. |
| 6,113,913 | A | 9/2000 | Brough et al. |

FOREIGN PATENT DOCUMENTS

| | | |
|---|---|---|
| EP | 2 350 268 | 8/2011 |
| EP | 2 536 829 | 12/2012 |
| WO | 98/39411 | 9/1998 |
| WO | 01/36615 | 5/2001 |
| WO | 2002/22080 | 3/2002 |
| WO | 2003/000283 | 1/2003 |
| WO | 2003/104467 | 12/2003 |
| WO | 2004/037189 | 5/2004 |
| WO | 2005/071093 | 8/2005 |
| WO | 2006/040330 | 4/2006 |
| WO | 2007/104792 | 9/2007 |
| WO | 2009/073104 | 6/2009 |
| WO | 2010/086189 | 8/2010 |
| WO | 2001/02607 | 1/2011 |
| WO | 2011/130627 | 10/2011 |
| WO | 2013/016591 | 1/2013 |
| WO | 2013/052859 | 4/2013 |
| WO | 2013/173702 | 11/2013 |

OTHER PUBLICATIONS

Altschul et al., "Basic Local Alignment Search Tool," (1990) J. Mol. Biol. 215: 403-410.
Altschul et al., "Gapped BLAST and PSI-BLAST: a new generation of protein database search programs," (1997) Nucleic Acids Res. 25: 3389-3402.
Barnes E, et al., "Novel Adenovirus-Based Vaccines Induce Broad and Sustained T Cell Responses to HCV in Man," 2012 Science translational medicine 4: 115ra1.
Fallaux et al., "New Helper Cells and Matched Early Region 1-Deleted Adenovirus Vectors Prevent Generation of Replication-Competent Adenovirus," 1998, Hum Gene Ther 9: 1909-17.
Gao et al., "A Cell Line for High-Yield Production of E1-Deleted Adenovirus Vectors without the Emergence of Replication-Competent Virus," 2000, Hum Gene Ther 11: 213-19.
Havenga et al., "Novel replication-incompetent adenoviral B-group vectors: high vector stability and yield in PER.C6 cells," J. Gen. Virol. 87(8):2135-43 (2006).
Henikoff & Henikoff, Proc. Natl. Acad. Sci. USA 89:10915 (1989).

(Continued)

*Primary Examiner* — Barry A Chestnut
(74) *Attorney, Agent, or Firm* — Ice Miller LLP

(57) ABSTRACT

Provided herein are adenoviral nucleic acid sequences and adenoviral vectors comprising said nucleic acid sequences. The provided adenoviral vectors can be used to induce a protective immune response in a subject.

17 Claims, 9 Drawing Sheets

Specification includes a Sequence Listing.

(56) References Cited

OTHER PUBLICATIONS

Karlin & Altschul, "Amino acid substitution matrices from protein blocks," Proc. Nat'l. Acad. Sci. USA, 90: 5873-5787 (1993).
Kovesdi et al., "Adenoviral Producer Cells," 2010, Viruses 2: 1681-703.
Letvin et al., "Prospects for Vaccine Protection Against HIV-1 Infection and AIDS," Ann. Rev. Immunol. 20:73 (2002).
Maizel et al., "The Polypeptides of Adenovirus," Virology, 36(1):115-25 (1968).
Needleman & Wunsch, "A General Method Applicable to the Search for Similarities in the Amino Acid Sequence of Two Proteins," J. Mol. Biol. 48:443 (1970).
Pearson & Lipman, "Improved tools for biological sequence comparison," Proc. Nat'l. Acad. Sci. USA 85:2444 (1988).
Peruzzi D, et al., A novel Chimpanzee serotype-based adenoviral vector as delivery tool for cancer vaccines, 2009 Vaccine 27: 1293-300.
Quinn KM, et al., "Comparative Analysis of the Magnitude, Quality, Phenotype, and Protective Capacity of Simian Immunodeficiency Virus Gag-Specific CD8 T Cells following Human-, Simian-, and Chimpanzee-Derived Recombinant Adenoviral Vector Immunization," 2013, J Immunol 190: 2720-35.
Shiver et al., "Replication-incompetent adenoviral vacccine vector elicits effective anti-immunodeficiency-virus immunity," Nature 415:331 (2002).
Shiver and Emini, "Recent Advances in the Development of HIV-1 Vaccines Using Replication-Incompetent Adenovirus Vectors," Ann. Rev. Med. 55:355 (2004).
Smith & Waterman, "Comparison of Biosequences," Adv. Appl. Math. 2:482 (1981).
Sprangers et al., "Quantifying Adenovirus-Neutralizing Antibodies by Luciferase Transgene Detection: Addressing Preexisting Immunity to Vaccine and Gene Therapy Vectors," 2003, J.CIin. Microbiol. 41:5046-5052.
Susan J. Morris et al., "Simian adenoviruses as vaccine vectors," Future Virology, 11(9):649-659, 2016.
R.R. Bradley et al., "Adenovirus Serotype 5 Neutralizing Antibodies Target both Hexon and Fiber following Vaccination and Natural Infection," Journal of Virology, 86(1):625-629, 2011.
S.C. Jacobs, "Characterization and manipulation of the human adenovirus 4 genome," Journal of General Virology, 85(11):3361-3366, 2004.
Roberts Diane M. et al., "Hexon-chimaeric adenovirus serotype 5 vectors circumvent pre-existing anti-vector immunity," Nature, Macmillan Journals Ltd., London, 441(7090):239-243, 2006.
Julio Alonso-Padilla et al., "Development of Novel Adenoviral Vectors to Overcome Challenges Observed with HAdV-5-based Constructs," Molecular Therapy: The Journal of the American Society of Gene Therapy, 24(1):6-16, 2015.
Mohan Babu Appaiahgari et al., "Adenoviruses as gene/vaccine delivery vectors: promises and pitfalls," Expert Opinion on Biological Therapy, 15(3):337-351, 2014.
Abbink et al., "Comparative Seroprevalence and Immunogenicity of Six Rare Serotype Recombinant Adenovirus Vaccine Vectors from Subgroups B and D," Journal of Virology, 81(9):4654-4663, 2007.
Alba et al., "Vector Systems for Prenatal Gene Therapy: Principles of Adenovirus Design and Production," Methods in Molecular Biology, 891:55-84, 2012.
Bradley, et al., "Adenovirus Serotype 5-Specific Neutralizing Antibodies Target Multiple Hexon Hypervariable Regions," Journal of Virology, 86:1267-72, 2012.
Bruder et al., "Modification of Ad5 Hexon Hypervaribable Regions Circumvents Pre-Existing Ad5 Neutralizing Antibodies and Induces Protective Immune Responses," PLoS ONE, 7(4):e33920, 2012.
Gall et al., "Construction and Characterization of Hexon-Chimeric Adenoviruses: Specification of Adenovirus Serotype," Journal of Virology, 72(12):10260-10264, 1998.
Ma et al., "Synergistic suppression effect on tumor growth of hepatocellular carcinoma by combining oncolytic adenovirus carrying XAF1 with cisplatin," J Cancer Res Clin Oncol, 141:419-429, 2015.
Roy et al., "Circumvention of Immunity to the Adenovirus Major Coat Protein Hexon," Journal of Virology, 72(8):6875-6879, 1998.
Roy et al., "Use of chimeric adenoviral vectors to assess capsid neutralization determinants," Virology, 333:207-214, 2005.
Wu et al., "Construction and Characterization of Adenovirus Serotype 5 Packages by Serotype 3 Hexon," Journal of Virology, 76(24):12775-12782, 2002.
Youil et al., "Hexon Gene Switch Strategy for the Generation of Chimeric Recombinant Adenovirus," Human Gene Therapy, 13:311-320, 2002.
Yu et al., "Chimeric hexon HVRs protein reflects partial function of adenovirus," Biochemical and Biophysical Research Communication, 421:170-176, 2012.
Wevers et al, "Novel Adenoviruses in Wild Primates: a High Level of Genetic Diversity and Evidence of Zoonotic Transmissions," Journal of Virology, 85(20):10774-10784, 2011.
Ma et al., "Manipulating Adenovirus Hexon Hypervariable Loops Dictates Immune Neutralisation and Coagulation Factor X-dependent Cell Interaction In Vitro and In Vivo," PLoS Pathog, 11(2):e1004673, 2015.

| Sera* | Adenoviral vectors: Ad35 (B) | Ad26 (D) | Ad49 (D) | Ad5 (C) | Ad4 (E) | BLY6 (E) |
|---|---|---|---|---|---|---|
| Ad35 (B) | 13384 | <16 | <16 | <16 | <16 | <16 |
| Ad26 (D) | <16 | 2786 | <16 | <16 | <16 | <16 |
| Ad49 (D) | <16 | <16 | [illegible] | <16 | <16 | <16 |
| Ad5 (C) | <16 | <16 | <16 | 6007 | <16 | <16 |
| Ad4 (E) | <16 | <16 | <16 | <16 | [illegible] | <16 |
| BLY6 (E) | <16 | 16.12 | <16 | <16 | <16 | [illegible] |

*Sera collected from mice immunized with the indicated serotypes

| Values | |
|---|---|
| <16 | No neutralization |
| 16 - 200 | Slight neutralization |
| 200 - 2000 | Neutralization |
| >2000 | Strong neutralization |

FIG. 3

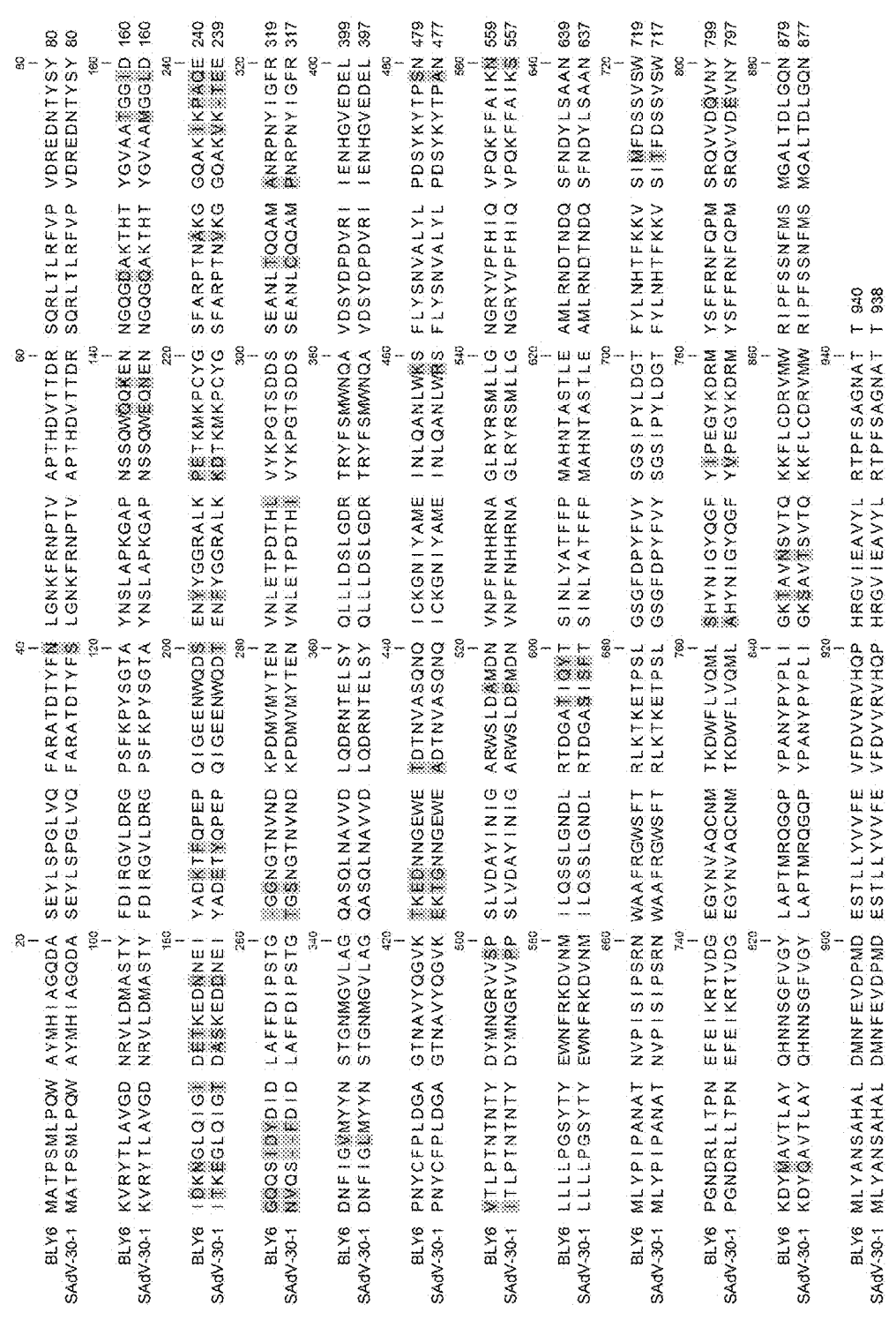

```
                                    20                    40                    60                    80
                                     |                     |                     |                     |
     BLY6 MATPSMLPQW AYMHIAGQDA SEYLSPGLVQ FARATDTYFN LGNKFRNPTV APTHDVTTDR SQRLTLRFVP VDREDNTYSY 80
SAdV-30-1 MATPSMLPQW AYMHIAGQDA SEYLSPGLVQ FARATDTYFS LGNKFRNPTV APTHDVTTDR SQRLTLRFVP VDREDNTYSY 80
                                   100                   120                   140                   160
                                     |                     |                     |                     |
     BLY6 KVRYTLAVGD NRVLDMASTY FDIRGVLDRG PSFKPYSGTA YNSLAPKGAP NSSQWQQKEN NGQGDAKTHT YGVAATGGID 160
SAdV-30-1 KVRYTLAVGD NRVLDMASTY FDIRGVLDRG PSFKPYSGTA YNSLAPKGAP NSSQWEQNEN NGQGQAKTHT YGVAAMGGLD 160
                                   180                   200                   220                   240
                                     |                     |                     |                     |
     BLY6 IDKNGLQIGI DETKEDNNEI YADKTFQPEP QIGEENWQDS ENYYGGRALK PETKMKPCYG SFARPTNAKG GQAKIKPAQE 240
SAdV-30-1 ITKEGLQIGT DASKEDDNEI YADETYQPEP QIGEENWQDT ENFYGGRALK KDTKMKPCYG SFARPTNVKG GQAKVK-TEE 239
                                   260                   280                   300                   320
                                     |                     |                     |                     |
     BLY6 GQQSIDYDID LAFFDIPSTG -GGNGTNVND KPDMVMYTEN VNLETPDTHL VYKPGTSDDS SEANLTQQAM ANRPNYIGFR 319
SAdV-30-1 NVQS--FDID LAFFDIPSTG TGSNGTNVND KPDMVMYTEN VNLETPDTHI VYKPGTSDDS SEANLCQQAM PNRPNYIGFR 317
                                   340                   360                   380                   400
                                     |                     |                     |                     |
     BLY6 DNFIGVMYYN STGNMGVLAG QASQLNAVVD LQDRNTELSY QLLLDSLGDR TRYFSMWNQA VDSYDPDVRI IENHGVEDEL 399
SAdV-30-1 DNFIGLMYYN STGNMGVLAG QASQLNAVVD LQDRNTELSY QLLLDSLGDR TRYFSMWNQA VDSYDPDVRI IENHGVEDEL 397
                                   420                   440                   460                   480
                                     |                     |                     |                     |
     BLY6 PNYCFPLDGA GTNAVYQGVK TKEDNNGEWE TDTNVASQNQ ICKGNIYAME INLQANLWKS FLYSNVALYL PDSYKYTPSN 479
SAdV-30-1 PNYCFPLDGA GTNAVYQGVK EKTGNNGEWE ADTNVASQNQ ICKGNIYAME INLQANLWRS FLYSNVALYL PDSYKYTPAN 477
                                   500                   520                   540                   560
                                     |                     |                     |                     |
     BLY6 VTLPTNTNTY DYMNGRVVSP SLVDAYINIG ARWSLDAMDN VNPFNHHRNA GLRYRSMLLG NGRYVPFHIQ VPQKFFAIKN 559
SAdV-30-1 ITLPTNTNTY DYMNGRVVPP SLVDAYINIG ARWSLDPMDN VNPFNHHRNA GLRYRSMLLG NGRYVPFHIQ VPQKFFAIKS 557
                                   580                   600                   620                   640
                                     |                     |                     |                     |
     BLY6 LLLLPGSYTY EWNFRKDVNM ILQSSLGNDL RTDGATIQYT SINLYATFFP MAHNTASTLE AMLRNDTNDQ SFNDYLSAAN 639
SAdV-30-1 LLLLPGSYTY EWNFRKDVNM ILQSSLGNDL RTDGASISET SINLYATFFP MAHNTASTLE AMLRNDTNDQ SFNDYLSAAN 637
                                   660                   680                   700                   720
                                     |                     |                     |                     |
     BLY6 MLYPIPANAT NVPISIPSRN WAAFRGWSFT RLKTKETPSL GSGFDPYFVY SGSIPYLDGT FYLNHTFKKV SIMFDSSVSW 719
SAdV-30-1 MLYPIPANAT NVPISIPSRN WAAFRGWSFT RLKTKETPSL GSGFDPYFVY SGSIPYLDGT FYLNHTFKKV SITFDSSVSW 717
                                   740                   760                   780                   800
                                     |                     |                     |                     |
     BLY6 PGNDRLLTPN EFEIKRTVDG EGYNVAQCNM TKDWFLVQML SHYNIGYQGF YIPEGYKDRM YSFFRNFQPM SRQVVDQVNY 799
SAdV-30-1 PGNDRLLTPN EFEIKRTVDG EGYNVAQCNM TKDWFLVQML AHYNIGYQGF YVPEGYKDRM YSFFRNFQPM SRQVVDEVNY 797
                                   820                   840                   860                   880
                                     |                     |                     |                     |
     BLY6 KDYMAVTLAY QHNNSGFVGY LAPTMRQGQP YPANYPYPLI GKTAVNSVTQ KKFLCDRVMW RIPFSSNFMS MGALTDLGQN 879
SAdV-30-1 KDYQAVTLAY QHNNSGFVGY LAPTMRQGQP YPANYPYPLI GKSAVTSVTQ KKFLCDRVMW RIPFSSNFMS MGALTDLGQN 877
                                   900                   920                   940
                                     |                     |                     |
     BLY6 MLYANSAHAL DMNFEVDPMD ESTLLYVVFE VFDVVRVHQP HRGVIEAVYL RTPFSAGNAT T 940
SAdV-30-1 MLYANSAHAL DMNFEVDPMD ESTLLYVVFE VFDVVRVHQP HRGVIEAVYL RTPFSAGNAT T 938
```

FIG. 7

ADENOVIRUS AND USES THEREOF

CROSS-REFERENCE TO RELATED APPLICATIONS

This application is a Section 371 of International Application No. PCT/EP2018/079713, filed Oct. 30, 2018, which was published in the English language on May 9, 2019 under International Publication No. WO 2019/086456 A1, and claims priority under 35 U.S.C. § 119(b) to European Application No. 17199348.8, filed Oct. 31, 2017, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065768.11633_SL," creation date of Apr. 29, 2020, and having a size of 451 KB. The sequence listing submitted via EFS-Web is part of the specification and is herein incorporated by reference in its entirety.

FIELD OF THE INVENTION

This invention relates to biotechnology. More particularly, to the field and use of adenoviral vectors, such as replication defective adenoviral vectors to deliver antigens and elicit an immune response in hosts.

BACKGROUND OF THE INVENTION

Recombinant adenoviral vectors are widely applied for gene therapy applications and vaccines. AdV-5 vector-based vaccines have been shown to elicit potent and protective immune responses in a variety of animal models (see, e.g., WO2001/02607; WO2002/22080; Shiver et al., Nature 415: 331 (2002); Letvin et al., Ann. Rev. Immunol. 20:73 (2002); Shiver and Emini, Ann. Rev. Med. 55:355 (2004)). However, the utility of recombinant AdV-5 vector-based vaccines will likely be limited by the high seroprevalence of AdV-5-specific neutralizing antibodies (NAbs) in human populations. The existence of anti-AdV-5 immunity has been shown to substantially suppress the immunogenicity of AdV-5-based vaccines in studies in mice, rhesus monkeys, and humans.

One promising strategy to circumvent the existence of pre-existing immunity in individuals previously infected or treated with the most common human adenovirus, e.g., AdV-5, involves the development of recombinant vectors from adenovirus serotypes that do not encounter such pre-existing immunities. One such strategy is based on the use of non-human simian adenoviruses since these do not typically infect humans and exhibit low seroprevalence in human samples. Non-human simian adenoviruses are applicable for human use since it was shown that these viruses could infect human cells in vitro (WO2003/000283; WO2004/037189).

Thus, there is a need in the field for alternative adenoviral vectors that are producible in large quantities, that do not encounter pre-existing immunities in the host, but that are still immunogenic and capable of inducing a strong immune response against the antigens encoded by the heterologous nucleic acids inserted in the vector.

BRIEF SUMMARY OF THE INVENTION

Provided are isolated nucleic acid sequences encoding hexon polypeptides. In certain embodiments, the hexon polypeptide or a functional derivative thereof comprises a hexon hypervariable regions-encompassing polypeptide having the amino acid sequence of SEQ ID NO:1 or an amino acid sequence which is at least 95% identical over its entire length to the amino acid sequence of SEQ ID NO:1.

In certain embodiments, the hexon polypeptide comprises a hexon hypervariable regions-encompassing polypeptide having the amino acid sequence of SEQ ID NO:1. In certain embodiments, the hexon polypeptide or the functional derivative thereof comprises the amino acid sequence of a BLY6 hexon polypeptide (SEQ ID NO:2) or an amino acid sequence which is at least 95% identical over its entire length to the amino acid sequence of SEQ ID NO:2.

Also provided are isolated nucleic acid sequences encoding a fiber polypeptide or a functional derivative thereof. In certain embodiments, the fiber polypeptide comprises at least one of a fiber knob polypeptide sequence comprising the amino acid sequence of SEQ ID NO:10; a fiber shaft polypeptide sequence comprising the amino acid sequence of SEQ ID NO:11; and a fiber tail polypeptide sequence comprising the amino acid sequence of SEQ ID NO:12. In certain embodiments, the fiber polypeptide or a functional derivative thereof comprises the amino acid sequence of a BLY6 fiber polypeptide (SEQ ID NO:3) or an amino acid sequence which is at least 95% identical over its entire length to the amino acid sequence of SEQ ID NO:3.

Embodiments of the invention also include isolated fiber and hexon polypeptides encoded by the fiber and hexon nucleic acid sequences of the invention.

Further provided herein are isolated nucleic acids comprising a hexon nucleic acid sequence encoding at least one of the hexon polypeptides disclosed herein, and a fiber nucleic acid sequence encoding at least one of the fiber polypeptides disclosed herein. In certain embodiments, provided herein are vectors comprising the isolated nucleic acids described herein. In one embodiment, the vector is a viral vector. In another embodiment, the vector is an expression vector. In one preferred embodiment, the vector is an adenoviral vector. More preferably, the vector further comprises a transgene.

Also provided are recombinant cells comprising the vectors described herein. Such cells can be used for recombinant protein production, recombinant protein expression, or the production of vectors or viral particles. Also provided are methods of producing a vector. The methods comprise (a) growing the recombinant cell disclosed herein under conditions for production of the vector; and (b) isolating the vector from the recombinant cell.

In certain embodiments, provided are immunogenic compositions comprising the vectors disclosed herein. Also provided are methods of inducing an immune response in a subject in need thereof, comprising administering to the subject the immunogenic compositions disclosed herein.

In certain embodiments, provided are adenoviral vectors comprising (a) at least one transgene; and (b) a nucleic acid sequence encoding a hexon polypeptide according to embodiments of the invention. The hexon polypeptide can, for example, comprise a hexon hypervariable regions-encompassing polypeptide having the amino acid sequence of SEQ ID NO:1 or an amino acid sequence which is at least 95% identical over its entire length to the amino acid sequence of SEQ ID NO:1. The hexon polypeptide can, for example, comprise an amino acid sequence having the amino acid sequence of SEQ ID NO:1. In certain embodiments, the hexon polypeptide comprises the amino acid sequence of a BLY6 hexon polypeptide (SEQ ID NO:2) or an amino acid sequence which is at least 95% identical over its entire length to the amino acid sequence of SEQ ID NO:2.

In certain embodiments, provided are adenoviral vectors comprising (a) at least one transgene; and (b) a nucleic acid sequence encoding a fiber polypeptide according to embodiments of the invention. In certain embodiments, the fiber polypeptide can comprise at least one of a fiber knob polypeptide sequence comprising the amino acid sequence of SEQ ID NO:10; a fiber shaft polypeptide sequence comprising the amino acid sequence of SEQ ID NO:11; and a fiber tail polypeptide sequence comprising the amino acid sequence of SEQ ID NO:12. In certain embodiments, the fiber polypeptide or a functional derivative thereof comprises the amino acid sequence of a BLY6 fiber polypeptide (SEQ ID NO:3) or an amino acid sequence which is at least 95% identical over its entire length to the amino acid sequence of SEQ ID NO:3. Embodiments of the invention also include adenoviral vectors comprising (a) at least one transgene; (b) a nucleic acid sequence encoding a hexon polypeptide according to embodiments of the invention; and (c) a nucleic acid sequence encoding a fiber polypeptide according to embodiments of the invention.

In certain embodiments, the adenoviral vectors provided herein are replication-defective adenovirus vectors (rAd). In one embodiment, the adenoviral vectors can comprise an E1 deletion. In certain embodiments, the adenoviral vectors provided herein can further comprise an E3 deletion. The adenoviral vectors can be simian adenoviral vectors comprising adenoviral nucleic acid sequences from one or more simian adenoviruses (SAdV), such as chimpanzee adenoviruses (e.g., ChAd3); gorilla adenoviruses; or rhesus adenoviruses (e.g., rhAd51, rhAd52 or rhAd53). The adenoviral vectors can be human adenoviral vectors comprising adenoviral sequences from one or more human adenoviruses (e.g., hAdV-4, hAdV-5, hAdV-26, hAdV-35). Preferably, the adenoviral vector is a chimeric adenoviral vector comprising one or more human adenoviral nucleic acid sequences. The human adenoviral nucleic acid sequences can, for example, be from human adenovirus-4 (hAdV-4), human adenovirus-5 (hAdV-5), human adenovirus-26 (hAdV-26), or human adenovirus-35 (hAdV-35). The adenoviral vectors can, for example, comprise a human adenovirus-5 (hAdV-5) E4 orf6 and orf 6/7.

In certain embodiments, the transgene is located adjacent to an inverted terminal repeat (ITR). In certain embodiments, a transgene is located at or adjacent to the E1 deletion, at or adjacent to the E3 deletion, and/or at or adjacent to the ITR, e.g., between the E4 region and the right ITR (RITR).

In certain embodiments, the adenoviral vectors provided herein comprises a nucleic acid sequence of SEQ ID NO:13 or SEQ ID NO:14.

Also provided are immunogenic compositions or vaccines comprising the adenoviral vectors described herein and a pharmaceutically acceptable carrier. Further provided are methods for inducing an immune response in a subject in need thereof. The methods comprise administering to the subject the vaccines disclosed herein. Further provided are methods of producing a vaccine. The methods comprise combining an adenoviral vector disclosed herein with a pharmaceutically acceptable carrier.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1A shows the experimental set-up. FIG. 1B shows the cellular immune response induced by Ad26.FLuc, BLY6.FLuc and Ad49.FLuc against the vector-encoded antigen (i.e. Fluc, firefly luciferase) as determined by Interferon gamma (IFN-γ) ELISPOT analysis. The y-axis shows the number of Spot Forming Units (SFU) per $10^6$ splenocytes and the dotted line indicates 95% percentile of the medium stimuli.

FIG. 2A shows the experimental set-up. FIG. 2B shows a graph of the results of a virus neutralization assay (VNA) performed at eight weeks after immunization with Ad26.RSVF-2A-GLuc or with BLY6.RSVF-2A-GLuc at three different concentrations ($10^8$, $10^9$ and $10^{10}$ vp), or with Ad26.FLuc or BLY6.FLuc at $10^{10}$ vp. FIG. 2C shows the cellular immune responses induced by Ad26.RSVF-2A-GLuc and BLY6.RSVF-2A-GLuc after immunization as determined by IFN-γ ELISPOT analysis. FIG. 2D shows a graph of RSVF-specific IgG binding antibodies induced by Ad26.RSVF-2A-GLuc or BLY6.RSVF-2A-GLuc in serum of immunized mice at 8 weeks post-immunization.

FIG. 3 shows homologous and heterologous adenovirus neutralization titers induced in mice immunized with adenoviral vectors Ad35, Ad26, Ad49, Ad5, Ad4, and BLY6.

FIG. 7 shows an alignment of BLY6 hexon polypeptide (SEQ ID NO:2) and SAdV-30-1 hexon polypeptide (SEQ ID NO:4) sequences.

DETAILED DESCRIPTION OF THE INVENTION

Figure 1A:
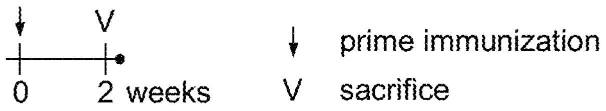
FIG. 1A-FIG. 1B show the cellular and humoral immune responses induced by BLY6.FLuc and Ad49.FLuc.

This disclosure is based upon, at least in part, the isolation and identification of a new gorilla adenovirus isolate, allocated into adenovirus species E, as well as construction and evaluation of vaccine vectors comprising nucleic acids encoding variable regions of the hexon and fiber polypeptides of said gorilla adenovirus. The adenoviral vectors are capable of eliciting an immune response and, furthermore, have low seroprevalence in humans. The adenoviral vectors can be formulated for vaccines and used to induce protective immunity against specific antigens of interest.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human, to whom will be or has been vaccinated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right", "left", "lower" and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., hexon and fiber polypeptides and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As used herein, the term "protective immunity" or "protective immune response" means that the vaccinated subject is able to control an infection with the pathogenic agent against which the vaccination was done. The pathogenic agent can, for example, be an antigenic gene product or antigenic protein, or a fragment thereof. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

The term "adjuvant" is defined as one or more substances that cause stimulation of the immune system. In this context, an adjuvant is used to enhance an immune response to the adenovirus vectors of the invention.

As used herein, the term "antigenic gene product or fragment thereof" or "antigenic protein" can include a bacterial, viral, parasitic, or fungal protein, or a fragment thereof. Preferably, an antigenic protein or antigenic gene product is capable of raising in a host a protective immune response, e.g., inducing an immune response against a disease or infection (e.g., a bacterial, viral, parasitic, or fungal disease or infection), and/or producing an immunity in (i.e., vaccinating) a subject against a disease or infection, that protects the subject against the disease or infection.

Adenoviral Vectors

Exposure to certain adenoviruses has resulted in immune responses against certain adenoviral serotypes, which can affect efficacy of adenoviral vectors. Because infections with human adenoviruses are common in humans, the prevalence of neutralizing antibodies against human adenoviruses in human populations is high. The presence of such neutralizing antibodies in individuals may be expected to reduce the efficacy of a gene transfer vector based on a human adenoviral backbone. One way to circumvent the reduction of efficacy is to replace the epitopes on the adenoviral capsid proteins that are the targets of neutralizing antibodies. The target sequences on the capsid proteins can be replaced with protein sequences from other adenoviruses which are of low prevalence, and therefore against which neutralizing antibodies are rare in human populations.

A "capsid protein" refers to a protein on the capsid of an adenovirus (e.g., BLY6, HAdV-4) or a functional fragment or derivative thereof that is involved in determining the serotype and/or tropism of a particular adenovirus. Capsid proteins typically include the fiber, penton and/or hexon proteins. In certain embodiments, the capsid protein is an entire or full length capsid protein of the adenovirus. In other embodiments, the capsid protein is a fragment or a derivative of a full length capsid protein of the adenovirus. In certain embodiments, the hexon, penton and fiber encoded by an adenoviral vector of the invention are of the same or different adenoviral background (i.e., a BLY6 hexon and BLY6 fiber, a BLY6 hexon and a human adenovirus fiber, a human adenovirus hexon and a BLY6 fiber, etc).

A "hexon polypeptide" refers to adenovirus hexon coat proteins, functional fragments, and derivatives thereof.

A "fiber polypeptide" refers to adenovirus fiber proteins, functional fragments, and derivatives thereof.

One target of neutralizing antibodies against adenoviruses is the major coat protein, the hexon protein. Replacing the hexon protein or the variable sequences within the hexon protein, which define serotype and bind to neutralizing antibodies, with the hexon protein or variable sequences within the hexon protein from adenoviruses that are rare in the human population, such as those gorilla sequences described herein, can allow for the construction of adenovirus vectors that would be less susceptible to neutralization by antibodies commonly found in humans.

A second target of neutralizing antibodies against adenoviruses is the fiber protein. Replacing the fiber protein or variable sequences within the fiber protein with the fiber protein or variable sequences within the fiber protein from adenoviruses that are rare in the human population, such as those gorilla sequences described herein, can also allow for the construction of adenovirus vectors that would be less susceptible to neutralization by antibodies commonly found in humans. A combination of the fiber replacement with hexon replacements described above can confer additional resistance to neutralization by antibodies commonly present in human populations.

This disclosure provides isolated nucleic acid sequences encoding hexon polypeptides and/or fiber polypeptides derived from an isolated simian adenovirus serotype and adenoviral vectors comprising at least one of the isolated nucleic acid sequences.

A "functional derivative" of a polypeptide suitably refers to a modified version of a polypeptide, e.g. wherein one or more amino acids of the polypeptide may be deleted, inserted, modified and/or substituted. A derivative of an unmodified adenoviral capsid protein is considered functional if, for example:

(a) an adenovirus comprising the derivative capsid protein within its capsid retains substantially the same or a lower seroprevalence compared to an adenovirus comprising the unmodified capsid protein; and/or (b) an adenovirus comprising the derivative capsid protein within its capsid retains substantially the same or a higher host cell infectivity compared to an adenovirus comprising the unmodified capsid protein; and/or (c) an adenovirus comprising the derivative capsid protein within its capsid retains substantially the same or a higher immunogenicity compared to an adenovirus comprising the unmodified capsid protein; and or (d) an adenovirus comprising the derivative capsid protein within its capsid retains substantially the same or a higher level of transgene productivity compared to an adenovirus comprising the unmodified capsid protein.

An "adenoviral vector" refers to a recombinant vector derived from or containing at least a portion of an adenoviral genome.

In preferred embodiments, the isolated nucleic acid sequences encode hexon polypeptides or a functional derivative thereof comprising a hexon hypervariable regions-encompassing polypeptide having the amino acid sequence of SEQ ID NO:1 or an amino acid sequence which is at least 95% identical over its entire length to the amino acid sequence of SEQ ID NO:1. In certain embodiments, the hexon polypeptides comprise a hexon hypervariable regions-encompassing polypeptide having the amino acid sequence of SEQ ID NO:1. In preferred embodiments, the hexon polypeptide or the functional derivative thereof comprises the amino acid sequence of a BLY6 hexon polypeptide (SEQ ID NO:2) or an amino acid sequence which is at least 95% identical over its entire length to the amino acid sequence of SEQ ID NO:2. In certain embodiments, the hexon polypeptide or functional derivative thereof comprises an amino acid sequence which is at least 95%, at least 96%, at least 97%, at least 98%, or at least 99% identical over its entire length to the amino acid sequence of SEQ ID NO:2.

In preferred embodiments, the isolated nucleic acid sequences encode fiber polypeptides or a functional derivative thereof. The fiber polypeptide can, for example, comprise at least one of a fiber knob polypeptide comprising the amino acid sequence of SEQ ID NO:10; a fiber shaft polypeptide comprising the amino acid sequence of SEQ ID NO:11; and a fiber tail polypeptide comprising the amino acid sequence of SEQ ID NO:12. In preferred embodiments, the fiber polypeptide or a functional derivative thereof comprise the amino acid sequence of a BLY6 fiber polypeptide (SEQ ID NO:3) or an amino acid sequence which is at least 95% identical over its entire length to the amino acid sequence of SEQ ID NO:3.

In preferred embodiments, provided is an isolated nucleic acid comprising a hexon nucleic acid sequence encoding at least one of the hexon polypeptides disclosed herein and a nucleic acid sequence encoding at least one of the fiber polypeptides disclosed herein.

In preferred embodiments, provided are vectors, preferably adenoviral vectors, comprising at least one of an isolated hexon nucleic acid sequence and/or an isolated fiber nucleic acid sequence according to embodiments of the invention. The adenoviral vectors can, for example, comprise at least one transgene; and a nucleic acid sequence encoding a hexon polypeptide and/or a fiber polypeptide, wherein the hexon polypeptide comprises a polypeptide comprising a hexon hypervariable regions-encompassing polypeptide disclosed herein and the fiber polypeptide comprises a fiber polypeptide described herein.

Typically, an adenoviral vector of the invention comprises the entire recombinant adenoviral genome on, e.g., a plasmid, cosmid, or baculovirus vector. The nucleic acid molecules of the invention can be in the form of RNA or in the form of DNA obtained by cloning or produced synthetically. The DNA can be double-stranded or single-stranded.

One of ordinary skill will recognize that elements derived from multiple serotypes can be combined in a single adenoviral vector, for example human or simian adenovirus. Thus, a chimeric adenovirus vector that combines desirable properties from different serotypes can be produced. Thus, in some embodiments, a chimeric adenovirus vector of the invention could combine the absence of pre-existing immunity of the simian hexon and/or fiber polypeptide sequences with the high level antigen delivery and presentation capacity of an existing adenoviral vectors, such as rAd4, rAd5, rAd26 or rAd35.

Advantages of adenoviral vectors for use as vaccines include ease of manipulation, good manufacturability at large scale, and an excellent safety record based on many years of experience in research, development, manufacturing and clinical trials with numerous adenoviral vectors that have been reported. Adenoviral vectors that are used as vaccines generally provide a good immune response to the transgene-encoded protein, including a cellular immune response. An adenoviral vector according to the invention can be based on any type of adenovirus, and in certain embodiments is a human adenovirus, which can be of any group or serotype. In preferred embodiments, the recombinant adenovirus is based upon a human adenovirus from group A, B, C, D, E, F or G. In other preferred embodiments, the recombinant adenovirus is based upon a human adenovirus serotype 5, 11, 26, 34, 35, 48, 49, or 50. In other embodiments, it is a simian adenovirus, such as chimpanzee or gorilla adenovirus, which can be of any serotype. In certain embodiments, the recombinant adenovirus is based upon chimpanzee adenovirus type 1, 3, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50, 67, or SA7P.

In a more preferred embodiment, the chimpanzee adenovirus vector of the second composition is ChAdV3. Recombinant chimpanzee adenovirus serotype 3 (ChAd3 or cAd3) is a subgroup C adenovirus with properties similar to those of human adenovirus serotype 5 (Ad5). ChAd3 has been shown to be safe and immunogenic in human studies evaluating candidate vaccines for hepatitis C virus (HCV) (Barnes E, et al. 2012 Science translational medicine 4: 115ral). It was reported that ChAd3-based vaccines were capable of inducing an immune response comparable to a human Ad5 vectored vaccine. See, e.g., Peruzzi D, et al. 2009 Vaccine 27: 1293-300 and Quinn K M, et al. 2013 J Immunol 190: 2720-35; WO 2005/071093; WO2011/0130627, etc.

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in *Virology*, B. N. Fields et al., eds 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual,* 2d ed., Cold Spring Harbor Press, Cold Spring Harbor, N.Y. (1989), Watson et al., *Recombinant DNA,* 2d ed., Scientific American Books (1992), and Ausubel et al., *Current Protocols in Molecular Biology*, Wiley Interscience Publishers, NY (1995), and other references mentioned herein.

In certain embodiments, the adenoviral vector comprises an E1 deletion and/or an E3 deletion. An E1 or E3 deletion can, for example, include a complete deletion of the gene or a partial deletion, which renders the E1 or E3 gene product functionally defective. Thus, in certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented. One or more of the E1, E2, E3 and E4 regions can also be inactivated by other means, such as by inserting a transgene of interest (usually linked to a promoter) into the regions to be inactivated.

A producer cell (sometimes also referred to in the art and herein as 'packaging cell' or 'complementing cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128), E1-transformed amniocytes (See EP patent 1230354), E1-transformed A549 cells (see e.g. WO 98/39411, U.S. Pat. No. 5,891,690), GH329:HeLa (Gao et al., 2000, *Hum Gene Ther* 11: 213-19), 293, and the like. In certain embodiments, the producer cells are for instance HEK293 cells, or PER.C6 cells, or 911 cells, or IT293SF cells, and the like. Production of adenoviral vectors in producer cells is reviewed in (Kovesdi et al., 2010, *Viruses* 2: 1681-703).

In certain embodiments, the adenoviral vector is a chimeric adenoviral vector comprising one or more human adenoviral nucleic acid sequences. The human adenoviral nucleic acids can, for example, be selected from human adenovirus-4 (Ad-4), human adenovirus-5 (Ad-5), human adenovirus-26 (Ad-26), or human adenovirus-35 (Ad-35). In certain embodiments, an E1-deficient adenoviral vector comprises the E4-orf6 coding sequence of an adenovirus of human Ad5. This allows propagation of such adenoviruses in well-known complementing cell lines that express the E1 genes of Ad5, such as for example 293 cells or PER.C6 cells (see, e.g. Fallaux et al., 1998, *Hum Gene Ther* 9: 1909-17, Havenga et al., 2006, *J Gen Virol* 87: 2135-43; WO 03/104467, incorporated in their entirety by reference herein).

In certain embodiments, the adenoviral vector comprises a transgene. A "transgene" refers to a heterologous nucleic acid, which is a nucleic acid that is not naturally present in the vector, and according to the present invention the transgene can encode an antigenic gene product or antigenic protein that elicits an immune response in the subject. The transgene can, for example, be introduced into the vector by standard molecular biology techniques. The transgene can, for example, be cloned into a deleted E1 or E3 region of an adenoviral vector, or in the region between the E4 region and the rITR. A transgene is generally operably linked to expression control sequences. In preferred embodiments, the transgene is inserted at a transgene insertion site.

If required, the nucleic acid sequences encoding hexon and/or fiber polypeptides according to embodiments of the invention, and/or the transgene can be codon-optimized to ensure proper expression in the treated host (e.g., human). Codon-optimization is a technology widely applied in the art.

The transgene can be under the control of (i.e., operably linked to) an adenovirus-derived promoter (e.g., the Major Late Promoter) or can be under the control of a heterologous promoter. Examples of suitable heterologous promoters include the CMV promoter and the RSV promoter. Preferably, the promoter is located upstream of the heterologous gene of interest within an expression cassette.

In preferred embodiments, the adenoviral vector comprises a nucleic acid sequence of SEQ ID NO:13 or SEQ ID NO:14.

Immunogenic Compositions

Immunogenic compositions are compositions comprising an immunologically effective amount of purified or partially purified human or simian (e.g., gorilla) adenoviral vectors for use in the invention. Said compositions can be formulated as a vaccine (also referred to as an "immunogenic composition") according to methods well known in the art. Such compositions can include adjuvants to enhance immune responses. The optimal ratios of each component in the formulation can be determined by techniques well known to those skilled in the art in view of the present disclosure.

The immunogenic compositions according to embodiments of the present invention can be made using methods known to those of skill in the art in view of the present disclosure. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

The immunogenic compositions useful in the invention can comprise adjuvants. Adjuvants suitable for co-administration in accordance with the invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, AS01, AS03, AS04, AS15, GcMAF, B-alethine, MPC-026, Adjuvax, CpG ODN, Betafectin, Alum, and MF59.

Other adjuvants that can be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-10, and IL-12 or encoding nucleic acids therefore.

The compositions of the invention can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intravenous, cutaneous, intramucosal (e.g., gut), intranasal or intraperitoneal routes.

Method for Inducing Protective Immunity

Another general aspect of the invention relates to a method of inducing an immune response in a subject in need thereof. The methods can, for example, comprise administering to the subject a vaccine comprising an adenoviral vector described herein and a pharmaceutically acceptable carrier. Also provided herein are methods of producing a vaccine. The methods comprise combining an adenoviral vector described herein with a pharmaceutically acceptable carrier.

Any of the immunogenic compositions according to embodiments of the invention, including but not limited to those described herein, can be used in methods of the invention as a vaccine.

Administration of the immunogenic compositions/vaccines comprising the vectors is typically intramuscular or subcutaneous. However other modes of administration such as intravenous, cutaneous, intradermal or nasal can be envisaged as well. Intramuscular administration of the immunogenic compositions can be achieved by using a needle to inject a suspension of the adenovirus vector. An alternative is the use of a needleless injection device to administer the composition (using, e.g., Biojector) or a freeze-dried powder containing the vaccine.

For intravenous, cutaneous or subcutaneous injection, or injection at the site of affliction, the vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed.

Typically, administration will have a prophylactic aim to generate an immune response against an antigen of interest (e.g., a bacterial, viral, parasitic, and/or fungal pathogen) before infection or development of symptoms. Diseases and disorders that can be treated or prevented in accordance with the invention include those in which an immune response can play a protective or therapeutic role. In other embodiments, the adenovirus vectors can be administered for post-exposure prophylactics.

The immunogenic compositions containing the human or simian (e.g., gorilla) adenovirus vectors are administered to a subject, giving rise to an immune response to the antigen of interest in the subject. An amount of a composition sufficient to induce a detectable immune response is defined to be an "immunologically effective dose" or an "effective amount" of the composition. The immunogenic compositions of the invention can induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus vectors and optional formulation of such particles into compositions, the vectors can be administered to an individual, particularly human or other primate. Administration can be to humans, or another mammal, e.g., mouse, rat, hamster, guinea pig, rabbit, sheep, goat, pig, horse, cow, donkey, monkey, dog or cat. Delivery to a non-human mammal need not be for a therapeutic purpose, but can be for use in an experimental context, for instance in investigation of mechanisms of immune responses to the adenovirus vectors.

In one exemplary regimen, the adenoviral vector is administered (e.g., intramuscularly) in a volume ranging between about 100 μl to about 10 ml containing concentrations of about $10^4$ to $10^{12}$ virus particles/ml. Preferably, the adenoviral vector is administered in a volume ranging between 0.1 and 2.0 ml. For example, the adenoviral vector can be administered with 100 μl, 500 μl, 1 ml, 2 ml. More preferably the adenoviral vector is administered in a volume of 0.5 ml. Optionally, the adenoviral vector can be administered in a concentration of about $10^7$ vp/ml, $10^8$ vp/ml, $10^9$ vp/ml, $10^{10}$ vp/ml, $5\times10^{10}$ vp/ml, $10^{11}$ vp/ml, or $10^{12}$ vp/ml. Typically, the adenoviral vector is administered in an amount of about $10^9$ to about $10^{12}$ viral particles (vp) to a human subject during one administration, more typically in an amount of about $10^{10}$ to about $10^{12}$ vp.

The initial vaccination can be followed by a boost or a kick from a vaccine/composition comprising the same adenoviral vector encoding an antigen of interest or a vaccine/composition comprising a different adenoviral vector encoding the same antigen of interest.

The composition can, if desired, be presented in a kit, pack or dispenser, which can contain one or more unit dosage forms containing the active ingredient. The kit, for example, can comprise metal or plastic foil, such as a blister pack. The kit, pack, or dispenser can be accompanied by instructions for administration.

The compositions of the invention can be administered alone or in combination with other treatments, either simultaneously or sequentially dependent upon the condition to be treated.

EMBODIMENTS

The invention provides also the following non-limiting embodiments.

Embodiment 1 is an isolated nucleic acid sequence encoding a hexon polypeptide or a functional derivative thereof comprising a hexon hypervariable regions-encompassing polypeptide having the amino acid sequence of SEQ ID NO:1 or an amino acid sequence which is at least 95% identical over its entire length to the amino acid sequence of SEQ ID NO:1.

Embodiment 2 is an isolated nucleic acid sequence encoding a hexon polypeptide comprising a hexon hypervariable regions-encompassing polypeptide having the amino acid sequence of SEQ ID NO:1.

Embodiment 3 is the isolated nucleic acid sequence of any one of embodiments 1-2, wherein the hexon polypeptide or the functional derivative thereof comprises the amino acid sequence of a BLY6 hexon polypeptide (SEQ ID NO:2) or an amino acid sequence which is at least 95% identical over its entire length to the amino acid sequence of SEQ ID NO:2.

Embodiment 4 is an isolated nucleic acid sequence comprising any one of the nucleic acid sequences of embodiments 1-3, and further comprising an isolated nucleic acid sequence encoding a fiber polypeptide or a functional derivative thereof.

Embodiment 5 is the isolated nucleic acid sequence of embodiment 4, wherein the fiber polypeptide comprises a fiber knob polypeptide sequence comprising the amino acid sequence of SEQ ID NO:10.

Embodiment 6 is the isolated nucleic acid sequence of embodiment 4, wherein the fiber polypeptide comprises a fiber shaft polypeptide sequence comprising the amino acid sequence of SEQ ID NO:11.

Embodiment 7 is the isolated nucleic acid sequence of embodiment 4, wherein the fiber polypeptide comprises a fiber tail polypeptide sequence comprising the amino acid sequence of SEQ ID NO:12.

Embodiment 8 is the isolated nucleic acid sequence of any one of embodiments 4-7, wherein the fiber polypeptide or a functional derivative thereof comprises the amino acid sequence of a BLY6 fiber polypeptide (SEQ ID NO:3) or an amino acid sequence which is at least 95% identical over its entire length to the amino acid sequence of SEQ ID NO:3.

Embodiment 9 is an isolated nucleic acid sequence encoding a fiber polypeptide comprising a fiber knob polypeptide sequence, wherein the fiber knob polypeptide sequence comprises the amino acid sequence of SEQ ID NO:10.

Embodiment 10 is an isolated nucleic acid sequence encoding a fiber polypeptide comprising a fiber shaft polypeptide sequence, wherein the fiber shaft polypeptide sequence comprises the amino acid sequence of SEQ ID NO:11.

Embodiment 11 is an isolated nucleic acid sequence encoding a fiber polypeptide comprising a fiber tail polypeptide sequence, wherein the fiber tail polypeptide sequence comprises the amino acid sequence of SEQ ID NO:12.

Embodiment 12 is the isolated nucleic acid sequence of any one of embodiments 9-11, wherein the fiber polypeptide comprises the amino acid sequence of a BLY6 fiber polypeptide (SEQ ID NO:3).

Embodiment 13 is a vector comprising the nucleic acid of any of embodiments 1-12.

Embodiment 14 is the vector of embodiment 13, being an adenoviral vector, and further comprising a transgene.

Embodiment 15 is a recombinant cell comprising the vector of embodiment 13 or 14.

Embodiment 16 is a method of producing a vector, comprising; (a) growing the recombinant cell of embodiment 15 under conditions for production of the vector; and (b) isolating the vector from the recombinant cell.

Embodiment 17 is an immunogenic composition comprising the vector of embodiment 14.

Embodiment 18 is a method of inducing an immune response in a subject in need thereof, comprising administering to the subject the immunogenic composition of embodiment 17.

Embodiment 19 is an adenoviral vector comprising (a) at least one transgene; and (b) a nucleic acid sequence encoding a hexon polypeptide comprising a hexon hypervariable regions-encompassing polypeptide having the amino acid sequence of SEQ ID NO:1.

Embodiment 20 is an adenoviral vector comprising (a) at least one transgene; and (b) a nucleic acid sequence encoding a hexon polypeptide comprising the amino acid sequence of a BLY6 hexon polypeptide (SEQ ID NO:2).

Embodiment 21 is an adenoviral vector comprising (a) at least one transgene; a nucleic acid sequence encoding a hexon polypeptide comprising the amino acid sequence of a BLY6 hexon polypeptide (SEQ ID NO:2); and (c) a nucleic acid sequence encoding a fiber polypeptide comprising the amino acid sequence of a BLY6 fiber polypeptide (SEQ ID NO:3).

EXAMPLES

Example 1: Generation of E1- and E3-Deleted Vectors Based on Novel Adenovirus Isolate BLY6

A novel gorilla adenovirus isolate, BLY6 (also designated JAd1-WT), was identified and sequenced. This gorilla adenovirus isolate was found to phylogenetically belong to the human adenovirus species E (HAdV-E). The full genome nucleotide sequence of BLY6 was determined to be SEQ ID NO:5.

Figure 5:
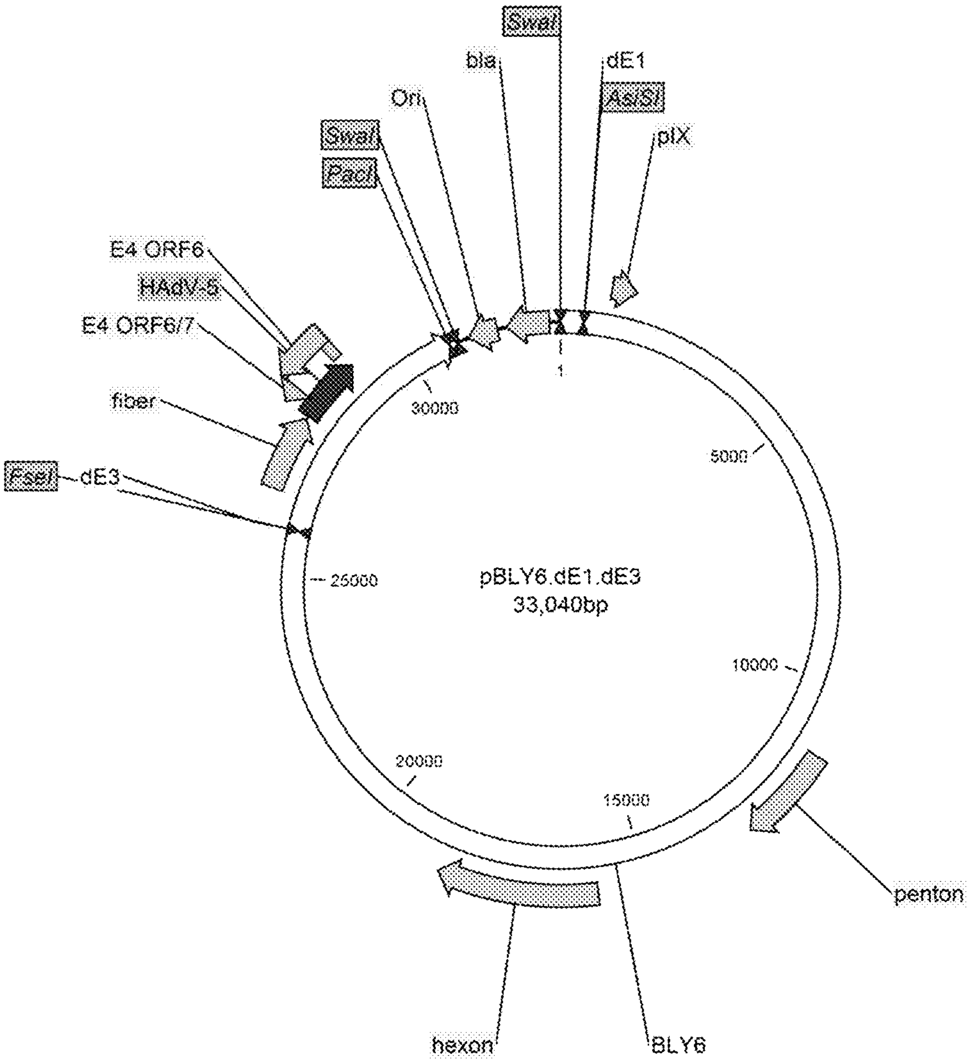
FIG. 5 shows a schematic of the plasmid pBLY6.dE1.dE3 (SEQ ID NO:8).
Figure 6:
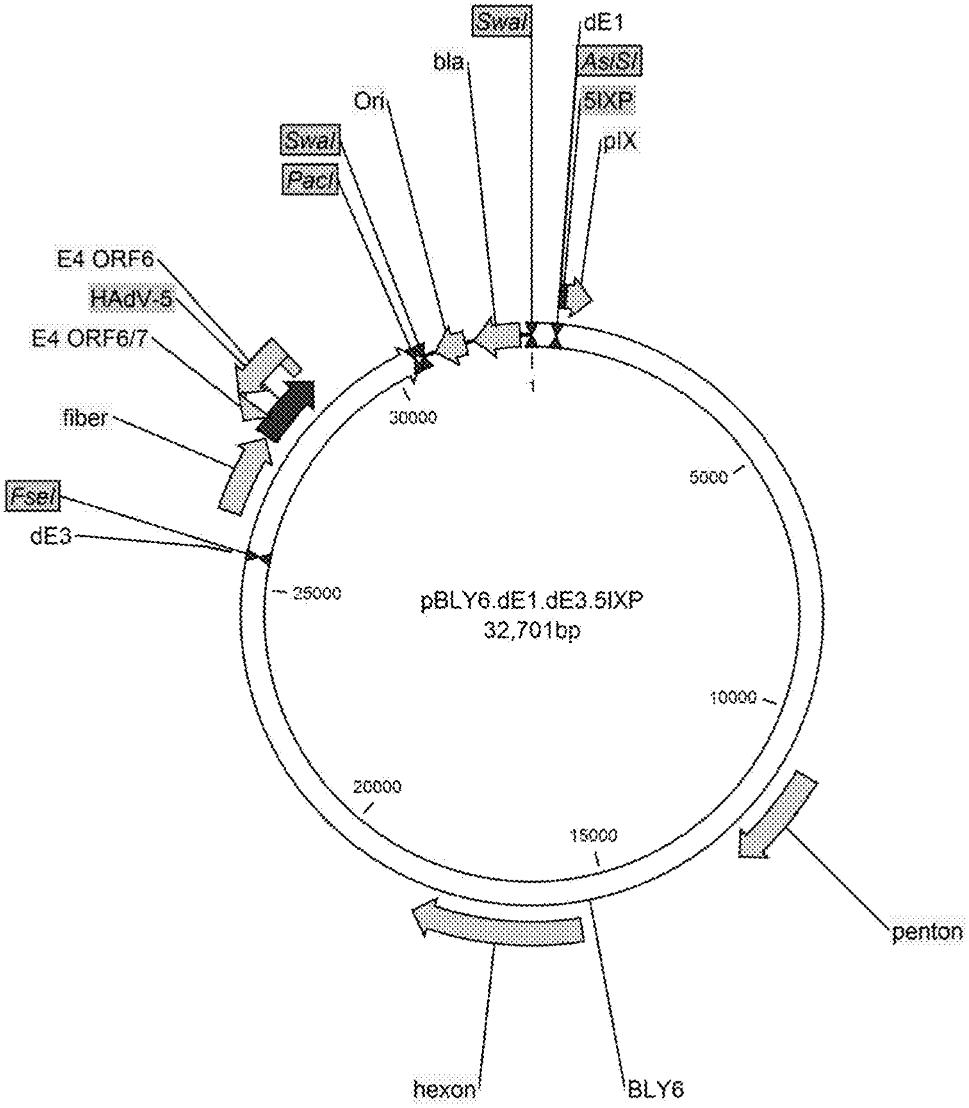
FIG. 6 shows a schematic of the plasmid pBLY6.dE1.dE3.5IXp (SEQ ID NO:9).

Description of the Single Plasmid System Used for the Generation of BLY6-Based Ad Vectors pBLY6.dE1.dE3 (SEQ ID NO:8; FIG. 5) and pBLY6.dE1.dE3.5IXP (SEQ ID NO:9; FIG. 6) are plasmids carrying full-length, E1- and E3-deleted adenoviral vector genomes based on isolate BLY6. The Ad vector genome sequences contained within these plasmids are set forth in SEQ ID NO:13 and SEQ ID NO:14, respectively. Within each of these plasmids, the adenoviral vector genome is flanked by two SwaI restriction enzyme sites (i.e. one SwaI site is located at either end of the vector genome). These SwaI sites are meant to facilitate excision of the Ad vector genome from the plasmid backbone prior to viral rescue by transfection of suitable E1-complementing cells (such as HEK293, 911, and PER.C6 cells). The Ad vector genomes comprised by these plasmids further carry certain restriction enzyme sites introduced in the location of the E1 deletion, in the E3 deletion, and adjacent to the right inverted terminal repeat (RITR). These restriction enzyme sites were selected to be unique in the context of the complete Ad genome plasmids. They represent "transgene insertion sites" that allow for the facile construction, by standard molecular cloning techniques, of Ad vectors carrying one or more transgene expression cassettes inserted at any of said respective locations or any combinations thereof. Ad vector designs and plasmid constructions are described in more detail in the sections below.

BLY6-Based Ad Vector Genome Design

BLY6-based Ad vector genomes were each designed to comprise an E1 deletion, an E3 deletion, different transgene insertion sites, and a replacement of the native E4 open reading frame (orf) 6 and orf6/7 with that of human adenovirus-5 (HAdV-5). The E1 region of each adenovirus was deleted and replaced with a transgene insertion site comprising an AsiSI restriction enzyme site sequence. The E3 region of each adenovirus was deleted and replaced with a transgene insertion site comprising an FseI restriction enzyme site sequence. Another transgene insertion site was created by insertion of a PacI restriction enzyme site sequence adjacent to the right inverted terminal repeat (ITR) of each adenovirus. The BLY6 sequences comprising E4 orf6 and orf6/7 coding sequences were replaced by SEQ ID NO:6. This replacing sequence comprises the E4 orf6 and orf6/7 coding sequences of human adenovirus-5 (HAdV-5) (base pairs 32914-34077 of GenBank sequence AC_000008).

Two types of E1 region deletions were designed and constructed. The BLY6-based Ad vector genome comprised by pBLY6.dE1.dE3 carries an E1 region deletion corresponding to removal of nucleotides 453 to 3016 of SEQ ID NO:5. By contrast, the BLY6-based Ad vector genome comprised by pBLY6.dE1.dE3.5IXP carries a larger E1 region-comprising sequence deletion that removes all the E1 coding sequences of BLY6 (i.e. nucleotides 453 to 3366 of SEQ ID NO:5). Furthermore, this latter Ad vector genome was additionally designed to carry a replacement of the non-coding sequence stretch between E1B 55K and pIX coding sequences by that of HAdV-5 (i.e. sequences corresponding to nucleotides 3367 to 3454 of SEQ ID NO:5 were replaced by nucleotides 3510-3608 of GenBank AC_000008 (i.e. by SEQ ID NO:7)).

Construction of Single Plasmids Comprising BLY6-Based Ad Vector Genomes pBLY6.dE1.dE3 (SEQ ID NO:8) was constructed by several steps of gene synthesis (performed by GenScript) and standard molecular cloning procedures. First, a 3586 bp DNA fragment (SEQ ID NO:15) containing the left end of the desired Ad vector genome (i.e. harboring the aforementioned E1 deletion) was synthesized and ligated, as an MfeI-NdeI restriction fragment, into EcoRI- and NdeI-digested pBR322 (GenBank accession number—J01749.1), leading to BLY6 intermediate plasmid 1. Second, A 4138 bp fragment (SEQ ID NO:16) containing the right end of the desired Ad vector genome (i.e. harboring the aforementioned E3 deletion, partial E4 sequence replacement, and transgene insertion site adjacent to the rITR) was synthesized and ligated, as a BamHI-NdeI restriction fragment, into BamHI- and NdeI-digested BLY6 intermediate plasmid 1, leading to BLY6 intermediate plasmid 2. Third, a 4563 bp fragment (SEQ ID NO:17) containing a middle Ad vector genome fragment was synthesized and ligated as a BamHI-MfeI restriction fragment into BamHI- and MfeI-digested BLY6 intermediate plasmid 2, leading to BLY6 intermediate plasmid 3 (SEQ ID NO:18). Fourth, the 18987 bp BsrGI-BsrGI restriction fragment of the BLY6 viral genome (SEQ ID NO:5) was ligated into BsrGI-digested BLY6 intermediate plasmid 3, leading to the final plasmid pBLY6.dE1.dE3 (SEQ ID NO:8).

pBLY6.dE1.dE3.5IXP (SEQ ID NO:9) was constructed in the same way as pBLY6.dE1.dE3 except that abovementioned BLY6 intermediate plasmid 3 (SEQ ID NO:18) was first modified to contain the desired E1 deletion and Ad5 pIX promoter insertion. This was done by synthesis of a 638 bp fragment (SEQ ID NO:19) that was subsequently ligated as an AsiSI-AgeI restriction fragment into AsiSI- and AgeI-digested BLY6 intermediate plasmid 3.

pBLY6.FLuc (SEQ ID NO:20) and pBLY6.RSVF-2A-GLuc (SEQ ID NO:21) are pBLY6.dE1.dE3-derived plasmids that each harbor a BLY6-based Ad vector genome equipped with a transgene expression cassette inserted at the location of the E1 deletion. The Ad vector genome sequences carried within these plasmids are set forth in SEQ ID NO:22 and SEQ ID NO:23, respectively. pBLY6.FLuc carries a transgene expression cassette for firefly luciferase (FLuc). This cassette is driven by the cytomegalovirus major immediate early promoter (i.e. the "CMV promoter") and contains an SV40-derived polyadenylation signal. pBLY6.RSVF-2A-Gluc carries a transgene expression cassette for "RSV-$F_{A2}$-2A-GLuc" (RSVF-2A-GLuc), which is a chimeric protein composed of the respiratory syncytial virus strain A2 fusion glycoprotein, a foot-and-mouth-disease virus 2A peptide, and Gaussia luciferase (GLuc). Like the Fluc cassette, this cassette is driven a CMV promoter and carries an SV40 polyadenlyation signal. In addition, this cassette contains within its 5'untranslated region a sequence comprising intron 2 of the human Apolipoprotein A1 gene. The Fluc and RSVF-2A-GLuc expression cassettes were each constructed by several standard gene synthesis and molecular cloning steps after which they were ligated into the unique AsiSI restriction enzyme site of pBLY6.dE1.dE3, generating pBLY6.FLuc and pBLY6.RSVF-2A-Gluc, respectively.

Generation and Production of BLY6-Based Adenoviral Vectors

Adenoviral vectors BLY6.Fluc (also designated JAd1NVT003) and BLY6.RSVF-2A-Gluc (also designated JAd1NVT001), which respectively comprise adenoviral vector genome sequences SEQ ID NO:22 and SEQ ID NO:23, were generated by transfection of the corresponding Ad vector genome plasmids (i.e. pBLY6.Fluc and pBLY6.RSVF-2A-Gluc) into E1-complementing PER.C6 cells. Prior to transfection into PER.C6 cells, which were grown as adherent cultures in Dulbecco's modified Eagle's medium (DMEM) supplemented with 10% fetal bovine serum (FBS) and 10 mM $MgCl_2$, the Ad vector genome plasmids were digested with SwaI to release the respective adenoviral vector genomes from the plasmid. The transfections were performed according to standard procedures using Lipofectamine transfection reagent (Invitrogen; Carlsbad, Calif.). After harvesting of the viral rescue transfections, the viruses were further amplified by several successive infection rounds on PER.C6 cell cultures. The viruses were purified from crude viral harvests using a two-step cesium chloride (CsCl) density gradient ultracentrifugation procedure as described before (Havenga et al., "Novel replication-incompetent adenoviral B-group vectors: high vector stability and yield in PER.C6 cells," J. Gen. Virol. 87(8):2135-43 (2006)). Viral particle (VP) titers were measured by a spectrophotometry-based procedure described previously (Maizel et al., "The polypeptides of adenovirus: I. Evidence for multiple protein components in the virion and a comparison of types 2, 7A, and 12," Virology, 36(1): 115-25 (1968)).

Cellular and Humoral Immune Responses Induced by Novel Adenoviral Vectors

Examples 2 and 3 describe experiments performed to assess the immunogenicity of the novel BLY6-based adenoviral vectors generated herein. In these experiments, the novel vectors were assessed for their abilities to induce humoral and cellular immune responses against vector-encoded (model) antigens in mice after intramuscular immunization. The vectors were tested using two different antigens: Firefly luciferase (FLuc) and RSV-$F_{A2}$-2A-GLuc (RSVF-2A-GLuc). RSVF-2A-GLuc is a chimeric protein composed of the respiratory syncytial virus strain A2 fusion glycoprotein, a foot-and-mouth-disease virus 2A peptide, and Gaussia luciferase (GLuc). Each vector was compared side-by-side with a benchmark vector based on human adenovirus type 26 (HAdV-26, also referred to herein as Ad26) or on human adenovirus type 49 (HAdV-49, also referred to herein as Ad49) carrying the same antigen-encoding transgene cassette. Immune responses against the respective antigens were measured using well-known immunological assays, such as enzyme-linked immunospot assay (ELISPOT), enzyme-linked immunosorbent assay (ELISA), and, in case of the RSVF-2A-GLuc antigen, a respiratory syncytial virus neutralization assay (VNA).

Example 2: Cellular Immune Responses Induced by BLY6.FLuc

Figure 1B:
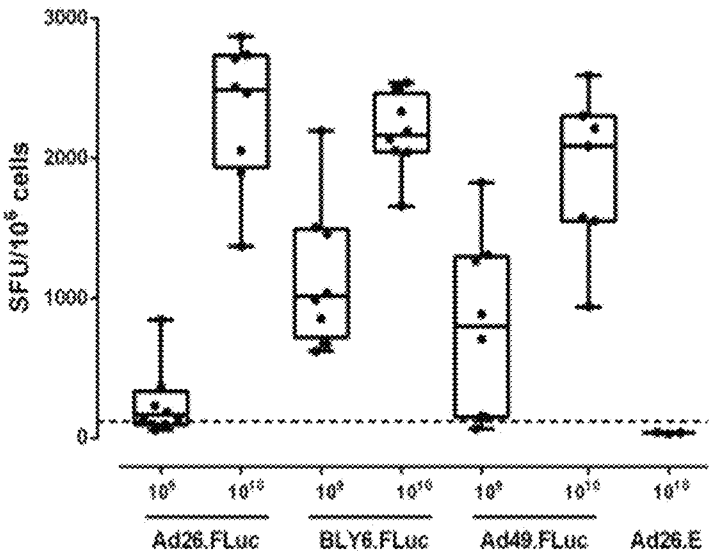

To evaluate the cellular immunogenicity of the novel adenoviral vector BLY6, Balb/C mice were immunized by intra-muscular injection with Ad26.FLuc, Ad49.Fluc (positive controls), a BLY6 vector expressing firefly luciferase (BLY6.FLuc), or with an adenovector not encoding a transgene (Ad26 empty). Two vector doses were tested for administration: $10^9$ and $10^{10}$ viral particles (vp) per mouse. Two weeks after immunization, mice were sacrificed and splenocytes were stimulated overnight with a 15mer overlapping FLuc peptide pool (experimental set up FIG. 1A). Cellular immune responses were determined by ex-vivo ELISPOT assay measuring the relative number of IFN-γ-secreting cells (FIG. 1B). The results show that at the higher-dose immunization ($10^{10}$), the cellular immune responses induced by BLY6 were about as high as the response seen for Ad26.Fluc. By contrast, at the lower-dose immunization ($10^9$), BLY6.Fluc gave a stronger response than Ad26.Fluc.

Overall, the cellular immune responses induced by the FLuc-expressing recombinant BLY6 adenoviral vector of the invention clearly indicate potent immunogenicity of this vector in mice.

Figure 2A:
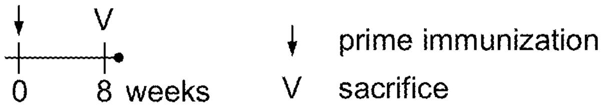
FIG. 2A-FIG. 2D show cellular and humoral immune responses induced by BLY6.RSVF-2A-GLuc.

Example 3: Cellular and Humoral Immune Responses Induced by BLY6.RSVF-2A-GLuc The immunogenicity of novel adenoviral vector BLY6 was further evaluated using RSV-$F_{A2}$-2A-GLuc (RSVF-2A-GLuc) as a vector-encoded (model) vaccine antigen. Balb/C mice were immunized intramuscularly with Ad26.RSVF-2A-GLuc (positive control) or BLY6.RSVF-2A-GLuc (both at $10^8$, $10^9$ and $10^{10}$ viral particles per mouse), or with Ad26.FLuc or BLY6.FLuc (both at $10^{10}$ viral particles per mouse). Mice were sacrificed after eight weeks and blood samples and splenocytes were collected (FIG. 2A). Different immune parameters were assessed as described below.

Figure 2B:
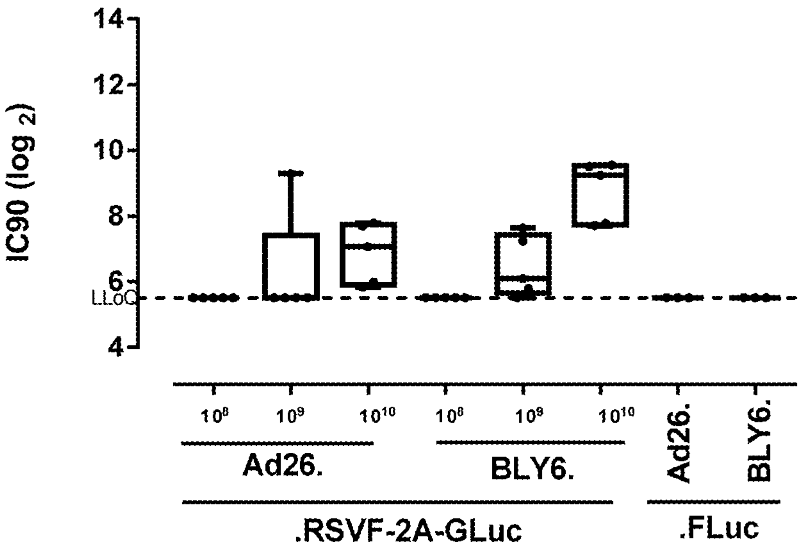

A virus neutralization assay was performed in order to assess the capacity of BLY6.RSVF-2A-GLuc to elicit respiratory syncytial virus-neutralizing-antibodies. FIG. 2B depicts the respiratory syncytial virus strain A2 (RSV A2) VNA titers measured for sera samples collected eight weeks after immunization. Each dot represents one mouse; the bars represent the group mean and the dotted line corresponds to the lower limit of quantification (LLOQ=6.88; mean endpoint titer of linearity samples). The results show that the $10^{10}$ vp-dose immunizations with BLY6.RSVF-2A-GLuc gave rise to higher RSV A2 neutralization titers as those found for the benchmark Ad26 vector encoding the same antigen. Titers against BLY6.RSVF-2A-GLuc were detected mainly at the highest dose used for immunization, $10^{10}$ vp. As expected, no RSV A2 specific responses were detected against the adenovectors encoding Firefly luciferase.

Figure 2C:
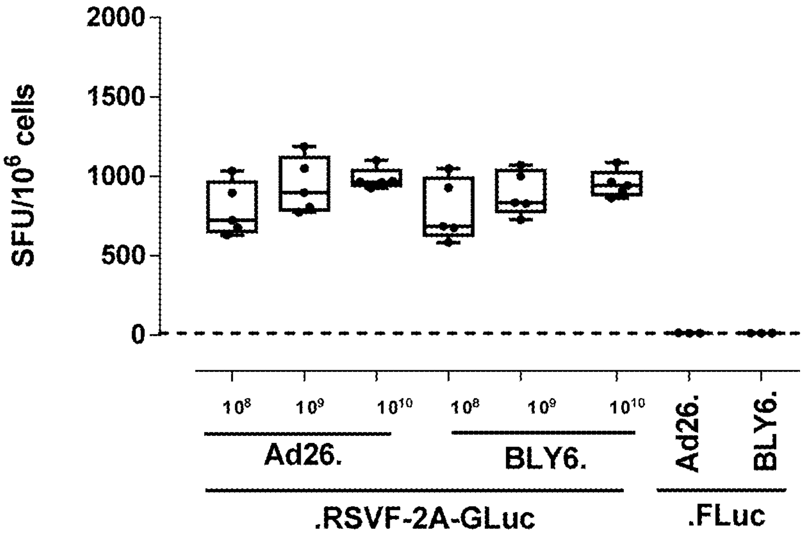

Induction of cellular immunity against the vector-encoded antigen was evaluated by an RSV-$F_{A2}$-specific ELISPOT assay. To this end, eight weeks after immunization, splenocytes from immunized mice were isolated and stimulated overnight with 15mer overlapping peptides spanning the RSV-$F_{A2}$ protein and cellular immune responses were determined by ex-vivo ELISPOT assay measuring the relative number of IFN-γ-secreting cells. The data show that the antigen-specific cellular immune responses elicited by the novel vector BLY6 encoding RSVF-2A-GLuc were dose-dependent and, per dose, similar in magnitude to those induced by the benchmark vector, Ad26.RSVF-2A-GLuc (FIG. 2C). As expected, no RSVF-$F_{A2}$-specific responses were measured from splenocytes of mice immunized with adenovectors encoding Firefly luciferase.

Figure 2D:
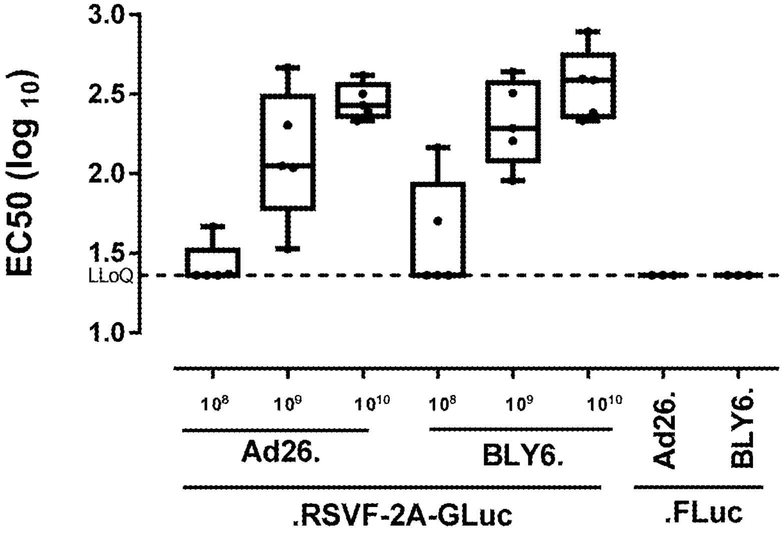

The ability of the RSVF-2A-GLuc-expressing vectors to elicit RSV-$F_{A2}$-specific IgG antibodies was assessed by ELISA. Sera collected 8 weeks post-immunization from the mice immunized with Ad26 (positive control) and BLY6 vectors expressing RSVF-2A-GLuc transgene or Firefly luciferase (control) were tested in an anti-RSV $F_{A2}$ IgG antibody ELISA. Specifically, this ELISA detects IgG antibodies capable of binding to a recombinant stable pre-fusion RSV-$F_{A2}$ protein (pre-RSV-F). The results show that BLY6.RSVF-2A-GLuc dose-dependently elicited higher pre-RSV-F-specific IgG antibody titers than those induced by Ad26.RSVF-2A-GLuc (FIG. 2D). As expected, no RSV-$F_{A2}$-specific antibody titers were detected in sera from mice immunized with vectors encoding Firefly luciferase only.

Altogether, the data show that the BLY6 vector induced potent cellular and humoral immune responses against the encoded antigens, similar to or higher than those induced by the benchmark vector based on HAdV-26. These immune responses clearly indicate potent immunogenicity of the BLY6 vector in mice.

Example 4: Evaluation of Serological Cross-Neutralization Among Novel and Existing Adenoviral Vectors For their potential utility as new adenoviral vaccine vectors, the novel BLY6 adenoviral vectors created herein would preferably be serologically distinct from existing adenoviral vectors currently already in development as vaccine vectors, such as vectors based on human adenovirus serotypes HAdV-5 and HAdV-35. Therefore, cross-neutralization tests were performed among the novel BLY6 adenoviral vectors and several existing vectors based on HAdV-4, HAdV-5, HAdV-26, HAdV-35 and HAdV49. To this end, mice antisera, each raised against one of these adenoviral vectors, were tested against each of the different vectors in an adenovirus neutralization assay. The mice antisera used for this assay were collected from Balb/C mice, two or eight weeks after their immunization with $10^{10}$ vector particles per mouse. The adenovirus neutralization assay was carried out as described previously (Spangers et al 2003. J. Clin. Microbiol. 41:5046-5052). Briefly, starting from a 1:16 dilution, the sera were 2-fold serially diluted, then pre-mixed with the adenoviral vectors expressing firefly luciferase (FLuc), and subsequently incubated overnight with A549 cells (at multiplicity of infection of 500 virus particles per cell). Luciferase activity levels in infected cell lysates measured 24 hours post-infection represented vector infection efficiencies. Neutralization titers against a given vector were defined as the highest serum dilution capable of giving a 90% reduction of vector infection efficiency. The neutralization titers were arbitrarily divided into the following categories: <16 (no neutralization), 16 to 200, 200 to 2,000, and >2,000. The results show no major cross-neutralization among the vectors tested (FIG. 3). There was only some slight, one-way cross-neutralization seen between vectors BLY6 and Ad26, with BLY6 antiserum displaying a neutralization titer against Ad26 of 16.12 (i.e. just above the lower limit of detection of 16) and Ad26 antiserum not showing a neutralization titer against BLY6. Thus, the new adenoviral vector BLY6 displayed no, or only very slight, cross-neutralization with the human adenoviral vectors included in the tested panel, i.e. Ad26, Ad35, Ad49, Ad5, and Ad4. Therefore, this vector could potentially be used in combination with one or more of these or other distinct adenoviral vectors in sequential immunizations, for example in the context of a heterologous prime-boost vaccination regimen or, alternatively or additionally, in the context of a series of two or more consecutive vaccination regimens against different diseases or antigens.

Example 5: Seroprevalence of Novel Adenoviral Vectors in Human Populations

Important for their potential use as efficacious vaccine vectors is that the novel adenoviral vectors described herein are not hampered by high levels of pre-existing anti-vector humoral immunity in vaccine target populations. Therefore, the BLY6 vector was evaluated for its seroprevalence within 200 human cohort serum samples from adults, ages 18 to 55 years, living in the United States (US) and the European Union (EU). The vector was tested for neutralization by the human serum samples by performing a standard adenovirus neutralization assay as carried out in Example 3 and described previously (Spangers et al 2003. J. Clin. Microbiol. 41:5046-5052). Briefly, starting from a 1:16 dilution, the sera were 2-fold serially diluted, then pre-mixed with the adenoviral vectors expressing firefly luciferase (FLuc), and subsequently incubated overnight with A549 cells (at a multiplicity of infection of 500 virus particles per cell). Luciferase activity levels in infected cell lysates, measured 24 hours post-infection, represented vector infection efficiencies. Neutralization titers against a given vector were defined as the highest serum dilution capable of giving a 90% reduction of vector infection efficiency. The neutralization titers were arbitrarily divided into the following categories: <16 (no neutralization), 16 to 300, 300 to 1,000, 1000 to 4000 and >4000.

Figure 4:
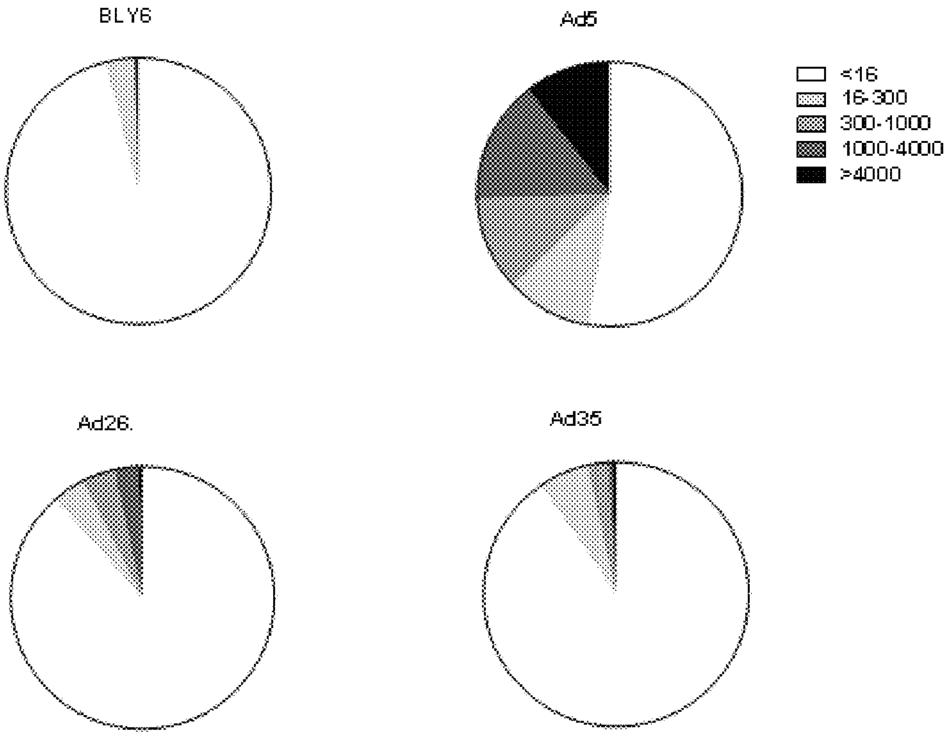
FIG. 4 shows the seroprevalence of Ad35, Ad26, Ad5 and BLY6 in 200 human cohort serum samples from adults, age 18 to 55 years, living in the United States (US) and European Union (EU). Neutralization titers measured in these sera against each vector were divided into four categories (<16 (negative), 16 to 300, 300 to 1,000, 1000 to 4000 and >4000), represented in the charts as indicated.

The results indicate that the BLY6 adenovirus vector has a considerably lower seroprevalence in the human subjects studied than the control Ad5 vector and benchmark Ad26 and Ad35 vectors (FIG. 4). Moreover, the positive neutralization titers that were seen against the novel BLY6 vectors were generally quite low, mostly not higher than 300. By contrast, most of the positive neutralization titers found against Ad26 and Ad5 were higher than 300.

Altogether, the above data indicate that pre-existing humoral anti-vector immunity against BLY6 vectors can be considered to be low in the evaluated vaccine target populations, suggesting that these vectors have potential as efficacious vaccine vectors in these populations.

Example 6: Adenoviral Vector Productivity in Suspension PER.C6 Cells

Adenovirus vectors to be used in clinical trials and beyond need to be readily producible to high titers in a scalable, serum-free adenovirus production platform. Suspension-adapted PER.C6® cells, also referred to herein as suspension PER.C6 cells or sPER.C6, represent such a platform as they have been shown to support large-scale manufacturing of adenoviral vectors in bioreactors, achieving large quantities of high-titer, clinical grade vector preparations, e.g. of E1-deleted vectors based on HAdV-26 or HAdV-35 (EP 2536829 B1, EP 2350268 B1).

As an initial assessment as to whether the novel vectors described herein would fit sPER.C6 cell-based production processes, small-scale vector productivity experiments were performed on sPER.C6 cells cultured in shaker flasks. These productivity experiments were carried out using the Fluc-encoding version of the novel Ad vector BLY6 described in Example 1. Taken along as a benchmark control was the HAdV-26-based vector Ad26.Fluc. Suspension PER.C6 cell cultures, seeded into shaker flasks at a density of $1\times10^6$ cells/ml in a total volume of 10 ml of PERMEXCIS® medium (available from Lonza) supplemented with 4 mM L-Glutamine (Lonza), were infected with the different vectors at different virus particle (VP)-to-cell ratios and then incubated for 4 days. The different VP-to-cell ratios used for infection were 70, 150 and 900. Samples of the infected cell cultures were taken every day and VP titers were determined in these samples by a quantitative PCR (qPCR)-based protocol that employs primers and probe that are specific for the CMV promoter (which is present in all the vectors tested). This protocol entails a DNAse treatment of the test samples prior to the qPCR to remove any free vector DNA (i.e. vector genomes that are not packaged into viral particles).

Figure 8:
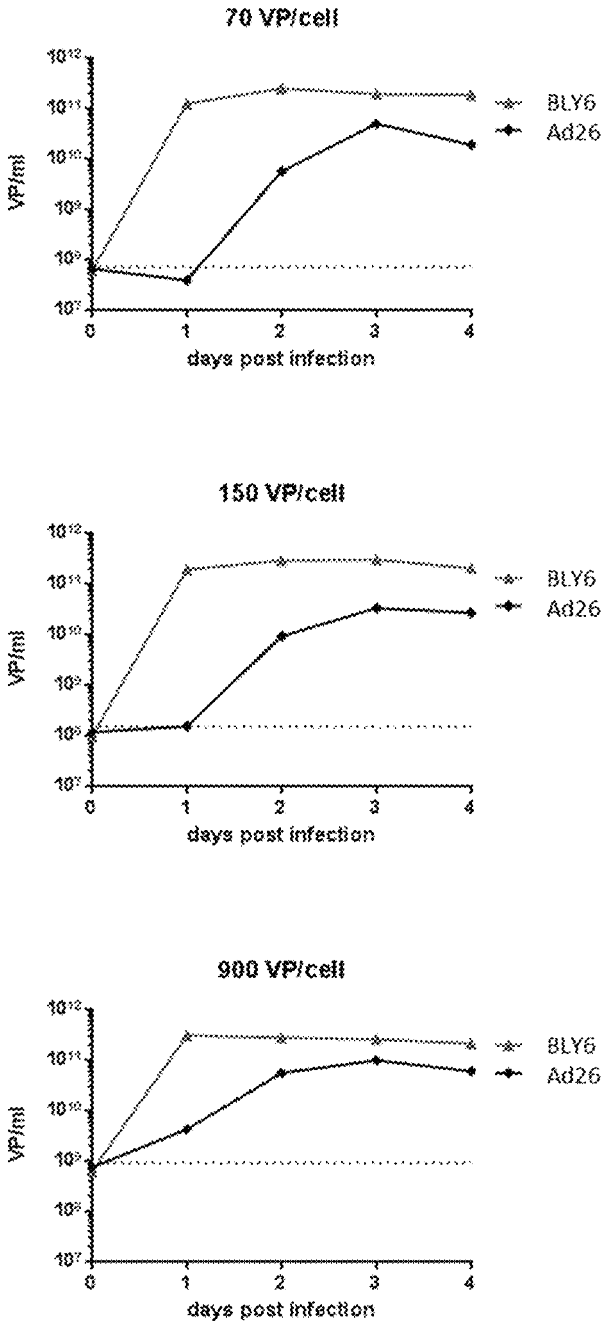
FIG. 8 shows productivity of novel vector BLY6.Fluc in production cell line sPER.C6.

The productivity results obtained for the novel vector BLY6.Fluc are shown in FIG. 8. BLY6.Fluc displayed higher VP titers than the benchmark control vector Ad26.Fluc at all VP-to-cell infection ratios and harvest time points tested. These results demonstrate good productivity of the novel BLY6 vector on a sPER.C6-based, serum-free suspension cell culture model.

Collectively, the studies of humoral and cellular immune responses induced by the novel recombinant BLY6-based adenoviral vectors of the invention, as presented above, clearly indicate potent immunogenicity of these vectors in mice. In addition, the vectors demonstrated to induce no, or only very limited, cross-neutralizing antibody responses against certain existing adenoviral vaccine vector candidates (e.g. Ad26 and Ad35) or vice versa. Furthermore, the new vectors showed low seroprevalence in humans. Finally, the new vectors can be readily produced at high yields. The combination of low seroprevalence, potent immunogenicity and producibility suggests that the novel adenoviral vectors of the invention can be useful as novel vaccine vector candidates against a variety of pathogens and may additionally have utility in gene therapy and/or diagnostics.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated nucleic acid sequence encoding a hexon polypeptide or a functional derivative thereof comprising a hexon hypervariable regions-encompassing polypeptide having the amino acid sequence of SEQ ID NO:1 or an amino acid sequence which is at least 95% identical over its entire length to the amino acid sequence of SEQ ID NO:1.

2. The isolated nucleic acid sequence of claim 1, wherein the hexon polypeptide comprises a hexon hypervariable regions-encompassing polypeptide having the amino acid sequence of SEQ ID NO:1.

3. The isolated nucleic acid sequence of claim 2, wherein the hexon polypeptide or the functional derivative thereof comprises the amino acid sequence of SEQ ID NO:2 or an amino acid sequence which is at least 95% identical over its entire length to the amino acid sequence of SEQ ID NO:2.

4. The isolated nucleic acid sequence of claim 1, further comprising a nucleic acid sequence encoding a fiber polypeptide or a functional derivative thereof.

5. The isolated nucleic acid sequence of claim 4, wherein the fiber polypeptide comprises at least one selected from the group consisting of: (1) a fiber knob polypeptide sequence comprising the amino acid sequence of SEQ ID NO:10, (2) a fiber shaft polypeptide sequence comprising the amino acid sequence of SEQ ID NO:11, and (3) a fiber tail polypeptide sequence comprising the amino acid sequence of SEQ ID NO:12, preferably, the fiber polypeptide or a functional derivative thereof comprises the amino acid sequence of SEQ ID NO:3 or an amino acid sequence which is at least 95% identical over its entire length to the amino acid sequence of SEQ ID NO:3.

6. An isolated nucleic acid sequence encoding a fiber polypeptide comprising at least one selected from the group consisting of: (1) a fiber knob polypeptide sequence comprising the amino acid sequence of SEQ ID NO:10; (2) a fiber shaft polypeptide sequence comprising the amino acid sequence of SEQ ID NO:11, and (3) a fiber tail polypeptide sequence comprising the amino acid sequence of SEQ ID NO:12.

7. The isolated nucleic acid sequence of claim 6, wherein the fiber polypeptide comprises the amino acid sequence of SEQ ID NO:3.

8. A vector comprising the nucleic acid of claim 1.

9. The vector of claim 8, being an adenoviral vector, and further comprising a transgene.

10. The adenoviral vector of claim 9, wherein the adenoviral vector further comprises at least one of an E1 deletion and an E3 deletion.

11. The adenoviral vector of claim 9, wherein the adenoviral vector is a chimeric adenoviral vector comprising one or more human adenoviral nucleic acid sequences, preferably the human adenoviral nucleic acid sequences are from at least one of human adenovirus-4, human adenovirus-5, human adenovirus-26, or human adenovirus-35.

12. The adenoviral vector of claim 9, wherein the adenoviral vector comprises a nucleic acid sequence selected from the group consisting of SEQ ID NO:13 and SEQ ID NO:14.

13. A recombinant cell comprising the vector of claim 8.

14. A method of producing a vector, comprising;

(a) growing the recombinant cell of claim 13 under conditions for production of the vector; and (b) isolating the vector from the recombinant cell.

15. An immunogenic composition comprising the adenoviral vector of claim 9.

16. A method of inducing an immune response in a subject in need thereof, comprising administering to the subject the immunogenic composition of claim 15.

17. A method of producing a vaccine, comprising combining an adenoviral vector according to claim 9 with a pharmaceutically acceptable carrier.

* * * * *

SEQUENCE LISTING

```
<160> NUMBER OF SEQ ID NOS: 23

<210> SEQ ID NO 1
<211> LENGTH: 300
```

<212> TYPE: PRT
<213> ORGANISM: Artificial Sequence
<220> FEATURE:
<223> OTHER INFORMATION: BLY6 hexon HVRs

<400> SEQUENCE: 1

```
Lys Glu Asn Asn Gly Gln Gly Asp Ala Lys Thr His Thr Tyr Gly Val
1               5                   10                  15

Ala Ala Thr Gly Gly Ile Asp Ile Asp Lys Asn Gly Leu Gln Ile Gly
            20                  25                  30

Ile Asp Glu Thr Lys Glu Asp Asn Asn Glu Ile Tyr Ala Asp Lys Thr
        35                  40                  45

Phe Gln Pro Glu Pro Gln Ile Gly Glu Glu Asn Trp Gln Asp Ser Glu
    50                  55                  60

Asn Tyr Tyr Gly Gly Arg Ala Leu Lys Pro Glu Thr Lys Met Lys Pro
65                  70                  75                  80

Cys Tyr Gly Ser Phe Ala Arg Pro Thr Asn Ala Lys Gly Gly Gln Ala
                85                  90                  95

Lys Ile Lys Pro Ala Gln Glu Gly Gln Gln Ser Ile Asp Tyr Asp Ile
            100                 105                 110

Asp Leu Ala Phe Phe Asp Ile Pro Ser Thr Gly Gly Gly Asn Gly Thr
        115                 120                 125

Asn Val Asn Asp Lys Pro Asp Met Val Met Tyr Thr Glu Asn Val Asn
    130                 135                 140

Leu Glu Thr Pro Asp Thr His Leu Val Tyr Lys Pro Gly Thr Ser Asp
145                 150                 155                 160

Asp Ser Ser Glu Ala Asn Leu Thr Gln Gln Ala Met Ala Asn Arg Pro
                165                 170                 175

Asn Tyr Ile Gly Phe Arg Asp Asn Phe Ile Gly Val Met Tyr Tyr Asn
            180                 185                 190

Ser Thr Gly Asn Met Gly Val Leu Ala Gly Gln Ala Ser Gln Leu Asn
        195                 200                 205

Ala Val Val Asp Leu Gln Asp Arg Asn Thr Glu Leu Ser Tyr Gln Leu
    210                 215                 220

Leu Leu Asp Ser Leu Gly Asp Arg Thr Arg Tyr Phe Ser Met Trp Asn
225                 230                 235                 240

Gln Ala Val Asp Ser Tyr Asp Pro Asp Val Arg Ile Ile Glu Asn His
                245                 250                 255

Gly Val Glu Asp Glu Leu Pro Asn Tyr Cys Phe Pro Leu Asp Gly Ala
            260                 265                 270

Gly Thr Asn Ala Val Tyr Gln Gly Val Lys Thr Lys Glu Asp Asn Asn
        275                 280                 285

Gly Glu Trp Glu Thr Asp Thr Asn Val Ala Ser Gln
    290                 295                 300
```

<210> SEQ ID NO 2
<211> LENGTH: 940
<212> TYPE: PRT
<213> ORGANISM: Artificial Sequence
<220> FEATURE:
<223> OTHER INFORMATION: BLY6 hexon

<400> SEQUENCE: 2

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30
```

-continued

```
Arg Ala Thr Asp Thr Tyr Phe Asn Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ser Ser Gln Trp Gln Gln Lys Glu Asn Asn Gly Gln Gly
    130                 135                 140

Asp Ala Lys Thr His Thr Tyr Gly Val Ala Ala Thr Gly Gly Ile Asp
145                 150                 155                 160

Ile Asp Lys Asn Gly Leu Gln Ile Gly Ile Asp Glu Thr Lys Glu Asp
                165                 170                 175

Asn Asn Glu Ile Tyr Ala Asp Lys Thr Phe Gln Pro Glu Pro Gln Ile
            180                 185                 190

Gly Glu Glu Asn Trp Gln Asp Ser Glu Asn Tyr Tyr Gly Gly Arg Ala
        195                 200                 205

Leu Lys Pro Glu Thr Lys Met Lys Pro Cys Tyr Gly Ser Phe Ala Arg
    210                 215                 220

Pro Thr Asn Ala Lys Gly Gly Gln Ala Lys Ile Lys Pro Ala Gln Glu
225                 230                 235                 240

Gly Gln Gln Ser Ile Asp Tyr Asp Ile Asp Leu Ala Phe Phe Asp Ile
                245                 250                 255

Pro Ser Thr Gly Gly Gly Asn Gly Thr Asn Val Asn Asp Lys Pro Asp
            260                 265                 270

Met Val Met Tyr Thr Glu Asn Val Asn Leu Glu Thr Pro Asp Thr His
        275                 280                 285

Leu Val Tyr Lys Pro Gly Thr Ser Asp Asp Ser Ser Glu Ala Asn Leu
    290                 295                 300

Thr Gln Gln Ala Met Ala Asn Arg Pro Asn Tyr Ile Gly Phe Arg Asp
305                 310                 315                 320

Asn Phe Ile Gly Val Met Tyr Tyr Asn Ser Thr Gly Asn Met Gly Val
                325                 330                 335

Leu Ala Gly Gln Ala Ser Gln Leu Asn Ala Val Val Asp Leu Gln Asp
            340                 345                 350

Arg Asn Thr Glu Leu Ser Tyr Gln Leu Leu Leu Asp Ser Leu Gly Asp
        355                 360                 365

Arg Thr Arg Tyr Phe Ser Met Trp Asn Gln Ala Val Asp Ser Tyr Asp
    370                 375                 380

Pro Asp Val Arg Ile Ile Glu Asn His Gly Val Glu Asp Glu Leu Pro
385                 390                 395                 400

Asn Tyr Cys Phe Pro Leu Asp Gly Ala Gly Thr Asn Ala Val Tyr Gln
                405                 410                 415

Gly Val Lys Thr Lys Glu Asp Asn Asn Gly Glu Trp Glu Thr Asp Thr
            420                 425                 430

Asn Val Ala Ser Gln Asn Gln Ile Cys Lys Gly Asn Ile Tyr Ala Met
        435                 440                 445
```

-continued

```
Glu Ile Asn Leu Gln Ala Asn Leu Trp Lys Ser Phe Leu Tyr Ser Asn
    450                 455                 460

Val Ala Leu Tyr Leu Pro Asp Ser Tyr Lys Tyr Thr Pro Ser Asn Val
465                 470                 475                 480

Thr Leu Pro Thr Asn Thr Asn Thr Tyr Asp Tyr Met Asn Gly Arg Val
                485                 490                 495

Val Ser Pro Ser Leu Val Asp Ala Tyr Ile Asn Ile Gly Ala Arg Trp
            500                 505                 510

Ser Leu Asp Ala Met Asp Asn Val Asn Pro Phe Asn His His Arg Asn
        515                 520                 525

Ala Gly Leu Arg Tyr Arg Ser Met Leu Leu Gly Asn Gly Arg Tyr Val
    530                 535                 540

Pro Phe His Ile Gln Val Pro Gln Lys Phe Phe Ala Ile Lys Asn Leu
545                 550                 555                 560

Leu Leu Leu Pro Gly Ser Tyr Thr Tyr Glu Trp Asn Phe Arg Lys Asp
                565                 570                 575

Val Asn Met Ile Leu Gln Ser Ser Leu Gly Asn Asp Leu Arg Thr Asp
            580                 585                 590

Gly Ala Thr Ile Gln Tyr Thr Ser Ile Asn Leu Tyr Ala Thr Phe Phe
        595                 600                 605

Pro Met Ala His Asn Thr Ala Ser Thr Leu Glu Ala Met Leu Arg Asn
    610                 615                 620

Asp Thr Asn Asp Gln Ser Phe Asn Asp Tyr Leu Ser Ala Ala Asn Met
625                 630                 635                 640

Leu Tyr Pro Ile Pro Ala Asn Ala Thr Asn Val Pro Ile Ser Ile Pro
                645                 650                 655

Ser Arg Asn Trp Ala Ala Phe Arg Gly Trp Ser Phe Thr Arg Leu Lys
            660                 665                 670

Thr Lys Glu Thr Pro Ser Leu Gly Ser Gly Phe Asp Pro Tyr Phe Val
        675                 680                 685

Tyr Ser Gly Ser Ile Pro Tyr Leu Asp Gly Thr Phe Tyr Leu Asn His
    690                 695                 700

Thr Phe Lys Lys Val Ser Ile Met Phe Asp Ser Ser Val Ser Trp Pro
705                 710                 715                 720

Gly Asn Asp Arg Leu Leu Thr Pro Asn Glu Phe Glu Ile Lys Arg Thr
                725                 730                 735

Val Asp Gly Glu Gly Tyr Asn Val Ala Gln Cys Asn Met Thr Lys Asp
            740                 745                 750

Trp Phe Leu Val Gln Met Leu Ser His Tyr Asn Ile Gly Tyr Gln Gly
        755                 760                 765

Phe Tyr Ile Pro Glu Gly Tyr Lys Asp Arg Met Tyr Ser Phe Phe Arg
    770                 775                 780

Asn Phe Gln Pro Met Ser Arg Gln Val Val Asp Gln Val Asn Tyr Lys
785                 790                 795                 800

Asp Tyr Met Ala Val Thr Leu Ala Tyr Gln His Asn Asn Ser Gly Phe
                805                 810                 815

Val Gly Tyr Leu Ala Pro Thr Met Arg Gln Gly Gln Pro Tyr Pro Ala
            820                 825                 830

Asn Tyr Pro Tyr Pro Leu Ile Gly Lys Thr Ala Val Asn Ser Val Thr
        835                 840                 845

Gln Lys Lys Phe Leu Cys Asp Arg Val Met Trp Arg Ile Pro Phe Ser
    850                 855                 860

Ser Asn Phe Met Ser Met Gly Ala Leu Thr Asp Leu Gly Gln Asn Met
```

-continued

```
865                 870                 875                 880

Leu Tyr Ala Asn Ser Ala His Ala Leu Asp Met Asn Phe Glu Val Asp
                885                 890                 895

Pro Met Asp Glu Ser Thr Leu Leu Tyr Val Val Phe Glu Val Phe Asp
            900                 905                 910

Val Val Arg Val His Gln Pro His Arg Gly Val Ile Glu Ala Val Tyr
        915                 920                 925

Leu Arg Thr Pro Phe Ser Ala Gly Asn Ala Thr Thr
    930                 935                 940


<210> SEQ ID NO 3
<211> LENGTH: 442
<212> TYPE: PRT
<213> ORGANISM: Artificial Sequence
<220> FEATURE:
<223> OTHER INFORMATION: BLY6 fiber

<400> SEQUENCE: 3

Met Ser Thr Lys Arg Ala Arg Val Glu Asp Asp Phe Asp Pro Val Tyr
1               5                   10                  15

Pro Tyr Asp Ala Glu Leu Ala Pro Ser Val Pro Phe Ile Ala Pro Pro
            20                  25                  30

Phe Val Ser Ser Asp Gly Phe Gln Glu Lys Pro Leu Gly Val Leu Ser
        35                  40                  45

Leu Arg Leu Ala Asn Pro Val Thr Thr Lys Asn Gly Glu Leu Thr Leu
    50                  55                  60

Lys Leu Gly Asp Gly Val Gly Ile Asp Ser Asp Gly Asn Leu Thr Ala
65                  70                  75                  80

Gln Thr Val Thr Lys Ala Thr Ser Pro Leu Thr Val Ser Asn Asn Ala
                85                  90                  95

Ile Ala Leu Asn Met Asp Lys Pro Phe Tyr Ser Ser Asn Gly Lys Leu
            100                 105                 110

Ser Leu Gln Val Thr Ser Pro Leu Lys Ile Val Asp Ser Leu Asn Thr
        115                 120                 125

Leu Ala Ile Gly Tyr Gly Gln Gly Leu Gly Leu Asn Asn Ser Ala Leu
    130                 135                 140

Ala Val Gln Leu Ala Ser Pro Leu Thr Phe Asp Ser Asn Ser Lys Ile
145                 150                 155                 160

Lys Ile Asn Leu Gly Ser Gly Pro Leu Lys Ile Asn Ala Asn Lys Leu
                165                 170                 175

Ser Ile Asn Cys Leu Arg Gly Val Tyr Val Thr Thr Asp Gly Thr Ser
            180                 185                 190

Ile Glu Thr Asn Ile Ser Trp Ala Lys Gly Met Arg Phe Glu Gly Asn
        195                 200                 205

Ala Met Ala Val Asn Val Asp Ser Thr Lys Gly Leu Gln Phe Gly Thr
    210                 215                 220

Thr Ser Thr Glu Ser Gly Val Thr Asn Ala Phe Pro Ile Gln Leu Lys
225                 230                 235                 240

Ile Gly Ser Gly Leu Ser Phe Asp Ser Thr Gly Ala Leu Val Ala Trp
                245                 250                 255

Asp Lys Asp Asn Asp Lys Leu Thr Leu Trp Thr Thr Ala Asp Pro Ser
            260                 265                 270

Pro Asn Cys Thr Ile Tyr Thr Asp Lys Asp Ala Lys Leu Thr Leu Cys
        275                 280                 285

Leu Thr Lys Cys Gly Ser Gln Ile Leu Gly Ser Val Ser Val Leu Ala
```

```
    290                 295                 300

Val Lys Ala Gly Thr Leu Gln Pro Ile Ser Glu Lys Ile Gly Thr Ala
305                 310                 315                 320

Leu Val Ser Leu Lys Phe Asn Asn Asn Gly Val Leu Leu Ser Asn Ser
                325                 330                 335

Thr Leu Ser Asn Glu Tyr Trp Asn Tyr Arg Lys Gly Asp Val Thr Pro
            340                 345                 350

Ala Glu Ala Tyr Thr Asn Ala Val Gly Phe Met Pro Asn Ile Lys Ala
        355                 360                 365

Tyr Pro Lys Asn Thr Asn Ser Ala Ser Lys Ser His Ile Val Gly Gln
    370                 375                 380

Val Tyr Leu Asn Gly Asp Glu Thr Lys Pro Met His Leu Ile Ile Thr
385                 390                 395                 400

Phe Asn Glu Thr Ser Asp Glu Thr Cys Thr Tyr Ser Ile Thr Phe Gln
                405                 410                 415

Trp Lys Trp Asn Ile Gly Thr Tyr Thr Ser Asp Thr Leu Ala Thr Ser
            420                 425                 430

Ser Phe Thr Phe Ser Tyr Ile Ala Gln Glu
        435                 440


<210> SEQ ID NO 4
<211> LENGTH: 938
<212> TYPE: PRT
<213> ORGANISM: Artificial Sequence
<220> FEATURE:
<223> OTHER INFORMATION: SAdV-30-1 hexon

<400> SEQUENCE: 4

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ser Ser Gln Trp Glu Gln Asn Glu Asn Asn Gly Gln Gly
    130                 135                 140

Gln Ala Lys Thr His Thr Tyr Gly Val Ala Ala Met Gly Gly Leu Asp
145                 150                 155                 160

Ile Thr Lys Glu Gly Leu Gln Ile Gly Thr Asp Ala Ser Lys Glu Asp
                165                 170                 175

Asp Asn Glu Ile Tyr Ala Asp Glu Thr Tyr Gln Pro Glu Pro Gln Ile
            180                 185                 190

Gly Glu Glu Asn Trp Gln Asp Thr Glu Asn Phe Tyr Gly Gly Arg Ala
        195                 200                 205

Leu Lys Lys Asp Thr Lys Met Lys Pro Cys Tyr Gly Ser Phe Ala Arg
```

-continued

```
    210                 215                 220

Pro Thr Asn Val Lys Gly Gly Gln Ala Lys Val Lys Thr Glu Glu Asn
225                 230                 235                 240

Val Gln Ser Phe Asp Ile Asp Leu Ala Phe Phe Asp Ile Pro Ser Thr
                245                 250                 255

Gly Thr Gly Ser Asn Gly Thr Asn Val Asn Asp Lys Pro Asp Met Val
            260                 265                 270

Met Tyr Thr Glu Asn Val Asn Leu Glu Thr Pro Asp Thr His Ile Val
        275                 280                 285

Tyr Lys Pro Gly Thr Ser Asp Asp Ser Ser Glu Ala Asn Leu Cys Gln
    290                 295                 300

Gln Ala Met Pro Asn Arg Pro Asn Tyr Ile Gly Phe Arg Asp Asn Phe
305                 310                 315                 320

Ile Gly Leu Met Tyr Tyr Asn Ser Thr Gly Asn Met Gly Val Leu Ala
                325                 330                 335

Gly Gln Ala Ser Gln Leu Asn Ala Val Val Asp Leu Gln Asp Arg Asn
            340                 345                 350

Thr Glu Leu Ser Tyr Gln Leu Leu Leu Asp Ser Leu Gly Asp Arg Thr
        355                 360                 365

Arg Tyr Phe Ser Met Trp Asn Gln Ala Val Asp Ser Tyr Asp Pro Asp
    370                 375                 380

Val Arg Ile Ile Glu Asn His Gly Val Glu Asp Glu Leu Pro Asn Tyr
385                 390                 395                 400

Cys Phe Pro Leu Asp Gly Ala Gly Thr Asn Ala Val Tyr Gln Gly Val
                405                 410                 415

Lys Glu Lys Thr Gly Asn Asn Gly Glu Trp Glu Ala Asp Thr Asn Val
            420                 425                 430

Ala Ser Gln Asn Gln Ile Cys Lys Gly Asn Ile Tyr Ala Met Glu Ile
        435                 440                 445

Asn Leu Gln Ala Asn Leu Trp Arg Ser Phe Leu Tyr Ser Asn Val Ala
    450                 455                 460

Leu Tyr Leu Pro Asp Ser Tyr Lys Tyr Thr Pro Ala Asn Ile Thr Leu
465                 470                 475                 480

Pro Thr Asn Thr Asn Thr Tyr Asp Tyr Met Asn Gly Arg Val Val Pro
                485                 490                 495

Pro Ser Leu Val Asp Ala Tyr Ile Asn Ile Gly Ala Arg Trp Ser Leu
            500                 505                 510

Asp Pro Met Asp Asn Val Asn Pro Phe Asn His His Arg Asn Ala Gly
        515                 520                 525

Leu Arg Tyr Arg Ser Met Leu Leu Gly Asn Gly Arg Tyr Val Pro Phe
    530                 535                 540

His Ile Gln Val Pro Gln Lys Phe Phe Ala Ile Lys Ser Leu Leu Leu
545                 550                 555                 560

Leu Pro Gly Ser Tyr Thr Tyr Glu Trp Asn Phe Arg Lys Asp Val Asn
                565                 570                 575

Met Ile Leu Gln Ser Ser Leu Gly Asn Asp Leu Arg Thr Asp Gly Ala
            580                 585                 590

Ser Ile Ser Phe Thr Ser Ile Asn Leu Tyr Ala Thr Phe Phe Pro Met
        595                 600                 605

Ala His Asn Thr Ala Ser Thr Leu Glu Ala Met Leu Arg Asn Asp Thr
    610                 615                 620

Asn Asp Gln Ser Phe Asn Asp Tyr Leu Ser Ala Ala Asn Met Leu Tyr
625                 630                 635                 640
```

```
Pro Ile Pro Ala Asn Ala Thr Asn Val Pro Ile Ser Ile Pro Ser Arg
                645                 650                 655

Asn Trp Ala Ala Phe Arg Gly Trp Ser Phe Thr Arg Leu Lys Thr Lys
            660                 665                 670

Glu Thr Pro Ser Leu Gly Ser Gly Phe Asp Pro Tyr Phe Val Tyr Ser
        675                 680                 685

Gly Ser Ile Pro Tyr Leu Asp Gly Thr Phe Tyr Leu Asn His Thr Phe
    690                 695                 700

Lys Lys Val Ser Ile Thr Phe Asp Ser Ser Val Ser Trp Pro Gly Asn
705                 710                 715                 720

Asp Arg Leu Leu Thr Pro Asn Glu Phe Glu Ile Lys Arg Thr Val Asp
                725                 730                 735

Gly Glu Gly Tyr Asn Val Ala Gln Cys Asn Met Thr Lys Asp Trp Phe
            740                 745                 750

Leu Val Gln Met Leu Ala His Tyr Asn Ile Gly Tyr Gln Gly Phe Tyr
        755                 760                 765

Val Pro Glu Gly Tyr Lys Asp Arg Met Tyr Ser Phe Phe Arg Asn Phe
    770                 775                 780

Gln Pro Met Ser Arg Gln Val Val Asp Glu Val Asn Tyr Lys Asp Tyr
785                 790                 795                 800

Gln Ala Val Thr Leu Ala Tyr Gln His Asn Asn Ser Gly Phe Val Gly
                805                 810                 815

Tyr Leu Ala Pro Thr Met Arg Gln Gly Gln Pro Tyr Pro Ala Asn Tyr
            820                 825                 830

Pro Tyr Pro Leu Ile Gly Lys Ser Ala Val Thr Ser Val Thr Gln Lys
        835                 840                 845

Lys Phe Leu Cys Asp Arg Val Met Trp Arg Ile Pro Phe Ser Ser Asn
    850                 855                 860

Phe Met Ser Met Gly Ala Leu Thr Asp Leu Gly Gln Asn Met Leu Tyr
865                 870                 875                 880

Ala Asn Ser Ala His Ala Leu Asp Met Asn Phe Glu Val Asp Pro Met
                885                 890                 895

Asp Glu Ser Thr Leu Leu Tyr Val Val Phe Glu Val Phe Asp Val Val
            900                 905                 910

Arg Val His Gln Pro His Arg Gly Val Ile Glu Ala Val Tyr Leu Arg
        915                 920                 925

Thr Pro Phe Ser Ala Gly Asn Ala Thr Thr
    930                 935
```

<210> SEQ ID NO 5
<211> LENGTH: 35873
<212> TYPE: DNA
<213> ORGANISM: Artificial Sequence
<220> FEATURE:
<223> OTHER INFORMATION: BLY6 genome

<400> SEQUENCE: 5

```
catcatcaat aatatacctt atatgggcag tgtgccaata tgcaaattag acgagtttga      60

attttgcggg atgtgcggtg attggcccgg ggtcaacggt cgcggggcgg ggcggcgtga     120

cgcggacgat gacgttttgg ggaggaggag ctatgttgca agtaatcgtg ggaaatgcga     180

cgtaaaacga ggtggagttt aaacacggaa gtagacaatt ttcccgcgct gtttgacagg     240

aaatgatgtg tttttgggcg gatgcaagtg aaaattctcc attttcgcgc gaaaactaaa     300

tgaggaagtg aaattctgag taattctgag gttatcacag ggcggagtat ttaccgaggg     360
```

```
ccgagtagac tttgacccat tacgtggagg tttcgattac tctatttttc acctaaattt    420
ccgcgtactg tgtcaaagtc cgtgttttta cgtaactgtc agctgatccc tagtgtattt    480
aaacctgtgc agttccgtca agaggccact cttgagtgcc agcgagaaga gttttctcct    540
ccgcagcgcg agtcaaatct acacttctaa gatgagacac cgagtgattc ctgaggagaa    600
attctctatt agcgccggac tggaaattct acagatggtg gtggatattc taacagaggg    660
agaaccggag gctgctaact ttaactacga tcctccttcg ctccacgatc tgtatgattt    720
agaggtaaat gaaccagaga ctgaggcatt tgtgaatgcc gcgtttcctg attctctcct    780
gagtaaagct gaggagagtg agggttccag cgagcctgca actccaagtc ctccgagacc    840
tggaataggc gaaaaaagat tgcctggatg tcataaatcg cctgttgggg aaatggactt    900
gatgtgttat gaggacggct ttcctccgag cgatgaggag gaagatacac agcaggtgct    960
tgaagcctcc actagtcatg gaacggaggt gtttaatctc gactgcccag agctgcccgg   1020
ccatggctgt aagtcttgtg attatcatcg aaagagcact ggcttggagg gattgttatg   1080
ctcgctttgc tatatgcgcc taaacagcca ttatattttc agtaagtttt tttaattttg   1140
gtttaaaggg acagcgcagc gtgtctgatt gtattaagat ttggaaactt aatgtttgtg   1200
tatgtgtttc ttatataggc cctgtgtctg actcagatga gaccccccacc ccagactcca   1260
ctacctcacc cccggaaatt cagatgcata ttccagagaa tgtgtgtaag ccaattcctt   1320
tgagacccac gcctggaaaa cgtcatgctg ttgaaagact tgaggactta ttgatgggtg   1380
gggatgaacc tttggacttg agcttgccta aacagccaag gcaataaaat gtccacacct   1440
gtgtttgctc aatgatgtca tgcaataaat tatgtcacat accaaaggtg tgttttatga   1500
ctaggggtgg ggctactggg tatataagta ggagcagact gttgtagtta gctgagagca   1560
gcgagctgtc tctatggagg tttgggctgc attggaagat ctccataaca ctagatccct   1620
gctagaaaac gcctcggacg gtgtctctag aatttggaga tactggtttg gtggcgagct   1680
agctagtgtg atctataggg ttaagcagga atataagggc gaatttgaag aacttttact   1740
ggactgtcct ggtcttttgg agtctttgaa tttaggtcat cagatccagt ttaacgagaa   1800
gattttatca gctttagatt tttcaacacc aggcagatct gcagcttctg ttgcttttat   1860
agttcacatt ttagacagat ggagtcagga aactcaccta agttgggggt acctcttgga   1920
tttcttagcg acagcgttgt ggagacaatg gaagagggtc agggcgagag taacctcaga   1980
ttattggccg gtgcagccgc tgggtgtagc acatctgctg agacacacca tggaactacc   2040
aacaattccg gaggaaccag ccctggagga gcaggaagag aacccgagag ccggcctgga   2100
ccctccaacg gaggaggagg aataagtgac ttgttccctg aactgcgacg ggtgcttact   2160
aggagtacat ctggaagggg ggatagggggc gtgaagcgag aaaggaagga gtctaatcct   2220
aaagtggatc ttacagttag cttgatgaat cgcaaccgtc cagaggttat tacatggact   2280
gaggtgcaac aggaatgcag ggatgaattt tccctttttac aggagaaata ctcattagaa   2340
caggtgaaga catattggct ggagccagaa gatgattggg aggcagtgat tagaaattat   2400
gctaaggtgg ctcttagacc agataaaaag tatatagtaa ctaaaaagat ctgtgttagg   2460
aatgcttgct acattgtggg taatggggca gaggttcaga taaacaccac agatagggtg   2520
gcttttagat gttgtatgat gggcatgaga cctggggtga gtgggatgga ggctgtgaca   2580
tttatgaata taaaattcag aggagatggg tttaatggca cagtgtttat ggccaatact   2640
aaattaattc tgcatgggtg cagtatgttt gggtttaata atacttgtgt ggaagcctgg   2700
```

-continued

```
ggggaggtga gcataagggg gtgcagtatc tttggttgtt ggacgggagt ggttggtagg   2760
acaaagagca tggtatctgt gaagaaatgt atgtttgaaa ggtgcacact gggtatcctg   2820
agcgagggag aagctaggat tcgcaactgt gctttcacag atagtgggtg tggcatactt   2880
gtgaagggaa atgccagtat aaagcataat atgttctgcg gaccatccga tgatcgatca   2940
taccagatgg tgacctgtgc cagtggcaat tgcgatttgc tggctactat tcacattgtg   3000
acccatcaac gcaaaagatg gcctgtgttt gagcataatg tactgaccag gtgtaacgtt   3060
catctgggtg gtcgtagagg aatgttcatg ccataccaat gcaattttaa tcatgtgagg   3120
atcttgatgg agccgcaagc gttttccaga gtcagcttga ctggaatctt tgacatgtgt   3180
gtggaagcat ggaagatctt aagatatgat gataccaaat ccagatgccg cgcatgcgag   3240
tgcgggggca ggcatgccag gttccaacct gtatgtgtgg aggtgaccga ggagctgaga   3300
ccagatcatt tggtgctgac ctgcactggt gcggagttcg gttccagtgg tgaagaaact   3360
gattaaagtg agtagtggga tgttataaaa gtgaccataa ggtgatgtga gatggacaaa   3420
tttggtaatt tttatgtatt tttgtcttgc agccatgagt gggagcgctt cctttgaagg   3480
gggcgtcttt agcccttatc tgacggggcg tctgcctcat tgggctggag tgcgtcagaa   3540
tgtgatgggg tctacagtgg atggaagacc tgttcagcct gctaattctt ctactctgac   3600
ttatgctact atgacttcct cgcctttgga tgcagctgca gctgctgccg cttctgctgc   3660
cgccaacact gttcggggga tggccttgga gatggggtat tatggaactg tagtggccaa   3720
caccactacc ccaaataacc ccacagcctt gaatgaggac aagctgctag ttctcatgtc   3780
ccagctggag tctttgaccc aacgcctggg cgatctagct cagcaggtgt cccagctgaa   3840
ggagcagact caagctgcaa ttaccactgc gaggggaaat taaaaaaatt caaagaatca   3900
ataaataaac cgagactttg ttgattttaa agtgtgtcat tctttattta atttttcgcg   3960
cgcgatatgc cctggaccac cggtctctat cattgaggac acggtggatc ttttctagaa   4020
cccgatagag gtgggattgg atgttgaggt acatgggcat aagaccatct ttggggtgta   4080
gatagctcca ctgcagagcc tcatgctccg gggtggtgtt gtatataacc cagtcatagc   4140
atgggcgttg ggcatgatgt tgcacaatat ctttaaggag gagactaatg gccactggga   4200
gacccttggt gtaagtgttt acaaatctat taagctggga cgggtgcatc cgaggtgaga   4260
taatgtgcat tttggattgg atttttagat tggcaatgtt tccccctaga tctctcctgg   4320
gattcatgtt atgcaagacc actagaacag tgtatccggt gcacttaggg aatttgtcat   4380
gaagtttgga ggggaaagca tgaaaaaatt tagacacacc cttgtgtcct cccaagttct   4440
ccatgcactc atccataata atggcaatgg gcccatgggc ggcggcacgg gcgaacacgt   4500
tcctgggatc tgacacatca tagttgtggt cttgggtcag gtcatcataa gccattttaa   4560
taaacttggg gcggagggtg ccagattggg ggatgaatgt tccctcgggc cccggaacat   4620
agtttccttc acatatttgc atttcccagg cttttagttc agaggggggg atcatgtcca   4680
cctgtggagc gatgaagaag acggtctcgg gggcgggggt gattaagtgg gaggacagca   4740
agttcctaag cagctgtgac ttgccacacc cagtgggacc gtagatgacc cctataacag   4800
gttgcagatg gtagtttagg gaaagacagc tgccgtcctc tcgcaggagg ggggcgacct   4860
cgttcatcat ttccctcaca tgcatgtttt cccgcacaag ttccgatagg aggcgctctc   4920
cacccaggga aaggagttct tgaagagatg agaaattttt caagggtttt aagccatcag   4980
ccatgggcat tttggagagg gtttgttgca agagttcaag gcggtcccag agttcggtga   5040
tgtgttctat ggcatctcga tccagcatac ttcctcgttt ctggggttgg gacggctgcg   5100
```

-continued ggagtatgga accaggcgat gggcgtccag cgctgccagt gtccggtcct tccacggtcg 5160
cagcgtccga gtcagggtcg tttccgtcac ggtgaagggg tgcgcgcctg gctgggcgct 5220
tgcgagggtg cgcttcaggc tcatcctgct cgtggagaac cgctgccgtt ctgcgccctg 5280
tgcatcggcc aggtagcaat taaccatgag ttcgtagttg agcgcctctg ccgcgtggcc 5340
tttggcgcgc agcttacctt tggaagtctt ctgacaggtg ggacagtaga gacacttgag 5400
agcatagagt tttggggcta gaaagaccga ttctggggag tatgcatcgg ccccacagga 5460
ggcgcagacg gtttcgcatt ccaccagcca tgtaagatcg ggctcgttgg ggtcaaaaac 5520
aagttttccg ccatgttttt tgatgcgttt cttacctttg ctttccatga gttcgtgccc 5580
ccgttgggtg acaaagaggc tgtccgtgtc cccgtagact gactttatgg gcctgtcctc 5640
gagcggcgtg ccgcggtcct cttcgtagag gaactcggac cactctgaga cgaaagcacg 5700
tgtccaggcc agcacaaagg aggctatatg ggaggggtag cgatcgttgt caaccaaggg 5760
gtctactttt tccaaggtgt gtaaacacat gtccccttct tccacatcca ggaaggtgat 5820
tggcttgtaa gtgtatgcca cgtgacctgg ggtcccagac ggggggtat aaaagggggc 5880
gggtctctgc tcgtcctcac tgtcttccgg atcgctgtcc aggagcgcca gctgttgagg 5940
taggtattcc ctctcgaagg cgggcataac ctccgcactc aggttgtcag tttctaggaa 6000
cgaggaggat ttgatattga cagtgcctgc cgagatgcct ttcatgagac tgtcgtccat 6060
ttggtcagaa aagacaatct ttttgttatc aagtttggtg gcgaaggatc catacagggc 6120
attggaaagc agtttggcaa tggagcgcat ggtttggttt ttttctttgt ctgcgcgctc 6180
tttggcggct atgttgagtt ggacatattc gcgggccaga catttccatt gtggaaatat 6240
ggtagttaat tcatctggga cgattctgac tttccagcct ctgttatgca gggtaatcag 6300
atccacactg gttgccactt ctcctctaag tggttcatta gtccagcata gtcgcccccc 6360
ttttcgagaa cagaaagggg gtaggggatc tagcatgagt tcgtctgggg ggtctgcatc 6420
tatggtgaaa atcccaggaa ggagatcttc gtcaaaatag ctgatggtgg cggggtcatc 6480
cagagacatt tgccattctc gagcagccag agcgcgctcg taggggttaa ggggagtccc 6540
ccatggcatg ggatgggtga gtgcagaagc atacatgcca cagatgtcat agacatagag 6600
cggctcttcc agaatcccta tgtaagtggg ataacatcgc ccccctctga tgctggctcg 6660
cacataatca tagagttcat gtgagggcgc tagaagaccc gagcccaggt tggtgcggtt 6720
gggtttttct gctctgtaga ggatctggcg aaagatggca tgggagtttg atgagatggt 6780
gggtctttgg aagatgttga aatgggcatg aggcagtccc acagagtccc ttatgaagtg 6840
agcataggag tcttgcagtt tggccaccag ctcggcggtg accagcacat ccaaagcaca 6900
gtagtcgagg gtctctttga tgatgtcata gttaggttcc cctttctttt cccacagctc 6960
gcggttgaga aggtattctt cgcgatcctt ccagtactct tcgagggggga acccgtcctt 7020
gtctgaacgg taagaaccca gcatgtaaaa ttgattgaca gctttgtagg cacaacaccc 7080
cttctccacg gggagtgagt atgcttgcgc ggctttgcgc agagaggtgt gagtaagggc 7140
gaaagtgtcc ctgaccatga ctttgaggaa ctgatgctta aagtctatgt catcgcaggc 7200
cccctgctcc cacagttgga agtccactcg ctttttgtag gcgggattgg gcaaagcgaa 7260
agtaacatcg ttgaatagga tctttccagc cctgggcatg aagttgcgag taatgcgaaa 7320
aggctgaggc acttctgccc tgttgttgat aacttgggca gccaagacga tctcgtcaaa 7380
gccgttgatg ttgtgaccca caatgtacag ttctacgaag cgtgggcgtc ccttgatgtg 7440

-continued

```
gggcagtttt ttaagctctt cgtaggtcaa gtcgtcaggg tcagcgattc catattgctc   7500
caaagcccag tcaggcaggt gaggattagc atgaaggaaa gaggtccaaa gatccacggc   7560
cagagctgtt tgtaagcggt ctctgtactg acggaaatgt cggcctaccg ccattttttc   7620
aggagtaaca cagtaaaagg tgcgcgggtc cttttcccag cgatcccatt gaagttgcaa   7680
ggctaggtcg tgggcgaggt tgacgagctg ttcgtccccc gaaagtttca tgaccagcat   7740
gaaagggaca agctgcttgc caaaggaccc catccaggtg taggtttcca catcgtaggt   7800
gaggaagagc ctttctgtgc gaggatgaga accgatcggg aagaactgga tttcctgcca   7860
ccagttggag gaatggctgt tgatatgatg gaagtagaac tccctacggc gcgccgagca   7920
ttcgtgcttg tgcttgtaca gacggccaca gtactcgcag cgctgcacgg gatgcacctg   7980
atgaatgagc tgtacctggc ttcctttgac aagaaatttc agtgggaagt tgaggcgtgg   8040
cgtctgcatc tcgtgttgta ttacgtcctg gctattggtc tggccatctt ctgtctcgat   8100
ggtggtcatg ctgacgagcc cgcgcgggag gcaggtccag acctccgcgc ggacgggtct   8160
gagagcgagg acgagagcgc gcaggccgga actgtccagg gtcctgagac gctgcggagt   8220
caggtcagta gggagagtac ataggtttac ttgcataagt tttccaggg catgtgggag   8280
gtcaagatga tatttgattt ctactggcga gttggtggag acatcgatgg cttgcagggt   8340
cccgtgcccc tggggtgcta ccaccgtccc tttttttttc ttgatcgggg gcggtgttgc   8400
ttcttgcatg gtaaggtcgt cttctagaag cggcggcgag gtcgcgcgcc gggtggcagt   8460
ggcggttctg gacctggagg tagaggcggt agaggtacgt cggcgccgcg cgcgggtagg   8520
ttctggtact gcgccctgag aagacttgcg tgagcgacga cgcggcggtt gacgtcctgg   8580
atctgacgcc tctgggtgaa tgctaccgga cccgtgagct tgaacctgaa agagagttca   8640
acagaatcaa tttcggtatc gttgacggct gcctgccgca ggatttcttg tacgtcgccc   8700
gagttgtctt ggtaggcgat ctcggccatg aactgctcga tctcttcttc ttggagatct   8760
ccgcggcccg ctcgttctac ggtggcagca aggtcgttgg agatgcgccc catgagctgt   8820
gagaatgcat tcatgcccgc ctcgttccag acgcgactgt agaccacggc tccctcggga   8880
tctctggcgc gcatgaccac ttgggcgagg tttagttcca cgtgtctggt gaagaccgca   8940
tagttgcaga gacgctggaa gaggtagttg agcgtggtgg cgatgtgctc ggtgacaaag   9000
aaatacatga tccagcgacg aagcggcatc tcgctgatat cgcccagggc ttccaaccgt   9060
tccatggctt cgtaaaagtc cacggcgaag ttgaaaaact gggagttgcg agcggacacg   9120
gtcaactcct cctccagaag acggatgagc tcggcgatgg tggcgcgcac ttcgcgctca   9180
aaggctcccg ggatctcttc ctcctcttct tcttccaact cttcctccac taacatctct   9240
tctacttcct cctcaggcgg cggggggtgga ggagggggcg cgcggcgacg ccggcgacgc   9300
acgggcagac gatcgatgaa gcgttcgatc acttctccgc ggcggcgacg catggtctcg   9360
gtgacggcgc gcccgtcctc cctgggtcgc agagtgaaga cgccgccgcg cagctccctg   9420
aaatggtgac tgggagggtc cccgtttggt agggacaggg cactgatgat gcatcttatt   9480
aattgccctg tagggactcc gcgcaaggac ctgagcgtct cgagatccac gggatctgaa   9540
aatctctgaa cgaaggcttc gagccagtcg cagtcgcaag gtaggctgag cactgtttct   9600
tcggggcggg ctgctgagct agagggttgt acgatgctgc tggtgatgaa gttaaaatag   9660
gcagttctga gacggcggat ggtggcgagg agcaccaggt ctttgggtcc ggcttgctgg   9720
atgcgcaggc ggtcggccat tccccatgca ttatcttggc acctggccag atctttatag   9780
tagtcttgca tgagtcgctc cacgggcact tcttcttcgc ccgctctgcc gtgcatgcgt   9840
```

gtgagtccgt accctctctg tggttggacg agcgccaggt cggcaacgac cctttcggct 9900
agaatggctt gctgcacctg ggtgagggtg ttctggaaat catcaaagtc cacaaagcgg 9960
tggtaggccc ccgtgttgat ggtgtaggag cagttggaca tgaccgacca gttgactgtc 10020
tggtgtcctg gtcgtacgag ttccgtgtac ctgagccgcg agtatgcgcg ggagtcgaag 10080
atgtaatcgt tgcaggttcg caccaggtac tggtagccga tgaggaagtg aggcggcggc 10140
tggcggtaga gaggccatcg ttcggtggcg ggcgcgccgg gcgctaggtc ttctagcatg 10200
agacggtggt atccgtagac gtacctggac atccaggtaa taccggcggc ggtggtggag 10260
gcgcgcggaa actctcgcac gcggttccag atgttgcgca gcggcatgaa gtagttcatg 10320
gtgggcacgg tctggcccgt gaggcgcgcg cagtcattga tgctctagat acgggcaaaa 10380
acgaaagcgt tgagcggttc ccttccgtgg cctggaggaa cgcgaacggg ttaggtcgca 10440
gcgtaccctg gttcgagact aaagaaagcg agcaactcga accggcagag tcgcggctaa 10500
cgggtattgg caatcccgtc tcgacccaag ccagcaaatc caggatacgg atgggggccc 10560
cttttgtttt tcagggcatg agtcaccggt taaggtttac aacggctgtt tcatgccttt 10620
agaagtggct cgcgcccgta gtctggagaa tcaatcgcca gggttgcgtt gcggcgtgcc 10680
ccggttcgag cctgcagctt gagtcggccg gtgaccgcgg caaacgaggg cgtggcggcc 10740
ccgtcgtttc taagaccttg ctagccgacc tctccagttt acgggaacga gccccctttt 10800 atttttttg tttttgccag atgcatcccg tactgcggca gatgcgccca cagcccccac 10860
agcagcagca gcaggctggc ctaccttctc tacctcagcc gctacctgca actaccgcgg 10920
tggccgctgt aagcggggcc ggacagcagg cggctcctca atatgaattg gacttggaag 10980
agggcgaggg attggcaaga ttgggggcgc cctcgcccga gcgccacccg cgggtgcaga 11040
tgaaaaagga cgttcgcgaa tcttacgtgc ccaagcagaa tctgttcaga gacagaagcg 11100
gcgaggagcc cgaggagatg cgcgcgtccc gttttaacgc gggtcgcgag ctgcgacaag 11160
gactggatcg aaaacgggtg ttgagggatg atgattttga ggtggatgaa atgacaggga 11220
tcagccccgc tcgcgctcac gtggctgcag ctaatctggt gacagcttat gagcagaccg 11280
tgaaggagga aagcaacttc cagaaatcat tcaataacca cgtgcgcacc ctgatcgcac 11340
gcgaggaggt gaccctgggc ctgatgcacc tgtgggatct gctggaagcc atagtgcaga 11400
accccactag caaacccctg actgctcaac tgtttctggt ggtgcagcac agcagggata 11460
atgaggcatt cagagaggcg ctgctgaata tcactgaacc tgaggggaga tggctgctgg 11520
atctggtgaa tatcctgcag agcattgtag tgcaggaacg cagcttgcct ttgtccgaga 11580
aggtggcggc gatcaattac tctgtgctga gtctgggcaa atactatgcc aggaagatct 11640
acaaaacccc ttacgtgccc atagacaagg aagtgaaaat agatgggttt tacatgcgca 11700
tgaccctgaa agtgctaacc ctgagcgatg acttgggagt gtaccgcaac gacaggatgc 11760
accgcgcggt gagcgccagc aggaggcgcg agctgagcga caaagaatta atgcacagct 11820
tgcaacgagc cctgacggga gccgggacgg agggggagaa ctactttgac atgggtgcag 11880
acttgcattg gctgcctagt cgcagggcat tggaagcggc aggcgatggg ccctatgtag 11940
aggaagtagt agacgaggac gatgaggagg gcgagtacct ggaagactga tggcgcgacc 12000
cgtatttttg ctagatggaa caggcgccgg accctgcgat gcgggcggcg ctgcagagcc 12060
agccgtccgg cattaattcc tcggacgatt ggacccaggc catgcaacgc atcatggcgc 12120
tgacgacccg caaccccgaa gcctttagac agcagcctca ggccaaccgc ctttcggcca 12180

```
tcctggaggc cgtggtgccc tctcgctcca accccaccca cgagaaggtt ctggccatcg  12240
tgaatgccct ggtggagaac aaggccatcc gctccgatga agccgggctg gtatacaacg  12300
ccttgctcga gcgcgtggct cgctacaaca gcagcaatgt ccagactaac ctggacagga  12360
tggtgaccga cgtgcgcgag gccgtgtccc agcgcgaacg gttccatcgc gagtctaacc  12420
tgggttccat ggtagcgctg aacgctttcc tcagttccca gcctgccaat gtgccccggg  12480
gacaggaaga ctataccaac tttattagcg ccctgagact catggtagcc gaggttcctc  12540
agagcgaggt gtaccagtcc ggtccagact actttttcca gacaagcagg aacggtatgc  12600
agacagtgaa cttaagccag gctttcaaga acctgcaagg gctgtgggga gtccaagctc  12660
cagtgggcga cagggcgacc gtgtcgagcc tgttgactcc aaattcccgt ttgctgctgc  12720
tgctggtgtc cccctcact gacagcggca gcataaacag aaactcctac ttgggctacc  12780
tgataaactt gtatcgcgaa gctataggtc aggcccacgt ggacgaacag acctatcagg  12840
agatcactaa tgtgagtcgc gctctgggcc aggacgaccc tggaaacctg gaagctactc  12900
taaactttct gctgaccaac cgctcgcaaa aaatccctcc tcagtataca ttaactgcgg  12960
aggaggaacg gatcttgaga tacgtgcagc agagcgtggg tctgttcctg atgcaagagg  13020
gtgcgacccc tagcgccgcg cttgatatga cagcgcgcaa catggagccc agcatgtatg  13080
ccagcaacag accattcatt aataaattga tggattactt ccatcgcgcg gccgctatga  13140
actctgatta cttcaccaat gctattctga acccccattg gctgcctccg cctggttttt  13200
atactggcga gtatgacatg cctgacccca acgatgggtt cttgtgggac gatgtggaca  13260
gcgtggcgtt ctcgcctacc gctcctcgta ctttttggaa gaaggaaggt agtgacagaa  13320
gaccctcctc cgtgctgtca ggacgtgagg gtgctgccgc ggcggtcccc gatgctgcaa  13380
gcccctttcc cagtctgcca ttttcactaa acagcgtgcg cagtagcgag ctggggagaa  13440
taacccgccc tcgcttgctg ggcgaggacg agtatttgaa tgactcccta ctgagacccg  13500
agcgggaaaa gaacttccct aataatggga ttgaaagcct ggtggataag atgagcagat  13560
ggaagaccta tgcccaggag cacagagatg agcctagaat cttgggtcct acagtaggca  13620
cccgcagacg ccagcgccat gatagacagc ggggtctggt gtgggacgat gaggattctg  13680
cagatgacag cagcgtgttg gacttgggcg ggaggggagg tgtgggcaac ccgttcgcac  13740
acttgcgtcc ccgtattgga cgcatgatgt aaaagtgaaa ataaaaaagg aactcaccaa  13800
ggccatggcg accagcgtgc gttcgttctt tctgttgttg tatctagtat gatgaggcgc  13860
accgtgctag gcggatcggt ggcgtatccg gagggtcctc ctccttcgta cgaaagcgtg  13920
atgcagcagg tggcggcggc ggcgatgcaa ccccccttgg aggctcctta cgtgcccccg  13980
cggtacctgg cacctaccga ggggagaaac agcattcgtt attcggaact cacacccttg  14040
tatgacacca cccggttgta cctggtggac aacaaatcgg cggacattgc ctcgttgaac  14100
tatcagaacg accacagcaa cttcttgaca acggtggtgc agaacaatga ctttaccccc  14160
acggaggcca gcacccagac catcaacttt gacgagcgct cccggtgggg cggtcagctg  14220
aagaccatca tgcacaccaa catgcccaac gtgaacgagt tcatgtttag caacaagttc  14280
agggctaggg tgatggtgtc cagaaccaca cctaaagagg tgacagtcac aacagactat  14340
gatggtagtc aggacatctt ggaatacgag tgggttgact ttgagttacc agaaggcaac  14400
ttctctgcca ccatgaccat agacctgatg aataatgcaa ttgttgataa ttacctaaaa  14460
gtgggtagac agaatggggt actggagagt gacataggtg ttaagtttga cactaggaac  14520
tttaggcttg gttgggaccc agtgacagag ttggtcatgc ctggggtcta caccaatgaa  14580
```

```
gctttccatc ctgacatagt cctactacct ggctgcggag tggacttcac tgagagccgc  14640
ctcagtaatc tgctaggcat tagaaagaaa cagccattcc aggaagggtt ccagatcatg  14700
tatgaggatc tggagggtgg taacatcccc gccctgcttg atgtaaatgc atatgagaag  14760
agcaaggaag ataatacaac caccacaaat gaagctgtgg ccgcggcttc atctactgaa  14820
gccaaagctg tggtagatgc ttccacttca acagaaaaca ccactgatga aaaagtcacc  14880
aggggagata catttgccac ccctgaacaa gagaaggcag ctgaggcaga gtctgatatt  14940
atgcttctgt ccaccgatga aaacgaaact aaaaaacaac tggttattcg agcggtgacc  15000
aaggatagta aggacaggag ttataatgta ttgtcagatg gaaagaacac agcttaccgt  15060
agttggtacc tggcatacaa ttatggcgac cgtgagaaag gggtgcgttc ttggacactg  15120
cttaccacct cggatgtcac ctgcggcgtg gagcaagtct attggtcgct accagatatg  15180
atgcaagatc cagtcacctt tcgctccaca cgccaagtta gcaactaccc agtggtgggc  15240
gcagagctgc tcccagtgca ttccagaagc ttctacaacg agcaagccgt ctactcgcaa  15300
cagctccgcc agtacacctc gctcacgcac gtcttcaacc gcttccccga gaatcagatc  15360
ctcgtccgcc cgcccgcgcc aaccattacc accgtcagtg aaaacgttcc tgctctcaca  15420
gatcacggga ccctgccgct gcgcagcagt atccggggag tccagcgcgt gaccgttact  15480
gacgccagac gccgcacctg tccatacgta tacaaggccc tgggcatagt cgcgccgcgc  15540
gtcctttcaa gccgcacttt ctaaaaaaat gtccattctc atctcgccca gtaataacac  15600
cggttggggc ctgcgcacac ctagcaagat gtatggaggc gctcgcagac gctccactca  15660
gcaccctgtg cgcgtgcgcg ggcatttccg cgctccctgg ggcgccctca agggacgctc  15720
tcgtactagg accaccgttg acgatgtgat cgaccaggtg gtcgccgatg cacgtaacta  15780
tacccccgca gccgcacctg catccaccgt ggatgcggtc attgacagcg tggtagccga  15840
tgcgcgcgcc tatgctcgcg ccaagagcag gaggcggcgt attgccaggc gtcaccgagc  15900
tactccagcc atgcgagctg caagagcttt attgcggaga gccagacgtg tggggcgaag  15960
agccatgcgt agagcggcca gacgcgcggc ttcaggtgcc agcgcaggca gggtccgcag  16020
gcgcgcggct acggcggcag cggcggccat cgctagcatg accaaaccac gaagaggcaa  16080
tgtgtattgg gtgcgcgacg ccgccaccgg ccagcgcgtg cccgtgcgca cacgcccccc  16140
tcgcacttag aagatactga gcagtctccg atgttgtgtc ccagcggcga gatgtccaag  16200
cgcaaattca aggaagagat gctccaggtc atcgcgcctg agatctacgg tcctgcggtg  16260
aaggatgaaa aaaagccccg caagatcaag cgggtcaaaa aggacaaaaa ggaagaagat  16320
ggtgatgatg ggctggtgga gtttgtgcgc gagtttgccc caaggaggcg cgtgcagtgg  16380
cgcgggcgca aagtgtggcc ggtgttgaga ccggggacca cagtggtctt tacgccaggc  16440
gagcgctcca gcaccgtttc caaacgctct tatgatgagg tgtacgggga cgatgatatt  16500
ctcgagcagg cggctgatcg ccttggcgag tttgcatatg gcaaacgcag ccgctcggga  16560
gccaaggaag aggcattgac catccccttg gatcatggaa atcccacccc aagcctcaaa  16620
cccgtgaccc tgcaacaagt gctgcccacg ccgccacgca agggcatcaa gcgcgagggc  16680
gaggatctgt atcccaccat gcagctgatg gtgcccaagc gccagaagct ggaagacgtg  16740
ctggagaaaa tgaaagtgga tcctgaaatc cagcctgaag tcaaagtgag gccaatcaag  16800
caggtggcgc ccggtttggg ggtacaaacc gtggatatca agatccccac cgagtccatg  16860
gaaattcaaa ccgaacccat gaagcccacc tccagcacca ttgaggtgca gacggatcct  16920
```

-continued

```
tggatgcccg cgcctgctcc tgttaccact actactcgaa gacctagaag aaagtatggt  16980
tcagccaacc tgataatgcc aaactatgct ctgcatccat caatcatacc cactcctggc  17040
taccgcggca ctcgctacta ccgcagtcac agcacccgcc gacgtaaagc acctgccacc  17100
cgccgccgtc gccgccgccg tgccactagc aaacttaccc cctcggctat ggtgcggaga  17160
gtgtaccgtg atgggcgcgc agctcctctg acactgccgc gcgcgcgcta ccatcctagc  17220
attgccattt aacaactctg cctccttgca gatatggccc tcacttgccg ccttcgtatt  17280
cctattgctg gctaccgcgg aagaaagtcg cgccgtagaa gagcagggtt gtctgggagc  17340
gggatgcgtc gccaccggcg gcggcgcgcc atcagcaaac ggttgggggg tggatttctt  17400
cccgctttga ttcccatcat cgccgcggcg atcggcgcga taccaggcat agcttccgtg  17460
gcggtgcagg cctcgcagcg ccactgacat tggaaaaaga tatcttataa ataaaaatag  17520
aatggactct gacgctcctg gtcctgtgat atgtttttgt agacgagatg gaagacatca  17580
atttttcatc cctggctccg cgacacggca cgcggccgta tatgggcacc tggagcgaca  17640
tcggcaacag ccaactgaac gggggagcct tcaattggag cagtctatgg agcgggctta  17700
aaaattttgg gtccactata aagacttatg ggaacaaagc ttggaacagc agcacagggc  17760
atgcgctgag acaaaagctt aaagatcaga atttccaaca gaaggtggtc gatggtatcg  17820
cctctggaat caatggggtg gtagatctgg ccaaccaggc cgtgcagaaa cagattaaca  17880
gtcgcctgga cccggctccc ccagctccta ttcatgagtt aatgcaagtg gaggaagagc  17940
tcccttcatt ggaaaagcgg ggcgataagc gacctcgtcc agatatggag gaaacgctgc  18000
tgaccaaggt ggatgagccg ccctcctatg aagaggctgt aaaactggga atgcccacta  18060
caaagcccat tatgcctctg gccactggag tgatgaagcc atctcagtct aaacctgcag  18120
ttgctgctac attggacttg cccgctcccg tggccacccc caaacctgtc gccgccccga  18180
agcccaccgc cgtgcaaccc gtggccgtgg ccagaccgcg tcccggtggt cggccgaatg  18240
caaactggca gagcactctg aacagcatcg tgggtttggg agtgcacagt gtgaagcgcc  18300
gtcgctgcta ttgattaaat atggagtagc gcttaacttg cttgtctgtg tgtgtatatg  18360
tcgatgccgc ccgccgtgct acagcaaaga gagaaggaga agaggcgccg ctgagttcct  18420
ttcaagatgg ccaccccatc gatgctgccc cagtgggcgt acatgcacat cgccggacag  18480
gacgcttcgg agtacctgag tccgggtctg gtgcagttcg cccgcgccac agatacctac  18540
ttcaatctgg ggaacaagtt taggaaccct accgtggctc ccacccacga tgtgaccacc  18600
gaccgtagcc agcgcctgac gctgcgcttt gtgcccgttg accgggagga caatacctac  18660
tcctacaaag tcagatacac cctggctgtg ggagacaaca gggtgttgga tatggccagc  18720
acctactttg acatcagggg cgtgttggac agaggaccta gcttcaaacc atactctggc  18780
actgcctaca actccctggc tccaaaagga gctccaaact ccagtcagtg gcaacaaaag  18840
gaaaacaatg gtcaaggtga tgcaaagact cacacctatg gtgtagctgc cactggaggt  18900
attgacattg acaaaaatgg tcttcaaatt ggaatcgatg aaactaaaga agataataac  18960
gaaatttatg cagacaaaac attccaacct gaacctcaaa ttggagaaga aaactggcaa  19020
gatagcgaaa actattatgg aggcagggct cttaaaccgg aaaccaagat gaagccttgc  19080
tatggttcct tcgctagacc aactaatgca aagggaggtc aagccaaaat taaaccagct  19140
caagagggtc aacagtctat agattatgac atagacctgg ctttctttga tattccaagc  19200
actggcggag gcaatggcac aaatgtaaat gacaagccag atatggttat gtatactgaa  19260
aatgtaaatc tggaaactcc agacactcat cttgtttaca agccaggaac ttcagatgac  19320
```

agttccgagg ccaatttaac tcagcaagcc atggctaaca gacccaacta tattgggttt 19380
agagataact ttattggcgt catgtactac aacagcactg gcaacatggg agtgcttgct 19440
ggtcaagcat cccagctaaa tgctgtggtg gacctgcaag acagaaacac cgagctgtct 19500
tatcagctat tacttgactc tctgggcgac agaaccaggt attttagtat gtggaatcag 19560
gcggtggaca gctatgatcc tgatgtgcgc attattgaaa accatggtgt ggaagatgaa 19620
ttgccaaact attgcttccc attggacgga gctggcacta atgctgttta ccaaggagtt 19680
aagacaaaag aggataataa tggcgaatgg gaaacagaca caaatgttgc atcgcagaat 19740
cagatatgca agggcaacat atatgctatg gagatcaacc tgcaagccaa cctgtggaaa 19800
agtttccttt actccaacgt ggctctgtac ctaccagact cctacaagta cactccatcc 19860
aacgtgacac tccctaccaa cactaacacc tatgactaca tgaatggcag ggtggtgtct 19920
ccatccctgg tggatgccta cattaacatt ggcgccaggt ggtctctgga tgccatggac 19980
aatgtcaacc ctttcaacca ccaccgcaat gccggcctgc gctaccggtc catgcttctg 20040
ggcaacggcc gatacgtgcc cttccacatc caagtgcccc agaaattctt cgctatcaag 20100
aacctgctgc ttctcccagg ctcatacacc tacgagtgga acttccgcaa ggatgtcaac 20160
atgatcctgc agagttccct tggcaatgac ctcagaaccg atggggccac catccagtac 20220
accagcatca atctctatgc caccttcttc cccatggctc acaacactgc ctccaccctg 20280
gaagccatgc tgcgcaatga caccaatgac cagtccttca atgactacct ctcagctgcc 20340
aacatgcttt accccatccc tgccaatgcc accaacgtgc ccatctccat cccatctcgt 20400
aactgggctg ccttcagggg ctggtctttc acccgcctca agaccaagga gaccccatct 20460
ctgggatcag ggttcgatcc ctacttcgtc tactcaggct ccattccata cctggatgga 20520
actttctacc ttaaccacac tttcaagaaa gtctccatca tgtttgactc ttctgtcagc 20580
tggccaggca atgacaggct gctgactccc aatgagttcg aaatcaagcg cactgttgat 20640
ggggaagggt acaatgtggc acaatgcaac atgaccaaag actggttcct ggttcagatg 20700
ctctcccact acaacattgg ctaccagggc ttctacatcc cagaaggata caaggaccgc 20760
atgtactcct tcttcagaaa cttccagccc atgagccgcc aggtggtcga tcaggtcaac 20820
tacaaagact acatggcagt caccccttgcc tatcagcaca acaactctgg ctttgtgggc 20880
tacctcgcgc ccaccatgcg acagggccaa ccctaccctg ctaactaccc atacccgctc 20940
attggcaaga ctgcagtcaa cagtgtcacc cagaaaaagt tcctctgcga cagggtcatg 21000
tggcgcatcc ccttctccag caacttcatg tccatggggg cccttaccga cctggggcaa 21060
aacatgcttt atgccaactc cgcccacgcg ctagacatga atttcgaagt agaccccatg 21120
gatgagtcca cccttctcta tgttgtcttc gaagtcttcg acgtggtcag agtgcaccag 21180
ccccaccgcg gcgtcatcga agctgtctac ctgcgcaccc ccttctcagc tggtaacgcc 21240
accacataag cgccttgctt cttgcaagtg gctgcagcag catggcctgt ggatcctcca 21300
ctggatccaa tgagcaagag ctcagggcca tcgccataga cctgggctgt ggaccctatt 21360
tcctgggaac ctttgacaag cggtttccag gcttcatggc tcctgacaag ctcgcctgtg 21420
ccattgtcaa cacggcaggg cgcgagactg gtggtgagca ctggctggct tttggatgga 21480
acccccgctc caatacctgc tatctctttg acccgtttgg gttttcagac gagcgcctca 21540
agcagatcta tcaattcgag tacgaggggc tcctgcgccg cagtgccctg gctactaagg 21600
accgatgcat cactctggaa aagtctaccc agaccgtgca gggtccgcgc tcggctgcct 21660

-continued

```
gcgggctctt ctgctgcatg ttcctccatg cttttgtgca ctggcccgac cgccccatgg  21720
acaacaaccc caccatgaat ttgctgacgg gggtacccaa caacatgctc caatcgcccc  21780
aagtagagcc caccctgcgc cacaaccagg aggcactcta tcgcttcctg aactcccact  21840
catcttactt tcgttctaac cgcgcgcgca ttgagaaggc cactgccttc gatcgaatga  21900
ataataacat gtaaaccaaa ttgtgtgtgg ctcaaataaa cagcacttta ttgtttacat  21960
gcactgaggc tctgggatga tcattttttta aaaatcgaag ggttctggc gggaatcagc  22020
atggccagat ggcagggaca cgttgcggaa ctggaacttg ttctgccact tgaactcggg  22080
aatcaccagc ctgggaactg gaatctctgg aaaggtatct tgccatagct ttctggtcag  22140
ttgcagagcg ccaagcaggt caggagcaga tatcttgaaa tcacagttgg ggccagaatt  22200
ctgggcgcgg gagttgcggt acactgggtt gcagcactgg aacaccataa gggcagggtg  22260
tctcacgctc gccagcacgg tctcgtcact gatgcaagac acatccaggt cttcagcatt  22320
ggccattcca aagggggtca tcttgcaggt ctgtctgccc atcacgggag cgcagccagg  22380
tttgtggttg caatcacaat gaagggggat cagcatcatc ttggcctggt cgggggtaat  22440
ccctgggtaa acagccttca tgaaggcttc atactgcttg aaagcttcct gggctttggt  22500
tccctcggtg tagaacactc cacaagactt gctggaaaac tgattagtag cgcagttggc  22560
atcattcaca cagcagcggg cgtcgttatt agccagctgg accacattcc tgccccagcg  22620
gttctgggtg atcttggctc gatctgggtt ctccttcaac gcgcgctggc cgttctcgct  22680
cgccacatcc atctcaatga catgttcctt ctggatcatg atgttgccat gcaggcatct  22740
aatcttgcct tcataatcag tgcagccatg aggccacagc gcgcacccgg tgcactccca  22800
attgttatgg gggatctggg aatggctatg aaccagccct tgcaggaatc ttcccatcat  22860
cacagccagg gtctttatgc tggtaaaggt cagcgggata ccgcggtgct cctcgttcac  22920
atactgctgg cagatgcgtc tgtagtgctc ggcctgctcg ggcatcagct tgaaagaggt  22980
tttcaactca ttatccagcc tgtatctctc catcatgatg gacattactt ccatgccctt  23040
ctcccaggca gaaacaatag ggagactcag ggattcttg acagtagaga caaccttact  23100
taaggggtca tcactgccaa tcttttcgat gcttctcttg ccatccttct cggtgatgcg  23160
caccggcggg tagctgaatc ccacagccac caactgagcc tcttcccttt cgtcttcgct  23220
gtcttgactg atgtcttgca gaggaacatg tttggttttc ctgggtttct tcttgggcgg  23280
cagctctgga ggactctggc tccgttccgg agaccccatg gatgagcgag agttgtcgct  23340
caccacttgg atctggctgc ctgtagaaga actggacccc acgcggcggt aggtgttcct  23400
cttggtaggc agaggtggag gcgacgggct ccggtccggt ctgggtggcg gatggctggc  23460
ggagcccctt ccgcgttcgg gggtgcgctc cagatggcgg tcgtctgact gacctccgcg  23520
gctggccatt gtgttctcct aggtagagaa acaagacatg gagactcagc catcgctgcc  23580
atcgccatcc accaccacaa gcaccgccga ggaggaggag tgtttaacca ccccaccatg  23640
cagccccgct accaccacca gcacccttga aagcgaggtc gacacggtcg tggaggattt  23700
acaggctatg gaagatattg aggcagctgt cgagcaagac cccggctatg tgacaccggc  23760
ggagcatgat gaggatctag cgcgctttct cgacggtgtg gagaaagcga aacaagatga  23820
ggacgaggaa gaggcagaag cacaaccatc ggtggccgac tacctcaccg gcctagggct  23880
agaagacgtg ctgcttaagc atcttgcaag gcagacagtc atagtcaaag acgccctgct  23940
agagcgctcc gaggtgccac tcagtgtgga agacctcagt cgcgcctatg agctaaacct  24000
cttctcgcct cgcaagcccc ccaagcgtca gcccaacggg acctgtgagc ccaatccgcg  24060
```

cctcaacttc tatccagcct tcactgtgcc cgaagtacta gctacctacc acatcttttt 24120
caagaaccaa aagatcccca tctcctgccg cgccaatcgc acccgcgcag atgccctact 24180
caacttgggg cccggcgctc gcatacctga tatcgcttcc ttggaagagg ttcctaagat 24240
ctttgagggt ctgggcaatg aggaaactcg ggcagcaaac gctctgcaaa gagaaacaga 24300
tgatggtgaa caccacagcg ctctggtgga gctccagggc gacaacgctc gtcttgcagt 24360
cctcaaacgc agcatcgagg tcacccattt cgcctacccc gcacttaatc tcccacccaa 24420
agtcatgagc tcggtcatgg acacgttgct catgaagcgc gcgagcccca tctccgagga 24480
tcagaacatg caggaccccg atgcctcaga tgaaggcaag cctgtagtca gcgacgagca 24540
actggctcgc tggctaggct ctgactcccc ccagtctttg gaggagcggc gcaagcttat 24600
gatggcagtg gtcctgatca cagcggagct ggagtgtctc cgccgcttct tcactgaccc 24660
agagaccctg cgcaagcttg aggagaacct gcattacaca ttcagtcatg ggttcgtgcg 24720
ccaggcgtgc aagatctcca acgttcaact caccaacctg gtctcctacc tgggcatctt 24780
gcatgaaaac cggctggggc agaacgtgct ccacaccacc ctgaaggggg aggcccgccg 24840
cgactatatc cgcgactgta tctacctcta cctatgctac acctggcaaa gcgggatggg 24900
tgtgtggcaa cagtgcttgg aagagcaaaa tctaaaagag ctggaaaagc tgcttcagaa 24960
atctcttaaa tctctgtgga ccgggttcga tgagcggacc accgcttcgg acatggccga 25020
tattatcttc cccgagcggc tcagacacac tctgcgcgac gggctgcctg actttgccag 25080
ccagagcatg ctacaaaact ttaggtcatt catcttggaa cgctccggga tcctgcccgc 25140
cacttgctgc gcactgccct ccgattttgt gcccatcacc taccgggagt gcccccccgcc 25200 gctatggagc cactgctacc tgttccgcct ggccaactac ttggcctacc actctgatgt 25260
gatagaagat gttagtggcg aagggctcct ggagtgccac tgccgctgca acctctgcac 25320
cccccaccgc tccctcgcct gcaatcccca gctgctgagc gaaacccaga tcatcggcac 25380
cttcgagttg caaggtccca gcggcgaagg cgaggggtcc tctccggggc aaagtctgaa 25440
actgactccg ggctatggga cctccgctta ccttcgcaag ttcgccccca aagactacca 25500
cccctatgag atcaggtttt atgaagacca atcacagccc cccaaggccg aactgacggc 25560
ctgcgtcatc acccaggggg caatcttggc ccaattgcaa gccatccaaa aatcccgcca 25620
agaatttttg ctgaaaaagg gacacgggat ctatctagac ccccagaccg gtgaggagct 25680
gaatacacgc ttccctcagg atgccccgag gaggcaagag aatgaaagtt cagatgccgc 25740
ccgaggagga gctggaagac tgggacagtc aggcagagga ggaagactgg gacagccagg 25800
cagaagagga ggacagcctg gaggaggaca gtctggagga aggcgaggag cccaaggaag 25860
aggcagccgc cgccagacca tcgtcctcgg cggtggagac aagcaaggtc ccagacagca 25920
cggctaccac ctccgctcca gctcaagggg ccgctcggcg acccaacagt agatgggacg 25980
agacgggtcg cttccagaac cccaccaccg tcaagaccgg taagcaggag cggcagggat 26040
acaagtcctg gcgggggcat aaaagtgcca tcatcgcttg cttgcaggag tgtgggggca 26100
atatatcctt tgccagacgc tacctgctat tccatcacgg ggtgaatttc ccccgcaaca 26160
tcttgcatta ctaccgtcac ctccacagcc cctactacca gcagcaagag acagcagagg 26220
aaaccagcgg caactccgag agttagaaaa ccagcagcta aaaaatccac agcggcggca 26280
gcaggtgcag gcggactgag gatcaccgcg aacgagccag ctcagaccag ggagttgagg 26340
aatcggatct ttcccaccct ctatgccata ttccaacaaa gtcggggtca ggaacaagaa 26400

-continued

```
ctgaaagtaa aaaacagatc tcttcgctcg ctcacccgca gttgtttgta tcacaagagc  26460
gaagaccaac ttcagcgcac tctcgaggac gccgaggctc tcttcaacaa gtactgcgcg  26520
ctgactctta aagagtagac tgcgcgcgct tggcgagaaa aggcgggaat tacgtcacct  26580
cttggccaca cctgtgcttc attatgagta aagaaattcc cacgccttac atgtggagct  26640
atcagcccca gatgggattg gccgctggcg ccgcccagga ctactccacc cgcatgaatt  26700
ggctcagcgc cggtcccgcg atgatctcac gggttaatgg tgtgagagag caccgaaacc  26760
agatactcct agaacagtcc gccctcaccg ccactccccg caatcacctc aacccccgta  26820
attggcccgc cgccctggtg taccaggaaa ctcctgctcc cactacagta ctacttcctc  26880
gtgacgccca ggccgaagtt cagatgacta actcaggtgt acagctggcg ggtggtgcca  26940
ccctgtgtcg tcaccggcca agaccgggta taaagggcct ggtgatcaga ggccgaggta  27000
ttcagctcaa cgacgagtcg gtgaactctt cgcttggtct gcgaccagac ggcatcttcc  27060
aaatagctgg ttgtgggaga tcttccttca ctcctcgtca ggctgtcctg actttggaga  27120
gttcgtcctc gcagccccgc tcgggcggca tcgggactct ccagttcgtg gaggagttta  27180
ctccctcggt ctacttcaac cccttctccg gttctcctgg gctttacccg gacgagttca  27240
tcccgaacta cgacgccatc agtgaagcgg tcgacggcta cgattaatgt ctaatggtgg  27300
cgcggctgag ctagctcgac tgcgacacct agaccactgc cggcgctttc gctgctttgc  27360
tcgggatctc tgcgagttca tctacttcga gtaccctgac gaacatcctc agggacctgc  27420
ccacggagtt cggattacca ttgaaggggc tatcgattct cacctgcttc ggatcttcac  27480
cgctcggcca gtgctagttg agcgcaacca gggcgacacc accatctccc tctgctgcat  27540
ttgtgacaac ccggattgc atgaaagctt ttgttgtctt ctttgtactg agtataataa  27600
aagctgaaat tagagactac tccggactct cttgtcgtct gaacaacacc aaccagaccc  27660
ttcacttcag cgggaaccag actactcttc actgtaaggc ttataactat aagtatctta  27720
cttggatata caaaggaaca ccgtttgctg tggtaaacag gtgctccaac gacggtgttc  27780
tcctcacctt cctaggcaac ttctccaact ttaccttttc tgttcgcaga aacaagctta  27840
ccctccttca gccctacttt cctgggatct atacctgcct cagtggacct tgcaaccaca  27900
cttttcacct gattgaaaac tctaccctta ccttcccagc gccaatccct actaacagct  27960
cggagtccaa ctcttccatt accgctgata ctaacactcc taaaaccgga ggtgagctcc  28020
gcagccttcc cccggctgca gataaccctt gggtggtagc gggatttgta gcgctaggaa  28080
tagttgcggg tgggctcgcg ttcgtcctct gctacctata ccttacctgc tgctcatatt  28140
tagtagtact gtgctgttgg tttagaaaat gggggcgcta ctaatcacac ttgctttact  28200
ttcgcttttg ggtctgagct cggctaatag cgagaaacca agctgtctag aaacaaactc  28260
tccagactgt gtggttcctc atgggctctc agacccagct gatgatccat gcttaacttt  28320
tgacccagaa aaaaactgct cggtgactat gcagccctat gcttacatgt gcacatctgt  28380
tataaagtgc ggatggggct gtaaaccgat tgaaattacc cacaaaggca aaacctggaa  28440
taatagtttg tttaacacat ggcagcctgg agacgagcag tggtatactg tcactgtccg  28500
tggtcctgac ggctcagtta aagctcatta caatctaacg ttcatgtttg cagaattgtg  28560
tgatctggct atgatcatgc aaagacagta caggctgtgg ccccccacta aggaaaacat  28620
tgttgagttc tccattgctt actgcatagg cacctgcttg gtcactgcta tcatgtgcgt  28680
ctgcattcac ctgcttgtaa tcattagacc caggaataac aatgaaaagg aaaaaatgcc  28740
ataatctttc taactttgtt ttcagccatg attactttta caactattct tgctatcatt  28800
```

-continued

```
agcattgtga ctgctcaaag gcacccacac acaacactaa acatttacac tggtcaaaac  28860
tatacattgt ggctaacaag caactactca aatgttatgt ggatatatca tacaaaatca  28920
tggaccaaca gccaaatgct atgtcgcggt accacaactt catacccaga gcttaagcac  28980
acttgtactg acacaaactt aacacttatt aatgtaaatg caaccttcaa tgccgactat  29040
tatgcatata gcggcaccca ttctttccaa tttacaattc acgttcacaa cttaaccaca  29100
ccaaaaccac caacaacact tacaacaact acaaccagca caaccacagc cagaactaaa  29160
cctacaacag gcaagcagtc cactaaaaca attcatacac ttggtttctt ggaaacattg  29220
ttttttgcta gaagcagttc taacaactct ggaaatgcaa cactagctga tgaagctcaa  29280
attcctggtt ctatgattgg aattgttatg gcagtagtga tagtaatggt gattattatc  29340
attagcatga tcacctatgc ttgctgctat aggaaattcc atcctacaaa agttgatcca  29400
ttattaaatt ttgattttta atcctacaga acaatgaaaa agctgcttat aattttgctt  29460
ttaaaattct catttggagg aaagttatac acgcgcataa caacaactga aggacaaaac  29520
ttaacattgc taggtgtaaa tgctattaat aataatgttt acaaaactgt caacataaca  29580
tgggaaactg aaattaatgg aactaggcaa aatgtgtgca aactaaacat aacaaaatat  29640
acatgtaagg cttatgattt aataatagtt aatgttacca cacttgattc aaaattatac  29700
gtagggcaaa gctacactgt tttgcaaaa ggattaacta aaggctatac tatacataac  29760
cttgcagcac accaagtgac agttattaaa gcaacaacac cccgcaccac aactgtcaca  29820
acacacaaaa gcaccgcttt gttacaatca atacacagta cgcctactat acctcaacca  29880
attgctgaag cagtgcactt taataatcat gaaaccaata tgcagactac tgaaaaaatc  29940
actagcaaaa aacataccac tattgctgtg cttatgccaa cacctgccaa aatctttttg  30000
atgccaatat cagttcaaat cgcaataatt gctgtaatag gcattgtgat tatttcttgt  30060
ctgctttatt atgttttctg ctgtcataaa cactatactg aaagaaaacc catttataga  30120
ccaatgatag gggatccaga acctcttaag gtggagggtg gtctaagaaa tcttctcttc  30180
tcttttacag tatggtgaac tgcaatcatg atccctaggc aatttttctt caccatacta  30240
atctgtgctt tgaatgtgtg tgcaactctc gctgtagtag ccaacacaaa cccagagtgt  30300
ctaggcccct tcgctaccta cctgctattt gtctttatta cctgcacctg catctgtagc  30360
atagtctgcc tgattattaa cttctttcaa ttcatagatt gggtatttgt gcgaatttgc  30420
taccttcgcc atcacccaga ataccgcaac aaagatgtcg ctgaactgct caggctgctc  30480
taaaatctgg caggctatga tactgctttt gcttcagctt ctgcttatac ttaccgcagc  30540
ttcagcagca acccctaccc ccaaacccga tgtaagcaag tgtaaattcc accagccatg  30600
gactttcctc caatgctacc atctcaaatc tgagttgccc tcttattaca ttgcgatcat  30660
tggaatcctc accatgctat catgcacatt cttctcattc atgatttacc ccacatttga  30720
ttttgggtgg aatgcaccag attcacttag gctcccacaa tacccagacc cagagccaga  30780
acacattgca ctacagaaca tgcccatacc catattagag tatgaagctg agccacaaca  30840
ccccatgctc cctgctatta gctacttcaa cctaactggt ggagatgact gaccccatgg  30900
aaaactcctc tgccaacgac ctggacatgg acggccgttc atctgagcag cgactggtcc  30960
agatgcgcat tcgccagaag caggaacgcg ccgccagaga gctcaaggat gccattgaaa  31020
ttcacctgtg caagaagggc atcttttgct tggttaagca agcaaagatt tcttatgaaa  31080
tcactgacaa cgaccaccgc ctgtattatg agctcggtcc acagcggcag aaattcacct  31140
```

-continued

```
gcatggttgg agtcaacccc atagtcatca ctcagcaggc tgcagaaatt aaagggtgca  31200
tccactgttc ctgtgattcc caagaatgcg tccacaccat agtcaagacc ctctgcggcc  31260
ttcgagatct tcttccaatg aactaacccc ttcccccaac ccaataaaac attggtttta  31320
atcataataa aaaatcactt actttaaatc tgaaacagtg tctccgtcca agttttcttg  31380
tagcaccact tcactcccct cttcccagct ctggtactgc aagccccggt gggctgcaaa  31440
ctttctccac accttaaaag ggatgtcaaa ttcctcttgt ccaacaatct tcattgtctc  31500
ttcctagatg tccacaaagc gcgcgcgggt ggaagatgac tttgaccctg tctacccata  31560
cgatgctgag ctggcaccgt ctgtaccctt catcgcccct cccttcgttt cgtcagacgg  31620
atttcaagaa aaacccctgg gagttctgtc cctaagacta gccaacccag tcactactaa  31680
aaatggggaa ctcacactta aactgggaga tggggtgggc atagactcag atggaaacct  31740
cacagcacag acagttacta aagcaacatc cccccttact gtttccaata acgcaattgc  31800
acttaacatg gacaaacctt tttacagtag caatggaaaa ctatccttac aagttacatc  31860
accattaaag atagtcgact ctttaaatac attggctatt ggctatgggc aaggcttagg  31920
actaaacaat agtgctcttg ctgtgcaatt agcatctccc cttacatttg acagcaacag  31980
caaaattaaa ataaatttgg gaagcgggcc attaaaaatt aatgcgaata aactgtcaat  32040
taactgccta aggggtgtat atgtaacaac tgacggaact tcaattgaaa caaatataag  32100
ctgggcaaaa ggaatgaggt ttgaaggtaa tgccatggct gtaaacgttg acagcaccaa  32160
aggtctacaa tttggcacta ccagcacaga atcaggagtc actaacgctt tccctatcca  32220
gttaaagatt ggatctggtc ttagttttga cagcacagga gcacttgtag cttgggataa  32280
ggataatgac aagcttacac tgtggacaac cgctgaccca tcacctaatt gtaccatata  32340
tacagacaag gatgctaaac ttacactttg tcttacaaaa tgtggcagtc aaatactagg  32400
cagtgtttca gtactggctg ttaaagctgg aaccctacag ccaatcagtg aaaaaatagg  32460
tactgctttg gtttcactaa aatttaataa caacggtgta ttgttaagca actccacatt  32520
aagtaatgaa tactggaact acaggaaggg agatgtcaca ccagccgaag cctatactaa  32580
tgctgtgggt tttatgccaa acatcaaggc atatcctaaa aacacaaact ctgcctcaaa  32640
aagccacatt gtaggacaag tgtaccttaa tggagatgaa actaaaccaa tgcatttaat  32700
cattacattt aatgaaacca gtgatgaaac atgcacatat tccataacgt tccaatggaa  32760
atggaacatt ggaacataca ccagcgacac ccttgcaaca agctccttta ccttttctta  32820
cattgcccaa gaataaaaac tgcagacaac aataaagttt aaatgtttta tttaaacagt  32880
tttacacgat tcgagtagtt attttgcctc ccccctccca tttaacagag taaactagtt  32940
tttgcccttg aacagcttta agcaatttta tcccactaga gatagataga tttttagttt  33000
ctacattcca cacagtttca aaacgagcaa atctaggatc agtaagggaa agaaattcat  33060
ctggacaatc ttttagggca gtggcttcac gatcttgctg ctggaaatgt tcatcagtag  33120
tagttgtagg aatcagagtc atctggaaga agaacggtgg gaatcataat ccgaaaatgg  33180
aattgggcga tggtgtctca ttaaaccctg gagcagtctc tgccgatgtc tctcagtgcg  33240
gctgctgctg atgggatctg gatccatagt ctctcgaagc ataatgccaa tagcctttag  33300
catcagcctt cttgtgcgcc ttgcacagca acgcatcctg atctcactca gatcccaaca  33360
gtaagtacag cataacacca caatgttatt tagcaaacca taattaaatg cactccatcc  33420
aaaactcatg gcagggataa cagagccggc atggccatca taccagattc ttacataaat  33480
cagatggcgc cccctaaaga aaacactgcc catgtacata atctctttag gcatgtgaag  33540
```

-continued

```
gtttacaacc cttcggtacc atggacagcg ctggttaatc atgcatcctt ctataatcct  33600
tctaaaccag atagccaaca cagcccctcc tgccatgcac tgaagggatc cctgattaga  33660
acagtgacaa tgaataaccc acctttccct cccatgaatt acttgggagt aaaaaatatc  33720
tattgtagca cagcacaagc agacattcat gcattttctc attactctaa actcctcagg  33780
tgttaacacc atatcccagg gtacaggaag ctcttgaatg acagtgaaca tagcagaaca  33840
aggtaaacct ctaacataac ttacactatg catagtcaag gtgttacaat ccggaaggta  33900
tggatgttcc tcagtcatag tagctctggt ctcagtctcc tcacatcgtg gtaactggac  33960
cctgtatggg tgacggcgag cggacgacgt cgatcgtccc cgcgacttcg ttgtagtgga  34020
gcgccttccg gacattctcg tactttgagt ggcaaaacct tgctctcgaa cagcacacgt  34080
ctcgtcgcct cctgtccctt ctcttcgcct tttcagtgtg atagttgtaa tacagccatt  34140
cacgaagctc agtcagaaga tcttcagcgt ctgttgtcaa aaacaatcca tccaatctga  34200
ttgctttcaa aacatcacaa acagtcgaat aagccaaacc catccaggca atgcaattat  34260
tttggttatc cacaatggga gggggcggaa gacatggaag aggcatattt aaatttttaa  34320
tccaatcgat cacgcagcac ttcaaaatga agatcgcgaa ggtgacacct ttcacccccca  34380
ctgtgttgat gaaaaataac agccaagtca aaattgatgc ggttttcaag gtgctcgact  34440
gtagcatcaa gcagagcttc cacacgcacg tccacaaata acagaatagc aaaagcggga  34500
ggaggaagta aatcctcaat catcatagta cagtccatca ccatccctaa ataattttca  34560
tccttccagc cttggactat atttttaaac tgctcttgta aatccaaacc acacatgtgg  34620
aaaagttccc aaagagctcc ctcaactacc attcttaagc acaccttcat agtgacaaaa  34680
tatcttgttc ctctgtcacc tgcagcaaat tacaaagtcc aatattagga tctatgccca  34740
gagatctaag ctcatccctc aattccaact gtaaaaaggc ttccagatct gccctaactt  34800
gttcagccag tgggctccct ggaataagcg tgggagaagc caaactgcaa aacagacgca  34860
tgccgccata attaccacca gaaaacacta cgttacagta tgcatgctga ttcattccag  34920
taatttcatc cagtgtattg gatacaaaaa aaggcaagca ctctctcact aattgtatta  34980
tggagacatt atcacacagg taacaattta aaggttgtgg aacaataatg cagtaagtaa  35040
ccacggtgcg ctccaacatg gttagtaatt tttagttctg aaaaacaaaa catacaaaaa  35100
attatatcat actcatttgg cgaactggtg gaaaaatgac cctatctagc acaaggcaag  35160
ccactggatc accaatgcgc ccctcataaa acctgtcatc atgattaaaa agcaacaccg  35220
aaagctcttc cctatgtcct gcatgaatga ttctagctga ggaatataag ccagcgcaat  35280
tagtatctgt taaagaaaaa aaacggccaa catagcctct aggaattagc acacttaatc  35340
ttaaagacat tactgccatc ccccttggat ttaaggtaaa atttacagga gcatagaaaa  35400
tatactgatt tccctcctgc acaggcagca tagcaccagg tccctctaaa aacacacaca  35460
aagcttctgc agccatagct taccgcgcaa accaggcaca gcagtgagct aaaaggacaa  35520
agctctaact cactagccaa cctggcgcac aatatatagt tagtccttac actgacgtaa  35580
ccgaccaaag tctaaaaacc ccgccaaaaa tacacacacg cccaaaaaac gccccgtgag  35640
tcaaaaaaca gtttcacttc ctcgttacac ccaaaacgtc gtcacttccg gattcccacg  35700
gttcgtcact tccggagctc cttgcaaccc cgcccaaaac gtcatcgtcc gcgtcacgcc  35760
gccccgcccc gcgaccgttg accccgggcc aatcaccgca catcccgcaa aattcaaact  35820
cgtctaattt gcatattggc acactgccca tataaggtat attattgatg atg         35873
```

<210> SEQ ID NO 6
<211> LENGTH: 1164
<212> TYPE: DNA
<213> ORGANISM: Artificial Sequence
<220> FEATURE:
<223> OTHER INFORMATION: HAdV-5 E4 orf 6/7

<400> SEQUENCE: 6
tcacagaacc ctagtattca acctgccacc tccctcccaa cacacagagt acacagtcct 60
ttctccccgg ctggccttaa aaagcatcat atcatgggta acagacatat tcttaggtgt 120
tatattccac acggtttcct gtcgagccaa acgctcatca gtgatattaa taaactcccc 180
gggcagctca cttaagttca tgtcgctgtc cagctgctga gccacaggct gctgtccaac 240
ttgcggttgc ttaacgggcg gcgaaggaga agtccacgcc tacatggggg tagagtcata 300
atcgtgcatc aggatagggc ggtggtgctg cagcagcgcg cgaataaact gctgccgccg 360
ccgctccgtc ctgcaggaat acaacatggc agtggtctcc tcagcgatga ttcgcaccgc 420
ccgcagcata aggcgccttg tcctccgggc acagcagcgc accctgatct cacttaaatc 480
agcacagtaa ctgcagcaca gcaccacaat attgttcaaa atcccacagt gcaaggcgct 540
gtatccaaag ctcatggcgg ggaccacaga acccacgtgg ccatcatacc acaagcgcag 600
gtagattaag tggcgacccc tcataaacac gctggacata aacattacct cttttggcat 660
gttgtaattc accacctccc ggtaccatat aaacctctga ttaaacatgg cgccatccac 720
caccatccta aaccagctgg ccaaaacctg cccgccggct atacactgca gggaaccggg 780
actggaacaa tgacagtgga gagcccagga ctcgtaacca tggatcatca tgctcgtcat 840
gatatcaatg ttggcacaac acaggcacac gtgcatacac ttcctcagga ttacaagctc 900
ctcccgcgtt agaaccatat cccagggaac aacccattcc tgaatcagcg taaatcccac 960
actgcaggga agacctcgca cgtaactcac gttgtgcatt gtcaaagtgt tacattcggg 1020
cagcagcgga tgatcctcca gtatggtagc gcgggtttct gtctcaaaag gaggtagacg 1080
atccctactg tacggagtgc gccgagacaa ccgagatcgt gttggtcgta gtgtcatgcc 1140
aaatggaacg ccggacgtag tcat 1164

<210> SEQ ID NO 7
<211> LENGTH: 99
<212> TYPE: DNA
<213> ORGANISM: Artificial Sequence
<220> FEATURE:
<223> OTHER INFORMATION: HAdV-5 protein IX promoter

<400> SEQUENCE: 7
ggtactgaaa tgtgtgggcg tggcttaagg gtgggaaaga atatataagg tgggggtctt 60
atgtagtttt gtatctgttt tgcagcagcc gccgccgcc 99

<210> SEQ ID NO 8
<211> LENGTH: 33040
<212> TYPE: DNA
<213> ORGANISM: Artificial Sequence
<220> FEATURE:
<223> OTHER INFORMATION: pBLY6.dE1.dE3

<400> SEQUENCE: 8
catcatcaat aatatacctt atatgggcag tgtgccaata tgcaaattag acgagtttga 60
attttgcggg atgtgcggtg attggcccgg ggtcaacggt cgcggggcgg ggcggcgtga 120
cgcggacgat gacgttttgg ggaggaggag ctatgttgca agtaatcgtg ggaaatgcga 180

-continued

```
cgtaaaacga ggtggagttt aaacacggaa gtagacaatt ttcccgcgct gtttgacagg    240
aaatgatgtg tttttgggcg gatgcaagtg aaaattctcc attttcgcgc gaaaactaaa    300
tgaggaagtg aaattctgag taattctgag gttatcacag ggcggagtat ttaccgaggg    360
ccgagtagac tttgacccat tacgtggagg tttcgattac tctatttttc acctaaattt    420
ccgcgtactg tgtcaaagtc cgtgttttta cgcgatcgcg atggcctgtg tttgagcata    480
atgtactgac caggtgtaac gttcatctgg gtggtcgtag aggaatgttc atgccatacc    540
aatgcaattt taatcatgtg aggatcttga tggagccgca agcgttttcc agagtcagct    600
tgactggaat ctttgacatg tgtgtggaag catggaagat cttaagatat gatgatacca    660
aatccagatg ccgcgcatgc gagtgcgggg gcaggcatgc caggttccaa cctgtatgtg    720
tggaggtgac cgaggagctg agaccagatc atttggtgct gacctgcact ggtgcggagt    780
tcggttccag tggtgaagaa actgattaaa gtgagtagtg ggatgttata aaagtgacca    840
taaggtgatg tgagatggac aaatttggta atttttatgt atttttgtct tgcagccatg    900
agtgggagcg cttcctttga agggggcgtc tttagccctt atctgacggg gcgtctgcct    960
cattgggctg gagtgcgtca gaatgtgatg ggtctacag tggatggaag acctgttcag   1020
cctgctaatt cttctactct gacttatgct actatgactt cctcgccttt ggatgcagct   1080
gcagctgctg ccgcttctgc tgccgccaac actgttcggg ggatggcctt ggagatgggg   1140
tattatggaa ctgtagtggc caacaccact accccaaata accccacagc cttgaatgag   1200
gacaagctgc tagttctcat gtcccagctg gagtctttga cccaacgcct gggcgatcta   1260
gctcagcagg tgtcccagct gaaggagcag actcaagctg caattaccac tgcgaggga    1320
aattaaaaaa attcaaagaa tcaataaata aaccgagact ttgttgattt taaagtgtgt   1380
cattctttat ttaatttttc gcgcgcgata tgccctggac caccggtctc tatcattgag   1440
gacacggtgg atcttttcta gaacccgata gaggtgggat tggatgttga ggtacatggg   1500
cataagacca tctttggggt gtagatagct ccactgcaga gcctcatgct ccggggtggt   1560
gttgtatata acccagtcat agcatgggcg ttgggcatga tgttgcacaa tatctttaag   1620
gaggagacta atggccactg ggagaccctt ggtgtaagtg tttacaaatc tattaagctg   1680
ggacgggtgc atccgaggtg agataatgtg cattttggat tggattttta gattggcaat   1740
gtttcccccct agatctctcc tgggattcat gttatgcaag accactagaa cagtgtatcc   1800
ggtgcactta gggaatttgt catgaagttt ggaggggaaa gcatgaaaaa atttagacac   1860
acccttgtgt cctcccaagt tctccatgca ctcatccata ataatggcaa tgggcccatg   1920
ggcggcggca cgggcgaaca cgttcctggg atctgacaca tcatagttgt ggtcttgggt   1980
caggtcatca taagccattt taataaactt ggggcggagg gtgccagatt gggggatgaa   2040
tgttccctcg ggccccggaa catagtttcc ttcacatatt tgcatttccc aggcttttag   2100
ttcagagggg gggatcatgt ccacctgtgg agcgatgaag aagacggtct cgggggcggg   2160
ggtgattaag tgggaggaca gcaagttcct aagcagctgt gacttgccac acccagtggg   2220
accgtagatg acccctataa caggttgcag atggtagttt agggaaagac agctgccgtc   2280
ctctcgcagg aggggggcga cctcgttcat catttccctc acatgcatgt tttcccgcac   2340
aagttccgat aggaggcgct ctccacccag ggaaaggagt tcttgaagag atgagaaatt   2400
tttcaagggt tttaagccat cagccatggg cattttggag agggtttgtt gcaagagttc   2460
aaggcggtcc cagagttcgg tgatgtgttc tatggcatct cgatccagca tacttcctcg   2520
```

-continued

```
tttctggggt tgggacggct gcgggagtat ggaaccaggc gatgggcgtc cagcgctgcc   2580
agtgtccggt ccttccacgg tcgcagcgtc cgagtcaggg tcgtttccgt cacggtgaag   2640
gggtgcgcgc ctggctgggc gcttgcgagg gtgcgcttca ggctcatcct gctcgtggag   2700
aaccgctgcc gttctgcgcc ctgtgcatcg gccaggtagc aattaaccat gagttcgtag   2760
ttgagcgcct ctgccgcgtg gcctttggcg cgcagcttac ctttggaagt cttctgacag   2820
gtgggacagt agagacactt gagagcatag agttttgggg ctagaaagac cgattctggg   2880
gagtatgcat cggccccaca ggaggcgcag acggtttcgc attccaccag ccatgtaaga   2940
tcgggctcgt tggggtcaaa aacaagtttt ccgccatgtt ttttgatgcg tttcttacct   3000
ttgctttcca tgagttcgtg cccccgttgg gtgacaaaga ggctgtccgt gtccccgtag   3060
actgacttta tgggcctgtc ctcgagcggc gtgccgcggt cctcttcgta gaggaactcg   3120
gaccactctg agacgaaagc acgtgtccag gccagcacaa aggaggctat atgggagggg   3180
tagcgatcgt tgtcaaccaa ggggtctact tttccaagg tgtgtaaaca catgtcccct    3240
tcttccacat ccaggaaggt gattggcttg taagtgtatg ccacgtgacc tggggtccca   3300
gacgggggg tataaaaggg ggcgggtctc tgctcgtcct cactgtcttc cggatcgctg    3360
tccaggagcg ccagctgttg aggtaggtat tccctctcga aggcgggcat aacctccgca   3420
ctcaggttgt cagtttctag gaacgaggag gatttgatat tgacagtgcc tgccgagatg   3480
cctttcatga gactgtcgtc catttggtca gaaaagacaa tctttttgtt atcaagtttg   3540
gtggcgaagg atccatacag ggcattggaa agcagtttgg caatggagcg catggtttgg   3600
tttttttctt tgtctgcgcg ctctttggcg gctatgttga gttggacata ttcgcgggcc   3660
agacatttcc attgtggaaa tatggtagtt aattcatctg ggacgattct gactttccag   3720
cctctgttat gcagggtaat cagatccaca ctggttgcca cttctcctct aagtggttca   3780
ttagtccagc atagtcgccc cccttttcga gaacagaaag gggggtagggg atctagcatg  3840
agttcgtctg gggggtctgc atctatggtg aaaatcccag gaaggagatc ttcgtcaaaa   3900
tagctgatgg tggcggggtc atccagagac atttgccatt ctcgagcagc cagagcgcgc   3960
tcgtaggggt taaggggagt cccccatggc atgggatggg tgagtgcaga agcatacatg   4020
ccacagatgt catagacata gagcggctct tccagaatcc ctatgtaagt gggataacat   4080
cgccccccctc tgatgctggc tcgcacataa tcatagagtt catgtgaggg cgctagaaga  4140
cccgagccca ggttggtgcg gttgggtttt tctgctctgt agaggatctg gcgaaagatg   4200
gcatgggagt ttgatgagat ggtgggtctt tggaagatgt tgaaatgggc atgaggcagt   4260
cccacagagt cccttatgaa gtgagcatag gagtcttgca gtttggccac cagctcggcg   4320
gtgaccagca catccaaagc acagtagtcg agggtctctt tgatgatgtc atagttaggt   4380
tccccttttct tttcccacag ctcgcggttg agaaggtatt cttcgcgatc cttccagtac  4440
tcttcgaggg ggaacccgtc cttgtctgaa cggtaagaac ccagcatgta aaattgattg   4500
acagctttgt aggcacaaca ccccttctcc acggggagtg agtatgcttg cgcggctttg   4560
cgcagagagg tgtgagtaag ggcgaaagtg tccctgacca tgactttgag gaactgatgc   4620
ttaaagtcta tgtcatcgca ggccccctgc tcccacagtt ggaagtccac tcgctttttg   4680
taggcgggat tgggcaaagc gaaagtaaca tcgttgaata ggatctttcc agccctgggc   4740
atgaagttgc gagtaatgcg aaaaggctga ggcacttctg ccctgttgtt gataacttgg   4800
gcagccaaga cgatctcgtc aaagccgttg atgttgtgac ccacaatgta aagttctacg   4860
aagcgtgggc gtcccttgat gtggggcagt tttttaagct cttcgtaggt caagtcgtca   4920
```

-continued

```
gggtcagcga ttccatattg ctccaaagcc cagtcaggca ggtgaggatt agcatgaagg   4980
aaagaggtcc aaagatccac ggccagagct gtttgtaagc ggtctctgta ctgacggaaa   5040
tgtcggccta ccgccatttt ttcaggagta acacagtaaa aggtgcgcgg gtcctttttcc   5100
cagcgatccc attgaagttg caaggctagg tcgtgggcga ggttgacgag ctgttcgtcc   5160
cccgaaagtt tcatgaccag catgaaaggg acaagctgct tgccaaagga ccccatccag   5220
gtgtaggttt ccacatcgta ggtgaggaag agcctttctg tgcgaggatg agaaccgatc   5280
gggaagaact ggatttcctg ccaccagttg gaggaatggc tgttgatatg atggaagtag   5340
aactccctac ggcgcgccga gcattcgtgc ttgtgcttgt acagacggcc acagtactcg   5400
cagcgctgca cgggatgcac ctgatgaatg agctgtacct ggcttccttt gacaagaaat   5460
ttcagtggga agttgaggcg tggcgtctgc atctcgtgtt gtattacgtc ctggctattg   5520
gtctggccat cttctgtctc gatggtggtc atgctgacga gcccgcgcgg gaggcaggtc   5580
cagacctccg cgcggacggg tctgagagcg aggacgagag cgcgcaggcc ggaactgtcc   5640
agggtcctga gacgctgcgg agtcaggtca gtagggagag tacataggtt tacttgcata   5700
agtttttcca gggcatgtgg gaggtcaaga tgatatttga tttctactgg cgagttggtg   5760
gagacatcga tggcttgcag ggtcccgtgc ccctggggtg ctaccaccgt cccttttttt   5820
ttcttgatcg gggcggtgt tgcttcttgc atggtaaggt cgtcttctag aagcggcggc   5880
gaggtcgcgc gccgggtggc agtggcggtt ctggacctgg aggtagaggc ggtagaggta   5940
cgtcggcgcc gcgcgcgggt aggttctggt actgcgccct gagaagactt gcgtgagcga   6000
cgacgcggcg gttgacgtcc tggatctgac gcctctgggt gaatgctacc ggacccgtga   6060
gcttgaacct gaaagagagt tcaacagaat caatttcggt atcgttgacg gctgcctgcc   6120
gcaggatttc ttgtacgtcg cccgagttgt cttggtaggc gatctcggcc atgaactgct   6180
cgatctcttc ttcttggaga tctccgcggc ccgctcgttc tacggtggca gcaaggtcgt   6240
tggagatgcg ccccatgagc tgtgagaatg cattcatgcc cgcctcgttc cagacgcgac   6300
tgtagaccac ggctccctcg ggatctctgg cgcgcatgac cacttgggcg aggtttagtt   6360
ccacgtgtct ggtgaagacc gcatagttgc agagacgctg gaagaggtag ttgagcgtgg   6420
tggcgatgtg ctcggtgaca aagaaataca tgatccagcg acgaagcggc atctcgctga   6480
tatcgcccag ggcttccaac cgttccatgg cttcgtaaaa gtccacggcg aagttgaaaa   6540
actgggagtt gcgagcggac acggtcaact cctcctccag aagacggatg agctcggcga   6600
tggtggcgcg cacttcgcgc tcaaaggctc ccgggatctc ttcctcctct tcttcttcca   6660
actcttcctc cactaacatc tcttctactt cctcctcagg cggcgggggt ggaggagggg   6720
gcgcgcggcg acgccggcga cgcacgggca gacgatcgat gaagcgttcg atcacttctc   6780
cgcggcggcg acgcatggtc tcggtgacgg cgcgcccgtc ctccctgggt cgcagagtga   6840
agacgccgcc gcgcagctcc ctgaaatggt gactgggagg gtccccgttt ggtagggaca   6900
gggcactgat gatgcatctt attaattgcc ctgtagggac tccgcgcaag gacctgagcg   6960
tctcgagatc cacgggatct gaaaatctct gaacgaaggc ttcgagccag tcgcagtcgc   7020
aaggtaggct gagcactgtt tcttcggggc gggctgctga gctagagggt tgtacgatgc   7080
tgctggtgat gaagttaaaa taggcagttc tgagacggcg gatggtggcg aggagcacca   7140
ggtctttggg tccggcttgc tggatgcgca ggcggtcggc cattccccat gcattatctt   7200
ggcacctggc cagatcttta tagtagtctt gcatgagtcg ctccacgggc acttcttctt   7260
```

-continued

```
cgcccgctct gccgtgcatg cgtgtgagtc cgtaccctct ctgtggttgg acgagcgcca   7320
ggtcggcaac gacccttttcg gctagaatgg cttgctgcac ctgggtgagg gtgttctgga   7380
aatcatcaaa gtccacaaag cggtggtagg cccccgtgtt gatggtgtag gagcagttgg   7440
acatgaccga ccagttgact gtctggtgtc ctggtcgtac gagttccgtg tacctgagcc   7500
gcgagtatgc gcgggagtcg aagatgtaat cgttgcaggt tcgcaccagg tactggtagc   7560
cgatgaggaa gtgaggcggc ggctggcggt agagaggcca tcgttcggtg gcgggcgcgc   7620
cgggcgctag gtcttctagc atgagacggt ggtatccgta gacgtacctg gacatccagg   7680
taataccggc ggcggtggtg gaggcgcgcg gaaactctcg cacgcggttc cagatgttgc   7740
gcagcggcat gaagtagttc atggtgggca cggtctggcc cgtgaggcgc gcgcagtcat   7800
tgatgctcta gatacgggca aaaacgaaag cgttgagcgg ttcccttccg tggcctggag   7860
gaacgcgaac gggttaggtc gcagcgtacc ctggttcgag actaaagaaa gcgagcaact   7920
cgaaccggca gagtcgcggc taacgggtat tggcaatccc gtctcgaccc aagccagcaa   7980
atccaggata cggatggggg ccccttttgt ttttcagggc atgagtcacc ggttaaggtt   8040
tacaacggct gtttcatgcc tttagaagtg gctcgcgccc gtagtctgga gaatcaatcg   8100
ccagggttgc gttgcggcgt gccccggttc gagcctgcag cttgagtcgg ccggtgaccg   8160
cggcaaacga gggcgtggcg gccccgtcgt ttctaagacc ttgctagccg acctctccag   8220
tttacgggaa cgagcccccct tttattttt ttgtttttgc cagatgcatc ccgtactgcg   8280
gcagatgcgc ccacagcccc cacagcagca gcagcaggct ggcctacctt ctctacctca   8340
gccgctacct gcaactaccg cggtggccgc tgtaagcggg gccggacagc aggcggctcc   8400
tcaatatgaa ttggacttgg aagagggcga gggattggca agattggggg cgccctcgcc   8460
cgagcgccac ccgcgggtgc agatgaaaaa ggacgttcgc gaatcttacg tgcccaagca   8520
gaatctgttc agagacagaa gcggcgagga gcccgaggag atgcgcgcgt cccgttttaa   8580
cgcgggtcgc gagctgcgac aaggactgga tcgaaaacgg gtgttgaggg atgatgattt   8640
tgaggtggat gaaatgacag ggatcagccc cgctcgcgct cacgtggctg cagctaatct   8700
ggtgacagct tatgagcaga ccgtgaagga ggaaagcaac ttccagaaat cattcaataa   8760
ccacgtgcgc accctgatcg cacgcgagga ggtgaccctg ggcctgatgc acctgtggga   8820
tctgctggaa gccatagtgc agaaccccac tagcaaaccc ctgactgctc aactgtttct   8880
ggtggtgcag cacagcaggg ataatgaggc attcagagag gcgctgctga atatcactga   8940
acctgagggg agatggctgc tggatctggt gaatatcctg cagagcattg tagtgcagga   9000
acgcagcttg cctttgtccg agaaggtggc ggcgatcaat tactctgtgc tgagtctggg   9060
caaatactat gccaggaaga tctacaaaac cccttacgtg cccatagaca aggaagtgaa   9120
aatagatggg ttttacatgc gcatgaccct gaaagtgcta accctgagcg atgacttggg   9180
agtgtaccgc aacgacagga tgcaccgcgc ggtgagcgcc agcaggaggc gcgagctgag   9240
cgacaaagaa ttaatgcaca gcttgcaacg agccctgacg ggagccggga cggaggggga   9300
gaactacttt gacatgggtg cagacttgca ttggctgcct agtcgcaggg cattggaagc   9360
ggcaggcgat gggccctatg tagaggaagt agtagacgag gacgatgagg agggcgagta   9420
cctggaagac tgatggcgcg acccgtattt ttgctagatg gaacaggcgc cggaccctgc   9480
gatgcgggcg gcgctgcaga gccagccgtc cggcattaat tcctcggacg attggaccca   9540
ggccatgcaa cgcatcatgg cgctgacgac ccgcaacccc gaagccttta gacagcagcc   9600
tcaggccaac cgcctttcgg ccatcctgga ggccgtggtg ccctctcgct ccaaccccac   9660
```

```
ccacgagaag gttctggcca tcgtgaatgc cctggtggag aacaaggcca tccgctccga   9720
tgaagccggg ctggtataca acgccttgct cgagcgcgtg gctcgctaca acagcagcaa   9780
tgtccagact aacctggaca ggatggtgac cgacgtgcgc gaggccgtgt cccagcgcga   9840
acggttccat cgcgagtcta acctgggttc catggtagcg ctgaacgctt tcctcagttc   9900
ccagcctgcc aatgtgcccc ggggacagga agactatacc aactttatta gcgccctgag   9960
actcatggta gccgaggttc ctcagagcga ggtgtaccag tccggtccag actacttttt  10020
ccagacaagc aggaacggta tgcagacagt gaacttaagc caggctttca agaacctgca  10080
agggctgtgg ggagtccaag ctccagtggg cgacagggcg accgtgtcga gcctgttgac  10140
tccaaattcc cgtttgctgc tgctgctggt gtccccctc actgacagcg gcagcataaa  10200
cagaaactcc tacttgggct acctgataaa cttgtatcgc gaagctatag gtcaggccca  10260
cgtggacgaa cagacctatc aggagatcac taatgtgagt cgcgctctgg gccaggacga  10320
ccctggaaac ctggaagcta ctctaaactt tctgctgacc aaccgctcgc aaaaaatccc  10380
tcctcagtat acattaactg cggaggagga acggatcttg agatacgtgc agcagagcgt  10440
gggtctgttc ctgatgcaag agggtgcgac ccctagcgcc gcgcttgata tgacagcgcg  10500
caacatggag cccagcatgt atgccagcaa cagaccattc attaataaat tgatggatta  10560
cttccatcgc gcggccgcta tgaactctga ttacttcacc aatgctattc tgaaccccca  10620
ttggctgcct ccgcctggtt tttatactgg cgagtatgac atgcctgacc ccaacgatgg  10680
gttcttgtgg gacgatgtgg acagcgtggc gttctcgcct accgctcctc gtactttttg  10740
gaagaaggaa ggtagtgaca gaagaccctc ctccgtgctg tcaggacgtg agggtgctgc  10800
cgcggcggtc cccgatgctg caagcccctt tcccagtctg ccattttcac taaacagcgt  10860
gcgcagtagc gagctgggga gaataacccg ccctcgcttg ctgggcgagg acgagtattt  10920
gaatgactcc ctactgagac ccgagcggga aaagaacttc cctaataatg ggattgaaag  10980
cctggtggat aagatgagca gatggaagac ctatgcccag gagcacagag atgagcctag  11040
aatcttgggt cctacagtag gcacccgcag acgccagcgc catgatagac agcggggtct  11100
ggtgtgggac gatgaggatt ctgcagatga cagcagcgtg ttggacttgg gcgggagggg  11160
aggtgtgggc aacccgttcg cacacttgcg tccccgtatt ggacgcatga tgtaaaagtg  11220
aaaataaaaa aggaactcac caaggccatg gcgaccagcg tgcgttcgtt ctttctgttg  11280
ttgtatctag tatgatgagg cgcaccgtgc taggcggatc ggtggcgtat ccggagggtc  11340
ctcctccttc gtacgaaagc gtgatgcagc aggtggcggc ggcggcgatg caacccccct  11400
tggaggctcc ttacgtgccc ccgcggtacc tggcacctac cgaggggaga aacagcattc  11460
gttattcgga actcacaccc ttgtatgaca ccacccggtt gtacctggtg gacaacaaat  11520
cggcggacat tgcctcgttg aactatcaga acgaccacag caacttcttg acaacggtgg  11580
tgcagaacaa tgactttacc cccacggagg ccagcaccca gaccatcaac tttgacgagc  11640
gctcccggtg gggcggtcag ctgaagacca tcatgcacac caacatgccc aacgtgaacg  11700
agttcatgtt tagcaacaag ttcagggcta gggtgatggt gtccagaacc acacctaaag  11760
aggtgacagt cacaacagac tatgatggta gtcaggacat cttggaatac gagtgggttg  11820
actttgagtt accagaaggc aacttctctg ccaccatgac catagacctg atgaataatg  11880
caattgttga taattaccta aaagtgggta gacagaatgg ggtactggag agtgacatag  11940
gtgttaagtt tgacactagg aactttaggc ttggttggga cccagtgaca gagttggtca  12000
```

tgcctggggt ctacaccaat gaagctttcc atcctgacat agtcctacta cctggctgcg 12060
gagtggactt cactgagagc cgcctcagta atctgctagg cattagaaag aaacagccat 12120
tccaggaagg gttccagatc atgtatgagg atctggaggg tggtaacatc cccgccctgc 12180
ttgatgtaaa tgcatatgag aagagcaagg aagataatac aaccaccaca aatgaagctg 12240
tggccgcggc ttcatctact gaagccaaag ctgtggtaga tgcttccact tcaacagaaa 12300
acaccactga tgaaaaagtc accaggggag atacatttgc caccccctgaa caagagaagg 12360
cagctgaggc agagtctgat attatgcttc tgtccaccga tgaaaacgaa actaaaaaac 12420
aactggttat tcgagcggtg accaaggata gtaaggacag gagttataat gtattgtcag 12480
atggaaagaa cacagcttac cgtagttggt acctggcata caattatggc gaccgtgaga 12540
aaggggtgcg ttcttggaca ctgcttacca cctcggatgt cacctgcggc gtggagcaag 12600
tctattggtc gctaccagat atgatgcaag atccagtcac ctttcgctcc acacgccaag 12660
ttagcaacta cccagtggtg ggcgcagagc tgctcccagt gcattccaga agcttctaca 12720
acgagcaagc cgtctactcg caacagctcc gccagtacac ctcgctcacg cacgtcttca 12780
accgcttccc cgagaatcag atcctcgtcc gcccgcccgc gccaaccatt accaccgtca 12840
gtgaaaacgt tcctgctctc acagatcacg ggaccctgcc gctgcgcagc agtatccggg 12900
gagtccagcg cgtgaccgtt actgacgcca gacgccgcac ctgtccatac gtatacaagg 12960
ccctgggcat agtcgcgccg cgcgtccttt caagccgcac tttctaaaaa aatgtccatt 13020
ctcatctcgc ccagtaataa caccggttgg ggcctgcgca cacctagcaa gatgtatgga 13080
ggcgctcgca gacgctccac tcagcaccct gtgcgcgtgc gcgggcattt ccgcgctccc 13140
tggggcgccc tcaagggacg ctctcgtact aggaccaccg ttgacgatgt gatcgaccag 13200
gtggtcgccg atgcacgtaa ctatacccc gcagccgcac ctgcatccac cgtggatgcg 13260
gtcattgaca gcgtggtagc cgatgcgcgc gcctatgctc gcgccaagag caggaggcgg 13320
cgtattgcca ggcgtcaccg agctactcca gccatgcgag ctgcaagagc tttattgcgg 13380
agagccagac gtgtggggcg aagagccatg cgtagagcgg ccagacgcgc ggcttcaggt 13440
gccagcgcag gcagggtccg caggcgcgcg gctacggcgg cagcggcggc catcgctagc 13500
atgaccaaac cacgaagagg caatgtgtat tgggtgcgcg acgccgccac cggccagcgc 13560
gtgcccgtgc gcacacgccc ccctcgcact tagaagatac tgagcagtct ccgatgttgt 13620
gtcccagcgg cgagatgtcc aagcgcaaat tcaaggaaga gatgctccag gtcatcgcgc 13680
ctgagatcta cggtcctgcg gtgaaggatg aaaaaaagcc ccgcaagatc aagcgggtca 13740
aaaaggacaa aaaggaagaa gatggtgatg atgggctggt ggagtttgtg cgcgagtttg 13800
ccccaaggag gcgcgtgcag tggcgcgggc gcaaagtgtg gccggtgttg agaccgggga 13860
ccacagtggt ctttacgcca ggcgagcgct ccagcaccgt ttccaaacgc tcttatgatg 13920
aggtgtacgg ggacgatgat attctcgagc aggcggctga tcgccttggc gagtttgcat 13980
atggcaaacg cagccgctcg ggagccaagg aagaggcatt gaccatcccc ttggatcatg 14040
gaaatcccac cccaagcctc aaacccgtga ccctgcaaca agtgctgccc acgccgccac 14100
gcaagggcat caagcgcgag ggcgaggatc tgtatcccac catgcagctg atggtgccca 14160
agcgccagaa gctggaagac gtgctggaga aaatgaaagt ggatcctgaa atccagcctg 14220
aagtcaaagt gaggccaatc aagcaggtgg cgcccggttt gggggtacaa accgtggata 14280
tcaagatccc caccgagtcc atggaaattc aaaccgaacc catgaagccc acctccagca 14340
ccattgaggt gcagacggat ccttggatgc ccgcgcctgc tcctgttacc actactactc 14400

```
gaagacctag aagaaagtat ggttcagcca acctgataat gccaaactat gctctgcatc  14460
catcaatcat acccactcct ggctaccgcg gcactcgcta ctaccgcagt cacagcaccc  14520
gccgacgtaa agcacctgcc acccgccgcc gtcgccgccg ccgtgccact agcaaactta  14580
ccccctcggc tatggtgcgg agagtgtacc gtgatgggcg cgcagctcct ctgacactgc  14640
cgcgcgcgcg ctaccatcct agcattgcca tttaacaact ctgcctcctt gcagatatgg  14700
ccctcacttg ccgccttcgt attcctattg ctggctaccg cggaagaaag tcgcgccgta  14760
gaagagcagg gttgtctggg agcgggatgc gtcgccaccg gcggcggcgc gccatcagca  14820
aacggttggg gggtggattt cttcccgctt tgattcccat catcgccgcg gcgatcggcg  14880
cgataccagg catagcttcc gtggcggtgc aggcctcgca gcgccactga cattggaaaa  14940
agatatctta taaataaaaa tagaatggac tctgacgctc ctggtcctgt gatatgtttt  15000
tgtagacgag atggaagaca tcaatttttc atccctggct ccgcgacacg gcacgcggcc  15060
gtatatgggc acctggagcg acatcggcaa cagccaactg aacgggggag ccttcaattg  15120
gagcagtcta tggagcgggc ttaaaaattt tgggtccact ataaagactt atgggaacaa  15180
agcttggaac agcagcacag ggcatgcgct gagacaaaag cttaaagatc agaatttcca  15240
acagaaggtg gtcgatggta tcgcctctgg aatcaatggg gtggtagatc tggccaacca  15300
ggccgtgcag aaacagatta acagtcgcct ggacccggct cccccagctc ctattcatga  15360
gttaatgcaa gtggaggaag agctcccttc attggaaaag cggggcgata agcgacctcg  15420
tccagatatg gaggaaacgc tgctgaccaa ggtggatgag ccgccctcct atgaagaggc  15480
tgtaaaactg ggaatgccca ctacaaagcc cattatgcct ctggccactg gagtgatgaa  15540
gccatctcag tctaaacctg cagttgctgc tacattggac ttgcccgctc ccgtggccac  15600
ccccaaacct gtcgccgccc cgaagcccac cgccgtgcaa cccgtggccg tggccagacc  15660
gcgtcccggt ggtcggccga atgcaaactg gcagagcact ctgaacagca tcgtgggttt  15720
gggagtgcac agtgtgaagc gccgtcgctg ctattgatta aatatggagt agcgcttaac  15780
ttgcttgtct gtgtgtgtat atgtcgatgc cgcccgccgt gctacagcaa agagagaagg  15840
agaagaggcg ccgctgagtt cctttcaaga tggccacccc atcgatgctg ccccagtggg  15900
cgtacatgca catcgccgga caggacgctt cggagtacct gagtccgggt ctggtgcagt  15960
tcgcccgcgc cacagatacc tacttcaatc tggggaacaa gtttaggaac cctaccgtgg  16020
ctcccaccca cgatgtgacc accgaccgta gccagcgcct gacgctgcgc tttgtgcccg  16080
ttgaccggga ggacaatacc tactcctaca aagtcagata caccctggct gtgggagaca  16140
acagggtgtt ggatatggcc agcacctact ttgacatcag ggcgtgttg gacagaggac  16200
ctagcttcaa accatactct ggcactgcct acaactccct ggctccaaaa ggagctccaa  16260
actccagtca gtggcaacaa aaggaaaaca atggtcaagg tgatgcaaag actcacacct  16320
atggtgtagc tgccactgga ggtattgaca ttgacaaaaa tggtcttcaa attggaatcg  16380
atgaaactaa agaagataat aacgaaattt atgcagacaa aacattccaa cctgaacctc  16440
aaattggaga agaaaactgg caagatagcg aaaactatta tggaggcagg gctcttaaac  16500
cggaaaccaa gatgaagcct tgctatggtt ccttcgctag accaactaat gcaaagggag  16560
gtcaagccaa aattaaacca gctcaagagg gtcaacagtc tatagattat gacatagacc  16620
tggctttctt tgatattcca agcactggcg gaggcaatgg cacaaatgta aatgacaagc  16680
cagatatggt tatgtatact gaaaatgtaa atctggaaac tccagacact catcttgttt  16740
```

-continued

```
acaagccagg aacttcagat gacagttccg aggccaattt aactcagcaa gccatggcta  16800
acagacccaa ctatattggg tttagagata actttattgg cgtcatgtac tacaacagca  16860
ctggcaacat gggagtgctt gctggtcaag catcccagct aaatgctgtg gtggacctgc  16920
aagacagaaa caccgagctg tcttatcagc tattacttga ctctctgggc gacagaacca  16980
ggtattttag tatgtggaat caggcggtgg acagctatga tcctgatgtg cgcattattg  17040
aaaaccatgg tgtggaagat gaattgccaa actattgctt cccattggac ggagctggca  17100
ctaatgctgt ttaccaagga gttaagacaa aagaggataa taatggcgaa tgggaaacag  17160
acacaaatgt tgcatcgcag aatcagatat gcaagggcaa catatatgct atggagatca  17220
acctgcaagc caacctgtgg aaaagtttcc tttactccaa cgtggctctg tacctaccag  17280
actcctacaa gtacactcca tccaacgtga cactccctac caacactaac acctatgact  17340
acatgaatgg cagggtggtg tctccatccc tggtggatgc ctacattaac attggcgcca  17400
ggtggtctct ggatgccatg gacaatgtca acccttcaa ccaccaccgc aatgccggcc  17460
tgcgctaccg gtccatgctt ctgggcaacg gccgatacgt gcccttccac atccaagtgc  17520
cccagaaatt cttcgctatc aagaacctgc tgcttctccc aggctcatac acctacgagt  17580
ggaacttccg caaggatgtc aacatgatcc tgcagagttc ccttggcaat gacctcagaa  17640
ccgatggggc caccatccag tacaccagca tcaatctcta tgccaccttc ttccccatgg  17700
ctcacaacac tgcctccacc ctggaagcca tgctgcgcaa tgacaccaat gaccagtcct  17760
tcaatgacta cctctcagct gccaacatgc tttaccccat ccctgccaat gccaccaacg  17820
tgcccatctc catcccatct cgtaactggg ctgccttcag ggctggtct ttcacccgcc  17880
tcaagaccaa ggagacccca tctctgggat cagggttcga tccctacttc gtctactcag  17940
gctccattcc atacctggat ggaactttct accttaacca cactttcaag aaagtctcca  18000
tcatgtttga ctcttctgtc agctggccag gcaatgacag gctgctgact cccaatgagt  18060
tcgaaatcaa gcgcactgtt gatggggaag ggtacaatgt ggcacaatgc aacatgacca  18120
aagactggtt cctggttcag atgctctccc actacaacat tggctaccag ggcttctaca  18180
tcccagaagg atacaaggac cgcatgtact ccttcttcag aaacttccag cccatgagcc  18240
gccaggtggt cgatcaggtc aactacaaag actacatggc agtcaccctt gcctatcagc  18300
acaacaactc tggctttgtg ggctacctcg cgcccaccat gcgacagggc caaccctacc  18360
ctgctaacta cccatacccg ctcattggca agactgcagt caacagtgtc acccagaaaa  18420
agttcctctg cgacagggtc atgtggcgca tccccttctc cagcaacttc atgtccatgg  18480
gggcccttac cgacctgggg caaaacatgc tttatgccaa ctccgcccac gcgctagaca  18540
tgaatttcga agtagacccc atggatgagt ccacccttct ctatgttgtc ttcgaagtct  18600
tcgacgtggt cagagtgcac cagccccacc gcggcgtcat cgaagctgtc tacctgcgca  18660
ccccctctc agctggtaac gccaccacat aagcgccttg cttcttgcaa gtggctgcag  18720
cagcatggcc tgtggatcct ccactggatc caatgagcaa gagctcaggg ccatcgccat  18780
agacctgggc tgtggaccct atttcctggg aacctttgac aagcggtttc caggcttcat  18840
ggctcctgac aagctcgcct gtgccattgt caacacggca gggcgcgaga ctggtggtga  18900
gcactggctg gcttttggat ggaaccccg ctccaatacc tgctatctct ttgacccgtt  18960
tgggttttca gacgagcgcc tcaagcagat ctatcaattc gagtacgagg ggctcctgcg  19020
ccgcagtgcc ctggctacta aggaccgatg catcactctg gaaaagtcta cccagaccgt  19080
gcagggtccg cgctcggctg cctgcgggct cttctgctgc atgttcctcc atgcttttgt  19140
```

-continued gcactggccc gaccgcccca tggacaacaa ccccaccatg aatttgctga cgggggtacc 19200
caacaacatg ctccaatcgc cccaagtaga gcccaccctg cgccacaacc aggaggcact 19260
ctatcgcttc ctgaactccc actcatctta ctttcgttct aaccgcgcgc gcattgagaa 19320
ggccactgcc ttcgatcgaa tgaataataa catgtaaacc aaattgtgtg tggctcaaat 19380
aaacagcact ttattgttta catgcactga ggctctggga tgatcatttt ttaaaaatcg 19440
aaggggttct ggcgggaatc agcatggcca gatggcaggg acacgttgcg gaactggaac 19500
ttgttctgcc acttgaactc gggaatcacc agcctgggaa ctggaatctc tggaaaggta 19560
tcttgccata gctttctggt cagttgcaga gcgccaagca ggtcaggagc agatatcttg 19620
aaatcacagt tggggccaga attctgggcg cgggagttgc ggtacactgg gttgcagcac 19680
tggaacacca taagggcagg gtgtctcacg ctcgccagca cggtctcgtc actgatgcaa 19740
gacacatcca ggtcttcagc attggccatt ccaaaggggg tcatcttgca ggtctgtctg 19800
cccatcacgg gagcgcagcc aggtttgtgg ttgcaatcac aatgaagggg gatcagcatc 19860
atcttggcct ggtcgggggt aatccctggg taaacagcct tcatgaaggc ttcatactgc 19920
ttgaaagctt cctgggcttt ggttccctcg gtgtagaaca ctccacaaga cttgctggaa 19980
aactgattag tagcgcagtt ggcatcattc acacagcagc gggcgtcgtt attagccagc 20040
tggaccacat tcctgcccca gcggttctgg gtgatcttgg ctcgatctgg gttctccttc 20100
aacgcgcgct ggccgttctc gctcgccaca tccatctcaa tgacatgttc cttctggatc 20160
atgatgttgc catgcaggca tctaatcttg ccttcataat cagtgcagcc atgaggccac 20220
agcgcgcacc cggtgcactc ccaattgtta tgggggatct gggaatggct atgaaccagc 20280
ccttgcagga atcttcccat catcacagcc agggtcttta tgctggtaaa ggtcagcggg 20340
ataccgcggt gctcctcgtt cacatactgc tggcagatgc gtctgtagtg ctcggcctgc 20400
tcgggcatca gcttgaaaga ggttttcaac tcattatcca gcctgtatct ctccatcatg 20460
atggacatta cttccatgcc cttctcccag gcagaaacaa tagggagact caggggattc 20520
ttgacagtag agacaacctt acttaagggg tcatcactgc caatcttttc gatgcttctc 20580
ttgccatcct tctcggtgat gcgcaccggc gggtagctga atcccacagc caccaactga 20640
gcctcttccc tttcgtcttc gctgtcttga ctgatgtctt gcagaggaac atgtttggtt 20700
ttcctgggtt tcttcttggg cggcagctct ggaggactct ggctccgttc cggagacccc 20760
atggatgagc gagagttgtc gctcaccact tggatctggc tgcctgtaga agaactggac 20820
cccacgcggc ggtaggtgtt cctcttggta ggcagaggtg gaggcgacgg gctccggtcc 20880
ggtctgggtg gcggatggct ggcggagccc cttccgcgtt cgggggtgcg ctccagatgg 20940
cggtcgtctg actgacctcc gcggctggcc attgtgttct cctaggtaga gaaacaagac 21000
atggagactc agccatcgct gccatcgcca tccaccacca caagcaccgc cgaggaggag 21060
gagtgtttaa ccaccccacc atgcagcccc gctaccacca ccagcaccct tgaaagcgag 21120
gtcgacacgg tcgtggagga tttacaggct atggaagata ttgaggcagc tgtcgagcaa 21180
gaccccggct atgtgacacc ggcggagcat gatgaggatc tagcgcgctt tctcgacggt 21240
gtggagaaag cgaaacaaga tgaggacgag gaagaggcag aagcacaacc atcggtggcc 21300
gactacctca ccggcctagg gctagaagac gtgctgctta agcatcttgc aaggcagaca 21360
gtcatagtca aagacgccct gctagagcgc tccgaggtgc cactcagtgt ggaagacctc 21420
agtcgcgcct atgagctaaa cctcttctcg cctcgcaagc cccccaagcg tcagcccaac 21480

-continued

```
gggacctgtg agcccaatcc gcgcctcaac ttctatccag ccttcactgt gcccgaagta  21540
ctagctacct accacatctt tttcaagaac caaaagatcc ccatctcctg ccgcgccaat  21600
cgcacccgcg cagatgccct actcaacttg gggcccggcg ctcgcatacc tgatatcgct  21660
tccttggaag aggttcctaa gatctttgag ggtctgggca atgaggaaac tcgggcagca  21720
aacgctctgc aaagagaaac agatgatggt gaacaccaca gcgctctggt ggagctccag  21780
ggcgacaacg ctcgtcttgc agtcctcaaa cgcagcatcg aggtcaccca tttcgcctac  21840
cccgcactta atctcccacc caaagtcatg agctcggtca tggacacgtt gctcatgaag  21900
cgcgcgagcc ccatctccga ggatcagaac atgcaggacc ccgatgcctc agatgaaggc  21960
aagcctgtag tcagcgacga gcaactggct cgctggctag gctctgactc cccccagtct  22020
ttggaggagc ggcgcaagct tatgatggca gtggtcctga tcacagcgga gctggagtgt  22080
ctccgccgct tcttcactga cccagagacc ctgcgcaagc ttgaggagaa cctgcattac  22140
acattcagtc atgggttcgt gcgccaggcg tgcaagatct ccaacgttca actcaccaac  22200
ctggtctcct acctgggcat cttgcatgaa aaccggctgg ggcagaacgt gctccacacc  22260
accctgaagg gggaggcccg ccgcgactat atccgcgact gtatctacct ctacctatgc  22320
tacacctggc aaagcgggat gggtgtgtgg caacagtgct tggaagagca aaatctaaaa  22380
gagctggaaa agctgcttca gaaatctctt aaatctctgt ggaccgggtt cgatgagcgg  22440
accaccgctt cggacatggc cgatattatc ttccccgagc ggctcagaca cactctgcgc  22500
gacgggctgc ctgactttgc cagccagagc atgctacaaa actttaggtc attcatcttg  22560
gaacgctccg ggatcctgcc cgccacttgc tgcgcactgc cctccgattt tgtgcccatc  22620
acctaccggg agtgcccccc gccgctatgg agccactgct acctgttccg cctggccaac  22680
tacttggcct accactctga tgtgatagaa gatgttagtg gcgaagggct cctggagtgc  22740
cactgccgct gcaacctctg caccccccac cgctccctcg cctgcaatcc ccagctgctg  22800
agcgaaaccc agatcatcgg caccttcgag ttgcaaggtc ccagcggcga aggcgagggg  22860
tcctctccgg ggcaaagtct gaaactgact ccggggctat ggacctccgc ttaccttcgc  22920
aagttcgccc ccaaagacta ccacccctat gagatcaggt tttatgaaga ccaatcacag  22980
ccccccaagg ccgaactgac ggcctgcgtc atcacccagg gggcaatctt ggcccaattg  23040
caagccatcc aaaaatcccg ccaagaattt ttgctgaaaa agggacacgg gatctatcta  23100
gacccccaga ccggtgagga gctgaataca cgcttccctc aggatgcccc gaggaggcaa  23160
gagaatgaaa gttcagatgc cgcccgagga ggagctggaa gactgggaca gtcaggcaga  23220
ggaggaagac tgggacagcc aggcagaaga ggaggacagc ctggaggagg acagtctgga  23280
ggaaggcgag gagcccaagg aagaggcagc cgccgccaga ccatcgtcct cggcggtgga  23340
gacaagcaag gtcccagaca gcacggctac cacctccgct ccagctcaag ggccgctcg   23400
gcgacccaac agtagatggg acgagacggg tcgcttccag aaccccacca ccgtcaagac  23460
cggtaagcag gagcggcagg gatacaagtc ctggcggggg cataaaagtg ccatcatcgc  23520
ttgcttgcag gagtgtgggg gcaatatatc ctttgccaga cgctacctgc tattccatca  23580
cggggtgaat ttcccccgca acatcttgca ttactaccgt cacctccaca gcccctacta  23640
ccagcagcaa gagacagcag aggaaaccag cggcaactcc gagagttaga aaaccagcag  23700
ctaaaaaatc cacagcggcg gcagcaggtg caggcggact gaggatcacc gcgaacgagc  23760
cagctcagac cagggagttg aggaatcgga tctttcccac cctctatgcc atattccaac  23820
aaagtcgggg tcaggaacaa gaactgaaag taaaaaacag atctcttcgc tcgctcaccc  23880
```

gcagttgttt gtatcacaag agcgaagacc aacttcagcg cactctcgag gacgccgagg 23940
ctctcttcaa caagtactgc gcgctgactc ttaaagagta gactgcgcgc gcttggcgag 24000
aaaaggcggg aattacgtca cctcttggcc acacctgtgc ttcattatga gtaaagaaat 24060
tcccacgcct tacatgtgga gctatcagcc ccagatggga ttggccgctg gcgccgccca 24120
ggactactcc acccgcatga attggctcag cgccggtccc gcgatgatct cacgggttaa 24180
tggtgtgaga gagcaccgaa accagatact cctagaacag tccgccctca ccgccactcc 24240
ccgcaatcac ctcaaccccc gtaattggcc cgccgccctg gtgtaccagg aaactcctgc 24300
tcccactaca gtactacttc ctcgtgacgc ccaggccgaa gttcagatga ctaactcagg 24360
tgtacagctg gcgggtggtg ccaccctgtg tcgtcaccgg ccaagaccgg gtataaaggg 24420
cctggtgatc agaggccgag gtattcagct caacgacgag tcggtgaact cttcgcttgg 24480
tctgcgacca gacggcatct tccaaatagc tggttgtggg agatcttcct tcactcctcg 24540
tcaggctgtc ctgactttgg agagttcgtc ctcgcagccc cgctcgggcg gcatcgggac 24600
tctccagttc gtggaggagt ttactccctc ggtctacttc aaccccttct ccggttctcc 24660
tgggctttac ccggacgagt tcatcccgaa ctacgacgcc atcagtgaag cggtcgacgg 24720
ctacgattaa tgtctaatgg tggcgcggct gagctagctc gactgcgaca cctagaccac 24780
tgccggcgct ttcgctgctt tgctcgggat ctctgcgagt tcatctactt cgagtaccct 24840
gacgaacatc ctcagggacc tgcccacgga gttcggatta ccattgaagg ggctatcgat 24900
tctcacctgc ttcggatctt caccgctcgg ccagtgctag ttgagcgcaa ccagggcgac 24960
accaccatct ccctctgctg catttgtgac aaccccggat tgcatgaaag cttttgttgt 25020
cttctttgta ctgagtataa taaaagctga aattagagac tactccggac tctcttgtcg 25080
tctgaacaac accaaccaga cccttcactt cagcgggaac cagactactc ttcactgtaa 25140
ggcttataac tataagtatc ttacttggat atacaaagga acaccgtttg ctgtggtaaa 25200
caggtgctcc aacgacggtg ttctcctcac cttcctaggc aacttctcca actttacctt 25260
ttctgttcgc agaaacaagc ttaccctcct tcagccctac tttcctggga tctatacctg 25320
cctcagtgga ccttgcaacc acacttttca cctgattgaa aactctaccc ttaccttccc 25380
agcgccaatc cctactaaca gctcggagtc caactcttcc attaccgctg atactaacac 25440
tcctaaaacc ggaggtgagc tccgcagcct tcccccggct gcagataacc cttgggtggt 25500
agcgggattt gtagcgctag gaatagttgc gggtgggctc gcgttcgtcc tctgctacct 25560
ataccttacc tgctgctcat atttagtagt actgtgctgt tggtttagaa aatgggggcg 25620
ctactaatca cacttgcttt actttcgctt ttgggtctga gctcggctaa tagcgagaaa 25680
ccaagctgtc tagaaacaaa ctctccagac tgtgtggttc ctcatgggct ctcagaccca 25740
gctgatgatc catgcttaac ttttgaccca gaaaaaaact gctcggtgac tatgcagccc 25800
tatgcttaca tgtgcacatc tgttataaag tgcggatggg gctgtaaacc gattgaaatt 25860
acccacaaag gcaaaacctg gaataatagt ttgtttaaca catggcagcc tggagacgag 25920
cagtggtata cggccggcca ctggtggaga tgactgaccc catggaaaac tcctctgcca 25980
acgacctgga catggacggc cgttcatctg agcagcgact ggtccagatg cgcattcgcc 26040
agaagcagga acgcgccgcc agagagctca aggatgccat tgaaattcac ctgtgcaaga 26100
agggcatctt ttgcttggtt aagcaagcaa agatttctta tgaaatcact gacaacgacc 26160
accgcctgta ttatgagctc ggtccacagc ggcagaaatt cacctgcatg gttggagtca 26220

-continued

```
accccatagt catcactcag caggctgcag aaattaaagg gtgcatccac tgttcctgtg  26280
attcccaaga atgcgtccac accatagtca agaccctctg cggccttcga gatcttcttc  26340
caatgaacta accccttccc ccaacccaat aaaacattgg ttttaatcat aataaaaaat  26400
cacttacttt aaatctgaaa cagtgtctcc gtccaagttt tcttgtagca ccacttcact  26460
cccctcttcc cagctctggt actgcaagcc ccggtgggct gcaaactttc tccacacctt  26520
aaaagggatg tcaaattcct cttgtccaac aatcttcatt gtctcttcct agatgtccac  26580
aaagcgcgcg cgggtggaag atgactttga ccctgtctac ccatacgatg ctgagctggc  26640
accgtctgta cccttcatcg cccctccctt cgtttcgtca gacggatttc aagaaaaacc  26700
cctgggagtt ctgtccctaa gactagccaa cccagtcact actaaaaatg gggaactcac  26760
acttaaactg ggagatgggg tgggcataga ctcagatgga aacctcacag cacagacagt  26820
tactaaagca acatcccccc ttactgtttc caataacgca attgcactta acatggacaa  26880
acctttttac agtagcaatg gaaaactatc cttacaagtt acatcaccat taaagatagt  26940
cgactcttta aatacattgg ctattggcta tgggcaaggc ttaggactaa acaatagtgc  27000
tcttgctgtg caattagcat ctccccttac atttgacagc aacagcaaaa ttaaaataaa  27060
tttgggaagc gggccattaa aattaatgc gaataaactg tcaattaact gcctaagggg  27120
tgtatatgta acaactgacg gaacttccat tgaaacaaat ataagctggg caaaaggaat  27180
gaggtttgaa ggtaatgcca tggctgtaaa cgttgacagc accaaaggtc tacaatttgg  27240
cactaccagc acagaatcag gagtcactaa cgctttccct atccagttaa agattggatc  27300
tggtcttagt tttgacagca caggagcact tgtagcttgg gataaggata atgacaagct  27360
tacactgtgg acaaccgctg acccatcacc taattgtacc atatatacag acaaggatgc  27420
taaacttaca ctttgtctta caaaatgtgg cagtcaaata ctaggcagtg tttcagtact  27480
ggctgttaaa gctggaaccc tacagccaat cagtgaaaaa ataggtactg ctttggtttc  27540
actaaaattt aataacaacg gtgtattgtt aagcaactcc acattaagta atgaatactg  27600
gaactacagg aagggagatg tcacaccagc cgaagcctat actaatgctg tgggttttat  27660
gccaaacatc aaggcatatc ctaaaaacac aaactctgcc tcaaaaagcc acattgtagg  27720
acaagtgtac cttaatggag atgaaactaa accaatgcat ttaatcatta catttaatga  27780
aaccagtgat gaaacatgca catattccat aacgttccaa tggaaatgga acattggaac  27840
atacaccagc gacacccttg caacaagctc ctttaccttt tcttacattg cccaagaata  27900
aaaactgcag acaacaataa agtttaaatg ttttatttaa acagtttcac agaaccctag  27960
tattcaacct gccacctccc tcccaacaca cagagtacac agtcctttct ccccggctgg  28020
ccttaaaaag catcatatca tgggtaacag acatattctt aggtgttata ttccacacgg  28080
tttcctgtcg agccaaacgc tcatcagtga tattaataaa ctccccgggc agctcactta  28140
agttcatgtc gctgtccagc tgctgagcca caggctgctg tccaacttgc ggttgcttaa  28200
cgggcggcga aggagaagtc cacgcctaca tgggggtaga gtcataatcg tgcatcagga  28260
tagggcggtg gtgctgcagc agcgcgcgaa taaactgctg ccgccgccgc tccgtcctgc  28320
aggaatacaa catggcagtg gtctcctcag cgatgattcg caccgcccgc agcataaggc  28380
gccttgtcct ccgggcacag cagcgcaccc tgatctcact taaatcagca cagtaactgc  28440
agcacagcac cacaatattg ttcaaaatcc cacagtgcaa ggcgctgtat ccaaagctca  28500
tggcggggac cacagaaccc acgtggccat cataccacaa gcgcaggtag attaagtggc  28560
gacccctcat aaacacgctg gacataaaca ttacctcttt tggcatgttg taattcacca  28620
```

-continued cctcccggta ccatataaac ctctgattaa acatggcgcc atccaccacc atcctaaacc 28680
agctggccaa aacctgcccg ccggctatac actgcaggga accgggactg gaacaatgac 28740
agtggagagc ccaggactcg taaccatgga tcatcatgct cgtcatgata tcaatgttgg 28800
cacaacacag gcacacgtgc atacacttcc tcaggattac aagctcctcc cgcgttagaa 28860
ccatatccca gggaacaacc cattcctgaa tcagcgtaaa tcccacactg cagggaagac 28920
ctcgcacgta actcacgttg tgcattgtca aagtgttaca ttcgggcagc agcggatgat 28980
cctccagtat ggtagcgcgg gtttctgtct caaaaggagg tagacgatcc ctactgtacg 29040
gagtgcgccg agacaaccga gatcgtgttg gtcgtagtgt catgccaaat ggaacgccgg 29100
acgtagtcat tctcgtactt tgagtggcaa aaccttgctc tcgaacagca cacgtctcgt 29160
cgcctcctgt cccttctctt cgccttttca gtgtgatagt tgtaatacag ccattcacga 29220
agctcagtca gaagatcttc agcgtctgtt gtcaaaaaca atccatccaa tctgattgct 29280
ttcaaaacat cacaaacagt cgaataagcc aaacccatcc aggcaatgca attattttgg 29340
ttatccacaa tgggaggggg cggaagacat ggaagaggca taattaattt tttaatccaa 29400
tcgatcacgc agcacttcaa aatgaagatc gcgaaggtga cacctttcac ccccactgtg 29460
ttgatgaaaa ataacagcca agtcaaaatt gatgcggttt tcaaggtgct cgactgtagc 29520
atcaagcaga gcttccacac gcacgtccac aaataacaga atagcaaaag cgggaggagg 29580
aagtaaatcc tcaatcatca tagtacagtc catcaccatc cctaaataat tttcatcctt 29640
ccagccttgg actatatttt taaactgctc ttgtaaatcc aaaccacaca tgtggaaaag 29700
ttcccaaaga gctccctcaa ctaccattct taagcacacc ttcatagtga caaaatatct 29760
tgttcctctg tcacctgcag caaattacaa agtccaatat taggatctat gcccagagat 29820
ctaagctcat ccctcaattc caactgtaaa aaggcttcca gatctgccct aacttgttca 29880
gccagtgggc tccctggaat aagcgtggga gaagccaaac tgcaaaacag acgcatgccg 29940
ccataattac caccagaaaa cactacgtta cagtatgcat gctgattcat tccagtaatt 30000
tcatccagtg tattggatac aaaaaaaggc aagcactctc tcactaattg tattatggag 30060
acattatcac acaggtaaca atttaaaggt tgtggaacaa taatgcagta agtaaccacg 30120
gtgcgctcca acatggttag taatttttag ttctgaaaaa caaaacatac aaaaaattat 30180
atcatactca tttggcgaac tggtggaaaa atgaccctat ctagcacaag gcaagccact 30240
ggatcaccaa tgcgcccctc ataaaacctg tcatcatgat taaaaagcaa caccgaaagc 30300
tcttccctat gtcctgcatg aatgattcta gctgaggaat ataagccagc gcaattagta 30360
tctgttaaag aaaaaaaacg gccaacatag cctctaggaa ttagcacact taatcttaaa 30420
gacattactg ccatccccct tggatttaag gtaaaattta caggagcata gaaaatatac 30480
tgatttccct cctgcacagg cagcatagca ccaggtccct ctaaaaacac acacaaagct 30540
tctgcagcca tagcttaccg cgcaaaccag gcacagcagt gagctaaaag gacaaagctc 30600
taactcacta gccaacctgg cgcacaatat atagttagtc cttacactga cgtaaccgac 30660
caaagtctaa aaaccccgcc aaaaatacac acacgcccaa aaaacgcccc gtgagtcaaa 30720
aaacagtttc acttcctcgt tacacccaaa acgtcgtcac ttccggattc ccacggttcg 30780
tcacttccgg agctccttgc ttaattaacc ccgcccaaaa cgtcatcgtc cgcgtcacgc 30840
cgccccgccc cgcgaccgtt gaccccgggc caatcaccgc acatcccgca aaattcaaac 30900
tcgtctaatt tgcatattgg cacactgccc atataaggta tattattgat gatgatttaa 30960

-continued

```
atcatatgcg gtgtgaaata ccgcacagat gcgtaaggag aaaataccgc atcaggcgct  31020
cttccgcttc ctcgctcact gactcgctgc gctcggtcgt tcggctgcgg cgagcggtat  31080
cagctcactc aaaggcggta atacggttat ccacagaatc aggggataac gcaggaaaga  31140
acatgtgagc aaaaggccag caaaaggcca ggaaccgtaa aaaggccgcg ttgctggcgt  31200
ttttccatag gctccgcccc cctgacgagc atcacaaaaa tcgacgctca agtcagaggt  31260
ggcgaaaccc gacaggacta taaagatacc aggcgtttcc ccctggaagc tccctcgtgc  31320
gctctcctgt tccgaccctg ccgcttaccg gatacctgtc cgcctttctc ccttcgggaa  31380
gcgtggcgct ttctcatagc tcacgctgta ggtatctcag ttcggtgtag gtcgttcgct  31440
ccaagctggg ctgtgtgcac gaaccccccg ttcagcccga ccgctgcgcc ttatccggta  31500
actatcgtct tgagtccaac ccggtaagac acgacttatc gccactggca gcagccactg  31560
gtaacaggat tagcagagcg aggtatgtag gcggtgctac agagttcttg aagtggtggc  31620
ctaactacgg ctacactaga aggacagtat ttggtatctg cgctctgctg aagccagtta  31680
ccttcggaaa aagagttggt agctcttgat ccggcaaaca aaccaccgct ggtagcggtg  31740
gtttttttgt ttgcaagcag cagattacgc gcagaaaaaa aggatctcaa gaagatcctt  31800
tgatcttttc tacggggtct gacgctcagt ggaacgaaaa ctcacgttaa gggattttgg  31860
tcatgagatt atcaaaaagg atcttcacct agatcctttt aaattaaaaa tgaagtttta  31920
aatcaatcta aagtatatat gagtaaactt ggtctgacag ttaccaatgc ttaatcagtg  31980
aggcacctat ctcagcgatc tgtctatttc gttcatccat agttgcctga ctccccgtcg  32040
tgtagataac tacgatacgg gagggcttac catctggccc cagtgctgca atgataccgc  32100
gagacccacg ctcaccggct ccagatttat cagcaataaa ccagccagcc ggaagggccg  32160
agcgcagaag tggtcctgca actttatccg cctccatcca gtctattaat tgttgccggg  32220
aagctagagt aagtagttcg ccagttaata gtttgcgcaa cgttgttgcc attgctgcag  32280
gcatcgtggt gtcacgctcg tcgtttggta tggcttcatt cagctccggt tcccaacgat  32340
caaggcgagt tacatgatcc cccatgttgt gcaaaaaagc ggttagctcc ttcggtcctc  32400
cgatcgttgt cagaagtaag ttggccgcag tgttatcact catggttatg gcagcactgc  32460
ataattctct tactgtcatg ccatccgtaa gatgcttttc tgtgactggt gagtactcaa  32520
ccaagtcatt ctgagaatag tgtatgcggc gaccgagttg ctcttgcccg gcgtcaacac  32580
gggataatac cgcgccacat agcagaactt taaaagtgct catcattgga aaacgttctt  32640
cggggcgaaa actctcaagg atcttaccgc tgttgagatc cagttcgatg taacccactc  32700
gtgcacccaa ctgatcttca gcatctttta ctttcaccag cgtttctggg tgagcaaaaa  32760
caggaaggca aaatgccgca aaaaagggaa taagggcgac acggaaatgt tgaatactca  32820
tactcttcct ttttcaatat tattgaagca tttatcaggg ttattgtctc atgagcggat  32880
acatatttga atgtatttag aaaaataaac aaataggggt tccgcgcaca tttccccgaa  32940
aagtgccacc tgacgtctaa gaaaccatta ttatcatgac attaacctat aaaaataggc  33000
gtatcacgag gccctttcgt cttcaagaat tgatttaaat                        33040
```

<210> SEQ ID NO 9
<211> LENGTH: 32701
<212> TYPE: DNA
<213> ORGANISM: Artificial Sequence
<220> FEATURE:
<223> OTHER INFORMATION: pBLY6.dE1.dE3.5IXP

<400> SEQUENCE: 9

-continued

```
catcatcaat aatatacctt atatgggcag tgtgccaata tgcaaattag acgagtttga     60
attttgcggg atgtgcggtg attggcccgg ggtcaacggt cgcggggcgg ggcggcgtga    120
cgcggacgat gacgttttgg ggaggaggag ctatgttgca agtaatcgtg ggaaatgcga    180
cgtaaaacga ggtggagttt aaacacggaa gtagacaatt ttcccgcgct gtttgacagg    240
aaatgatgtg tttttgggcg gatgcaagtg aaaattctcc attttcgcgc gaaaactaaa    300
tgaggaagtg aaattctgag taattctgag gttatcacag ggcggagtat ttaccgaggg    360
ccgagtagac tttgacccat tacgtggagg tttcgattac tctatttttc acctaaattt    420
ccgcgtactg tgtcaaagtc cgtgttttta cgcgatcgcg gtactgaaat gtgtgggcgt    480
ggcttaaggg tgggaaagaa tatataaggt gggggtctta tgtagttttg tatctgtttt    540
gcagcagccg ccgccgccat gagtgggagc gcttcctttg aagggggcgt ctttagccct    600
tatctgacgg ggcgtctgcc tcattgggct ggagtgcgtc agaatgtgat ggggtctaca    660
gtggatggaa gacctgttca gcctgctaat tcttctactc tgacttatgc tactatgact    720
tcctcgcctt tggatgcagc tgcagctgct gccgcttctg ctgccgccaa cactgttcgg    780
gggatggcct tggagatggg gtattatgga actgtagtgg ccaacaccac taccccaaat    840
aaccccacag ccttgaatga ggacaagctg ctagttctca tgtcccagct ggagtctttg    900
acccaacgcc tgggcgatct agctcagcag gtgtcccagc tgaaggagca gactcaagct    960
gcaattacca ctgcgagggg aaattaaaaa aattcaaaga atcaataaat aaaccgagac   1020
tttgttgatt ttaaagtgtg tcattcttta tttaattttt cgcgcgcgat atgccctgga   1080
ccaccggtct ctatcattga ggacacggtg gatctttttct agaacccgat agaggtggga   1140
ttggatgttg aggtacatgg gcataagacc atctttgggg tgtagatagc tccactgcag   1200
agcctcatgc tccggggtgg tgttgtatat aacccagtca tagcatgggc gttgggcatg   1260
atgttgcaca atatctttaa ggaggagact aatggccact gggagaccct tggtgtaagt   1320
gtttacaaat ctattaagct gggacgggtg catccgaggt gagataatgt gcattttgga   1380
ttggattttt agattggcaa tgtttccccc tagatctctc ctgggattca tgttatgcaa   1440
gaccactaga acagtgtatc cggtgcactt agggaatttg tcatgaagtt tggaggggaa   1500
agcatgaaaa aatttagaca caccccttgtg tcctcccaag ttctccatgc actcatccat   1560
aataatggca atgggcccat gggcggcggc acgggcgaac acgttcctgg gatctgacac   1620
atcatagttg tggtcttggg tcaggtcatc ataagccatt ttaataaact tggggcggag   1680
ggtgccagat tgggggatga atgttccctc gggccccgga acatagtttc cttcacatat   1740
ttgcatttcc caggctttta gttcagaggg ggggatcatg tccacctgtg gagcgatgaa   1800
gaagacggtc tcgggggcgg gggtgattaa gtgggaggac agcaagttcc taagcagctg   1860
tgacttgcca cacccagtgg gaccgtagat gacccctata acaggttgca gatggtagtt   1920
tagggaaaga cagctgccgt cctctcgcag gaggggggcg acctcgttca tcatttccct   1980
cacatgcatg ttttcccgca caagttccga taggaggcgc tctccaccca gggaaaggag   2040
ttcttgaaga gatgagaaat tttcaaggg ttttaagcca tcagccatgg gcattttgga    2100
gagggtttgt tgcaagagtt caaggcggtc ccagagttcg gtgatgtgtt ctatggcatc   2160
tcgatccagc atacttcctc gtttctgggg ttgggacggc tgcgggagta tggaaccagg   2220
cgatgggcgt ccagcgctgc cagtgtccgg tccttccacg gtcgcagcgt ccgagtcagg   2280
gtcgtttccg tcacggtgaa ggggtgcgcg cctggctggg cgcttgcgag ggtgcgcttc   2340
```

-continued

```
aggctcatcc tgctcgtgga gaaccgctgc cgttctgcgc cctgtgcatc ggccaggtag   2400
caattaacca tgagttcgta gttgagcgcc tctgccgcgt ggcctttggc gcgcagctta   2460
cctttggaag tcttctgaca ggtgggacag tagagacact tgagagcata gagttttggg   2520
gctagaaaga ccgattctgg ggagtatgca tcggccccac aggaggcgca gacggtttcg   2580
cattccacca gccatgtaag atcgggctcg ttggggtcaa aaacaagttt tccgccatgt   2640
tttttgatgc gtttcttacc tttgctttcc atgagttcgt gcccccgttg ggtgacaaag   2700
aggctgtccg tgtccccgta gactgacttt atgggcctgt cctcgagcgg cgtgccgcgg   2760
tcctcttcgt agaggaactc ggaccactct gagacgaaag cacgtgtcca ggccagcaca   2820
aaggaggcta tatgggaggg gtagcgatcg ttgtcaacca aggggtctac tttttccaag   2880
gtgtgtaaac acatgtcccc ttcttccaca tccaggaagg tgattggctt gtaagtgtat   2940
gccacgtgac ctggggtccc agacgggggg gtataaaagg gggcgggtct ctgctcgtcc   3000
tcactgtctt ccggatcgct gtccaggagc gccagctgtt gaggtaggta ttccctctcg   3060
aaggcgggca taacctccgc actcaggttg tcagtttcta ggaacgagga ggatttgata   3120
ttgacagtgc ctgccgagat gcctttcatg agactgtcgt ccatttggtc agaaaagaca   3180
atctttttgt tatcaagttt ggtggcgaag gatccataca gggcattgga aagcagtttg   3240
gcaatggagc gcatggtttg gtttttttct ttgtctgcgc gctctttggc ggctatgttg   3300
agttggacat attcgcgggc cagacatttc cattgtggaa atatggtagt taattcatct   3360
gggacgattc tgactttcca gcctctgtta tgcagggtaa tcagatccac actggttgcc   3420
acttctcctc taagtggttc attagtccag catagtcgcc cccttttcg agaacagaaa   3480
gggggtaggg gatctagcat gagttcgtct gggggtctg catctatggt gaaaatccca   3540
ggaaggagat cttcgtcaaa atagctgatg gtggcggggt catccagaga catttgccat   3600
tctcgagcag ccagagcgcg ctcgtagggg ttaaggggag tcccccatgg catgggatgg   3660
gtgagtgcag aagcatacat gccacagatg tcatagacat agagcggctc ttccagaatc   3720
cctatgtaag tgggataaca tcgccccct ctgatgctgg ctcgcacata atcatagagt   3780
tcatgtgagg gcgctagaag acccgagccc aggttggtgc ggttgggttt ttctgctctg   3840
tagaggatct ggcgaaagat ggcatgggag tttgatgaga tggtgggtct ttggaagatg   3900
ttgaaatggg catgaggcag tcccacagag tcccttatga agtgagcata ggagtcttgc   3960
agtttggcca ccagctcggc ggtgaccagc acatccaaag cacagtagtc gagggtctct   4020
ttgatgatgt catagttagg ttccccttc ttttcccaca gctcgcggtt gagaaggtat   4080
tcttcgcgat ccttccagta ctcttcgagg gggaacccgt ccttgtctga acggtaagaa   4140
cccagcatgt aaaattgatt gacagctttg taggcacaac accccttctc cacggggagt   4200
gagtatgctt gcgcggcttt gcgcagagag gtgtgagtaa gggcgaaagt gtccctgacc   4260
atgactttga ggaactgatg cttaaagtct atgtcatcgc aggccccctg ctcccacagt   4320
tggaagtcca ctcgcttttt gtaggcggga ttgggcaaag cgaaagtaac atcgttgaat   4380
aggatctttc cagccctggg catgaagttg cgagtaatgc gaaaaggctg aggcacttct   4440
gccctgttgt tgataacttg ggcagccaag acgatctcgt caaagccgtt gatgttgtga   4500
cccacaatgt aaagttctac gaagcgtggg cgtcccttga tgtggggcag ttttttaagc   4560
tcttcgtagg tcaagtcgtc agggtcagcg attccatatt gctccaaagc ccagtcaggc   4620
aggtgaggat tagcatgaag gaaagaggtc caaagatcca cggccagagc tgtttgtaag   4680
cggtctctgt actgacggaa atgtcggcct accgccattt tttcaggagt aacacagtaa   4740
```

-continued

```
aaggtgcgcg ggtccttttc ccagcgatcc cattgaagtt gcaaggctag gtcgtgggcg   4800
aggttgacga gctgttcgtc ccccgaaagt ttcatgacca gcatgaaagg gacaagctgc   4860
ttgccaaagg accccatcca ggtgtaggtt tccacatcgt aggtgaggaa gagcctttct   4920
gtgcgaggat gagaaccgat cgggaagaac tggatttcct gccaccagtt ggaggaatgg   4980
ctgttgatat gatggaagta gaactcccta cggcgcgccg agcattcgtg cttgtgcttg   5040
tacagacggc cacagtactc gcagcgctgc acgggatgca cctgatgaat gagctgtacc   5100
tggcttcctt tgacaagaaa tttcagtggg aagttgaggc gtggcgtctg catctcgtgt   5160
tgtattacgt cctggctatt ggtctggcca tcttctgtct cgatggtggt catgctgacg   5220
agcccgcgcg ggaggcaggt ccagacctcc gcgcggacgg gtctgagagc gaggacgaga   5280
gcgcgcaggc cggaactgtc cagggtcctg agacgctgcg gagtcaggtc agtagggaga   5340
gtacataggt ttacttgcat aagtttttcc agggcatgtg ggaggtcaag atgatatttg   5400
atttctactg gcgagttggt ggagacatcg atggcttgca gggtcccgtg cccctggggt   5460
gctaccaccg tccctttttt tttcttgatc gggggcggtg ttgcttcttg catggtaagg   5520
tcgtcttcta gaagcggcgg cgaggtcgcg cgccgggtgg cagtggcggt tctggacctg   5580
gaggtagagg cggtagaggt acgtcggcgc cgcgcgcggg taggttctgg tactgcgccc   5640
tgagaagact tgcgtgagcg acgacgcggc ggttgacgtc ctggatctga cgcctctggg   5700
tgaatgctac cggacccgtg agcttgaacc tgaaagagag ttcaacagaa tcaatttcgg   5760
tatcgttgac ggctgcctgc cgcaggattt cttgtacgtc gcccgagttg tcttggtagg   5820
cgatctcggc catgaactgc tcgatctctt cttcttggag atctccgcgg cccgctcgtt   5880
ctacggtggc agcaaggtcg ttggagatgc gccccatgag ctgtgagaat gcattcatgc   5940
ccgcctcgtt ccagacgcga ctgtagacca cggctccctc gggatctctg gcgcgcatga   6000
ccacttgggc gaggtttagt tccacgtgtc tggtgaagac cgcatagttg cagagacgct   6060
ggaagaggta gttgagcgtg gtggcgatgt gctcggtgac aaagaaatac atgatccagc   6120
gacgaagcgg catctcgctg atatcgccca gggcttccaa ccgttccatg gcttcgtaaa   6180
agtccacggc gaagttgaaa aactgggagt tgcgagcgga cacggtcaac tcctcctcca   6240
gaagacggat gagctcggcg atggtggcgc gcacttcgcg ctcaaaggct cccgggatct   6300
cttcctcctc ttcttcttcc aactcttcct ccactaacat ctcttctact tcctcctcag   6360
gcggcggggg tggaggaggg ggcgcgcggc gacgccggcg acgcacgggc agacgatcga   6420
tgaagcgttc gatcacttct ccgcggcggc gacgcatggt ctcggtgacg gcgcgcccgt   6480
cctccctggg tcgcagagtg aagacgccgc cgcgcagctc cctgaaatgg tgactgggag   6540
ggtccccgtt tggtagggac agggcactga tgatgcatct tattaattgc cctgtaggga   6600
ctccgcgcaa ggacctgagc gtctcgagat ccacgggatc tgaaaatctc tgaacgaagg   6660
cttcgagcca gtcgcagtcg caaggtaggc tgagcactgt ttcttcgggg cgggctgctg   6720
agctagaggg ttgtacgatg ctgctggtga tgaagttaaa ataggcagtt ctgagacggc   6780
ggatggtggc gaggagcacc aggtctttgg gtccggcttg ctggatgcgc aggcggtcgg   6840
ccattcccca tgcattatct tggcacctgg ccagatcttt atagtagtct tgcatgagtc   6900
gctccacggg cacttcttct tcgcccgctc tgccgtgcat gcgtgtgagt ccgtaccctc   6960
tctgtggttg gacgagcgcc aggtcggcaa cgaccctttc ggctagaatg gcttgctgca   7020
cctgggtgag ggtgttctgg aaatcatcaa agtccacaaa gcggtggtag gcccccgtgt   7080
```

-continued

```
tgatggtgta ggagcagttg gacatgaccg accagttgac tgtctggtgt cctggtcgta   7140
cgagttccgt gtacctgagc cgcgagtatg cgcgggagtc gaagatgtaa tcgttgcagg   7200
ttcgcaccag gtactggtag ccgatgagga agtgaggcgg cggctggcgg tagagaggcc   7260
atcgttcggt ggcgggcgcg ccgggcgcta ggtcttctag catgagacgg tggtatccgt   7320
agacgtacct ggacatccag gtaataccgg cggcggtggt ggaggcgcgc ggaaactctc   7380
gcacgcggtt ccagatgttg cgcagcggca tgaagtagtt catggtgggc acggtctggc   7440
ccgtgaggcg cgcgcagtca ttgatgctct agatacgggc aaaaacgaaa gcgttgagcg   7500
gttcccttcc gtggcctgga ggaacgcgaa cgggttaggt cgcagcgtac cctggttcga   7560
gactaaagaa agcgagcaac tcgaaccggc agagtcgcgg ctaacgggta ttggcaatcc   7620
cgtctcgacc caagccagca aatccaggat acggatgggg gccccttttg tttttcaggg   7680
catgagtcac cggttaaggt ttacaacggc tgtttcatgc ctttagaagt ggctcgcgcc   7740
cgtagtctgg agaatcaatc gccagggttg cgttgcggcg tgccccggtt cgagcctgca   7800
gcttgagtcg gccggtgacc gcggcaaacg agggcgtggc ggccccgtcg tttctaagac   7860
cttgctagcc gacctctcca gtttacggga acgagccccc ttttattttt tttgtttttg   7920
ccagatgcat cccgtactgc ggcagatgcg cccacagccc ccacagcagc agcagcaggc   7980
tggcctacct tctctacctc agccgctacc tgcaactacc gcggtggccg ctgtaagcgg   8040
ggccggacag caggcggctc ctcaatatga attggacttg gaagagggcg agggattggc   8100
aagattgggg gcgccctcgc ccgagcgcca cccgcgggtg cagatgaaaa aggacgttcg   8160
cgaatcttac gtgcccaagc agaatctgtt cagagacaga agcggcgagg agcccgagga   8220
gatgcgcgcg tcccgtttta acgcgggtcg cgagctgcga caaggactgg atcgaaaacg   8280
ggtgttgagg gatgatgatt ttgaggtgga tgaaatgaca gggatcagcc ccgctcgcgc   8340
tcacgtggct gcagctaatc tggtgacagc ttatgagcag accgtgaagg aggaaagcaa   8400
cttccagaaa tcattcaata accacgtgcg caccctgatc gcacgcgagg aggtgaccct   8460
gggcctgatg cacctgtggg atctgctgga agccatagtg cagaacccca ctagcaaacc   8520
cctgactgct caactgtttc tggtggtgca gcacagcagg gataatgagg cattcagaga   8580
ggcgctgctg aatatcactg aacctgaggg gagatggctg ctggatctgg tgaatatcct   8640
gcagagcatt gtagtgcagg aacgcagctt gcctttgtcc gagaaggtgg cggcgatcaa   8700
ttactctgtg ctgagtctgg gcaaatacta tgccaggaag atctacaaaa ccccttacgt   8760
gcccatagac aaggaagtga aaatagatgg gttttacatg cgcatgaccc tgaaagtgct   8820
aaccctgagc gatgacttgg gagtgtaccg caacgacagg atgcaccgcg cggtgagcgc   8880
cagcaggagg cgcgagctga gcgacaaaga attaatgcac agcttgcaac gagccctgac   8940
gggagccggg acggaggggg agaactactt tgacatgggt gcagacttgc attggctgcc   9000
tagtcgcagg gcattggaag cggcaggcga tgggccctat gtagaggaag tagtagacga   9060
ggacgatgag gagggcgagt acctggaaga ctgatggcgc gacccgtatt tttgctagat   9120
ggaacaggcg ccggaccctg cgatgcgggc ggcgctgcag agccagccgt ccggcattaa   9180
ttcctcggac gattggaccc aggccatgca acgcatcatg gcgctgacga cccgcaaccc   9240
cgaagccttt agacagcagc ctcaggccaa ccgcctttcg gccatcctgg aggccgtggt   9300
gccctctcgc tccaacccca cccacgagaa ggttctggcc atcgtgaatg ccctggtgga   9360
gaacaaggcc atccgctccg atgaagccgg gctggtatac aacgccttgc tcgagcgcgt   9420
ggctcgctac aacagcagca atgtccagac taacctggac aggatggtga ccgacgtgcg   9480
```

-continued

```
cgaggccgtg tcccagcgcg aacggttcca tcgcgagtct aacctgggtt ccatggtagc   9540
gctgaacgct ttcctcagtt cccagcctgc caatgtgccc cggggacagg aagactatac   9600
caactttatt agcgccctga gactcatggt agccgaggtt cctcagagcg aggtgtacca   9660
gtccggtcca gactactttt tccagacaag caggaacggt atgcagacag tgaacttaag   9720
ccaggctttc aagaacctgc aagggctgtg ggagtccaa gctccagtgg gcgacagggc   9780
gaccgtgtcg agcctgttga ctccaaattc ccgtttgctg ctgctgctgg tgtccccctt   9840
cactgacagc ggcagcataa acagaaactc ctacttgggc tacctgataa acttgtatcg   9900
cgaagctata ggtcaggccc acgtggacga acagacctat caggagatca ctaatgtgag   9960
tcgcgctctg ggccaggacg accctggaaa cctggaagct actctaaact ttctgctgac  10020
caaccgctcg caaaaaatcc ctcctcagta tacattaact gcggaggagg aacggatctt  10080
gagatacgtg cagcagagcg tgggtctgtt cctgatgcaa gagggtgcga cccctagcgc  10140
cgcgcttgat atgacagcgc gcaacatgga gcccagcatg tatgccagca acagaccatt  10200
cattaataaa ttgatggatt acttccatcg cgcggccgct atgaactctg attacttcac  10260
caatgctatt ctgaaccccc attggctgcc tccgcctggt ttttatactg gcgagtatga  10320
catgcctgac cccaacgatg ggttcttgtg ggacgatgtg gacagcgtgg cgttctcgcc  10380
taccgctcct cgtacttttt ggaagaagga aggtagtgac agaagaccct cctccgtgct  10440
gtcaggacgt gagggtgctg ccgcggcggt ccccgatgct gcaagcccct ttcccagtct  10500
gccattttca ctaaacagcg tgcgcagtag cgagctgggg agaataaccc gccctcgctt  10560
gctgggcgag gacgagtatt tgaatgactc cctactgaga cccgagcggg aaaagaactt  10620
ccctaataat gggattgaaa gcctggtgga taagatgagc agatggaaga cctatgccca  10680
ggagcacaga gatgagccta gaatcttggg tcctacagta ggcacccgca gacgccagcg  10740
ccatgataga cagcggggtc tggtgtggga cgatgaggat tctgcagatg acagcagcgt  10800
gttggacttg ggcgggaggg gaggtgtggg caacccgttc gcacacttgc gtccccgtat  10860
tggacgcatg atgtaaaagt gaaaataaaa aaggaactca ccaaggccat ggcgaccagc  10920
gtgcgttcgt tctttctgtt gttgtatcta gtatgatgag gcgcaccgtg ctaggcggat  10980
cggtggcgta tccggagggt cctcctcctt cgtacgaaag cgtgatgcag caggtggcgg  11040
cggcggcgat gcaacccccc ttggaggctc cttacgtgcc cccgcggtac ctggcaccta  11100
ccgaggggag aaacagcatt cgttattcgg aactcacacc cttgtatgac accacccggt  11160
tgtacctggt ggacaacaaa tcggcggaca ttgcctcgtt gaactatcag aacgaccaca  11220
gcaacttctt gacaacggtg gtgcagaaca atgactttac ccccacggag gccagcaccc  11280
agaccatcaa ctttgacgag cgctcccggt ggggcggtca gctgaagacc atcatgcaca  11340
ccaacatgcc caacgtgaac gagttcatgt ttagcaacaa gttcagggct agggtgatgg  11400
tgtccagaac cacacctaaa gaggtgacag tcacaacaga ctatgatggt agtcaggaca  11460
tcttggaata cgagtgggtt gactttgagt taccagaagg caacttctct gccaccatga  11520
ccatagacct gatgaataat gcaattgttg ataattacct aaaagtgggt agacagaatg  11580
gggtactgga gagtgacata ggtgttaagt ttgacactag gaactttagg cttggttggg  11640
acccagtgac agagttggtc atgcctgggg tctacaccaa tgaagctttc catcctgaca  11700
tagtcctact acctggctgc ggagtggact tcactgagag ccgcctcagt aatctgctag  11760
gcattagaaa gaaacagcca ttccaggaag ggttccagat catgtatgag gatctggagg  11820
```

-continued gtggtaacat ccccgccctg cttgatgtaa atgcatatga gaagagcaag gaagataata 11880
caaccaccac aaatgaagct gtggccgcgg cttcatctac tgaagccaaa gctgtggtag 11940
atgcttccac ttcaacagaa aacaccactg atgaaaaagt caccagggga gatacatttg 12000
ccacccctga acaagagaag gcagctgagg cagagtctga tattatgctt ctgtccaccg 12060
atgaaaacga aactaaaaaa caactggtta ttcgagcggt gaccaaggat agtaaggaca 12120
ggagttataa tgtattgtca gatggaaaga acacagctta ccgtagttgg tacctggcat 12180
acaattatgg cgaccgtgag aaaggggtgc gttcttggac actgcttacc acctcggatg 12240
tcacctgcgg cgtggagcaa gtctattggt cgctaccaga tatgatgcaa gatccagtca 12300
cctttcgctc cacacgccaa gttagcaact acccagtggt gggcgcagag ctgctcccag 12360
tgcattccag aagcttctac aacgagcaag ccgtctactc gcaacagctc cgccagtaca 12420
cctcgctcac gcacgtcttc aaccgcttcc ccgagaatca gatcctcgtc cgcccgcccg 12480
cgccaaccat taccaccgtc agtgaaaacg ttcctgctct cacagatcac gggaccctgc 12540
cgctgcgcag cagtatccgg ggagtccagc gcgtgaccgt tactgacgcc agacgccgca 12600
cctgtccata cgtatacaag gccctgggca tagtcgcgcc gcgcgtcctt tcaagccgca 12660
ctttctaaaa aaatgtccat tctcatctcg cccagtaata acaccggttg gggcctgcgc 12720
acacctagca agatgtatgg aggcgctcgc agacgctcca ctcagcaccc tgtgcgcgtg 12780
cgcgggcatt tccgcgctcc ctggggcgcc ctcaagggac gctctcgtac taggaccacc 12840
gttgacgatg tgatcgacca ggtggtcgcc gatgcacgta actatacccc cgcagccgca 12900
cctgcatcca ccgtggatgc ggtcattgac agcgtggtag ccgatgcgcg cgcctatgct 12960
cgcgccaaga gcaggaggcg gcgtattgcc aggcgtcacc gagctactcc agccatgcga 13020
gctgcaagag ctttattgcg gagagccaga cgtgtggggc gaagagccat gcgtagagcg 13080
gccagacgcg cggcttcagg tgccagcgca ggcagggtcc gcaggcgcgc ggctacggcg 13140
gcagcggcgg ccatcgctag catgaccaaa ccacgaagag gcaatgtgta ttgggtgcgc 13200
gacgccgcca ccggccagcg cgtgcccgtg cgcacacgcc cccctcgcac ttagaagata 13260
ctgagcagtc tccgatgttg tgtcccagcg gcgagatgtc caagcgcaaa ttcaaggaag 13320
agatgctcca ggtcatcgcg cctgagatct acggtcctgc ggtgaaggat gaaaaaaagc 13380
cccgcaagat caagcgggtc aaaaaggaca aaaaggaaga agatggtgat gatgggctgg 13440
tggagtttgt gcgcgagttt gccccaagga ggcgcgtgca gtggcgcggg cgcaaagtgt 13500
ggccggtgtt gagaccgggg accacagtgg tctttacgcc aggcgagcgc tccagcaccg 13560
tttccaaacg ctcttatgat gaggtgtacg gggacgatga tattctcgag caggcggctg 13620
atcgccttgg cgagtttgca tatggcaaac gcagccgctc gggagccaag gaagaggcat 13680
tgaccatccc cttggatcat ggaaatccca ccccaagcct caaacccgtg accctgcaac 13740
aagtgctgcc cacgccgcca cgcaagggca tcaagcgcga gggcgaggat ctgtatccca 13800
ccatgcagct gatggtgccc aagcgccaga agctggaaga cgtgctggag aaaatgaaag 13860
tggatcctga aatccagcct gaagtcaaag tgaggccaat caagcaggtg gcgcccggtt 13920
tgggggtaca aaccgtggat atcaagatcc ccaccgagtc catggaaatt caaaccgaac 13980
ccatgaagcc cacctccagc accattgagg tgcagacgga tccttggatg cccgcgcctg 14040
ctcctgttac cactactact cgaagaccta gaagaaagta tggttcagcc aacctgataa 14100
tgccaaacta tgctctgcat ccatcaatca tacccactcc tggctaccgc ggcactcgct 14160
actaccgcag tcacagcacc cgccgacgta aagcacctgc cacccgccgc cgtcgccgcc 14220

-continued gccgtgccac tagcaaactt acccccctcgg ctatggtgcg gagagtgtac cgtgatgggc 14280
gcgcagctcc tctgacactg ccgcgcgcgc gctaccatcc tagcattgcc atttaacaac 14340
tctgcctcct tgcagatatg gccctcactt gccgccttcg tattcctatt gctggctacc 14400
gcggaagaaa gtcgcgccgt agaagagcag ggttgtctgg gagcgggatg cgtcgccacc 14460
ggcggcggcg cgccatcagc aaacggttgg ggggtggatt tcttcccgct ttgattccca 14520
tcatcgccgc ggcgatcggc gcgataccag gcatagcttc cgtggcggtg caggcctcgc 14580
agcgccactg acattggaaa aagatatctt ataaataaaa atagaatgga ctctgacgct 14640
cctggtcctg tgatatgttt ttgtagacga gatggaagac atcaattttt catccctggc 14700
tccgcgacac ggcacgcggc cgtatatggg cacctggagc gacatcggca acagccaact 14760
gaacggggga gccttcaatt ggagcagtct atggagcggg cttaaaaatt ttgggtccac 14820
tataaagact tatgggaaca aagcttggaa cagcagcaca gggcatgcgc tgagacaaaa 14880
gcttaaagat cagaatttcc aacagaaggt ggtcgatggt atcgcctctg gaatcaatgg 14940
ggtggtagat ctggccaacc aggccgtgca gaaacagatt aacagtcgcc tggacccggc 15000
tcccccagct cctattcatg agttaatgca agtggaggaa gagctccctt cattggaaaa 15060
gcggggcgat aagcgacctc gtccagatat ggaggaaacg ctgctgacca aggtggatga 15120
gccgccctcc tatgaagagg ctgtaaaact gggaatgccc actacaaagc ccattatgcc 15180
tctggccact ggagtgatga agccatctca gtctaaacct gcagttgctg ctacattgga 15240
cttgcccgct cccgtggcca cccccaaacc tgtcgccgcc ccgaagccca ccgccgtgca 15300
acccgtggcc gtggccagac cgcgtcccgg tggtcggccg aatgcaaact ggcagagcac 15360
tctgaacagc atcgtgggtt tgggagtgca cagtgtgaag cgccgtcgct gctattgatt 15420
aaatatggag tagcgcttaa cttgcttgtc tgtgtgtgta tatgtcgatg ccgcccgccg 15480
tgctacagca aagagagaag gagaagaggc gccgctgagt tcctttcaag atggccaccc 15540
catcgatgct gccccagtgg gcgtacatgc acatcgccgg acaggacgct tcggagtacc 15600
tgagtccggg tctggtgcag ttcgcccgcg ccacagatac ctacttcaat ctggggaaca 15660
agtttaggaa ccctaccgtg gctcccaccc acgatgtgac caccgaccgt agccagcgcc 15720
tgacgctgcg ctttgtgccc gttgaccggg aggacaatac ctactcctac aaagtcagat 15780
acaccctggc tgtgggagac aacagggtgt tggatatggc cagcacctac tttgacatca 15840
ggggcgtgtt ggacagagga cctagcttca aaccatactc tggcactgcc tacaactccc 15900
tggctccaaa aggagctcca aactccagtc agtggcaaca aaaggaaaac aatggtcaag 15960
gtgatgcaaa gactcacacc tatggtgtag ctgccactgg aggtattgac attgacaaaa 16020
atggtcttca aattggaatc gatgaaacta aagaagataa taacgaaatt tatgcagaca 16080
aaacattcca acctgaacct caaattggag aagaaaactg gcaagatagc gaaaactatt 16140
atggaggcag ggctcttaaa ccggaaacca agatgaagcc ttgctatggt tccttcgcta 16200
gaccaactaa tgcaaaggga ggtcaagcca aaattaaacc agctcaagag ggtcaacagt 16260
ctatagatta tgacatagac ctggctttct ttgatattcc aagcactggc ggaggcaatg 16320
gcacaaatgt aaatgacaag ccagatatgg ttatgtatac tgaaaatgta aatctggaaa 16380
ctccagacac tcatcttgtt tacaagccag gaacttcaga tgacagttcc gaggccaatt 16440
taactcagca agccatggct aacagaccca actatattgg gtttagagat aactttattg 16500
gcgtcatgta ctacaacagc actggcaaca tgggagtgct tgctggtcaa gcatcccagc 16560
taaatgctgt ggtggacctg caagacagaa acaccgagct gtcttatcag ctattacttg 16620
actctctggg cgacagaacc aggtatttta gtatgtggaa tcaggcggtg gacagctatg 16680
atcctgatgt gcgcattatt gaaaaccatg gtgtggaaga tgaattgcca aactattgct 16740
tcccattgga cggagctggc actaatgctg tttaccaagg agttaagaca aaagaggata 16800
ataatggcga atgggaaaca gacacaaatg ttgcatcgca gaatcagata tgcaagggca 16860
acatatatgc tatggagatc aacctgcaag ccaacctgtg gaaaagtttc ctttactcca 16920
acgtggctct gtacctacca gactcctaca agtacactcc atccaacgtg acactcccta 16980
ccaacactaa cacctatgac tacatgaatg gcagggtggt gtctccatcc ctggtggatg 17040
cctacattaa cattggcgcc aggtggtctc tggatgccat ggacaatgtc aacccctttca 17100 accaccaccg caatgccggc ctgcgctacc ggtccatgct tctgggcaac ggccgatacg 17160
tgcccttcca catccaagtg ccccagaaat tcttcgctat caagaacctg ctgcttctcc 17220
caggctcata cacctacgag tggaacttcc gcaaggatgt caacatgatc ctgcagagtt 17280
cccttggcaa tgacctcaga accgatgggg ccaccatcca gtacaccagc atcaatctct 17340
atgccacctt cttccccatg gctcacaaca ctgcctccac cctggaagcc atgctgcgca 17400
atgacaccaa tgaccagtcc ttcaatgact acctctcagc tgccaacatg ctttacccca 17460
tccctgccaa tgccaccaac gtgcccatct ccatcccatc tcgtaactgg gctgccttca 17520
ggggctggtc tttcacccgc ctcaagacca aggagacccc atctctggga tcagggttcg 17580
atccctactt cgtctactca ggctccattc catacctgga tggaactttc taccttaacc 17640
acactttcaa gaaagtctcc atcatgtttg actcttctgt cagctggcca ggcaatgaca 17700
ggctgctgac tcccaatgag ttcgaaatca agcgcactgt tgatggggaa gggtacaatg 17760
tggcacaatg caacatgacc aaagactggt tcctggttca gatgctctcc cactacaaca 17820
ttggctacca gggcttctac atcccagaag gatacaagga ccgcatgtac tccttcttca 17880
gaaacttcca gcccatgagc cgccaggtgg tcgatcaggt caactacaaa gactacatgg 17940
cagtcaccct tgcctatcag cacaacaact ctggctttgt gggctacctc gcgcccacca 18000
tgcgacaggg ccaaccctac cctgctaact acccataccc gctcattggc aagactgcag 18060
tcaacagtgt cacccagaaa aagttcctct gcgacagggt catgtggcgc atccccttct 18120
ccagcaactt catgtccatg gggggcccta ccgacctggg gcaaaacatg ctttatgcca 18180
actccgccca cgcgctagac atgaatttcg aagtagaccc catggatgag tccacccttc 18240
tctatgttgt cttcgaagtc ttcgacgtgg tcagagtgca ccagccccac cgcggcgtca 18300
tcgaagctgt ctacctgcgc accccccttct cagctggtaa cgccaccaca taagcgcctt 18360
gcttcttgca agtggctgca gcagcatggc ctgtggatcc tccactggat ccaatgagca 18420
agagctcagg gccatcgcca tagacctggg ctgtggaccc tatttcctgg gaacctttga 18480
caagcggttt ccaggcttca tggctcctga caagctcgcc tgtgccattg tcaacacggc 18540
agggcgcgag actggtggtg agcactggct ggcttttgga tggaaccccc gctccaatac 18600
ctgctatctc tttgacccgt ttgggttttc agacgagcgc ctcaagcaga tctatcaatt 18660
cgagtacgag gggctcctgc gccgcagtgc cctggctact aaggaccgat gcatcactct 18720
ggaaaagtct acccagaccg tgcagggtcc gcgctcggct gcctgcgggc tcttctgctg 18780
catgttcctc catgcttttg tgcactggcc cgaccgcccc atggacaaca accccaccat 18840
gaatttgctg acgggggtac ccaacaacat gctccaatcg ccccaagtag agcccaccct 18900
gcgccacaac caggaggcac tctatcgctt cctgaactcc cactcatctt actttcgttc 18960
taaccgcgcg cgcattgaga aggccactgc cttcgatcga atgaataata acatgtaaac 19020
caaattgtgt gtggctcaaa taaacagcac tttattgttt acatgcactg aggctctggg 19080
atgatcattt tttaaaaatc gaaggggttc tggcgggaat cagcatggcc agatggcagg 19140
gacacgttgc ggaactggaa cttgttctgc cacttgaact cgggaatcac cagcctggga 19200
actggaatct ctggaaaggt atcttgccat agctttctgg tcagttgcag agcgccaagc 19260
aggtcaggag cagatatctt gaaatcacag ttggggccag aattctgggc gcgggagttg 19320
cggtacactg ggttgcagca ctggaacacc ataagggcag ggtgtctcac gctcgccagc 19380
acggtctcgt cactgatgca agacacatcc aggtcttcag cattggccat tccaaagggg 19440
gtcatcttgc aggtctgtct gcccatcacg ggagcgcagc caggtttgtg gttgcaatca 19500
caatgaaggg ggatcagcat catcttggcc tggtcggggg taatccctgg gtaaacagcc 19560
ttcatgaagg cttcatactg cttgaaagct tcctgggctt tggttccctc ggtgtagaac 19620
actccacaag acttgctgga aaactgatta gtagcgcagt tggcatcatt cacacagcag 19680
cgggcgtcgt tattagccag ctggaccaca ttcctgcccc agcggttctg ggtgatcttg 19740
gctcgatctg ggttctcctt caacgcgcgc tggccgttct cgctcgccac atccatctca 19800
atgacatgtt ccttctggat catgatgttg ccatgcaggc atctaatctt gccttcataa 19860
tcagtgcagc catgaggcca cagcgcgcac ccggtgcact cccaattgtt atgggggatc 19920
tgggaatggc tatgaaccag cccttgcagg aatcttccca tcatcacagc cagggtcttt 19980
atgctggtaa aggtcagcgg gataccgcgg tgctcctcgt tcacatactg ctggcagatg 20040
cgtctgtagt gctcggcctg ctcgggcatc agcttgaaag aggttttcaa ctcattatcc 20100
agcctgtatc tctccatcat gatggacatt acttccatgc ccttctccca ggcagaaaca 20160
atagggagac tcaggggatt cttgacagta gagacaacct tacttaaggg gtcatcactg 20220
ccaatctttt cgatgcttct cttgccatcc ttctcggtga tgcgcaccgg cgggtagctg 20280
aatcccacag ccaccaactg agcctcttcc ctttcgtctt cgctgtcttg actgatgtct 20340
tgcagaggaa catgtttggt tttcctgggt ttcttcttgg gcggcagctc tggaggactc 20400
tggctccgtt ccggagaccc catggatgag cgagagttgt cgctcaccac ttggatctgg 20460
ctgcctgtag aagaactgga ccccacgcgg cggtaggtgt tcctcttggt aggcagaggt 20520
ggaggcgacg ggctccggtc cggtctgggt ggcggatggc tggcggagcc ccttccgcgt 20580
tcgggggtgc gctccagatg gcggtcgtct gactgacctc cgcggctggc cattgtgttc 20640
tcctaggtag agaaacaaga catggagact cagccatcgc tgccatcgcc atccaccacc 20700
acaagcaccg ccgaggagga ggagtgttta accaccccac catgcagccc cgctaccacc 20760
accagcaccc ttgaaagcga ggtcgacacg gtcgtggagg atttacaggc tatggaagat 20820
attgaggcag ctgtcgagca agaccccggc tatgtgacac cggcggagca tgatgaggat 20880
ctagcgcgct ttctcgacgg tgtggagaaa gcgaaacaag atgaggacga ggaagaggca 20940
gaagcacaac catcggtggc cgactacctc accggcctag ggctagaaga cgtgctgctt 21000
aagcatcttg caaggcagac agtcatagtc aaagacgccc tgctagagcg ctccgaggtg 21060
ccactcagtg tggaagacct cagtcgcgcc tatgagctaa acctcttctc gcctcgcaag 21120
ccccccaagc gtcagcccaa cgggacctgt gagcccaatc cgcgcctcaa cttctatcca 21180
gccttcactg tgcccgaagt actagctacc taccacatct tttcaagaa ccaaaagatc 21240
cccatctcct gccgcgccaa tcgcacccgc gcagatgccc tactcaactt ggggcccggc 21300
gctcgcatac ctgatatcgc ttccttggaa gaggttccta agatctttga gggtctgggc 21360
aatgaggaaa ctcgggcagc aaacgctctg caaagagaaa cagatgatgg tgaacaccac 21420
agcgctctgg tggagctcca gggcgacaac gctcgtcttg cagtcctcaa acgcagcatc 21480
gaggtcaccc atttcgccta ccccgcactt aatctcccac ccaaagtcat gagctcggtc 21540
atggacacgt tgctcatgaa gcgcgcgagc cccatctccg aggatcagaa catgcaggac 21600
cccgatgcct cagatgaagg caagcctgta gtcagcgacg agcaactggc tcgctggcta 21660
ggctctgact ccccccagtc tttggaggag cggcgcaagc ttatgatggc agtggtcctg 21720
atcacagcgg agctggagtg tctccgccgc ttcttcactg acccagagac cctgcgcaag 21780
cttgaggaga acctgcatta cacattcagt catgggttcg tgcgccaggc gtgcaagatc 21840
tccaacgttc aactcaccaa cctggtctcc tacctgggca tcttgcatga aaaccggctg 21900
gggcagaacg tgctccacac caccctgaag ggggaggccc gccgcgacta tatccgcgac 21960
tgtatctacc tctacctatg ctacacctgg caaagcggga tgggtgtgtg gcaacagtgc 22020
ttggaagagc aaaatctaaa agagctggaa aagctgcttc agaaatctct taaatctctg 22080
tggaccgggt tcgatgagcg gaccaccgct tcggacatgg ccgatattat cttccccgag 22140
cggctcagac acactctgcg cgacgggctg cctgactttg ccagccagag catgctacaa 22200
aactttaggt cattcatctt ggaacgctcc gggatcctgc ccgccacttg ctgcgcactg 22260
ccctccgatt ttgtgcccat cacctaccgg gagtgccccc cgccgctatg gagccactgc 22320
tacctgttcc gcctggccaa ctacttggcc taccactctg atgtgataga agatgttagt 22380
ggcgaagggc tcctggagtg ccactgccgc tgcaacctct gcaccccca ccgctccctc 22440
gcctgcaatc cccagctgct gagcgaaacc cagatcatcg gcaccttcga gttgcaaggt 22500
cccagcggcg aaggcgaggg gtcctctccg gggcaaagtc tgaaactgac tccggggcta 22560
tggacctccg cttaccttcg caagttcgcc cccaaagact accacccta tgagatcagg 22620
ttttatgaag accaatcaca gcccccaag gccgaactga cggcctgcgt catcacccag 22680
ggggcaatct tggcccaatt gcaagccatc caaaaatccc gccaagaatt tttgctgaaa 22740
aagggacacg ggatctatct agacccccag accggtgagg agctgaatac acgcttccct 22800
caggatgccc cgaggaggca agagaatgaa agttcagatg ccgcccgagg aggagctgga 22860
agactgggac agtcaggcag aggaggaaga ctgggacagc caggcagaag aggaggacag 22920
cctggaggag gacagtctgg aggaaggcga ggagcccaag gaagaggcag ccgccgccag 22980
accatcgtcc tcggcggtgg agacaagcaa ggtcccagac agcacggcta ccacctccgc 23040
tccagctcaa ggggccgctc ggcgacccaa cagtagatgg gacgagacgg gtcgcttcca 23100
gaaccccacc accgtcaaga ccggtaagca ggagcggcag ggatacaagt cctggcgggg 23160
gcataaaagt gccatcatcg cttgcttgca ggagtgtggg ggcaatatat cctttgccag 23220
acgctacctg ctattccatc acggggtgaa tttcccccgc aacatcttgc attactaccg 23280
tcacctccac agcccctact accagcagca agagacagca gaggaaacca gcggcaactc 23340
cgagagttag aaaaccagca gctaaaaaat ccacagcggc ggcagcaggt gcaggcggac 23400
tgaggatcac cgcgaacgag ccagctcaga ccagggagtt gaggaatcgg atctttccca 23460
ccctctatgc catattccaa caaagtcggg gtcaggaaca agaactgaaa gtaaaaaaca 23520
gatctcttcg ctcgctcacc cgcagttgtt tgtatcacaa gagcgaagac caacttcagc 23580
gcactctcga ggacgccgag gctctcttca acaagtactg cgcgctgact cttaaagagt 23640
agactgcgcg cgcttggcga gaaaaggcgg gaattacgtc acctcttggc cacacctgtg 23700
cttcattatg agtaaagaaa ttcccacgcc ttacatgtgg agctatcagc cccagatggg 23760
attggccgct ggcgccgccc aggactactc cacccgcatg aattggctca gcgccggtcc 23820
cgcgatgatc tcacgggtta atggtgtgag agagcaccga aaccagatac tcctagaaca 23880
gtccgccctc accgccactc cccgcaatca cctcaacccc cgtaattggc ccgccgccct 23940
ggtgtaccag gaaactcctg ctcccactac agtactactt cctcgtgacg cccaggccga 24000
agttcagatg actaactcag gtgtacagct ggcgggtggt gccaccctgt gtcgtcaccg 24060
gccaagaccg ggtataaagg gcctggtgat cagaggccga ggtattcagc tcaacgacga 24120
gtcggtgaac tcttcgcttg gtctgcgacc agacggcatc ttccaaatag ctggttgtgg 24180
gagatcttcc ttcactcctc gtcaggctgt cctgactttg gagagttcgt cctcgcagcc 24240
ccgctcgggc ggcatcggga ctctccagtt cgtggaggag tttactccct cggtctactt 24300
caaccccttc tccggttctc ctgggcttta cccggacgag ttcatcccga actacgacgc 24360
catcagtgaa gcggtcgacg gctacgatta atgtctaatg gtggcgcggc tgagctagct 24420
cgactgcgac acctagacca ctgccggcgc tttcgctgct ttgctcggga tctctgcgag 24480
ttcatctact tcgagtaccc tgacgaacat cctcagggac ctgcccacgg agttcggatt 24540
accattgaag ggcctatcga ttctcacctg cttcggatct tcaccgctcg gccagtgcta 24600
gttgagcgca accagggcga caccaccatc tccctctgct gcatttgtga caaccccgga 24660
ttgcatgaaa gcttttgttg tcttctttgt actgagtata ataaaagctg aaattagaga 24720
ctactccgga ctctcttgtc gtctgaacaa caccaaccag acccttcact tcagcgggaa 24780
ccagactact cttcactgta aggcttataa ctataagtat cttacttgga tatacaaagg 24840
aacaccgttt gctgtggtaa acaggtgctc caacgacggt gttctcctca ccttcctagg 24900
caacttctcc aactttacct tttctgttcg cagaaacaag cttaccctcc ttcagcccta 24960
ctttcctggg atctatacct gcctcagtgg accttgcaac cacacttttc acctgattga 25020
aaactctacc cttaccttcc cagcgccaat ccctactaac agctcggagt ccaactcttc 25080
cattaccgct gatactaaca ctcctaaaac cggaggtgag ctccgcagcc ttcccccggc 25140
tgcagataac ccttgggtgg tagcgggatt tgtagcgcta ggaatagttg cgggtgggct 25200
cgcgttcgtc ctctgctacc tataccttac ctgctgctca tatttagtag tactgtgctg 25260
ttggtttaga aaatgggggc gctactaatc acacttgctt tactttcgct tttgggtctg 25320
agctcggcta atagcgagaa accaagctgt ctagaaacaa actctccaga ctgtgtggtt 25380
cctcatgggc tctcagaccc agctgatgat ccatgcttaa cttttgaccc agaaaaaaac 25440
tgctcggtga ctatgcagcc ctatgcttac atgtgcacat ctgttataaa gtgcggatgg 25500
ggctgtaaac cgattgaaat tacccacaaa ggcaaaacct ggaataatag tttgtttaac 25560
acatggcagc ctggagacga gcagtggtat acggccggcc actggtggag atgactgacc 25620
ccatggaaaa ctcctctgcc aacgacctgg acatggacgg ccgttcatct gagcagcgac 25680
tggtccagat gcgcattcgc cagaagcagg aacgcgccgc cagagagctc aaggatgcca 25740
ttgaaattca cctgtgcaag aagggcatct tttgcttggt taagcaagca aagatttctt 25800
atgaaatcac tgacaacgac caccgcctgt attatgagct cggtccacag cggcagaaat 25860
tcacctgcat ggttggagtc aaccccatag tcatcactca gcaggctgca gaaattaaag 25920
ggtgcatcca ctgttcctgt gattcccaag aatgcgtcca caccatagtc aagaccctct 25980
gcggccttcg agatcttctt ccaatgaact aacccccttcc cccaacccaa taaaacattg 26040

-continued

```
gttttaatca taataaaaaa tcacttactt taaatctgaa acagtgtctc cgtccaagtt  26100
ttcttgtagc accacttcac tcccctcttc ccagctctgg tactgcaagc cccggtgggc  26160
tgcaaacttt ctccacacct taaaagggat gtcaaattcc tcttgtccaa caatcttcat  26220
tgtctcttcc tagatgtcca caaagcgcgc gcgggtggaa gatgactttg accctgtcta  26280
cccatacgat gctgagctgg caccgtctgt acccttcatc gcccctccct tcgtttcgtc  26340
agacggattt caagaaaaac ccctgggagt tctgtcccta agactagcca acccagtcac  26400
tactaaaaat ggggaactca cacttaaact gggagatggg gtgggcatag actcagatgg  26460
aaacctcaca gcacagacag ttactaaagc aacatccccc cttactgttt ccaataacgc  26520
aattgcactt aacatggaca aacctttttta cagtagcaat ggaaaactat ccttacaagt  26580
tacatcacca ttaaagatag tcgactcttt aaatacattg gctattggct atgggcaagg  26640
cttaggacta aacaatagtg ctcttgctgt gcaattagca tctcccctta catttgacag  26700
caacagcaaa attaaaataa atttgggaag cgggccatta aaaattaatg cgaataaact  26760
gtcaattaac tgcctaaggg gtgtatatgt aacaactgac ggaacttcca ttgaaacaaa  26820
tataagctgg gcaaaaggaa tgaggtttga aggtaatgcc atggctgtaa acgttgacag  26880
caccaaaggt ctacaatttg gcactaccag cacagaatca ggagtcacta acgctttccc  26940
tatccagtta aagattggat ctggtcttag ttttgacagc acaggagcac ttgtagcttg  27000
ggataaggat aatgacaagc ttacactgtg gacaaccgct gacccatcac ctaattgtac  27060
catatataca gacaaggatg ctaaacttac actttgtctt acaaaatgtg gcagtcaaat  27120
actaggcagt gtttcagtac tggctgttaa agctggaacc ctacagccaa tcagtgaaaa  27180
aataggtact gctttggttt cactaaaatt taataacaac ggtgtattgt taagcaactc  27240
cacattaagt aatgaatact ggaactacag gaagggagat gtcacaccag ccgaagccta  27300
tactaatgct gtgggtttta tgccaaacat caaggcatat cctaaaaaca caaactctgc  27360
ctcaaaaagc cacattgtag gacaagtgta ccttaatgga gatgaaacta aaccaatgca  27420
tttaatcatt acatttaatg aaaccagtga tgaaacatgc acatattcca taacgttcca  27480
atggaaatgg aacattggaa catacaccag cgacaccctt gcaacaagct cctttacctt  27540
ttcttacatt gcccaagaat aaaaactgca gacaacaata aagtttaaat gttttattta  27600
aacagtttca cagaacccta gtattcaacc tgccacctcc ctcccaacac acagagtaca  27660
cagtcctttc tccccggctg gccttaaaaa gcatcatatc atgggtaaca gacatattct  27720
taggtgttat attccacacg gtttcctgtc gagccaaacg ctcatcagtg atattaataa  27780
actccccggg cagctcactt aagttcatgt cgctgtccag ctgctgagcc acaggctgct  27840
gtccaacttg cggttgctta acgggcggcg aaggagaagt ccacgcctac atgggggtag  27900
agtcataatc gtgcatcagg atagggcggt ggtgctgcag cagcgcgcga ataaactgct  27960
gccgccgccg ctccgtcctg caggaataca acatggcagt ggtctcctca gcgatgattc  28020
gcaccgcccg cagcataagg cgccttgtcc tccgggcaca gcagcgcacc ctgatctcac  28080
ttaaatcagc acagtaactg cagcacagca ccacaatatt gttcaaaatc ccacagtgca  28140
aggcgctgta tccaaagctc atggcgggga ccacagaacc cacgtggcca tcataccaca  28200
agcgcaggta gattaagtgg cgacccctca taaacacgct ggacataaac attacctctt  28260
ttggcatgtt gtaattcacc acctcccggt accatataaa cctctgatta aacatggcgc  28320
catccaccac catcctaaac cagctggcca aaacctgccc gccggctata cactgcaggg  28380
aaccgggact ggaacaatga cagtggagag cccaggactc gtaaccatgg atcatcatgc  28440
```

-continued

```
tcgtcatgat atcaatgttg gcacaacaca ggcacacgtg catacacttc ctcaggatta  28500
caagctcctc ccgcgttaga accatatccc agggaacaac ccattcctga atcagcgtaa  28560
atcccacact gcagggaaga cctcgcacgt aactcacgtt gtgcattgtc aaagtgttac  28620
attcgggcag cagcggatga tcctccagta tggtagcgcg ggtttctgtc tcaaaaggag  28680
gtagacgatc cctactgtac ggagtgcgcc gagacaaccg agatcgtgtt ggtcgtagtg  28740
tcatgccaaa tggaacgccg gacgtagtca ttctcgtact ttgagtggca aaaccttgct  28800
ctcgaacagc acacgtctcg tcgcctcctg tcccttctct tcgccttttc agtgtgatag  28860
ttgtaataca gccattcacg aagctcagtc agaagatctt cagcgtctgt tgtcaaaaac  28920
aatccatcca atctgattgc tttcaaaaca tcacaaacag tcgaataagc caaacccatc  28980
caggcaatgc aattattttg gttatccaca atgggagggg gcggaagaca tggaagaggc  29040
ataattaatt ttttaatcca atcgatcacg cagcacttca aaatgaagat cgcgaaggtg  29100
acacctttca cccccactgt gttgatgaaa aataacagcc aagtcaaaat tgatgcggtt  29160
ttcaaggtgc tcgactgtag catcaagcag agcttccaca cgcacgtcca caaataacag  29220
aatagcaaaa gcgggaggag gaagtaaatc ctcaatcatc atagtacagt ccatcaccat  29280
ccctaaataa ttttcatcct tccagccttg gactatattt ttaaactgct cttgtaaatc  29340
caaaccacac atgtggaaaa gttcccaaag agctccctca actaccattc ttaagcacac  29400
cttcatagtg acaaaatatc ttgttcctct gtcacctgca gcaaattaca aagtccaata  29460
ttaggatcta tgcccagaga tctaagctca tccctcaatt ccaactgtaa aaaggcttcc  29520
agatctgccc taacttgttc agccagtggg ctccctggaa taagcgtggg agaagccaaa  29580
ctgcaaaaca gacgcatgcc gccataatta ccaccagaaa acactacgtt acagtatgca  29640
tgctgattca ttccagtaat ttcatccagt gtattggata caaaaaaagg caagcactct  29700
ctcactaatt gtattatgga gacattatca cacaggtaac aatttaaagg ttgtggaaca  29760
ataatgcagt aagtaaccac ggtgcgctcc aacatggtta gtaattttta gttctgaaaa  29820
acaaaacata caaaaaatta tatcatactc atttggcgaa ctggtggaaa aatgacccta  29880
tctagcacaa ggcaagccac tggatcacca atgcgcccct cataaaacct gtcatcatga  29940
ttaaaaagca acaccgaaag ctcttcccta tgtcctgcat gaatgattct agctgaggaa  30000
tataagccag cgcaattagt atctgttaaa gaaaaaaaac ggccaacata gcctctagga  30060
attagcacac ttaatcttaa agacattact gccatccccc ttggatttaa ggtaaaattt  30120
acaggagcat agaaaatata ctgatttccc tcctgcacag gcagcatagc accaggtccc  30180
tctaaaaaca cacacaaagc ttctgcagcc atagcttacc gcgcaaacca ggcacagcag  30240
tgagctaaaa ggacaaagct ctaactcact agccaacctg gcgcacaata tatagttagt  30300
ccttacactg acgtaaccga ccaaagtcta aaaaccccgc caaaaataca cacacgccca  30360
aaaaacgccc cgtgagtcaa aaaacagttt cacttcctcg ttacacccaa aacgtcgtca  30420
cttccggatt cccacggttc gtcacttccg gagctccttg cttaattaac cccgcccaaa  30480
acgtcatcgt ccgcgtcacg ccgccccgcc ccgcgaccgt tgaccccggg ccaatcaccg  30540
cacatcccgc aaaattcaaa ctcgtctaat ttgcatattg gcacactgcc catataaggt  30600
atattattga tgatgattta aatcatatgc ggtgtgaaat accgcacaga tgcgtaagga  30660
gaaaataccg catcaggcgc tcttccgctt cctcgctcac tgactcgctg cgctcggtcg  30720
ttcggctgcg gcgagcggta tcagctcact caaaggcggt aatacggtta tccacagaat  30780
```

cagggggataa cgcaggaaag aacatgtgag caaaaggcca gcaaaaggcc aggaaccgta 30840
aaaaggccgc gttgctggcg tttttccata ggctccgccc ccctgacgag catcacaaaa 30900
atcgacgctc aagtcagagg tggcgaaacc cgacaggact ataaagatac caggcgtttc 30960
cccctggaag ctccctcgtg cgctctcctg ttccgaccct gccgcttacc ggatacctgt 31020
ccgcctttct cccttcggga agcgtggcgc tttctcatag ctcacgctgt aggtatctca 31080
gttcggtgta ggtcgttcgc tccaagctgg gctgtgtgca cgaacccccc gttcagcccg 31140
accgctgcgc cttatccggt aactatcgtc ttgagtccaa cccggtaaga cacgacttat 31200
cgccactggc agcagccact ggtaacagga ttagcagagc gaggtatgta ggcggtgcta 31260
cagagttctt gaagtggtgg cctaactacg gctacactag aaggacagta tttggtatct 31320
gcgctctgct gaagccagtt accttcggaa aaagagttgg tagctcttga tccggcaaac 31380
aaaccaccgc tggtagcggt ggtttttttg tttgcaagca gcagattacg cgcagaaaaa 31440
aaggatctca agaagatcct ttgatctttt ctacggggtc tgacgctcag tggaacgaaa 31500
actcacgtta agggattttg gtcatgagat tatcaaaaag gatcttcacc tagatccttt 31560
taaattaaaa atgaagtttt aaatcaatct aaagtatata tgagtaaact tggtctgaca 31620
gttaccaatg cttaatcagt gaggcaccta tctcagcgat ctgtctattt cgttcatcca 31680
tagttgcctg actccccgtc gtgtagataa ctacgatacg ggagggctta ccatctggcc 31740
ccagtgctgc aatgataccg cgagacccac gctcaccggc tccagattta tcagcaataa 31800
accagccagc cggaagggcc gagcgcagaa gtggtcctgc aactttatcc gcctccatcc 31860
agtctattaa ttgttgccgg gaagctagag taagtagttc gccagttaat agtttgcgca 31920
acgttgttgc cattgctgca ggcatcgtgg tgtcacgctc gtcgtttggt atggcttcat 31980
tcagctccgg ttcccaacga tcaaggcgag ttacatgatc ccccatgttg tgcaaaaaag 32040
cggttagctc cttcggtcct ccgatcgttg tcagaagtaa gttggccgca gtgttatcac 32100
tcatggttat ggcagcactg cataattctc ttactgtcat gccatccgta agatgctttt 32160
ctgtgactgg tgagtactca accaagtcat tctgagaata gtgtatgcgg cgaccgagtt 32220
gctcttgccc ggcgtcaaca cgggataata ccgcgccaca tagcagaact ttaaaagtgc 32280
tcatcattgg aaaacgttct tcggggcgaa aactctcaag gatcttaccg ctgttgagat 32340
ccagttcgat gtaacccact cgtgcaccca actgatcttc agcatctttt actttcacca 32400
gcgtttctgg gtgagcaaaa acaggaaggc aaaatgccgc aaaaaaggga ataagggcga 32460
cacggaaatg ttgaatactc atactcttcc tttttcaata ttattgaagc atttatcagg 32520
gttattgtct catgagcgga tacatatttg aatgtattta gaaaaataaa caaatagggg 32580
ttccgcgcac atttccccga aaagtgccac ctgacgtcta agaaaccatt attatcatga 32640
cattaaccta taaaaatagg cgtatcacga ggccctttcg tcttcaagaa ttgatttaaa 32700
t 32701

<210> SEQ ID NO 10
<211> LENGTH: 179
<212> TYPE: PRT
<213> ORGANISM: Artificial Sequence
<220> FEATURE:
<223> OTHER INFORMATION: BLY6 fiber knob

<400> SEQUENCE: 10

Thr Leu Trp Thr Thr Ala Asp Pro Ser Pro Asn Cys Thr Ile Tyr Thr
1 5 10 15

-continued

Asp Lys Asp Ala Lys Leu Thr Leu Cys Leu Thr Lys Cys Gly Ser Gln
20 25 30

Ile Leu Gly Ser Val Ser Val Leu Ala Val Lys Ala Gly Thr Leu Gln
35 40 45

Pro Ile Ser Glu Lys Ile Gly Thr Ala Leu Val Ser Leu Lys Phe Asn
50 55 60

Asn Asn Gly Val Leu Leu Ser Asn Ser Thr Leu Ser Asn Glu Tyr Trp
65 70 75 80

Asn Tyr Arg Lys Gly Asp Val Thr Pro Ala Glu Ala Tyr Thr Asn Ala
85 90 95

Val Gly Phe Met Pro Asn Ile Lys Ala Tyr Pro Lys Asn Thr Asn Ser
100 105 110

Ala Ser Lys Ser His Ile Val Gly Gln Val Tyr Leu Asn Gly Asp Glu
115 120 125

Thr Lys Pro Met His Leu Ile Ile Thr Phe Asn Glu Thr Ser Asp Glu
130 135 140

Thr Cys Thr Tyr Ser Ile Thr Phe Gln Trp Lys Trp Asn Ile Gly Thr
145 150 155 160

Tyr Thr Ser Asp Thr Leu Ala Thr Ser Ser Phe Thr Phe Ser Tyr Ile
165 170 175

Ala Gln Glu

<210> SEQ ID NO 11
<211> LENGTH: 219
<212> TYPE: PRT
<213> ORGANISM: Artificial Sequence
<220> FEATURE:
<223> OTHER INFORMATION: BLY6 fiber shaft

<400> SEQUENCE: 11

Gly Val Leu Ser Leu Arg Leu Ala Asn Pro Val Thr Thr Lys Asn Gly
1 5 10 15

Glu Leu Thr Leu Lys Leu Gly Asp Gly Val Gly Ile Asp Ser Asp Gly
20 25 30

Asn Leu Thr Ala Gln Thr Val Thr Lys Ala Thr Ser Pro Leu Thr Val
35 40 45

Ser Asn Asn Ala Ile Ala Leu Asn Met Asp Lys Pro Phe Tyr Ser Ser
50 55 60

Asn Gly Lys Leu Ser Leu Gln Val Thr Ser Pro Leu Lys Ile Val Asp
65 70 75 80

Ser Leu Asn Thr Leu Ala Ile Gly Tyr Gly Gln Gly Leu Gly Leu Asn
85 90 95

Asn Ser Ala Leu Ala Val Gln Leu Ala Ser Pro Leu Thr Phe Asp Ser
100 105 110

Asn Ser Lys Ile Lys Ile Asn Leu Gly Ser Gly Pro Leu Lys Ile Asn
115 120 125

Ala Asn Lys Leu Ser Ile Asn Cys Leu Arg Gly Val Tyr Val Thr Thr
130 135 140

Asp Gly Thr Ser Ile Glu Thr Asn Ile Ser Trp Ala Lys Gly Met Arg
145 150 155 160

Phe Glu Gly Asn Ala Met Ala Val Asn Val Asp Ser Thr Lys Gly Leu
165 170 175

Gln Phe Gly Thr Thr Ser Thr Glu Ser Gly Val Thr Asn Ala Phe Pro
180 185 190

Ile Gln Leu Lys Ile Gly Ser Gly Leu Ser Phe Asp Ser Thr Gly Ala

```
        195                 200                 205

Leu Val Ala Trp Asp Lys Asp Asn Asp Lys Leu
    210                 215
```

<210> SEQ ID NO 12
<211> LENGTH: 44
<212> TYPE: PRT
<213> ORGANISM: Artificial Sequence
<220> FEATURE:
<223> OTHER INFORMATION: BLY6 fiber tail

<400> SEQUENCE: 12

```
Met Ser Thr Lys Arg Ala Arg Val Glu Asp Asp Phe Asp Pro Val Tyr
1               5                   10                  15

Pro Tyr Asp Ala Glu Leu Ala Pro Ser Val Pro Phe Ile Ala Pro Pro
            20                  25                  30

Phe Val Ser Ser Asp Gly Phe Gln Glu Lys Pro Leu
        35                  40
```

<210> SEQ ID NO 13
<211> LENGTH: 30954
<212> TYPE: DNA
<213> ORGANISM: Artificial Sequence
<220> FEATURE:
<223> OTHER INFORMATION: BLY6.dE1.dE3 Ad vector genome

<400> SEQUENCE: 13

```
catcatcaat aatatacctt atatgggcag tgtgccaata tgcaaattag acgagtttga     60

attttgcggg atgtgcggtg attggcccgg ggtcaacggt cgcggggcgg ggcggcgtga    120

cgcggacgat gacgttttgg ggaggaggag ctatgttgca agtaatcgtg ggaaatgcga    180

cgtaaaacga ggtggagttt aaacacggaa gtagacaatt ttcccgcgct gtttgacagg    240

aaatgatgtg tttttgggcg gatgcaagtg aaaattctcc attttcgcgc gaaaactaaa    300

tgaggaagtg aaattctgag taattctgag gttatcacag ggcggagtat ttaccgaggg    360

ccgagtagac tttgacccat tacgtggagg tttcgattac tctatttttc acctaaattt    420

ccgcgtactg tgtcaaagtc cgtgttttta cgcgatcgcg atggcctgtg tttgagcata    480

atgtactgac caggtgtaac gttcatctgg gtggtcgtag aggaatgttc atgccatacc    540

aatgcaattt taatcatgtg aggatcttga tggagccgca agcgttttcc agagtcagct    600

tgactggaat ctttgacatg tgtgtggaag catggaagat cttaagatat gatgatacca    660

aatccagatg ccgcgcatgc gagtgcgggg gcaggcatgc caggttccaa cctgtatgtg    720

tggaggtgac cgaggagctg agaccagatc atttggtgct gacctgcact ggtgcggagt    780

tcggttccag tggtgaagaa actgattaaa gtgagtagtg ggatgttata aaagtgacca    840

taaggtgatg tgagatggac aaatttggta atttttatgt atttttgtct tgcagccatg    900

agtgggagcg cttcctttga agggggcgtc tttagccctt atctgacggg gcgtctgcct    960

cattgggctg gagtgcgtca gaatgtgatg ggtctacag tggatggaag acctgttcag   1020

cctgctaatt cttctactct gacttatgct actatgactt cctcgccttt ggatgcagct   1080

gcagctgctg ccgcttctgc tgccgccaac actgttcggg ggatggcctt ggagatgggg   1140

tattatggaa ctgtagtggc caacaccact accccaaata accccacagc cttgaatgag   1200

gacaagctgc tagttctcat gtcccagctg gagtctttga cccaacgcct gggcgatcta   1260

gctcagcagg tgtcccagct gaaggagcag actcaagctg caattaccac tgcgagggga   1320

aattaaaaaa attcaaagaa tcaataaata aaccgagact ttgttgattt taaagtgtgt   1380
```

cattctttat ttaatttttc gcgcgcgata tgccctggac caccggtctc tatcattgag 1440
gacacggtgg atcttttcta gaacccgata gaggtgggat tggatgttga ggtacatggg 1500
cataagacca tctttggggt gtagatagct ccactgcaga gcctcatgct ccggggtggt 1560
gttgtatata acccagtcat agcatgggcg ttgggcatga tgttgcacaa tatctttaag 1620
gaggagacta atggccactg ggagaccctt ggtgtaagtg tttacaaatc tattaagctg 1680
ggacgggtgc atccgaggtg agataatgtg cattttggat tggattttta gattggcaat 1740
gtttcccccct agatctctcc tgggattcat gttatgcaag accactagaa cagtgtatcc 1800
ggtgcactta gggaatttgt catgaagttt ggaggggaaa gcatgaaaaa atttagacac 1860
acccttgtgt cctcccaagt tctccatgca ctcatccata ataatggcaa tgggcccatg 1920
ggcggcggca cgggcgaaca cgttcctggg atctgacaca tcatagttgt ggtcttgggt 1980
caggtcatca taagccattt taataaactt ggggcggagg gtgccagatt gggggatgaa 2040
tgttccctcg ggccccggaa catagtttcc ttcacatatt tgcatttccc aggcttttag 2100
ttcagagggg gggatcatgt ccacctgtgg agcgatgaag aagacggtct cgggggcggg 2160
ggtgattaag tgggaggaca gcaagttcct aagcagctgt gacttgccac acccagtggg 2220
accgtagatg accccctataa caggttgcag atggtagttt agggaaagac agctgccgtc 2280
ctctcgcagg aggggggcga cctcgttcat catttccctc acatgcatgt ttcccgcac 2340
aagttccgat aggaggcgct ctccacccag ggaaaggagt tcttgaagag atgagaaatt 2400
tttcaagggt tttaagccat cagccatggg cattttggag agggtttgtt gcaagagttc 2460
aaggcggtcc cagagttcgg tgatgtgttc tatggcatct cgatccagca tacttcctcg 2520
tttctggggt tgggacggct gcgggagtat ggaaccaggc gatgggcgtc cagcgctgcc 2580
agtgtccggt ccttccacgg tcgcagcgtc cgagtcaggg tcgtttccgt cacggtgaag 2640
gggtgcgcgc ctggctgggc gcttgcgagg gtgcgcttca ggctcatcct gctcgtggag 2700
aaccgctgcc gttctgcgcc ctgtgcatcg gccaggtagc aattaaccat gagttcgtag 2760
ttgagcgcct ctgccgcgtg gcctttggcg cgcagcttac ctttggaagt cttctgacag 2820
gtgggacagt agagacactt gagagcatag agttttgggg ctagaaagac cgattctggg 2880
gagtatgcat cggccccaca ggaggcgcag acggtttcgc attccaccag ccatgtaaga 2940
tcgggctcgt tggggtcaaa aacaagtttt ccgccatgtt ttttgatgcg tttcttacct 3000
ttgctttcca tgagttcgtg cccccgttgg gtgacaaaga ggctgtccgt gtccccgtag 3060
actgacttta tgggcctgtc ctcgagcggc gtgccgcggt cctcttcgta gaggaactcg 3120
gaccactctg agacgaaagc acgtgtccag gccagcacaa aggaggctat atgggagggg 3180
tagcgatcgt tgtcaaccaa ggggtctact tttccaagg tgtgtaaaca catgtcccct 3240
tcttccacat ccaggaaggt gattggcttg taagtgtatg ccacgtgacc tggggtccca 3300
gacgggggg tataaaaggg ggcgggtctc tgctcgtcct cactgtcttc cggatcgctg 3360
tccaggagcg ccagctgttg aggtaggtat tccctctcga aggcgggcat aacctccgca 3420
ctcaggttgt cagtttctag gaacgaggag gatttgatat tgacagtgcc tgccgagatg 3480
cctttcatga gactgtcgtc catttggtca gaaaagacaa tctttttgtt atcaagtttg 3540
gtggcgaagg atccatacag ggcattggaa agcagtttgg caatggagcg catggtttgg 3600
tttttttctt tgtctgcgcg ctctttggcg gctatgttga gttggacata ttcgcgggcc 3660
agacatttcc attgtggaaa tatggtagtt aattcatctg ggacgattct gactttccag 3720

-continued

```
cctctgttat gcagggtaat cagatccaca ctggttgcca cttctcctct aagtggttca   3780
ttagtccagc atagtcgccc ccctttttcga gaacagaaag ggggtagggg atctagcatg   3840
agttcgtctg gggggtctgc atctatggtg aaaatcccag gaaggagatc ttcgtcaaaa   3900
tagctgatgg tggcggggtc atccagagac atttgccatt ctcgagcagc cagagcgcgc   3960
tcgtaggggt taaggggagt cccccatggc atgggatggg tgagtgcaga agcatacatg   4020
ccacagatgt catagacata gagcggctct tccagaatcc ctatgtaagt gggataacat   4080
cgccccccctc tgatgctggc tcgcacataa tcatagagtt catgtgaggg cgctagaaga   4140
cccgagccca ggttggtgcg gttgggtttt tctgctctgt agaggatctg gcgaaagatg   4200
gcatgggagt ttgatgagat ggtgggtctt tggaagatgt tgaaatgggc atgaggcagt   4260
cccacagagt cccttatgaa gtgagcatag gagtcttgca gtttggccac cagctcggcg   4320
gtgaccagca catccaaagc acagtagtcg agggtctctt tgatgatgtc atagttaggt   4380
tccccttttct tttcccacag ctcgcggttg agaaggtatt cttcgcgatc cttccagtac   4440
tcttcgaggg ggaacccgtc cttgtctgaa cggtaagaac ccagcatgta aaattgattg   4500
acagctttgt aggcacaaca ccccttctcc acggggagtg agtatgcttg cgcggctttg   4560
cgcagagagg tgtgagtaag ggcgaaagtg tccctgacca tgactttgag gaactgatgc   4620
ttaaagtcta tgtcatcgca ggccccctgc tcccacagtt ggaagtccac tcgctttttg   4680
taggcgggat tgggcaaagc gaaagtaaca tcgttgaata ggatctttcc agccctgggc   4740
atgaagttgc gagtaatgcg aaaaggctga ggcacttctg ccctgttgtt gataacttgg   4800
gcagccaaga cgatctcgtc aaagccgttg atgttgtgac ccacaatgta aagttctacg   4860
aagcgtgggc gtcccttgat gtggggcagt tttttaagct cttcgtaggt caagtcgtca   4920
gggtcagcga ttccatattg ctccaaagcc cagtcaggca ggtgaggatt agcatgaagg   4980
aaagaggtcc aaagatccac ggccagagct gtttgtaagc ggtctctgta ctgacggaaa   5040
tgtcggccta ccgccatttt ttcaggagta acacagtaaa aggtgcgcgg gtcctttttcc  5100
cagcgatccc attgaagttg caaggctagg tcgtgggcga ggttgacgag ctgttcgtcc   5160
cccgaaagtt tcatgaccag catgaaaggg acaagctgct tgccaaagga ccccatccag   5220
gtgtaggttt ccacatcgta ggtgaggaag agcctttctg tgcgaggatg agaaccgatc   5280
gggaagaact ggatttcctg ccaccagttg gaggaatggc tgttgatatg atggaagtag   5340
aactccctac ggcgcgccga gcattcgtgc ttgtgcttgt acagacggcc acagtactcg   5400
cagcgctgca cgggatgcac ctgatgaatg agctgtacct ggcttccttt gacaagaaat   5460
ttcagtggga agttgaggcg tggcgtctgc atctcgtgtt gtattacgtc ctggctattg   5520
gtctggccat cttctgtctc gatggtggtc atgctgacga gcccgcgcgg gaggcaggtc   5580
cagacctccg cgcggacggg tctgagagcg aggacgagag cgcgcaggcc ggaactgtcc   5640
agggtcctga gacgctgcgg agtcaggtca gtagggagag tacataggtt tacttgcata   5700
agtttttcca gggcatgtgg gaggtcaaga tgatatttga tttctactgg cgagttggtg   5760
gagacatcga tggcttgcag ggtcccgtgc ccctggggtg ctaccaccgt cccttttttt   5820
ttcttgatcg gggggcggtgt tgcttcttgc atggtaaggt cgtcttctag aagcggcggc  5880
gaggtcgcgc gccgggtggc agtggcggtt ctggacctgg aggtagaggc ggtagaggta   5940
cgtcggcgcc gcgcgcgggt aggttctggt actgcgccct gagaagactt gcgtgagcga   6000
cgacgcggcg gttgacgtcc tggatctgac gcctctgggt gaatgctacc ggacccgtga   6060
gcttgaacct gaaagagagt tcaacagaat caatttcggt atcgttgacg gctgcctgcc   6120
```

```
gcaggatttc ttgtacgtcg cccgagttgt cttggtaggc gatctcggcc atgaactgct   6180
cgatctcttc ttcttggaga tctccgcggc ccgctcgttc tacggtggca gcaaggtcgt   6240
tggagatgcg ccccatgagc tgtgagaatg cattcatgcc cgcctcgttc cagacgcgac   6300
tgtagaccac ggctccctcg ggatctctgg cgcgcatgac cacttgggcg aggtttagtt   6360
ccacgtgtct ggtgaagacc gcatagttgc agagacgctg gaagaggtag ttgagcgtgg   6420
tggcgatgtg ctcggtgaca aagaaataca tgatccagcg acgaagcggc atctcgctga   6480
tatcgcccag ggcttccaac cgttccatgg cttcgtaaaa gtccacggcg aagttgaaaa   6540
actgggagtt gcgagcggac acggtcaact cctcctccag aagacggatg agctcggcga   6600
tggtggcgcg cacttcgcgc tcaaaggctc ccgggatctc ttcctcctct tcttcttcca   6660
actcttcctc cactaacatc tcttctactt cctcctcagg cggcgggggt ggaggagggg   6720
gcgcgcggcg acgccggcga cgcacgggca gacgatcgat gaagcgttcg atcacttctc   6780
cgcggcggcg acgcatggtc tcggtgacgg cgcgcccgtc ctccctgggt cgcagagtga   6840
agacgccgcc gcgcagctcc ctgaaatggt gactgggagg gtccccgttt ggtagggaca   6900
gggcactgat gatgcatctt attaattgcc ctgtagggac tccgcgcaag gacctgagcg   6960
tctcgagatc cacgggatct gaaaatctct gaacgaaggc ttcgagccag tcgcagtcgc   7020
aaggtaggct gagcactgtt tcttcggggc gggctgctga gctagagggt tgtacgatgc   7080
tgctggtgat gaagttaaaa taggcagttc tgagacggcg gatggtggcg aggagcacca   7140
ggtctttggg tccggcttgc tggatgcgca ggcggtcggc cattccccat gcattatctt   7200
ggcacctggc cagatcttta tagtagtctt gcatgagtcg ctccacgggc acttcttctt   7260
cgcccgctct gccgtgcatg cgtgtgagtc cgtaccctct ctgtggttgg acgagcgcca   7320
ggtcggcaac gaccctttcg gctagaatgg cttgctgcac ctgggtgagg gtgttctgga   7380
aatcatcaaa gtccacaaag cggtggtagg cccccgtgtt gatggtgtag gagcagttgg   7440
acatgaccga ccagttgact gtctggtgtc ctggtcgtac gagttccgtg tacctgagcc   7500
gcgagtatgc gcgggagtcg aagatgtaat cgttgcaggt tcgcaccagg tactggtagc   7560
cgatgaggaa gtgaggcggc ggctggcggt agagaggcca tcgttcggtg gcgggcgcgc   7620
cgggcgctag gtcttctagc atgagacggt ggtatccgta gacgtacctg gacatccagg   7680
taataccggc ggcggtggtg gaggcgcgcg gaaactctcg cacgcggttc cagatgttgc   7740
gcagcggcat gaagtagttc atggtgggca cggtctggcc cgtgaggcgc gcgcagtcat   7800
tgatgctcta gatacgggca aaaacgaaag cgttgagcgg ttcccttccg tggcctggag   7860
gaacgcgaac gggttaggtc gcagcgtacc ctggttcgag actaaagaaa gcgagcaact   7920
cgaaccggca gagtcgcggc taacgggtat tggcaatccc gtctcgaccc aagccagcaa   7980
atccaggata cggatggggg ccccttttgt ttttcagggc atgagtcacc ggttaaggtt   8040
tacaacggct gtttcatgcc tttagaagtg gctcgcgccc gtagtctgga gaatcaatcg   8100
ccagggttgc gttgcggcgt gccccggttc gagcctgcag cttgagtcgg ccggtgaccg   8160
cggcaaacga gggcgtggcg gccccgtcgt ttctaagacc ttgctagccg acctctccag   8220
tttacgggaa cgagcccccct tttatttttt ttgtttttgc cagatgcatc ccgtactgcg   8280
gcagatgcgc ccacagcccc cacagcagca gcagcaggct ggcctacctt ctctacctca   8340
gccgctacct gcaactaccg cggtggccgc tgtaagcggg gccggacagc aggcggctcc   8400
tcaatatgaa ttggacttgg aagagggcga gggattggca agattggggg cgccctcgcc   8460
```

-continued

```
cgagcgccac ccgcgggtgc agatgaaaaa ggacgttcgc gaatcttacg tgcccaagca   8520
gaatctgttc agagacagaa gcggcgagga gcccgaggag atgcgcgcgt cccgttttaa   8580
cgcgggtcgc gagctgcgac aaggactgga tcgaaaacgg gtgttgaggg atgatgattt   8640
tgaggtggat gaaatgacag ggatcagccc cgctcgcgct cacgtggctg cagctaatct   8700
ggtgacagct tatgagcaga ccgtgaagga ggaaagcaac ttccagaaat cattcaataa   8760
ccacgtgcgc accctgatcg cacgcgagga ggtgaccctg ggcctgatgc acctgtggga   8820
tctgctggaa gccatagtgc agaaccccac tagcaaaccc ctgactgctc aactgtttct   8880
ggtggtgcag cacagcaggg ataatgaggc attcagagag gcgctgctga atatcactga   8940
acctgagggg agatggctgc tggatctggt gaatatcctg cagagcattg tagtgcagga   9000
acgcagcttg cctttgtccg agaaggtggc ggcgatcaat tactctgtgc tgagtctggg   9060
caaatactat gccaggaaga tctacaaaac cccttacgtg cccatagaca aggaagtgaa   9120
aatagatggg ttttacatgc gcatgaccct gaaagtgcta accctgagcg atgacttggg   9180
agtgtaccgc aacgacagga tgcaccgcgc ggtgagcgcc agcaggaggc gcgagctgag   9240
cgacaaagaa ttaatgcaca gcttgcaacg agccctgacg ggagccggga cggaggggga   9300
gaactacttt gacatgggtg cagacttgca ttggctgcct agtcgcaggg cattggaagc   9360
ggcaggcgat gggccctatg tagaggaagt agtagacgag gacgatgagg agggcgagta   9420
cctggaagac tgatggcgcg acccgtattt ttgctagatg gaacaggcgc cggaccctgc   9480
gatgcgggcg gcgctgcaga gccagccgtc cggcattaat tcctcggacg attggaccca   9540
ggccatgcaa cgcatcatgg cgctgacgac ccgcaacccc gaagccttta gacagcagcc   9600
tcaggccaac cgcctttcgg ccatcctgga ggccgtggtg ccctctcgct ccaaccccac   9660
ccacgagaag gttctggcca tcgtgaatgc cctggtggag aacaaggcca tccgctccga   9720
tgaagccggg ctggtataca acgccttgct cgagcgcgtg gctcgctaca acagcagcaa   9780
tgtccagact aacctggaca ggatggtgac cgacgtgcgc gaggccgtgt cccagcgcga   9840
acggttccat cgcgagtcta acctgggttc catggtagcg ctgaacgctt tcctcagttc   9900
ccagcctgcc aatgtgcccc ggggacagga agactatacc aactttatta gcgccctgag   9960
actcatggta gccgaggttc ctcagagcga ggtgtaccag tccggtccag actacttttt  10020
ccagacaagc aggaacggta tgcagacagt gaacttaagc caggctttca agaacctgca  10080
agggctgtgg ggagtccaag ctccagtggg cgacagggcg accgtgtcga gcctgttgac  10140
tccaaattcc cgtttgctgc tgctgctggt gtccccccttc actgacagcg gcagcataaa  10200
cagaaactcc tacttgggct acctgataaa cttgtatcgc gaagctatag gtcaggccca  10260
cgtggacgaa cagacctatc aggagatcac taatgtgagt cgcgctctgg gccaggacga  10320
ccctggaaac ctggaagcta ctctaaactt tctgctgacc aaccgctcgc aaaaaatccc  10380
tcctcagtat acattaactg cggaggagga acggatcttg agatacgtgc agcagagcgt  10440
gggtctgttc ctgatgcaag agggtgcgac ccctagcgcc gcgcttgata tgacagcgcg  10500
caacatggag cccagcatgt atgccagcaa cagaccattc attaataaat tgatggatta  10560
cttccatcgc gcggccgcta tgaactctga ttacttcacc aatgctattc tgaaccccca  10620
ttggctgcct ccgcctggtt tttatactgg cgagtatgac atgcctgacc ccaacgatgg  10680
gttcttgtgg gacgatgtgg acagcgtggc gttctcgcct accgctcctc gtactttttg  10740
gaagaaggaa ggtagtgaca gaagaccctc ctccgtgctg tcaggacgtg agggtgctgc  10800
cgcggcggtc cccgatgctg caagcccctt tcccagtctg ccattttcac taaacagcgt  10860
```

```
gcgcagtagc gagctgggga gaataacccg ccctcgcttg ctgggcgagg acgagtattt    10920

gaatgactcc ctactgagac ccgagcggga aaagaacttc cctaataatg ggattgaaag    10980

cctggtggat aagatgagca gatggaagac ctatgcccag gagcacagag atgagcctag    11040

aatcttgggt cctacagtag gcacccgcag acgccagcgc catgatagac agcggggtct    11100

ggtgtgggac gatgaggatt ctgcagatga cagcagcgtg ttggacttgg gcgggagggg    11160

aggtgtgggc aacccgttcg cacacttgcg tccccgtatt ggacgcatga tgtaaaagtg    11220

aaaataaaaa aggaactcac caaggccatg gcgaccagcg tgcgttcgtt ctttctgttg    11280

ttgtatctag tatgatgagg cgcaccgtgc taggcggatc ggtggcgtat ccggagggtc    11340

ctcctccttc gtacgaaagc gtgatgcagc aggtggcggc ggcggcgatg caacccccct    11400

tggaggctcc ttacgtgccc ccgcggtacc tggcacctac cgaggggaga aacagcattc    11460

gttattcgga actcacaccc ttgtatgaca ccacccggtt gtacctggtg gacaacaaat    11520

cggcggacat tgcctcgttg aactatcaga acgaccacag caacttcttg acaacggtgg    11580

tgcagaacaa tgactttacc cccacggagg ccagcaccca gaccatcaac tttgacgagc    11640

gctcccggtg gggcggtcag ctgaagacca tcatgcacac caacatgccc aacgtgaacg    11700

agttcatgtt tagcaacaag ttcagggcta gggtgatggt gtccagaacc acacctaaag    11760

aggtgacagt cacaacagac tatgatggta gtcaggacat cttggaatac gagtgggttg    11820

actttgagtt accagaaggc aacttctctg ccaccatgac catagacctg atgaataatg    11880

caattgttga taattaccta aaagtgggta gacagaatgg ggtactggag agtgacatag    11940

gtgttaagtt tgacactagg aactttaggc ttggttggga cccagtgaca gagttggtca    12000

tgcctggggt ctacaccaat gaagctttcc atcctgacat agtcctacta cctggctgcg    12060

gagtggactt cactgagagc cgcctcagta atctgctagg cattagaaag aaacagccat    12120

tccaggaagg gttccagatc atgtatgagg atctggaggg tggtaacatc cccgccctgc    12180

ttgatgtaaa tgcatatgag aagagcaagg aagataatac aaccaccaca aatgaagctg    12240

tggccgcggc ttcatctact gaagccaaag ctgtggtaga tgcttccact tcaacagaaa    12300

acaccactga tgaaaaagtc accaggggag atacatttgc caccccctgaa caagagaagg    12360

cagctgaggc agagtctgat attatgcttc tgtccaccga tgaaaacgaa actaaaaaac    12420

aactggttat tcgagcggtg accaaggata gtaaggacag gagttataat gtattgtcag    12480

atggaaagaa cacagcttac cgtagttggt acctggcata caattatggc gaccgtgaga    12540

aaggggtgcg ttcttggaca ctgcttacca cctcggatgt cacctgcggc gtggagcaag    12600

tctattggtc gctaccagat atgatgcaag atccagtcac ctttcgctcc acacgccaag    12660

ttagcaacta cccagtggtg ggcgcagagc tgctcccagt gcattccaga agcttctaca    12720

acgagcaagc cgtctactcg caacagctcc gccagtacac ctcgctcacg cacgtcttca    12780

accgcttccc cgagaatcag atcctcgtcc gcccgcccgc gccaaccatt accaccgtca    12840

gtgaaaacgt tcctgctctc acagatcacg ggaccctgcc gctgcgcagc agtatccggg    12900

gagtccagcg cgtgaccgtt actgacgcca gacgccgcac ctgtccatac gtatacaagg    12960

ccctgggcat agtcgcgccg cgcgtccttt caagccgcac tttctaaaaa aatgtccatt    13020

ctcatctcgc ccagtaataa caccggttgg ggcctgcgca cacctagcaa gatgtatgga    13080

ggcgctcgca gacgctccac tcagcaccct gtgcgcgtgc gcgggcattt ccgcgctccc    13140

tggggcgccc tcaagggacg ctctcgtact aggaccaccg ttgacgatgt gatcgaccag    13200
```

-continued

```
gtggtcgccg atgcacgtaa ctataccccc gcagccgcac ctgcatccac cgtggatgcg  13260
gtcattgaca gcgtggtagc cgatgcgcgc gcctatgctc gcgccaagag caggaggcgg  13320
cgtattgcca ggcgtcaccg agctactcca gccatgcgag ctgcaagagc tttattgcgg  13380
agagccagac gtgtggggcg aagagccatg cgtagagcgg ccagacgcgc ggcttcaggt  13440
gccagcgcag gcagggtccg caggcgcgcg gctacggcgg cagcggcggc catcgctagc  13500
atgaccaaac cacgaagagg caatgtgtat tgggtgcgcg acgccgccac cggccagcgc  13560
gtgcccgtgc gcacacgccc ccctcgcact tagaagatac tgagcagtct ccgatgttgt  13620
gtcccagcgg cgagatgtcc aagcgcaaat tcaaggaaga gatgctccag gtcatcgcgc  13680
ctgagatcta cggtcctgcg gtgaaggatg aaaaaaagcc ccgcaagatc aagcgggtca  13740
aaaaggacaa aaaggaagaa gatggtgatg atgggctggt ggagtttgtg cgcgagtttg  13800
ccccaaggag gcgcgtgcag tggcgcgggc gcaaagtgtg gccggtgttg agaccgggga  13860
ccacagtggt ctttacgcca ggcgagcgct ccagcaccgt ttccaaacgc tcttatgatg  13920
aggtgtacgg ggacgatgat attctcgagc aggcggctga tcgccttggc gagtttgcat  13980
atggcaaacg cagccgctcg ggagccaagg aagaggcatt gaccatcccc ttggatcatg  14040
gaaatcccac cccaagcctc aaacccgtga ccctgcaaca agtgctgccc acgccgccac  14100
gcaagggcat caagcgcgag ggcgaggatc tgtatcccac catgcagctg atggtgccca  14160
agcgccagaa gctggaagac gtgctggaga aaatgaaagt ggatcctgaa atccagcctg  14220
aagtcaaagt gaggccaatc aagcaggtgg cgcccggttt gggggtacaa accgtggata  14280
tcaagatccc caccgagtcc atggaaattc aaaccgaacc catgaagccc acctccagca  14340
ccattgaggt gcagacggat ccttggatgc ccgcgcctgc tcctgttacc actactactc  14400
gaagacctag aagaaagtat ggttcagcca acctgataat gccaaactat gctctgcatc  14460
catcaatcat acccactcct ggctaccgcg gcactcgcta ctaccgcagt cacagcaccc  14520
gccgacgtaa agcacctgcc acccgccgcc gtcgccgccg ccgtgccact agcaaactta  14580
ccccctcggc tatggtgcgg agagtgtacc gtgatgggcg cgcagctcct ctgacactgc  14640
cgcgcgcgcg ctaccatcct agcattgcca tttaacaact ctgcctcctt gcagatatgg  14700
ccctcacttg ccgccttcgt attcctattg ctggctaccg cggaagaaag tcgcgccgta  14760
gaagagcagg gttgtctggg agcgggatgc gtcgccaccg gcggcggcgc gccatcagca  14820
aacggttggg gggtggattt cttcccgctt tgattcccat catcgccgcg gcgatcggcg  14880
cgataccagg catagcttcc gtggcggtgc aggcctcgca gcgccactga cattggaaaa  14940
agatatctta taaataaaaa tagaatggac tctgacgctc ctggtcctgt gatatgtttt  15000
tgtagacgag atggaagaca tcaatttttc atccctggct ccgcgacacg gcacgcggcc  15060
gtatatgggc acctggagcg acatcggcaa cagccaactg aacgggggag ccttcaattg  15120
gagcagtcta tggagcgggc ttaaaaattt tgggtccact ataaagactt atgggaacaa  15180
agcttggaac agcagcacag ggcatgcgct gagacaaaag cttaaagatc agaatttcca  15240
acagaaggtg gtcgatggta tcgcctctgg aatcaatggg gtggtagatc tggccaacca  15300
ggccgtgcag aaacagatta acagtcgcct ggacccggct cccccagctc ctattcatga  15360
gttaatgcaa gtggaggaag agctcccttc attggaaaag cggggcgata agcgacctcg  15420
tccagatatg gaggaaacgc tgctgaccaa ggtggatgag ccgccctcct atgaagaggc  15480
tgtaaaactg ggaatgccca ctacaaagcc cattatgcct ctggccactg gagtgatgaa  15540
gccatctcag tctaaacctg cagttgctgc tacattggac ttgcccgctc ccgtggccac  15600
```

-continued

```
ccccaaacct gtcgccgccc cgaagcccac cgccgtgcaa cccgtggccg tggccagacc  15660
gcgtcccggt ggtcggccga atgcaaactg gcagagcact ctgaacagca tcgtgggttt  15720
gggagtgcac agtgtgaagc gccgtcgctg ctattgatta aatatggagt agcgcttaac  15780
ttgcttgtct gtgtgtgtat atgtcgatgc cgcccgccgt gctacagcaa agagagaagg  15840
agaagaggcg ccgctgagtt cctttcaaga tggccacccc atcgatgctg ccccagtggg  15900
cgtacatgca catcgccgga caggacgctt cggagtacct gagtccgggt ctggtgcagt  15960
tcgcccgcgc cacagatacc tacttcaatc tggggaacaa gtttaggaac cctaccgtgg  16020
ctcccaccca cgatgtgacc accgaccgta gccagcgcct gacgctgcgc tttgtgcccg  16080
ttgaccggga ggacaatacc tactcctaca aagtcagata caccctggct gtgggagaca  16140
acagggtgtt ggatatggcc agcacctact ttgacatcag gggcgtgttg gacagaggac  16200
ctagcttcaa accatactct ggcactgcct acaactccct ggctccaaaa ggagctccaa  16260
actccagtca gtggcaacaa aaggaaaaca atggtcaagg tgatgcaaag actcacacct  16320
atggtgtagc tgccactgga ggtattgaca ttgacaaaaa tggtcttcaa attggaatcg  16380
atgaaactaa agaagataat aacgaaattt atgcagacaa aacattccaa cctgaacctc  16440
aaattggaga agaaaactgg caagatagcg aaaactatta tggaggcagg gctcttaaac  16500
cggaaaccaa gatgaagcct tgctatggtt ccttcgctag accaactaat gcaaagggag  16560
gtcaagccaa aattaaacca gctcaagagg gtcaacagtc tatagattat gacatagacc  16620
tggctttctt tgatattcca agcactggcg gaggcaatgg cacaaatgta aatgacaagc  16680
cagatatggt tatgtatact gaaaatgtaa atctggaaac tccagacact catcttgttt  16740
acaagccagg aacttcagat gacagttccg aggccaattt aactcagcaa gccatggcta  16800
acagacccaa ctatattggg tttagagata actttattgg cgtcatgtac tacaacagca  16860
ctggcaacat gggagtgctt gctggtcaag catcccagct aaatgctgtg gtggacctgc  16920
aagacagaaa caccgagctg tcttatcagc tattacttga ctctctgggc gacagaacca  16980
ggtattttag tatgtggaat caggcggtgg acagctatga tcctgatgtg cgcattattg  17040
aaaaccatgg tgtggaagat gaattgccaa actattgctt cccattggac ggagctggca  17100
ctaatgctgt ttaccaagga gttaagacaa aagaggataa taatggcgaa tgggaaacag  17160
acacaaatgt tgcatcgcag aatcagatat gcaagggcaa catatatgct atggagatca  17220
acctgcaagc caacctgtgg aaaagtttcc tttactccaa cgtggctctg tacctaccag  17280
actcctacaa gtacactcca tccaacgtga cactccctac caacactaac acctatgact  17340
acatgaatgg cagggtggtg tctccatccc tggtggatgc ctacattaac attggcgcca  17400
ggtggtctct ggatgccatg gacaatgtca accctttcaa ccaccaccgc aatgccggcc  17460
tgcgctaccg gtccatgctt ctgggcaacg gccgatacgt gcccttccac atccaagtgc  17520
cccagaaatt cttcgctatc aagaacctgc tgcttctccc aggctcatac acctacgagt  17580
ggaacttccg caaggatgtc aacatgatcc tgcagagttc ccttggcaat gacctcagaa  17640
ccgatggggc caccatccag tacaccagca tcaatctcta tgccaccttc ttccccatgg  17700
ctcacaacac tgcctccacc ctggaagcca tgctgcgcaa tgacaccaat gaccagtcct  17760
tcaatgacta cctctcagct gccaacatgc tttaccccat ccctgccaat gccaccaacg  17820
tgcccatctc catcccatct cgtaactggg ctgccttcag gggctggtct ttcacccgcc  17880
tcaagaccaa ggagacccca tctctgggat cagggttcga tccctacttc gtctactcag  17940
```

```
gctccattcc atacctggat ggaactttct accttaacca cactttcaag aaagtctcca  18000
tcatgtttga ctcttctgtc agctggccag gcaatgacag gctgctgact cccaatgagt  18060
tcgaaatcaa gcgcactgtt gatggggaag ggtacaatgt ggcacaatgc aacatgacca  18120
aagactggtt cctggttcag atgctctccc actacaacat tggctaccag ggcttctaca  18180
tcccagaagg atacaaggac cgcatgtact ccttcttcag aaacttccag cccatgagcc  18240
gccaggtggt cgatcaggtc aactacaaag actacatggc agtcaccctt gcctatcagc  18300
acaacaactc tggctttgtg ggctacctcg cgcccaccat gcgacagggc caaccctacc  18360
ctgctaacta cccatacccg ctcattggca agactgcagt caacagtgtc acccagaaaa  18420
agttcctctg cgacagggtc atgtggcgca tccccttctc cagcaacttc atgtccatgg  18480
gggcccttac cgacctgggg caaaacatgc tttatgccaa ctccgcccac gcgctagaca  18540
tgaatttcga agtagacccc atggatgagt ccacccttct ctatgttgtc ttcgaagtct  18600
tcgacgtggt cagagtgcac cagccccacc gcggcgtcat cgaagctgtc tacctgcgca  18660
ccccttctc agctggtaac gccaccacat aagcgccttg cttcttgcaa gtggctgcag  18720
cagcatggcc tgtggatcct ccactggatc caatgagcaa gagctcaggg ccatcgccat  18780
agacctgggc tgtggaccct atttcctggg aacctttgac aagcggtttc caggcttcat  18840
ggctcctgac aagctcgcct gtgccattgt caacacggca gggcgcgaga ctggtggtga  18900
gcactggctg gcttttggat ggaacccccg ctccaatacc tgctatctct ttgacccgtt  18960
tgggttttca gacgagcgcc tcaagcagat ctatcaattc gagtacgagg ggctcctgcg  19020
ccgcagtgcc ctggctacta aggaccgatg catcactctg gaaaagtcta cccagaccgt  19080
gcagggtccg cgctcggctg cctgcgggct cttctgctgc atgttcctcc atgcttttgt  19140
gcactggccc gaccgcccca tggacaacaa ccccaccatg aatttgctga cgggggtacc  19200
caacaacatg ctccaatcgc cccaagtaga gcccaccctg cgccacaacc aggaggcact  19260
ctatcgcttc ctgaactccc actcatctta ctttcgttct aaccgcgcgc gcattgagaa  19320
ggccactgcc ttcgatcgaa tgaataataa catgtaaacc aaattgtgtg tggctcaaat  19380
aaacagcact ttattgttta catgcactga ggctctggga tgatcatttt ttaaaaatcg  19440
aaggggttct ggcgggaatc agcatggcca gatggcaggg acacgttgcg gaactggaac  19500
ttgttctgcc acttgaactc gggaatcacc agcctgggaa ctggaatctc tggaaaggta  19560
tcttgccata gctttctggt cagttgcaga gcgccaagca ggtcaggagc agatatcttg  19620
aaatcacagt tggggccaga attctgggcg cgggagttgc ggtacactgg gttgcagcac  19680
tggaacacca taagggcagg gtgtctcacg ctcgccagca cggtctcgtc actgatgcaa  19740
gacacatcca ggtcttcagc attggccatt ccaaaggggg tcatcttgca ggtctgtctg  19800
cccatcacgg gagcgcagcc aggtttgtgg ttgcaatcac aatgaagggg gatcagcatc  19860
atcttggcct ggtcgggggt aatccctggg taaacagcct tcatgaaggc ttcatactgc  19920
ttgaaagctt cctgggcttt ggttccctcg gtgtagaaca ctccacaaga cttgctggaa  19980
aactgattag tagcgcagtt ggcatcattc acacagcagc gggcgtcgtt attagccagc  20040
tggaccacat tcctgcccca gcggttctgg gtgatcttgg ctcgatctgg gttctccttc  20100
aacgcgcgct ggccgttctc gctcgccaca tccatctcaa tgacatgttc cttctggatc  20160
atgatgttgc catgcaggca tctaatcttg ccttcataat cagtgcagcc atgaggccac  20220
agcgcgcacc cggtgcactc ccaattgtta tgggggatct gggaatggct atgaaccagc  20280
ccttgcagga atcttcccat catcacagcc agggtcttta tgctggtaaa ggtcagcggg  20340
```

-continued

```
ataccgcggt gctcctcgtt cacatactgc tggcagatgc gtctgtagtg ctcggcctgc  20400
tcgggcatca gcttgaaaga ggttttcaac tcattatcca gcctgtatct ctccatcatg  20460
atggacatta cttccatgcc cttctcccag gcagaaacaa tagggagact caggggattc  20520
ttgacagtag agacaacctt acttaagggg tcatcactgc caatcttttc gatgcttctc  20580
ttgccatcct tctcggtgat gcgcaccggc gggtagctga atcccacagc caccaactga  20640
gcctcttccc tttcgtcttc gctgtcttga ctgatgtctt gcagaggaac atgtttggtt  20700
ttcctgggtt tcttcttggg cggcagctct ggaggactct ggctccgttc cggagacccc  20760
atggatgagc gagagttgtc gctcaccact tggatctggc tgcctgtaga agaactggac  20820
cccacgcggc ggtaggtgtt cctcttggta ggcagaggtg gaggcgacgg gctccggtcc  20880
ggtctgggtg gcggatggct ggcggagccc cttccgcgtt cgggggtgcg ctccagatgg  20940
cggtcgtctg actgacctcc gcggctggcc attgtgttct cctaggtaga gaaacaagac  21000
atggagactc agccatcgct gccatcgcca tccaccacca caagcaccgc cgaggaggag  21060
gagtgtttaa ccaccccacc atgcagcccc gctaccacca ccagcaccct tgaaagcgag  21120
gtcgacacgg tcgtggagga tttacaggct atggaagata ttgaggcagc tgtcgagcaa  21180
gaccccggct atgtgacacc ggcggagcat gatgaggatc tagcgcgctt tctcgacggt  21240
gtggagaaag cgaaacaaga tgaggacgag gaagaggcag aagcacaacc atcggtggcc  21300
gactacctca ccggcctagg gctagaagac gtgctgctta agcatcttgc aaggcagaca  21360
gtcatagtca aagacgccct gctagagcgc tccgaggtgc cactcagtgt ggaagacctc  21420
agtcgcgcct atgagctaaa cctcttctcg cctcgcaagc cccccaagcg tcagcccaac  21480
gggacctgtg agcccaatcc gcgcctcaac ttctatccag ccttcactgt gcccgaagta  21540
ctagctacct accacatctt tttcaagaac caaaagatcc ccatctcctg ccgcgccaat  21600
cgcacccgcg cagatgccct actcaacttg gggcccggcg ctcgcatacc tgatatcgct  21660
tccttggaag aggttcctaa gatctttgag ggtctgggca atgaggaaac tcgggcagca  21720
aacgctctgc aaagagaaac agatgatggt gaacaccaca gcgctctggt ggagctccag  21780
ggcgacaacg ctcgtcttgc agtcctcaaa cgcagcatcg aggtcaccca tttcgcctac  21840
cccgcactta atctcccacc caaagtcatg agctcggtca tggacacgtt gctcatgaag  21900
cgcgcgagcc ccatctccga ggatcagaac atgcaggacc ccgatgcctc agatgaaggc  21960
aagcctgtag tcagcgacga gcaactggct cgctggctag gctctgactc cccccagtct  22020
ttggaggagc ggcgcaagct tatgatggca gtggtcctga tcacagcgga gctggagtgt  22080
ctccgccgct tcttcactga cccagagacc ctgcgcaagc ttgaggagaa cctgcattac  22140
acattcagtc atgggttcgt gcgccaggcg tgcaagatct ccaacgttca actcaccaac  22200
ctggtctcct acctgggcat cttgcatgaa aaccggctgg ggcagaacgt gctccacacc  22260
accctgaagg gggaggcccg ccgcgactat atccgcgact gtatctacct ctacctatgc  22320
tacacctggc aaagcgggat gggtgtgtgg caacagtgct tggaagagca aaatctaaaa  22380
gagctggaaa agctgcttca gaaatctctt aaatctctgt ggaccgggtt cgatgagcgg  22440
accaccgctt cggacatggc cgatattatc ttccccgagc ggctcagaca cactctgcgc  22500
gacgggctgc ctgactttgc cagccagagc atgctacaaa actttaggtc attcatcttg  22560
gaacgctccg ggatcctgcc cgccacttgc tgcgcactgc cctccgattt tgtgcccatc  22620
acctaccggg agtgcccccc gccgctatgg agccactgct acctgttccg cctggccaac  22680
```

-continued

```
tacttggcct accactctga tgtgatagaa gatgttagtg gcgaagggct cctggagtgc  22740
cactgccgct gcaacctctg cacccccac cgctccctcg cctgcaatcc ccagctgctg  22800
agcgaaaccc agatcatcgg caccttcgag ttgcaaggtc ccagcggcga aggcgagggg  22860
tcctctccgg ggcaaagtct gaaactgact ccggggctat ggacctccgc ttaccttcgc  22920
aagttcgccc ccaaagacta ccacccctat gagatcaggt tttatgaaga ccaatcacag  22980
ccccccaagg ccgaactgac ggcctgcgtc atcacccagg gggcaatctt ggcccaattg  23040
caagccatcc aaaaatcccg ccaagaattt ttgctgaaaa agggacacgg gatctatcta  23100
gacccccaga ccggtgagga gctgaataca cgcttccctc aggatgcccc gaggaggcaa  23160
gagaatgaaa gttcagatgc cgcccgagga ggagctggaa gactgggaca gtcaggcaga  23220
ggaggaagac tgggacagcc aggcagaaga ggaggacagc ctggaggagg acagtctgga  23280
ggaaggcgag gagcccaagg aagaggcagc cgccgccaga ccatcgtcct cggcggtgga  23340
gacaagcaag gtcccagaca gcacggctac cacctccgct ccagctcaag ggccgctcg  23400
gcgacccaac agtagatggg acgagacggg tcgcttccag aaccccacca ccgtcaagac  23460
cggtaagcag gagcggcagg gatacaagtc ctggcggggg cataaaagtg ccatcatcgc  23520
ttgcttgcag gagtgtgggg gcaatatatc ctttgccaga cgctacctgc tattccatca  23580
cggggtgaat ttcccccgca acatcttgca ttactaccgt cacctccaca gcccctacta  23640
ccagcagcaa gagacagcag aggaaaccag cggcaactcc gagagttaga aaaccagcag  23700
ctaaaaaatc cacagcggcg gcagcaggtg caggcggact gaggatcacc gcgaacgagc  23760
cagctcagac cagggagttg aggaatcgga tctttcccac cctctatgcc atattccaac  23820
aaagtcgggg tcaggaacaa gaactgaaag taaaaaacag atctcttcgc tcgctcaccc  23880
gcagttgttt gtatcacaag agcgaagacc aacttcagcg cactctcgag gacgccgagg  23940
ctctcttcaa caagtactgc gcgctgactc ttaaagagta gactgcgcgc gcttggcgag  24000
aaaaggcggg aattacgtca cctcttggcc acacctgtgc ttcattatga gtaaagaaat  24060
tcccacgcct tacatgtgga gctatcagcc ccagatggga ttggccgctg gcgccgccca  24120
ggactactcc acccgcatga attggctcag cgccggtccc gcgatgatct cacgggttaa  24180
tggtgtgaga gagcaccgaa accagatact cctagaacag tccgccctca ccgccactcc  24240
ccgcaatcac ctcaacccc gtaattggcc cgccgccctg gtgtaccagg aaactcctgc  24300
tcccactaca gtactacttc ctcgtgacgc ccaggccgaa gttcagatga ctaactcagg  24360
tgtacagctg gcgggtggtg ccaccctgtg tcgtcaccgg ccaagaccgg gtataaaggg  24420
cctggtgatc agaggccgag gtattcagct caacgacgag tcggtgaact cttcgcttgg  24480
tctgcgacca gacggcatct tccaaatagc tggttgtggg agatcttcct tcactcctcg  24540
tcaggctgtc ctgactttgg agagttcgtc ctcgcagccc cgctcgggcg gcatcgggac  24600
tctccagttc gtggaggagt ttactccctc ggtctacttc aacccttct ccggttctcc  24660
tgggctttac ccggacgagt tcatcccgaa ctacgacgcc atcagtgaag cggtcgacgg  24720
ctacgattaa tgtctaatgg tggcgcggct gagctagctc gactgcgaca cctagaccac  24780
tgccggcgct ttcgctgctt tgctcgggat ctctgcgagt tcatctactt cgagtaccct  24840
gacgaacatc ctcagggacc tgcccacgga gttcggatta ccattgaagg ggctatcgat  24900
tctcacctgc ttcggatctt caccgctcgg ccagtgctag ttgagcgcaa ccagggcgac  24960
accaccatct ccctctgctg catttgtgac aaccccggat tgcatgaaag cttttgttgt  25020
cttctttgta ctgagtataa taaaagctga aattagagac tactccggac tctcttgtcg  25080
```

tctgaacaac accaaccaga cccttcactt cagcgggaac cagactactc ttcactgtaa 25140
ggcttataac tataagtatc ttacttggat atacaaagga acaccgtttg ctgtggtaaa 25200
caggtgctcc aacgacggtg ttctcctcac cttcctaggc aacttctcca actttacctt 25260
ttctgttcgc agaaacaagc ttaccctcct tcagccctac tttcctggga tctatacctg 25320
cctcagtgga ccttgcaacc acacttttca cctgattgaa aactctaccc ttaccttccc 25380
agcgccaatc cctactaaca gctcggagtc caactcttcc attaccgctg atactaacac 25440
tcctaaaacc ggaggtgagc tccgcagcct tcccccggct gcagataacc cttgggtggt 25500
agcgggattt gtagcgctag gaatagttgc gggtgggctc gcgttcgtcc tctgctacct 25560
ataccttacc tgctgctcat atttagtagt actgtgctgt tggtttagaa aatgggggcg 25620
ctactaatca cacttgcttt actttcgctt ttgggtctga gctcggctaa tagcgagaaa 25680
ccaagctgtc tagaaacaaa ctctccagac tgtgtggttc ctcatgggct ctcagaccca 25740
gctgatgatc catgcttaac ttttgaccca gaaaaaaact gctcggtgac tatgcagccc 25800
tatgcttaca tgtgcacatc tgttataaag tgcggatggg gctgtaaacc gattgaaatt 25860
acccacaaag gcaaaacctg gaataatagt ttgtttaaca catggcagcc tggagacgag 25920
cagtggtata cggccggcca ctggtggaga tgactgaccc catggaaaac tcctctgcca 25980
acgacctgga catggacggc cgttcatctg agcagcgact ggtccagatg cgcattcgcc 26040
agaagcagga acgcgccgcc agagagctca aggatgccat tgaaattcac ctgtgcaaga 26100
agggcatctt ttgcttggtt aagcaagcaa agatttctta tgaaatcact gacaacgacc 26160
accgcctgta ttatgagctc ggtccacagc ggcagaaatt cacctgcatg gttggagtca 26220
accccatagt catcactcag caggctgcag aaattaaagg gtgcatccac tgttcctgtg 26280
attcccaaga atgcgtccac accatagtca agaccctctg cggccttcga gatcttcttc 26340
caatgaacta accccttccc ccaacccaat aaaacattgg ttttaatcat aataaaaaat 26400
cacttacttt aaatctgaaa cagtgtctcc gtccaagttt tcttgtagca ccacttcact 26460
cccctcttcc cagctctggt actgcaagcc ccggtgggct gcaaactttc tccacacctt 26520
aaaagggatg tcaaattcct cttgtccaac aatcttcatt gtctcttcct agatgtccac 26580
aaagcgcgcg cgggtggaag atgactttga ccctgtctac ccatacgatg ctgagctggc 26640
accgtctgta cccttcatcg cccctccctt cgtttcgtca gacggatttc aagaaaaacc 26700
cctgggagtt ctgtccctaa gactagccaa cccagtcact actaaaaatg ggaactcac 26760
acttaaactg ggagatgggg tgggcataga ctcagatgga aacctcacag cacagacagt 26820
tactaaagca acatcccccc ttactgtttc caataacgca attgcactta acatggacaa 26880
acctttttac agtagcaatg gaaaactatc cttacaagtt acatcaccat taaagatagt 26940
cgactcttta aatacattgg ctattggcta tgggcaaggc ttaggactaa acaatagtgc 27000
tcttgctgtg caattagcat ctccccttac atttgacagc aacagcaaaa ttaaaataaa 27060
tttgggaagc gggccattaa aaattaatgc gaataaactg tcaattaact gcctaagggg 27120
tgtatatgta acaactgacg gaacttccat tgaaacaaat ataagctggg caaaaggaat 27180
gaggtttgaa ggtaatgcca tggctgtaaa cgttgacagc accaaaggtc tacaatttgg 27240
cactaccagc acagaatcag gagtcactaa cgctttccct atccagttaa agattggatc 27300
tggtcttagt tttgacagca caggagcact tgtagcttgg gataaggata atgacaagct 27360
tacactgtgg acaaccgctg acccatcacc taattgtacc atatatacag acaaggatgc 27420

-continued

```
taaacttaca ctttgtctta caaaatgtgg cagtcaaata ctaggcagtg tttcagtact  27480
ggctgttaaa gctggaaccc tacagccaat cagtgaaaaa ataggtactg ctttggtttc  27540
actaaaattt aataacaacg gtgtattgtt aagcaactcc acattaagta atgaatactg  27600
gaactacagg aagggagatg tcacaccagc cgaagcctat actaatgctg tgggttttat  27660
gccaaacatc aaggcatatc ctaaaaacac aaactctgcc tcaaaaagcc acattgtagg  27720
acaagtgtac cttaatggag atgaaactaa accaatgcat ttaatcatta catttaatga  27780
aaccagtgat gaaacatgca catattccat aacgttccaa tggaaatgga acattggaac  27840
atacaccagc gacacccttg caacaagctc ctttaccttt tcttacattg cccaagaata  27900
aaaactgcag acaacaataa agtttaaatg ttttatttaa acagtttcac agaaccctag  27960
tattcaacct gccacctccc tcccaacaca cagagtacac agtcctttct ccccggctgg  28020
ccttaaaaag catcatatca tgggtaacag acatattctt aggtgttata ttccacacgg  28080
tttcctgtcg agccaaacgc tcatcagtga tattaataaa ctccccgggc agctcactta  28140
agttcatgtc gctgtccagc tgctgagcca caggctgctg tccaacttgc ggttgcttaa  28200
cgggcggcga aggagaagtc cacgcctaca tgggggtaga gtcataatcg tgcatcagga  28260
tagggcggtg gtgctgcagc agcgcgcgaa taaactgctg ccgccgccgc tccgtcctgc  28320
aggaatacaa catggcagtg gtctcctcag cgatgattcg caccgcccgc agcataaggc  28380
gccttgtcct ccgggcacag cagcgcaccc tgatctcact taaatcagca cagtaactgc  28440
agcacagcac cacaatattg ttcaaaatcc cacagtgcaa ggcgctgtat ccaaagctca  28500
tggcggggac cacagaaccc acgtggccat cataccacaa gcgcaggtag attaagtggc  28560
gacccctcat aaacacgctg gacataaaca ttacctcttt tggcatgttg taattcacca  28620
cctcccggta ccatataaac ctctgattaa acatggcgcc atccaccacc atcctaaacc  28680
agctggccaa aacctgcccg ccggctatac actgcaggga accgggactg gaacaatgac  28740
agtggagagc ccaggactcg taaccatgga tcatcatgct cgtcatgata tcaatgttgg  28800
cacaacacag gcacacgtgc atacacttcc tcaggattac aagctcctcc cgcgttagaa  28860
ccatatccca gggaacaacc cattcctgaa tcagcgtaaa tcccacactg cagggaagac  28920
ctcgcacgta actcacgttg tgcattgtca aagtgttaca ttcgggcagc agcggatgat  28980
cctccagtat ggtagcgcgg gtttctgtct caaaaggagg tagacgatcc ctactgtacg  29040
gagtgcgccg agacaaccga gatcgtgttg gtcgtagtgt catgccaaat ggaacgccgg  29100
acgtagtcat tctcgtactt tgagtggcaa aaccttgctc tcgaacagca cacgtctcgt  29160
cgcctcctgt cccttctctt cgccttttca gtgtgatagt tgtaatacag ccattcacga  29220
agctcagtca gaagatcttc agcgtctgtt gtcaaaaaca atccatccaa tctgattgct  29280
ttcaaaacat cacaaacagt cgaataagcc aaacccatcc aggcaatgca attattttgg  29340
ttatccacaa tgggaggggg cggaagacat ggaagaggca taattaattt tttaatccaa  29400
tcgatcacgc agcacttcaa aatgaagatc gcgaaggtga cacctttcac ccccactgtg  29460
ttgatgaaaa ataacagcca agtcaaaatt gatgcggttt tcaaggtgct cgactgtagc  29520
atcaagcaga gcttccacac gcacgtccac aaataacaga atagcaaaag cgggaggagg  29580
aagtaaatcc tcaatcatca tagtacagtc catcaccatc cctaaataat tttcatcctt  29640
ccagccttgg actatatttt taaactgctc ttgtaaatcc aaaccacaca tgtggaaaag  29700
ttcccaaaga gctccctcaa ctaccattct taagcacacc ttcatagtga caaaatatct  29760
tgttcctctg tcacctgcag caaattacaa agtccaatat taggatctat gcccagagat  29820
```

```
ctaagctcat ccctcaattc caactgtaaa aaggcttcca gatctgccct aacttgttca  29880
gccagtgggc tccctggaat aagcgtggga gaagccaaac tgcaaaacag acgcatgccg  29940
ccataattac caccagaaaa cactacgtta cagtatgcat gctgattcat tccagtaatt  30000
tcatccagtg tattggatac aaaaaaaggc aagcactctc tcactaattg tattatggag  30060
acattatcac acaggtaaca atttaaaggt tgtggaacaa taatgcagta agtaaccacg  30120
gtgcgctcca acatggttag taatttttag ttctgaaaaa caaaacatac aaaaaattat  30180
atcatactca tttggcgaac tggtggaaaa atgaccctat ctagcacaag gcaagccact  30240
ggatcaccaa tgcgcccctc ataaaacctg tcatcatgat taaaaagcaa caccgaaagc  30300
tcttccctat gtcctgcatg aatgattcta gctgaggaat ataagccagc gcaattagta  30360
tctgttaaag aaaaaaaacg gccaacatag cctctaggaa ttagcacact taatcttaaa  30420
gacattactg ccatccccct tggatttaag gtaaaattta caggagcata gaaaatatac  30480
tgatttccct cctgcacagg cagcatagca ccaggtccct ctaaaaacac acacaaagct  30540
tctgcagcca tagcttaccg cgcaaaccag gcacagcagt gagctaaaag gacaaagctc  30600
taactcacta gccaacctgg cgcacaatat atagttagtc cttacactga cgtaaccgac  30660
caaagtctaa aaaccccgcc aaaaatacac acacgcccaa aaaacgcccc gtgagtcaaa  30720
aaacagtttc acttcctcgt tacacccaaa acgtcgtcac ttccggattc ccacggttcg  30780
tcacttccgg agctccttgc ttaattaacc ccgcccaaaa cgtcatcgtc cgcgtcacgc  30840
cgccccgccc cgcgaccgtt gaccccgggc caatcaccgc acatcccgca aaattcaaac  30900
tcgtctaatt tgcatattgg cacactgccc atataaggta tattattgat gatg        30954
```

<210> SEQ ID NO 14
<211> LENGTH: 30615
<212> TYPE: DNA
<213> ORGANISM: Artificial Sequence
<220> FEATURE:
<223> OTHER INFORMATION: BLY6.dE1.dE3.5IXP Ad vector genome

<400> SEQUENCE: 14

```
catcatcaat aatatacctt atatgggcag tgtgccaata tgcaaattag acgagtttga     60
attttgcggg atgtgcggtg attggcccgg ggtcaacggt cgcggggcgg ggcggcgtga    120
cgcggacgat gacgttttgg ggaggaggag ctatgttgca agtaatcgtg ggaaatgcga    180
cgtaaaacga ggtggagttt aaacacggaa gtagacaatt ttcccgcgct gtttgacagg    240
aaatgatgtg tttttgggcg gatgcaagtg aaaattctcc attttcgcgc gaaaactaaa    300
tgaggaagtg aaattctgag taattctgag gttatcacag ggcggagtat ttaccgaggg    360
ccgagtagac tttgacccat tacgtggagg tttcgattac tctatttttc acctaaattt    420
ccgcgtactg tgtcaaagtc cgtgttttta cgcgatcgcg gtactgaaat gtgtgggcgt    480
ggcttaaggg tgggaaagaa tatataaggt gggggtctta tgtagttttg tatctgtttt    540
gcagcagccg ccgccgccat gagtgggagc gcttcctttg aagggggcgt ctttagccct    600
tatctgacgg ggcgtctgcc tcattgggct ggagtgcgtc agaatgtgat ggggtctaca    660
gtggatggaa gacctgttca gcctgctaat tcttctactc tgacttatgc tactatgact    720
tcctcgcctt tggatgcagc tgcagctgct gccgcttctg ctgccgccaa cactgttcgg    780
gggatggcct tggagatggg gtattatgga actgtagtgg ccaacaccac taccccaaat    840
aaccccacag ccttgaatga ggacaagctg ctagttctca tgtcccagct ggagtctttg    900
```

-continued

```
acccaacgcc tgggcgatct agctcagcag gtgtcccagc tgaaggagca gactcaagct    960
gcaattacca ctgcgagggg aaattaaaaa aattcaaaga atcaataaat aaaccgagac   1020
tttgttgatt ttaaagtgtg tcattcttta tttaattttt cgcgcgcgat atgccctgga   1080
ccaccggtct ctatcattga ggacacggtg gatcttttct agaacccgat agaggtggga   1140
ttggatgttg aggtacatgg gcataagacc atctttgggg tgtagatagc tccactgcag   1200
agcctcatgc tccggggtgg tgttgtatat aacccagtca tagcatgggc gttgggcatg   1260
atgttgcaca atatctttaa ggaggagact aatggccact gggagaccct tggtgtaagt   1320
gtttacaaat ctattaagct gggacgggtg catccgaggt gagataatgt gcattttgga   1380
ttggattttt agattggcaa tgtttccccc tagatctctc ctgggattca tgttatgcaa   1440
gaccactaga acagtgtatc cggtgcactt agggaatttg tcatgaagtt tggaggggaa   1500
agcatgaaaa aatttagaca caccccttgtg tcctcccaag ttctccatgc actcatccat   1560
aataatggca atgggcccat gggcggcggc acgggcgaac acgttcctgg gatctgacac   1620
atcatagttg tggtcttggg tcaggtcatc ataagccatt ttaataaact tggggcggag   1680
ggtgccagat tgggggatga atgttccctc gggccccgga acatagtttc cttcacatat   1740
ttgcatttcc caggctttta gttcagaggg ggggatcatg tccacctgtg gagcgatgaa   1800
gaagacggtc tcgggggcgg gggtgattaa gtgggaggac agcaagttcc taagcagctg   1860
tgacttgcca cacccagtgg gaccgtagat gacccctata acaggttgca gatggtagtt   1920
tagggaaaga cagctgccgt cctctcgcag gagggggggcg acctcgttca tcatttccct   1980
cacatgcatg ttttcccgca caagttccga taggaggcgc tctccaccca gggaaaggag   2040
ttcttgaaga gatgagaaat ttttcaaggg ttttaagcca tcagccatgg gcattttgga   2100
gagggtttgt tgcaagagtt caaggcggtc ccagagttcg gtgatgtgtt ctatggcatc   2160
tcgatccagc atacttcctc gtttctgggg ttgggacggc tgcgggagta tggaaccagg   2220
cgatgggcgt ccagcgctgc cagtgtccgg tccttccacg gtcgcagcgt ccgagtcagg   2280
gtcgtttccg tcacggtgaa ggggtgcgcg cctggctggg cgcttgcgag ggtgcgcttc   2340
aggctcatcc tgctcgtgga gaaccgctgc cgttctgcgc cctgtgcatc ggccaggtag   2400
caattaacca tgagttcgta gttgagcgcc tctgccgcgt ggcctttggc gcgcagctta   2460
cctttggaag tcttctgaca ggtgggacag tagagacact tgagagcata gagttttggg   2520
gctagaaaga ccgattctgg ggagtatgca tcggccccac aggaggcgca gacggtttcg   2580
cattccacca gccatgtaag atcgggctcg ttggggtcaa aaacaagttt tccgccatgt   2640
tttttgatgc gtttcttacc tttgctttcc atgagttcgt gcccccgttg ggtgacaaag   2700
aggctgtccg tgtccccgta gactgacttt atgggcctgt cctcgagcgg cgtgccgcgg   2760
tcctcttcgt agaggaactc ggaccactct gagacgaaag cacgtgtcca ggccagcaca   2820
aaggaggcta tatgggaggg gtagcgatcg ttgtcaacca aggggtctac tttttccaag   2880
gtgtgtaaac acatgtcccc ttcttccaca tccaggaagg tgattggctt gtaagtgtat   2940
gccacgtgac ctggggtccc agacgggggg gtataaaagg gggcgggtct ctgctcgtcc   3000
tcactgtctt ccggatcgct gtccaggagc gccagctgtt gaggtaggta ttccctctcg   3060
aaggcgggca taacctccgc actcaggttg tcagtttcta ggaacgagga ggatttgata   3120
ttgacagtgc ctgccgagat gcctttcatg agactgtcgt ccatttggtc agaaaagaca   3180
atctttttgt tatcaagttt ggtggcgaag gatccataca gggcattgga aagcagtttg   3240
gcaatggagc gcatggtttg gttttttttct ttgtctgcgc gctctttggc ggctatgttg   3300
```

-continued agttggacat attcgcgggc cagacatttc cattgtggaa atatggtagt taattcatct 3360
gggacgattc tgactttcca gcctctgtta tgcagggtaa tcagatccac actggttgcc 3420
acttctcctc taagtggttc attagtccag catagtcgcc ccccttttcg agaacagaaa 3480
gggggtaggg gatctagcat gagttcgtct ggggggtctg catctatggt gaaaatccca 3540
ggaaggagat cttcgtcaaa atagctgatg gtggcggggt catccagaga catttgccat 3600
tctcgagcag ccagagcgcg ctcgtagggg ttaaggggag tcccccatgg catgggatgg 3660
gtgagtgcag aagcatacat gccacagatg tcatagacat agagcggctc ttccagaatc 3720
cctatgtaag tgggataaca tcgccccct ctgatgctgg ctcgcacata atcatagagt 3780
tcatgtgagg gcgctagaag acccgagccc aggttggtgc ggttgggttt ttctgctctg 3840
tagaggatct ggcgaaagat ggcatgggag tttgatgaga tggtgggtct ttggaagatg 3900
ttgaaatggg catgaggcag tcccacagag tcccttatga agtgagcata ggagtcttgc 3960
agtttggcca ccagctcggc ggtgaccagc acatccaaag cacagtagtc gagggtctct 4020
ttgatgatgt catagttagg ttcccctttc ttttcccaca gctcgcggtt gagaaggtat 4080
tcttcgcgat ccttccagta ctcttcgagg gggaacccgt ccttgtctga acggtaagaa 4140
cccagcatgt aaaattgatt gacagctttg taggcacaac acccttctc cacggggagt 4200 gagtatgctt gcgcggcttt gcgcagagag gtgtgagtaa gggcgaaagt gtccctgacc 4260
atgactttga ggaactgatg cttaaagtct atgtcatcgc aggccccctg ctcccacagt 4320
tggaagtcca ctcgcttttt gtaggcggga ttgggcaaag cgaaagtaac atcgttgaat 4380
aggatctttc cagccctggg catgaagttg cgagtaatgc gaaaaggctg aggcacttct 4440
gccctgttgt tgataacttg ggcagccaag acgatctcgt caaagccgtt gatgttgtga 4500
cccacaatgt aaagttctac gaagcgtggg cgtcccttga tgtggggcag ttttttaagc 4560
tcttcgtagg tcaagtcgtc agggtcagcg attccatatt gctccaaagc ccagtcaggc 4620
aggtgaggat tagcatgaag gaaagaggtc caaagatcca cggccagagc tgtttgtaag 4680
cggtctctgt actgacggaa atgtcggcct accgccattt tttcaggagt aacacagtaa 4740
aaggtgcgcg ggtccttttc ccagcgatcc cattgaagtt gcaaggctag gtcgtgggcg 4800
aggttgacga gctgttcgtc cccgaaagt ttcatgacca gcatgaaagg gacaagctgc 4860
ttgccaaagg accccatcca ggtgtaggtt tccacatcgt aggtgaggaa gagcctttct 4920
gtgcgaggat gagaaccgat cggaagaac tggatttcct gccaccagtt ggaggaatgg 4980
ctgttgatat gatggaagta gaactcccta cggcgcgccg agcattcgtg cttgtgcttg 5040
tacagacggc cacagtactc gcagcgctgc acgggatgca cctgatgaat gagctgtacc 5100
tggcttcctt tgacaagaaa tttcagtggg aagttgaggc gtggcgtctg catctcgtgt 5160
tgtattacgt cctggctatt ggtctggcca tcttctgtct cgatggtggt catgctgacg 5220
agcccgcgcg ggaggcaggt ccagacctcc gcgcggacgg gtctgagagc gaggacgaga 5280
gcgcgcaggc cggaactgtc cagggtcctg agacgctgcg gagtcaggtc agtagggaga 5340
gtacataggt ttacttgcat aagtttttcc agggcatgtg ggaggtcaag atgatatttg 5400
atttctactg gcgagttggt ggagacatcg atggcttgca gggtcccgtg cccctggggt 5460
gctaccaccg tcccttttt tttcttgatc gggggcggtg ttgcttcttg catggtaagg 5520
tcgtcttcta gaagcggcgg cgaggtcgcg cgccgggtgg cagtggcggt tctggacctg 5580
gaggtagagg cggtagaggt acgtcggcgc cgcgcgcggg taggttctgg tactgcgccc 5640

```
tgagaagact tgcgtgagcg acgacgcggc ggttgacgtc ctggatctga cgcctctggg   5700
tgaatgctac cggacccgtg agcttgaacc tgaaagagag ttcaacagaa tcaatttcgg   5760
tatcgttgac ggctgcctgc cgcaggattt cttgtacgtc gcccgagttg tcttggtagg   5820
cgatctcggc catgaactgc tcgatctctt cttcttggag atctccgcgg cccgctcgtt   5880
ctacggtggc agcaaggtcg ttggagatgc gccccatgag ctgtgagaat gcattcatgc   5940
ccgcctcgtt ccagacgcga ctgtagacca cggctccctc gggatctctg gcgcgcatga   6000
ccacttgggc gaggtttagt tccacgtgtc tggtgaagac cgcatagttg cagagacgct   6060
ggaagaggta gttgagcgtg gtggcgatgt gctcggtgac aaagaaatac atgatccagc   6120
gacgaagcgg catctcgctg atatcgccca gggcttccaa ccgttccatg gcttcgtaaa   6180
agtccacggc gaagttgaaa aactgggagt tgcgagcgga cacggtcaac tcctcctcca   6240
gaagacggat gagctcggcg atggtggcgc gcacttcgcg ctcaaaggct cccgggatct   6300
cttcctcctc ttcttcttcc aactcttcct ccactaacat ctcttctact tcctcctcag   6360
gcggcggggg tggaggaggg ggcgcgcggc gacgccggcg acgcacgggc agacgatcga   6420
tgaagcgttc gatcacttct ccgcggcggc gacgcatggt ctcggtgacg gcgcgcccgt   6480
cctccctggg tcgcagagtg aagacgccgc cgcgcagctc cctgaaatgg tgactgggag   6540
ggtccccgtt tggtagggac agggcactga tgatgcatct tattaattgc cctgtaggga   6600
ctccgcgcaa ggacctgagc gtctcgagat ccacgggatc tgaaaatctc tgaacgaagg   6660
cttcgagcca gtcgcagtcg caaggtaggc tgagcactgt ttcttcgggg cgggctgctg   6720
agctagaggg ttgtacgatg ctgctggtga tgaagttaaa ataggcagtt ctgagacggc   6780
ggatggtggc gaggagcacc aggtctttgg gtccggcttg ctggatgcgc aggcggtcgg   6840
ccattcccca tgcattatct tggcacctgg ccagatcttt atagtagtct tgcatgagtc   6900
gctccacggg cacttcttct tcgcccgctc tgccgtgcat gcgtgtgagt ccgtaccctc   6960
tctgtggttg gacgagcgcc aggtcggcaa cgaccctttc ggctagaatg gcttgctgca   7020
cctgggtgag ggtgttctgg aaatcatcaa agtccacaaa gcggtggtag gcccccgtgt   7080
tgatggtgta ggagcagttg gacatgaccg accagttgac tgtctggtgt cctggtcgta   7140
cgagttccgt gtacctgagc cgcgagtatg cgcgggagtc gaagatgtaa tcgttgcagg   7200
ttcgcaccag gtactggtag ccgatgagga agtgaggcgg cggctggcgg tagagaggcc   7260
atcgttcggt ggcgggcgcg ccgggcgcta ggtcttctag catgagacgg tggtatccgt   7320
agacgtacct ggacatccag gtaataccgg cggcggtggt ggaggcgcgc ggaaactctc   7380
gcacgcggtt ccagatgttg cgcagcggca tgaagtagtt catggtgggc acggtctggc   7440
ccgtgaggcg cgcgcagtca ttgatgctct agatacgggc aaaaacgaaa gcgttgagcg   7500
gttcccttcc gtggcctgga ggaacgcgaa cgggttaggt cgcagcgtac cctggttcga   7560
gactaaagaa agcgagcaac tcgaaccggc agagtcgcgg ctaacgggta ttggcaatcc   7620
cgtctcgacc caagccagca aatccaggat acggatgggg gcccctttg tttttcaggg   7680
catgagtcac cggttaaggt ttacaacggc tgtttcatgc ctttagaagt ggctcgcgcc   7740
cgtagtctgg agaatcaatc gccagggttg cgttgcggcg tgccccggtt cgagcctgca   7800
gcttgagtcg gccggtgacc gcggcaaacg agggcgtggc ggccccgtcg tttctaagac   7860
cttgctagcc gacctctcca gtttacggga acgagccccc ttttattttt tttgtttttg   7920
ccagatgcat cccgtactgc ggcagatgcg cccacagccc ccacagcagc agcagcaggc   7980
tggcctacct tctctacctc agccgctacc tgcaactacc gcggtggccg ctgtaagcgg   8040
```

ggccggacag caggcggctc ctcaatatga attggacttg gaagagggcg agggattggc 8100
aagattgggg gcgccctcgc ccgagcgcca cccgcgggtg cagatgaaaa aggacgttcg 8160
cgaatcttac gtgcccaagc agaatctgtt cagagacaga agcggcgagg agcccgagga 8220
gatgcgcgcg tcccgtttta acgcgggtcg cgagctgcga caaggactgg atcgaaaacg 8280
ggtgttgagg gatgatgatt ttgaggtgga tgaaatgaca gggatcagcc ccgctcgcgc 8340
tcacgtggct gcagctaatc tggtgacagc ttatgagcag accgtgaagg aggaaagcaa 8400
cttccagaaa tcattcaata accacgtgcg caccctgatc gcacgcgagg aggtgaccct 8460
gggcctgatg cacctgtggg atctgctgga agccatagtg cagaacccca ctagcaaacc 8520
cctgactgct caactgtttc tggtggtgca gcacagcagg gataatgagg cattcagaga 8580
ggcgctgctg aatatcactg aacctgaggg gagatggctg ctggatctgg tgaatatcct 8640
gcagagcatt gtagtgcagg aacgcagctt gcctttgtcc gagaaggtgg cggcgatcaa 8700
ttactctgtg ctgagtctgg gcaaatacta tgccaggaag atctacaaaa ccccttacgt 8760
gcccatagac aaggaagtga aaatagatgg gttttacatg cgcatgaccc tgaaagtgct 8820
aaccctgagc gatgacttgg gagtgtaccg caacgacagg atgcaccgcg cggtgagcgc 8880
cagcaggagg cgcgagctga gcgacaaaga attaatgcac agcttgcaac gagccctgac 8940
gggagccggg acggaggggg agaactactt tgacatgggt gcagacttgc attggctgcc 9000
tagtcgcagg gcattggaag cggcaggcga tgggccctat gtagaggaag tagtagacga 9060
ggacgatgag gagggcgagt acctggaaga ctgatggcgc gacccgtatt tttgctagat 9120
ggaacaggcg ccggaccctg cgatgcgggc ggcgctgcag agccagccgt ccggcattaa 9180
ttcctcggac gattggaccc aggccatgca acgcatcatg gcgctgacga cccgcaaccc 9240
cgaagccttt agacagcagc ctcaggccaa ccgcctttcg gccatcctgg aggccgtggt 9300
gccctctcgc tccaacccca cccacgagaa ggttctggcc atcgtgaatg ccctggtgga 9360
gaacaaggcc atccgctccg atgaagccgg gctggtatac aacgccttgc tcgagcgcgt 9420
ggctcgctac aacagcagca atgtccagac taacctggac aggatggtga ccgacgtgcg 9480
cgaggccgtg tcccagcgcg aacggttcca tcgcgagtct aacctgggtt ccatggtagc 9540
gctgaacgct ttcctcagtt cccagcctgc caatgtgccc cggggacagg aagactatac 9600
caactttatt agcgccctga gactcatggt agccgaggtt cctcagagcg aggtgtacca 9660
gtccggtcca gactactttt tccagacaag caggaacggt atgcagacag tgaacttaag 9720
ccaggctttc aagaacctgc aagggctgtg gggagtccaa gctccagtgg gcgacagggc 9780
gaccgtgtcg agcctgttga ctccaaattc ccgtttgctg ctgctgctgg tgtcccccctt 9840 cactgacagc ggcagcataa acagaaactc ctacttgggc tacctgataa acttgtatcg 9900
cgaagctata ggtcaggccc acgtggacga acagacctat caggagatca ctaatgtgag 9960
tcgcgctctg ggccaggacg accctggaaa cctggaagct actctaaact ttctgctgac 10020
caaccgctcg caaaaaatcc ctcctcagta tacattaact gcggaggagg aacggatctt 10080
gagatacgtg cagcagagcg tgggtctgtt cctgatgcaa gagggtgcga cccctagcgc 10140
cgcgcttgat atgacagcgc gcaacatgga gcccagcatg tatgccagca acagaccatt 10200
cattaataaa ttgatggatt acttccatcg cgcggccgct atgaactctg attacttcac 10260
caatgctatt ctgaaccccc attggctgcc tccgcctggt ttttatactg gcgagtatga 10320
catgcctgac cccaacgatg ggttcttgtg ggacgatgtg gacagcgtgg cgttctcgcc 10380

-continued

```
taccgctcct cgtacttttt ggaagaagga aggtagtgac agaagaccct cctccgtgct  10440
gtcaggacgt gagggtgctg ccgcggcggt ccccgatgct gcaagcccct ttcccagtct  10500
gccattttca ctaaacagcg tgcgcagtag cgagctgggg agaataaccc gccctcgctt  10560
gctgggcgag gacgagtatt tgaatgactc cctactgaga cccgagcggg aaaagaactt  10620
ccctaataat gggattgaaa gcctggtgga taagatgagc agatggaaga cctatgccca  10680
ggagcacaga gatgagccta gaatcttggg tcctacagta ggcacccgca gacgccagcg  10740
ccatgataga cagcggggtc tggtgtggga cgatgaggat tctgcagatg acagcagcgt  10800
gttggacttg ggcgggaggg gaggtgtggg caacccgttc gcacacttgc gtccccgtat  10860
tggacgcatg atgtaaaagt gaaaataaaa aaggaactca ccaaggccat ggcgaccagc  10920
gtgcgttcgt tctttctgtt gttgtatcta gtatgatgag gcgcaccgtg ctaggcggat  10980
cggtggcgta tccggagggt cctcctcctt cgtacgaaag cgtgatgcag caggtggcgg  11040
cggcggcgat gcaacccccc ttggaggctc cttacgtgcc cccgcggtac ctggcaccta  11100
ccgaggggag aaacagcatt cgttattcgg aactcacacc cttgtatgac accacccggt  11160
tgtacctggt ggacaacaaa tcggcggaca ttgcctcgtt gaactatcag aacgaccaca  11220
gcaacttctt gacaacggtg gtgcagaaca atgactttac ccccacggag gccagcaccc  11280
agaccatcaa ctttgacgag cgctcccggt ggggcggtca gctgaagacc atcatgcaca  11340
ccaacatgcc caacgtgaac gagttcatgt ttagcaacaa gttcagggct agggtgatgg  11400
tgtccagaac cacacctaaa gaggtgacag tcacaacaga ctatgatggt agtcaggaca  11460
tcttggaata cgagtgggtt gactttgagt taccagaagg caacttctct gccaccatga  11520
ccatagacct gatgaataat gcaattgttg ataattacct aaaagtgggt agacagaatg  11580
gggtactgga gagtgacata ggtgttaagt ttgacactag gaactttagg cttggttggg  11640
acccagtgac agagttggtc atgcctgggg tctacaccaa tgaagctttc catcctgaca  11700
tagtcctact acctggctgc ggagtggact tcactgagag ccgcctcagt aatctgctag  11760
gcattagaaa gaaacagcca ttccaggaag ggttccagat catgtatgag gatctggagg  11820
gtggtaacat ccccgccctg cttgatgtaa atgcatatga gaagagcaag gaagataata  11880
caaccaccac aaatgaagct gtggccgcgg cttcatctac tgaagccaaa gctgtggtag  11940
atgcttccac ttcaacagaa aacaccactg atgaaaaagt caccagggga gatacatttg  12000
ccacccctga acaagagaag gcagctgagg cagagtctga tattatgctt ctgtccaccg  12060
atgaaaacga aactaaaaaa caactggtta ttcgagcggt gaccaaggat agtaaggaca  12120
ggagttataa tgtattgtca gatggaaaga acacagctta ccgtagttgg tacctggcat  12180
acaattatgg cgaccgtgag aaaggggtgc gttcttggac actgcttacc acctcggatg  12240
tcacctgcgg cgtggagcaa gtctattggt cgctaccaga tatgatgcaa gatccagtca  12300
cctttcgctc cacacgccaa gttagcaact acccagtggt gggcgcagag ctgctcccag  12360
tgcattccag aagcttctac aacgagcaag ccgtctactc gcaacagctc cgccagtaca  12420
cctcgctcac gcacgtcttc aaccgcttcc ccgagaatca gatcctcgtc cgcccgcccg  12480
cgccaaccat taccaccgtc agtgaaaacg ttcctgctct cacagatcac gggaccctgc  12540
cgctgcgcag cagtatccgg ggagtccagc gcgtgaccgt tactgacgcc agacgccgca  12600
cctgtccata cgtatacaag gccctgggca tagtcgcgcc gcgcgtcctt tcaagccgca  12660
ctttctaaaa aaatgtccat tctcatctcg cccagtaata acaccggttg ggcctgcgc   12720
acacctagca agatgtatgg aggcgctcgc agacgctcca ctcagcaccc tgtgcgcgtg  12780
```

cgcgggcatt tccgcgctcc ctggggcgcc ctcaagggac gctctcgtac taggaccacc 12840
gttgacgatg tgatcgacca ggtggtcgcc gatgcacgta actatacccc cgcagccgca 12900
cctgcatcca ccgtggatgc ggtcattgac agcgtggtag ccgatgcgcg cgcctatgct 12960
cgcgccaaga gcaggaggcg gcgtattgcc aggcgtcacc gagctactcc agccatgcga 13020
gctgcaagag ctttattgcg gagagccaga cgtgtggggc gaagagccat gcgtagagcg 13080
gccagacgcg cggcttcagg tgccagcgca ggcagggtcc gcaggcgcgc ggctacggcg 13140
gcagcggcgg ccatcgctag catgaccaaa ccacgaagag gcaatgtgta ttgggtgcgc 13200
gacgccgcca ccggccagcg cgtgcccgtg cgcacacgcc cccctcgcac ttagaagata 13260
ctgagcagtc tccgatgttg tgtcccagcg gcgagatgtc caagcgcaaa ttcaaggaag 13320
agatgctcca ggtcatcgcg cctgagatct acggtcctgc ggtgaaggat gaaaaaaagc 13380
cccgcaagat caagcgggtc aaaaaggaca aaaaggaaga agatggtgat gatgggctgg 13440
tggagtttgt gcgcgagttt gccccaagga ggcgcgtgca gtggcgcggg cgcaaagtgt 13500
ggccggtgtt gagaccgggg accacagtgg tctttacgcc aggcgagcgc tccagcaccg 13560
tttccaaacg ctcttatgat gaggtgtacg gggacgatga tattctcgag caggcggctg 13620
atcgccttgg cgagtttgca tatggcaaac gcagccgctc gggagccaag gaagaggcat 13680
tgaccatccc cttggatcat ggaaatccca ccccaagcct caaacccgtg accctgcaac 13740
aagtgctgcc cacgccgcca cgcaagggca tcaagcgcga gggcgaggat ctgtatccca 13800
ccatgcagct gatggtgccc aagcgccaga agctggaaga cgtgctggag aaaatgaaag 13860
tggatcctga aatccagcct gaagtcaaag tgaggccaat caagcaggtg gcgcccggtt 13920
tgggggtaca aaccgtggat atcaagatcc ccaccgagtc catggaaatt caaaccgaac 13980
ccatgaagcc cacctccagc accattgagg tgcagacgga tccttggatg cccgcgcctg 14040
ctcctgttac cactactact cgaagaccta gaagaaagta tggttcagcc aacctgataa 14100
tgccaaacta tgctctgcat ccatcaatca tacccactcc tggctaccgc ggcactcgct 14160
actaccgcag tcacagcacc cgccgacgta aagcacctgc cacccgccgc cgtcgccgcc 14220
gccgtgccac tagcaaactt acccccctcgg ctatggtgcg gagagtgtac cgtgatgggc 14280
gcgcagctcc tctgacactg ccgcgcgcgc gctaccatcc tagcattgcc atttaacaac 14340
tctgcctcct tgcagatatg gccctcactt gccgccttcg tattcctatt gctggctacc 14400
gcggaagaaa gtcgcgccgt agaagagcag ggttgtctgg gagcgggatg cgtcgccacc 14460
ggcggcggcg cgccatcagc aaacggttgg ggggtggatt tcttcccgct ttgattccca 14520
tcatcgccgc ggcgatcggc gcgataccag gcatagcttc cgtggcggtg caggcctcgc 14580
agcgccactg acattggaaa aagatatctt ataaataaaa atagaatgga ctctgacgct 14640
cctggtcctg tgatatgttt ttgtagacga gatggaagac atcaattttt catccctggc 14700
tccgcgacac ggcacgcggc cgtatatggg cacctggagc gacatcggca acagccaact 14760
gaacgggggga gccttcaatt ggagcagtct atggagcggg cttaaaaatt ttgggtccac 14820
tataaagact tatgggaaca aagcttggaa cagcagcaca gggcatgcgc tgagacaaaa 14880
gcttaaagat cagaatttcc aacagaaggt ggtcgatggt atcgcctctg gaatcaatgg 14940
ggtggtagat ctggccaacc aggccgtgca gaaacagatt aacagtcgcc tggacccggc 15000
tcccccagct cctattcatg agttaatgca agtggaggaa gagctccctt cattggaaaa 15060
gcggggcgat aagcgacctc gtccagatat ggaggaaacg ctgctgacca aggtggatga 15120

-continued gccgccctcc tatgaagagg ctgtaaaact gggaatgccc actacaaagc ccattatgcc 15180
tctggccact ggagtgatga agccatctca gtctaaacct gcagttgctg ctacattgga 15240
cttgcccgct cccgtggcca cccccaaacc tgtcgccgcc ccgaagccca ccgccgtgca 15300
acccgtggcc gtggccagac cgcgtcccgg tggtcggccg aatgcaaact ggcagagcac 15360
tctgaacagc atcgtgggtt tgggagtgca cagtgtgaag cgccgtcgct gctattgatt 15420
aaatatggag tagcgcttaa cttgcttgtc tgtgtgtgta tatgtcgatg ccgcccgccg 15480
tgctacagca aagagagaag gagaagaggc gccgctgagt tcctttcaag atggccaccc 15540
catcgatgct gccccagtgg gcgtacatgc acatcgccgg acaggacgct tcggagtacc 15600
tgagtccggg tctggtgcag ttcgcccgcg ccacagatac ctacttcaat ctggggaaca 15660
agtttaggaa ccctaccgtg gctcccaccc acgatgtgac caccgaccgt agccagcgcc 15720
tgacgctgcg ctttgtgccc gttgaccggg aggacaatac ctactcctac aaagtcagat 15780
acaccctggc tgtgggagac aacagggtgt tggatatggc cagcacctac tttgacatca 15840
ggggcgtgtt ggacagagga cctagcttca aaccatactc tggcactgcc tacaactccc 15900
tggctccaaa aggagctcca aactccagtc agtggcaaca aaaggaaaac aatggtcaag 15960
gtgatgcaaa gactcacacc tatggtgtag ctgccactgg aggtattgac attgacaaaa 16020
atggtcttca aattggaatc gatgaaacta aagaagataa taacgaaatt tatgcagaca 16080
aaacattcca acctgaacct caaattggag aagaaaactg gcaagatagc gaaaactatt 16140
atggaggcag ggctcttaaa ccggaaacca agatgaagcc ttgctatggt tccttcgcta 16200
gaccaactaa tgcaaaggga ggtcaagcca aaattaaacc agctcaagag ggtcaacagt 16260
ctatagatta tgacatagac ctggctttct ttgatattcc aagcactggc ggaggcaatg 16320
gcacaaatgt aaatgacaag ccagatatgg ttatgtatac tgaaaatgta aatctggaaa 16380
ctccagacac tcatcttgtt tacaagccag gaacttcaga tgacagttcc gaggccaatt 16440
taactcagca agccatggct aacagaccca actatattgg gtttagagat aactttattg 16500
gcgtcatgta ctacaacagc actggcaaca tgggagtgct tgctggtcaa gcatcccagc 16560
taaatgctgt ggtggacctg caagacagaa acaccgagct gtcttatcag ctattacttg 16620
actctctggg cgacagaacc aggtatttta gtatgtggaa tcaggcggtg gacagctatg 16680
atcctgatgt gcgcattatt gaaaaccatg gtgtggaaga tgaattgcca aactattgct 16740
tcccattgga cggagctggc actaatgctg tttaccaagg agttaagaca aaagaggata 16800
ataatggcga atgggaaaca gacacaaatg ttgcatcgca gaatcagata tgcaagggca 16860
acatatatgc tatggagatc aacctgcaag ccaacctgtg gaaaagtttc ctttactcca 16920
acgtggctct gtacctacca gactcctaca agtacactcc atccaacgtg acactcccta 16980
ccaacactaa cacctatgac tacatgaatg gcagggtggt gtctccatcc ctggtggatg 17040
cctacattaa cattggcgcc aggtggtctc tggatgccat ggacaatgtc aacccctttca 17100 accaccaccg caatgccggc ctgcgctacc ggtccatgct tctgggcaac ggccgatacg 17160
tgcccttcca catccaagtg ccccagaaat tcttcgctat caagaacctg ctgcttctcc 17220
caggctcata cacctacgag tggaacttcc gcaaggatgt caacatgatc ctgcagagtt 17280
cccttggcaa tgacctcaga accgatgggg ccaccatcca gtacaccagc atcaatctct 17340
atgccacctt cttccccatg gctcacaaca ctgcctccac cctggaagcc atgctgcgca 17400
atgacaccaa tgaccagtcc ttcaatgact acctctcagc tgccaacatg ctttacccca 17460
tccctgccaa tgccaccaac gtgcccatct ccatcccatc tcgtaactgg gctgccttca 17520

```
ggggctggtc tttcacccgc ctcaagacca aggagacccc atctctggga tcagggttcg  17580
atccctactt cgtctactca ggctccattc catacctgga tggaactttc taccttaacc  17640
acactttcaa gaaagtctcc atcatgtttg actcttctgt cagctggcca ggcaatgaca  17700
ggctgctgac tcccaatgag ttcgaaatca agcgcactgt tgatggggaa gggtacaatg  17760
tggcacaatg caacatgacc aaagactggt tcctggttca gatgctctcc cactacaaca  17820
ttggctacca gggcttctac atcccagaag gatacaagga ccgcatgtac tccttcttca  17880
gaaacttcca gcccatgagc cgccaggtgg tcgatcaggt caactacaaa gactacatgg  17940
cagtcaccct tgcctatcag cacaacaact ctggctttgt gggctacctc gcgcccacca  18000
tgcgacaggg ccaaccctac cctgctaact acccataccc gctcattggc aagactgcag  18060
tcaacagtgt cacccagaaa aagttcctct gcgacagggt catgtggcgc atccccttct  18120
ccagcaactt catgtccatg gggggccctta ccgacctggg gcaaaacatg ctttatgcca  18180
actccgccca cgcgctagac atgaatttcg aagtagaccc catggatgag tccacccttc  18240
tctatgttgt cttcgaagtc ttcgacgtgg tcagagtgca ccagccccac cgcggcgtca  18300
tcgaagctgt ctacctgcgc accccttct cagctggtaa cgccaccaca taagcgcctt  18360
gcttcttgca agtggctgca gcagcatggc ctgtggatcc tccactggat ccaatgagca  18420
agagctcagg gccatcgcca tagacctggg ctgtggaccc tatttcctgg gaacctttga  18480
caagcggttt ccaggcttca tggctcctga caagctcgcc tgtgccattg tcaacacggc  18540
agggcgcgag actggtggtg agcactggct ggcttttgga tggaaccccc gctccaatac  18600
ctgctatctc tttgacccgt ttgggttttc agacgagcgc ctcaagcaga tctatcaatt  18660
cgagtacgag gggctcctgc gccgcagtgc cctggctact aaggaccgat gcatcactct  18720
ggaaaagtct acccagaccg tgcagggtcc gcgctcggct gcctgcgggc tcttctgctg  18780
catgttcctc catgcttttg tgcactggcc cgaccgcccc atggacaaca accccaccat  18840
gaatttgctg acgggggtac ccaacaacat gctccaatcg ccccaagtag agcccaccct  18900
gcgccacaac caggaggcac tctatcgctt cctgaactcc cactcatctt actttcgttc  18960
taaccgcgcg cgcattgaga aggccactgc cttcgatcga atgaataata acatgtaaac  19020
caaattgtgt gtggctcaaa taaacagcac tttattgttt acatgcactg aggctctggg  19080
atgatcattt tttaaaaatc gaaggggttc tggcgggaat cagcatggcc agatggcagg  19140
gacacgttgc ggaactggaa cttgttctgc cacttgaact cgggaatcac cagcctggga  19200
actggaatct ctggaaaggt atcttgccat agctttctgg tcagttgcag agcgccaagc  19260
aggtcaggag cagatatctt gaaatcacag ttggggccag aattctgggc gcgggagttg  19320
cggtacactg ggttgcagca ctggaacacc ataagggcag ggtgtctcac gctcgccagc  19380
acggtctcgt cactgatgca agacacatcc aggtcttcag cattggccat tccaaagggg  19440
gtcatcttgc aggtctgtct gcccatcacg ggagcgcagc caggtttgtg gttgcaatca  19500
caatgaaggg ggatcagcat catcttggcc tggtcggggg taatccctgg gtaaacagcc  19560
ttcatgaagg cttcatactg cttgaaagct tcctgggctt tggttccctc ggtgtagaac  19620
actccacaag acttgctgga aaactgatta gtagcgcagt tggcatcatt cacacagcag  19680
cgggcgtcgt tattagccag ctggaccaca ttcctgcccc agcggttctg ggtgatcttg  19740
gctcgatctg ggttctcctt caacgcgcgc tggccgttct cgctcgccac atccatctca  19800
atgacatgtt ccttctggat catgatgttg ccatgcaggc atctaatctt gccttcataa  19860
```

tcagtgcagc catgaggcca cagcgcgcac ccggtgcact cccaattgtt atgggggatc 19920
tgggaatggc tatgaaccag cccttgcagg aatcttccca tcatcacagc cagggtcttt 19980
atgctggtaa aggtcagcgg gataccgcgg tgctcctcgt tcacatactg ctggcagatg 20040
cgtctgtagt gctcggcctg ctcgggcatc agcttgaaag aggttttcaa ctcattatcc 20100
agcctgtatc tctccatcat gatggacatt acttccatgc ccttctccca ggcagaaaca 20160
atagggagac tcaggggatt cttgacagta gagacaacct tacttaaggg gtcatcactg 20220
ccaatctttt cgatgcttct cttgccatcc ttctcggtga tgcgcaccgg cgggtagctg 20280
aatcccacag ccaccaactg agcctcttcc ctttcgtctt cgctgtcttg actgatgtct 20340
tgcagaggaa catgtttggt tttcctgggt ttcttcttgg gcggcagctc tggaggactc 20400
tggctccgtt ccggagaccc catggatgag cgagagttgt cgctcaccac ttggatctgg 20460
ctgcctgtag aagaactgga ccccacgcgg cggtaggtgt tcctcttggt aggcagaggt 20520
ggaggcgacg ggctccggtc cggtctgggt ggcggatggc tggcggagcc ccttccgcgt 20580
tcgggggtgc gctccagatg gcggtcgtct gactgacctc cgcggctggc cattgtgttc 20640
tcctaggtag agaaacaaga catggagact cagccatcgc tgccatcgcc atccaccacc 20700
acaagcaccg ccgaggagga ggagtgttta accaccccac catgcagccc cgctaccacc 20760
accagcaccc ttgaaagcga ggtcgacacg gtcgtggagg atttacaggc tatggaagat 20820
attgaggcag ctgtcgagca agaccccggc tatgtgacac cggcggagca tgatgaggat 20880
ctagcgcgct ttctcgacgg tgtggagaaa gcgaaacaag atgaggacga ggaagaggca 20940
gaagcacaac catcggtggc cgactacctc accggcctag ggctagaaga cgtgctgctt 21000
aagcatcttg caaggcagac agtcatagtc aaagacgccc tgctagagcg ctccgaggtg 21060
ccactcagtg tggaagacct cagtcgcgcc tatgagctaa acctcttctc gcctcgcaag 21120
ccccccaagc gtcagcccaa cgggacctgt gagcccaatc cgcgcctcaa cttctatcca 21180
gccttcactg tgcccgaagt actagctacc taccacatct tttcaagaa ccaaaagatc 21240 cccatctcct gccgcgccaa tcgcacccgc gcagatgccc tactcaactt ggggcccggc 21300
gctcgcatac ctgatatcgc ttccttggaa gaggttccta agatctttga gggtctgggc 21360
aatgaggaaa ctcgggcagc aaacgctctg caaagagaaa cagatgatgg tgaacaccac 21420
agcgctctgg tggagctcca gggcgacaac gctcgtcttg cagtcctcaa acgcagcatc 21480
gaggtcaccc atttcgccta ccccgcactt aatctcccac ccaaagtcat gagctcggtc 21540
atggacacgt tgctcatgaa gcgcgcgagc cccatctccg aggatcagaa catgcaggac 21600
cccgatgcct cagatgaagg caagcctgta gtcagcgacg agcaactggc tcgctggcta 21660
ggctctgact ccccccagtc tttggaggag cggcgcaagc ttatgatggc agtggtcctg 21720
atcacagcgg agctggagtg tctccgccgc ttcttcactg acccagagac cctgcgcaag 21780
cttgaggaga acctgcatta cacattcagt catgggttcg tgcgccaggc gtgcaagatc 21840
tccaacgttc aactcaccaa cctggtctcc tacctgggca tcttgcatga aaaccggctg 21900
gggcagaacg tgctccacac caccctgaag ggggaggccc gccgcgacta tatccgcgac 21960
tgtatctacc tctacctatg ctacacctgg caaagcggga tgggtgtgtg gcaacagtgc 22020
ttggaagagc aaaatctaaa agagctggaa aagctgcttc agaaatctct taaatctctg 22080
tggaccgggt tcgatgagcg gaccaccgct tcggacatgg ccgatattat cttccccgag 22140
cggctcagac acactctgcg cgacgggctg cctgactttg ccagccagag catgctacaa 22200
aactttaggt cattcatctt ggaacgctcc gggatcctgc ccgccacttg ctgcgcactg 22260
ccctccgatt ttgtgcccat cacctaccgg gagtgccccc cgccgctatg gagccactgc 22320
tacctgttcc gcctggccaa ctacttggcc taccactctg atgtgataga agatgttagt 22380
ggcgaagggc tcctggagtg ccactgccgc tgcaacctct gcacccccca ccgctccctc 22440
gcctgcaatc cccagctgct gagcgaaacc cagatcatcg gcaccttcga gttgcaaggt 22500
cccagcggcg aaggcgaggg gtcctctccg gggcaaagtc tgaaactgac tccggggcta 22560
tggacctccg cttaccttcg caagttcgcc cccaaagact accacccccta tgagatcagg 22620
ttttatgaag accaatcaca gccccccaag gccgaactga cggcctgcgt catcacccag 22680
ggggcaatct tggcccaatt gcaagccatc caaaaatccc gccaagaatt tttgctgaaa 22740
aagggacacg ggatctatct agacccccag accggtgagg agctgaatac acgcttccct 22800
caggatgccc cgaggaggca agagaatgaa agttcagatg ccgcccgagg aggagctgga 22860
agactgggac agtcaggcag aggaggaaga ctgggacagc caggcagaag aggaggacag 22920
cctggaggag gacagtctgg aggaaggcga ggagcccaag gaagaggcag ccgccgccag 22980
accatcgtcc tcggcggtgg agacaagcaa ggtcccagac agcacggcta ccacctccgc 23040
tccagctcaa ggggccgctc ggcgacccaa cagtagatgg gacgagacgg gtcgcttcca 23100
gaaccccacc accgtcaaga ccggtaagca ggagcggcag ggatacaagt cctggcgggg 23160
gcataaaagt gccatcatcg cttgcttgca ggagtgtggg ggcaatatat cctttgccag 23220
acgctacctg ctattccatc acggggtgaa tttccccccgc aacatcttgc attactaccg 23280
tcacctccac agcccctact accagcagca agagacagca gaggaaacca gcggcaactc 23340
cgagagttag aaaaccagca gctaaaaaat ccacagcggc ggcagcaggt gcaggcggac 23400
tgaggatcac cgcgaacgag ccagctcaga ccagggagtt gaggaatcgg atctttccca 23460
ccctctatgc catattccaa caaagtcggg gtcaggaaca agaactgaaa gtaaaaaaca 23520
gatctcttcg ctcgctcacc cgcagttgtt tgtatcacaa gagcgaagac caacttcagc 23580
gcactctcga ggacgccgag gctctcttca acaagtactg cgcgctgact cttaaagagt 23640
agactgcgcg cgcttggcga gaaaaggcgg gaattacgtc acctcttggc cacacctgtg 23700
cttcattatg agtaaagaaa ttcccacgcc ttacatgtgg agctatcagc cccagatggg 23760
attggccgct ggcgccgccc aggactactc cacccgcatg aattggctca gcgccggtcc 23820
cgcgatgatc tcacgggtta atggtgtgag agagcaccga aaccagatac tcctagaaca 23880
gtccgccctc accgccactc cccgcaatca cctcaacccc cgtaattggc ccgccgccct 23940
ggtgtaccag gaaactcctg ctcccactac agtactactt cctcgtgacg cccaggccga 24000
agttcagatg actaactcag gtgtacagct ggcgggtggt gccaccctgt gtcgtcaccg 24060
gccaagaccg ggtataaagg gcctggtgat cagaggccga ggtattcagc tcaacgacga 24120
gtcggtgaac tcttcgcttg gtctgcgacc agacggcatc ttccaaatag ctggttgtgg 24180
gagatcttcc ttcactcctc gtcaggctgt cctgactttg gagagttcgt cctcgcagcc 24240
ccgctcgggc ggcatcggga ctctccagtt cgtggaggag tttactccct cggtctactt 24300
caaccccttc tccggttctc ctgggcttta cccggacgag ttcatcccga actacgacgc 24360
catcagtgaa gcggtcgacg gctacgatta atgtctaatg gtggcgcggc tgagctagct 24420
cgactgcgac acctagacca ctgccggcgc tttcgctgct ttgctcggga tctctgcgag 24480
ttcatctact tcgagtaccc tgacgaacat cctcagggac ctgcccacgg agttcggatt 24540
accattgaag ggctatcga ttctcacctg cttcggatct tcaccgctcg gccagtgcta 24600

-continued

```
gttgagcgca accagggcga caccaccatc tccctctgct gcatttgtga caaccccgga  24660
ttgcatgaaa gcttttgttg tcttctttgt actgagtata ataaaagctg aaattagaga  24720
ctactccgga ctctcttgtc gtctgaacaa caccaaccag acccttcact tcagcgggaa  24780
ccagactact cttcactgta aggcttataa ctataagtat cttacttgga tatacaaagg  24840
aacaccgttt gctgtggtaa acaggtgctc caacgacggt gttctcctca ccttcctagg  24900
caacttctcc aactttacct tttctgttcg cagaaacaag cttaccctcc ttcagcccta  24960
ctttcctggg atctatacct gcctcagtgg accttgcaac cacacttttc acctgattga  25020
aaactctacc cttaccttcc cagcgccaat ccctactaac agctcggagt ccaactcttc  25080
cattaccgct gatactaaca ctcctaaaac cggaggtgag ctccgcagcc ttccccccggc  25140
tgcagataac ccttgggtgg tagcgggatt tgtagcgcta ggaatagttg cgggtgggct  25200
cgcgttcgtc ctctgctacc tataccttac ctgctgctca tatttagtag tactgtgctg  25260
ttggtttaga aaatgggggc gctactaatc acacttgctt tactttcgct tttgggtctg  25320
agctcggcta atagcgagaa accaagctgt ctagaaacaa actctccaga ctgtgtggtt  25380
cctcatgggc tctcagaccc agctgatgat ccatgcttaa cttttgaccc agaaaaaaac  25440
tgctcggtga ctatgcagcc ctatgcttac atgtgcacat ctgttataaa gtgcggatgg  25500
ggctgtaaac cgattgaaat tacccacaaa ggcaaaacct ggaataatag tttgtttaac  25560
acatggcagc ctggagacga gcagtggtat acggccggcc actggtggag atgactgacc  25620
ccatggaaaa ctcctctgcc aacgacctgg acatggacgg ccgttcatct gagcagcgac  25680
tggtccagat gcgcattcgc cagaagcagg aacgcgccgc cagagagctc aaggatgcca  25740
ttgaaattca cctgtgcaag aagggcatct tttgcttggt taagcaagca aagatttctt  25800
atgaaatcac tgacaacgac caccgcctgt attatgagct cggtccacag cggcagaaat  25860
tcacctgcat ggttggagtc aaccccatag tcatcactca gcaggctgca gaaattaaag  25920
ggtgcatcca ctgttcctgt gattcccaag aatgcgtcca caccatagtc aagaccctct  25980
gcggccttcg agatcttctt ccaatgaact aacccccttcc cccaacccaa taaaacattg  26040
gttttaatca taataaaaaa tcacttactt taaatctgaa acagtgtctc cgtccaagtt  26100
ttcttgtagc accacttcac tcccctcttc ccagctctgg tactgcaagc cccggtgggc  26160
tgcaaacttt ctccacacct taaaagggat gtcaaattcc tcttgtccaa caatcttcat  26220
tgtctcttcc tagatgtcca caaagcgcgc gcgggtggaa gatgactttg accctgtcta  26280
cccatacgat gctgagctgg caccgtctgt acccttcatc gcccctccct tcgtttcgtc  26340
agacggattt caagaaaaac ccctgggagt tctgtcccta agactagcca acccagtcac  26400
tactaaaaat ggggaactca cacttaaact gggagatggg gtgggcatag actcagatgg  26460
aaacctcaca gcacagacag ttactaaagc aacatccccc cttactgttt ccaataacgc  26520
aattgcactt aacatggaca aacctttttta cagtagcaat ggaaaactat ccttacaagt  26580
tacatcacca ttaaagatag tcgactcttt aaatacattg gctattggct atgggcaagg  26640
cttaggacta aacaatagtg ctcttgctgt gcaattagca tctcccctta catttgacag  26700
caacagcaaa attaaaataa atttgggaag cgggccatta aaaattaatg cgaataaact  26760
gtcaattaac tgcctaaggg gtgtatatgt aacaactgac ggaacttcca ttgaaacaaa  26820
tataagctgg gcaaaaggaa tgaggtttga aggtaatgcc atggctgtaa acgttgacag  26880
caccaaaggt ctacaatttg gcactaccag cacagaatca ggagtcacta acgctttccc  26940
tatccagtta aagattggat ctggtcttag ttttgacagc acaggagcac ttgtagcttg  27000
```

```
ggataaggat aatgacaagc ttacactgtg gacaaccgct gacccatcac ctaattgtac  27060
catatataca gacaaggatg ctaaacttac actttgtctt acaaaatgtg gcagtcaaat  27120
actaggcagt gtttcagtac tggctgttaa agctggaacc ctacagccaa tcagtgaaaa  27180
aataggtact gctttggttt cactaaaatt taataacaac ggtgtattgt taagcaactc  27240
cacattaagt aatgaatact ggaactacag gaagggagat gtcacaccag ccgaagccta  27300
tactaatgct gtgggtttta tgccaaacat caaggcatat cctaaaaaca caaactctgc  27360
ctcaaaaagc cacattgtag gacaagtgta ccttaatgga gatgaaacta aaccaatgca  27420
tttaatcatt acatttaatg aaaccagtga tgaaacatgc acatattcca taacgttcca  27480
atggaaatgg aacattggaa catacaccag cgacaccctt gcaacaagct cctttacctt  27540
ttcttacatt gcccaagaat aaaaactgca gacaacaata aagtttaaat gttttattta  27600
aacagtttca cagaacccta gtattcaacc tgccacctcc ctcccaacac acagagtaca  27660
cagtcctttc tccccggctg gccttaaaaa gcatcatatc atgggtaaca gacatattct  27720
taggtgttat attccacacg gtttcctgtc gagccaaacg ctcatcagtg atattaataa  27780
actccccggg cagctcactt aagttcatgt cgctgtccag ctgctgagcc acaggctgct  27840
gtccaacttg cggttgctta acgggcggcg aaggagaagt ccacgcctac atgggggtag  27900
agtcataatc gtgcatcagg atagggcggt ggtgctgcag cagcgcgcga ataaactgct  27960
gccgccgccg ctccgtcctg caggaataca acatggcagt ggtctcctca gcgatgattc  28020
gcaccgcccg cagcataagg cgccttgtcc tccgggcaca gcagcgcacc ctgatctcac  28080
ttaaatcagc acagtaactg cagcacagca ccacaatatt gttcaaaatc ccacagtgca  28140
aggcgctgta tccaaagctc atggcgggga ccacagaacc cacgtggcca tcataccaca  28200
agcgcaggta gattaagtgg cgacccctca taaacacgct ggacataaac attacctctt  28260
ttggcatgtt gtaattcacc acctcccggt accatataaa cctctgatta aacatggcgc  28320
catccaccac catcctaaac cagctggcca aaacctgccc gccggctata cactgcaggg  28380
aaccgggact ggaacaatga cagtggagag cccaggactc gtaaccatgg atcatcatgc  28440
tcgtcatgat atcaatgttg gcacaacaca ggcacacgtg catacacttc ctcaggatta  28500
caagctcctc ccgcgttaga accatatccc agggaacaac ccattcctga atcagcgtaa  28560
atcccacact gcagggaaga cctcgcacgt aactcacgtt gtgcattgtc aaagtgttac  28620
attcgggcag cagcggatga tcctccagta tggtagcgcg ggtttctgtc tcaaaaggag  28680
gtagacgatc cctactgtac ggagtgcgcc gagacaaccg agatcgtgtt ggtcgtagtg  28740
tcatgccaaa tggaacgccg gacgtagtca ttctcgtact ttgagtggca aaaccttgct  28800
ctcgaacagc acacgtctcg tcgcctcctg tcccttctct tcgccttttc agtgtgatag  28860
ttgtaataca gccattcacg aagctcagtc agaagatctt cagcgtctgt tgtcaaaaac  28920
aatccatcca atctgattgc tttcaaaaca tcacaaacag tcgaataagc caaacccatc  28980
caggcaatgc aattattttg gttatccaca atgggagggg gcggaagaca tggaagaggc  29040
ataattaatt ttttaatcca atcgatcacg cagcacttca aaatgaagat cgcgaaggtg  29100
acacctttca cccccactgt gttgatgaaa aataacagcc aagtcaaaat tgatgcggtt  29160
ttcaaggtgc tcgactgtag catcaagcag agcttccaca cgcacgtcca caaataacag  29220
aatagcaaaa gcgggaggag gaagtaaatc ctcaatcatc atagtacagt ccatcaccat  29280
ccctaaataa ttttcatcct tccagccttg gactatattt ttaaactgct cttgtaaatc  29340
```

caaaccacac atgtggaaaa gttcccaaag agctccctca actaccattc ttaagcacac 29400
cttcatagtg acaaaatatc ttgttcctct gtcacctgca gcaaattaca aagtccaata 29460
ttaggatcta tgcccagaga tctaagctca tccctcaatt ccaactgtaa aaaggcttcc 29520
agatctgccc taacttgttc agccagtggg ctccctggaa taagcgtggg agaagccaaa 29580
ctgcaaaaca gacgcatgcc gccataatta ccaccagaaa acactacgtt acagtatgca 29640
tgctgattca ttccagtaat ttcatccagt gtattggata caaaaaaagg caagcactct 29700
ctcactaatt gtattatgga gacattatca cacaggtaac aatttaaagg ttgtggaaca 29760
ataatgcagt aagtaaccac ggtgcgctcc aacatggtta gtaattttta gttctgaaaa 29820
acaaaacata caaaaaatta tatcatactc atttggcgaa ctggtggaaa aatgacccta 29880
tctagcacaa ggcaagccac tggatcacca atgcgcccct cataaaacct gtcatcatga 29940
ttaaaaagca acaccgaaag ctcttcccta tgtcctgcat gaatgattct agctgaggaa 30000
tataagccag cgcaattagt atctgttaaa gaaaaaaaac ggccaacata gcctctagga 30060
attagcacac ttaatcttaa agacattact gccatccccc ttggatttaa ggtaaaattt 30120
acaggagcat agaaaatata ctgatttccc tcctgcacag gcagcatagc accaggtccc 30180
tctaaaaaca cacacaaagc ttctgcagcc atagcttacc gcgcaaacca ggcacagcag 30240
tgagctaaaa ggacaaagct ctaactcact agccaacctg gcgcacaata tatagttagt 30300
ccttacactg acgtaaccga ccaaagtcta aaaaccccgc caaaaataca cacacgccca 30360
aaaaacgccc cgtgagtcaa aaaacagttt cacttcctcg ttacacccaa aacgtcgtca 30420
cttccggatt cccacggttc gtcacttccg gagctccttg cttaattaac cccgcccaaa 30480
acgtcatcgt ccgcgtcacg ccgccccgcc ccgcgaccgt tgaccccggg ccaatcaccg 30540
cacatcccgc aaaattcaaa ctcgtctaat ttgcatattg gcacactgcc catataaggt 30600
atattattga tgatg 30615

<210> SEQ ID NO 15
<211> LENGTH: 3586
<212> TYPE: DNA
<213> ORGANISM: Artificial Sequence
<220> FEATURE:
<223> OTHER INFORMATION: BLY6 vector left end

<400> SEQUENCE: 15
caattgattt aaatcatcat caataatata ccttatatgg gcagtgtgcc aatatgcaaa 60
ttagacgagt ttgaattttg cgggatgtgc ggtgattggc ccggggtcaa cggtcgcggg 120
gcggggcggc gtgacgcgga cgatgacgtt ttggggagga ggagctatgt tgcaagtaat 180
cgtgggaaat gcgacgtaaa acgaggtgga gtttaaacac ggaagtagac aattttcccg 240
cgctgtttga caggaaatga tgtgtttttg ggcggatgca agtgaaaatt ctccattttc 300
gcgcgaaaac taaatgagga agtgaaattc tgagtaattc tgaggttatc acagggcgga 360
gtatttaccg agggccgagt agactttgac ccattacgtg gaggtttcga ttactctatt 420
tttcacctaa atttccgcgt actgtgtcaa agtccgtgtt tttacgcgat cgcgatggcc 480
tgtgtttgag cataatgtac tgaccaggtg taacgttcat ctgggtggtc gtagaggaat 540
gttcatgcca taccaatgca attttaatca tgtgaggatc ttgatggagc cgcaagcgtt 600
ttccagagtc agcttgactg gaatctttga catgtgtgtg gaagcatgga agatcttaag 660
atatgatgat accaaatcca gatgccgcgc atgcgagtgc gggggcaggc atgccaggtt 720
ccaacctgta tgtgtggagg tgaccgagga gctgagacca gatcatttgg tgctgacctg 780

-continued

```
cactggtgcg gagttcggtt ccagtggtga agaaactgat taaagtgagt agtgggatgt    840
tataaaagtg accataaggt gatgtgagat ggacaaattt ggtaattttt atgtattttt    900
gtcttgcagc catgagtggg agcgcttcct ttgaaggggg cgtctttagc ccttatctga    960
cggggcgtct gcctcattgg gctggagtgc gtcagaatgt gatggggtct acagtggatg   1020
gaagacctgt tcagcctgct aattcttcta ctctgactta tgctactatg acttcctcgc   1080
ctttggatgc agctgcagct gctgccgctt ctgctgccgc caacactgtt cgggggatgg   1140
ccttggagat ggggtattat ggaactgtag tggccaacac cactacccca aataacccca   1200
cagccttgaa tgaggacaag ctgctagttc tcatgtccca gctggagtct ttgacccaac   1260
gcctgggcga tctagctcag caggtgtccc agctgaagga gcagactcaa gctgcaatta   1320
ccactgcgag gggaaattaa aaaaattcaa agaatcaata aataaaccga gactttgttg   1380
attttaaagt gtgtcattct ttatttaatt tttcgcgcgc gatatgccct ggaccaccgg   1440
tctctatcat tgaggacacg gtggatcttt tctagaaccc gatagaggtg ggattggatg   1500
ttgaggtaca tgggcataag accatctttg gggtgtagat agctccactg cagagcctca   1560
tgctccgggg tggtgttgta tataacccag tcatagcatg ggcgttgggc atgatgttgc   1620
acaatatctt taaggaggag actaatggcc actgggagac ccttggtgta agtgtttaca   1680
aatctattaa gctgggacgg gtgcatccga ggtgagataa tgtgcatttt ggattggatt   1740
tttagattgg caatgtttcc ccctagatct ctcctgggat tcatgttatg caagaccact   1800
agaacagtgt atccggtgca cttagggaat ttgtcatgaa gtttggaggg gaaagcatga   1860
aaaaatttag acacaccctt gtgtcctccc aagttctcca tgcactcatc cataataatg   1920
gcaatgggcc catgggcggc ggcacgggcg aacacgttcc tgggatctga cacatcatag   1980
ttgtggtctt gggtcaggtc atcataagcc attttaataa acttggggcg gagggtgcca   2040
gattggggga tgaatgttcc ctcgggcccc ggaacatagt ttccttcaca tatttgcatt   2100
tcccaggctt ttagttcaga ggggggggatc atgtccacct gtggagcgat gaagaagacg   2160
gtctcggggg cgggggtgat taagtgggag gacagcaagt tcctaagcag ctgtgacttg   2220
ccacacccag tgggaccgta gatgacccct ataacaggtt gcagatggta gtttagggaa   2280
agacagctgc cgtcctctcg caggaggggg gcgacctcgt tcatcatttc cctcacatgc   2340
atgttttccc gcacaagttc cgataggagg cgctctccac ccagggaaag gagttcttga   2400
agagatgaga atttttcaa gggttttaag ccatcagcca tgggcatttt ggagagggtt   2460
tgttgcaaga gttcaaggcg gtcccagagt tcggtgatgt gttctatggc atctcgatcc   2520
agcatacttc ctcgtttctg gggttgggac ggctgcggga gtatggaacc aggcgatggg   2580
cgtccagcgc tgccagtgtc cggtccttcc acggtcgcag cgtccgagtc agggtcgttt   2640
ccgtcacggt gaaggggtgc gcgcctggct gggcgcttgc gagggtgcgc ttcaggctca   2700
tcctgctcgt ggagaaccgc tgccgttctg cgccctgtgc atcggccagg tagcaattaa   2760
ccatgagttc gtagttgagc gcctctgccg cgtggccttt ggcgcgcagc ttacctttgg   2820
aagtcttctg acaggtggga cagtagagac acttgagagc atagagtttt ggggctagaa   2880
agaccgattc tggggagtat gcatcggccc cacaggaggc gcagacggtt tcgcattcca   2940
ccagccatgt aagatcgggc tcgttggggt caaaaacaag ttttccgcca tgttttttga   3000
tgcgtttctt acctttgctt tccatgagtt cgtgccccg ttgggtgaca aagaggctgt   3060
ccgtgtcccc gtagactgac tttatgggcc tgtcctcgag cggcgtgccg cggtcctctt   3120
```

-continued

```
cgtagaggaa ctcggaccac tctgagacga aagcacgtgt ccaggccagc acaaaggagg   3180

ctatatggga ggggtagcga tcgttgtcaa ccaaggggtc tactttttcc aaggtgtgta   3240

aacacatgtc cccttcttcc acatccagga aggtgattgg cttgtaagtg tatgccacgt   3300

gacctggggt cccagacggg ggggtataaa agggggcggg tctctgctcg tcctcactgt   3360

cttccggatc gctgtccagg agcgccagct gttgaggtag gtattccctc tcgaaggcgg   3420

gcataacctc cgcactcagg ttgtcagttt ctaggaacga ggaggatttg atattgacag   3480

tgcctgccga gatgcctttc atgagactgt cgtccatttg gtcagaaaag acaatctttt   3540

tgttatcaag tttggtggcg aaggatccga tcgatcgatc catatg                  3586
```

<210> SEQ ID NO 16
<211> LENGTH: 4138
<212> TYPE: DNA
<213> ORGANISM: Artificial Sequence
<220> FEATURE:
<223> OTHER INFORMATION: BLY6 vector right end

<400> SEQUENCE: 16

```
ggatccccc ttactgtttc caataacgca attgcactta acatggacaa accttttac      60

agtagcaatg gaaaactatc cttacaagtt acatcaccat taaagatagt cgactcttta    120

aatacattgg ctattggcta tgggcaaggc ttaggactaa acaatagtgc tcttgctgtg    180

caattagcat ctccccttac atttgacagc aacagcaaaa ttaaaataaa tttgggaagc    240

gggccattaa aaattaatgc gaataaactg tcaattaact gcctaagggg tgtatatgta    300

acaactgacg gaacttccat tgaaacaaat ataagctggg caaaaggaat gaggtttgaa    360

ggtaatgcca tggctgtaaa cgttgacagc accaaaggtc tacaatttgg cactaccagc    420

acagaatcag gagtcactaa cgctttccct atccagttaa agattggatc tggtcttagt    480

tttgacagca caggagcact tgtagcttgg gataaggata atgacaagct tacactgtgg    540

acaaccgctg acccatcacc taattgtacc atatatacag acaaggatgc taaacttaca    600

ctttgtctta caaaatgtgg cagtcaaata ctaggcagtg tttcagtact ggctgttaaa    660

gctggaaccc tacagccaat cagtgaaaaa ataggtactg ctttggtttc actaaaattt    720

aataacaacg gtgtattgtt aagcaactcc acattaagta atgaatactg gaactacagg    780

aagggagatg tcacaccagc cgaagcctat actaatgctg tgggttttat gccaaacatc    840

aaggcatatc ctaaaaacac aaactctgcc tcaaaaagcc acattgtagg acaagtgtac    900

cttaatggag atgaaactaa accaatgcat ttaatcatta catttaatga aaccagtgat    960

gaaacatgca catattccat aacgttccaa tggaaatgga acattggaac atacaccagc   1020

gacacccttg caacaagctc ctttaccttt tcttacattg cccaagaata aaaactgcag   1080

acaacaataa agtttaaatg ttttatttaa acagtttcac agaaccctag tattcaacct   1140

gccacctccc tcccaacaca cagagtacac agtcctttct ccccggctgg ccttaaaaag   1200

catcatatca tgggtaacag acatattctt aggtgttata ttccacacgg tttcctgtcg   1260

agccaaacgc tcatcagtga tattaataaa ctccccgggc agctcactta agttcatgtc   1320

gctgtccagc tgctgagcca caggctgctg tccaacttgc ggttgcttaa cgggcggcga   1380

aggagaagtc cacgcctaca tgggggtaga gtcataatcg tgcatcagga tagggcggtg   1440

gtgctgcagc agcgcgcgaa taaactgctg ccgccgccgc tccgtcctgc aggaatacaa   1500

catggcagtg gtctcctcag cgatgattcg caccgcccgc agcataaggc gccttgtcct   1560

ccgggcacag cagcgcaccc tgatctcact taaatcagca cagtaactgc agcacagcac   1620
```

-continued

```
cacaatattg ttcaaaatcc cacagtgcaa ggcgctgtat ccaaagctca tggcggggac   1680
cacagaaccc acgtggccat cataccacaa gcgcaggtag attaagtggc gacccctcat   1740
aaacacgctg gacataaaca ttacctcttt tggcatgttg taattcacca cctcccggta   1800
ccatataaac ctctgattaa acatggcgcc atccaccacc atcctaaacc agctggccaa   1860
aacctgcccg ccggctatac actgcaggga accgggactg gaacaatgac agtggagagc   1920
ccaggactcg taaccatgga tcatcatgct cgtcatgata tcaatgttgg cacaacacag   1980
gcacacgtgc atacacttcc tcaggattac aagctcctcc cgcgttagaa ccatatccca   2040
gggaacaacc cattcctgaa tcagcgtaaa tcccacactg cagggaagac ctcgcacgta   2100
actcacgttg tgcattgtca aagtgttaca ttcgggcagc agcggatgat cctccagtat   2160
ggtagcgcgg gtttctgtct caaaaggagg tagacgatcc ctactgtacg gagtgcgccg   2220
agacaaccga gatcgtgttg gtcgtagtgt catgccaaat ggaacgccgg acgtagtcat   2280
tctcgtactt tgagtggcaa aaccttgctc tcgaacagca cacgtctcgt cgcctcctgt   2340
cccttctctt cgccttttca gtgtgatagt tgtaatacag ccattcacga agctcagtca   2400
gaagatcttc agcgtctgtt gtcaaaaaca atccatccaa tctgattgct ttcaaaacat   2460
cacaaacagt cgaataagcc aaacccatcc aggcaatgca attattttgg ttatccacaa   2520
tgggaggggg cggaagacat ggaagaggca taattaattt tttaatccaa tcgatcacgc   2580
agcacttcaa aatgaagatc gcgaaggtga cacctttcac ccccactgtg ttgatgaaaa   2640
ataacagcca agtcaaaatt gatgcggttt tcaaggtgct cgactgtagc atcaagcaga   2700
gcttccacac gcacgtccac aaataacaga atagcaaaag cgggaggagg aagtaaatcc   2760
tcaatcatca tagtacagtc catcaccatc cctaaataat tttcatcctt ccagccttgg   2820
actatatttt taaactgctc ttgtaaatcc aaaccacaca tgtggaaaag ttcccaaaga   2880
gctccctcaa ctaccattct taagcacacc ttcatagtga caaaatatct tgttcctctg   2940
tcacctgcag caaattacaa agtccaatat taggatctat gcccagagat ctaagctcat   3000
ccctcaattc caactgtaaa aaggcttcca gatctgccct aacttgttca gccagtgggc   3060
tccctggaat aagcgtggga gaagccaaac tgcaaaacag acgcatgccg ccataattac   3120
caccagaaaa cactacgtta cagtatgcat gctgattcat tccagtaatt tcatccagtg   3180
tattggatac aaaaaaaggc aagcactctc tcactaattg tattatggag acattatcac   3240
acaggtaaca atttaaaggt tgtggaacaa taatgcagta agtaaccacg gtgcgctcca   3300
acatggttag taatttttag ttctgaaaaa caaaacatac aaaaaattat atcatactca   3360
tttggcgaac tggtggaaaa atgaccctat ctagcacaag gcaagccact ggatcaccaa   3420
tgcgcccctc ataaaacctg tcatcatgat taaaaagcaa caccgaaagc tcttccctat   3480
gtcctgcatg aatgattcta gctgaggaat ataagccagc gcaattagta tctgttaaag   3540
aaaaaaaacg gccaacatag cctctaggaa ttagcacact taatcttaaa gacattactg   3600
ccatccccct tggatttaag gtaaaattta caggagcata gaaaatatac tgatttccct   3660
cctgcacagg cagcatagca ccaggtccct ctaaaaacac acacaaagct tctgcagcca   3720
tagcttaccg cgcaaaccag gcacagcagt gagctaaaag gacaaagctc taactcacta   3780
gccaacctgg cgcacaatat atagttagtc cttacactga cgtaaccgac caaagtctaa   3840
aaaccccgcc aaaaatacac acacgcccaa aaaacgcccc gtgagtcaaa aaacagtttc   3900
acttcctcgt tacacccaaa acgtcgtcac ttccggattc ccacggttcg tcacttccgg   3960
```

agctccttgc ttaattaacc ccgcccaaaa cgtcatcgtc cgcgtcacgc cgccccgccc 4020
cgcgaccgtt gaccccgggc caatcaccgc acatcccgca aaattcaaac tcgtctaatt 4080
tgcatattgg cacactgccc atataaggta tattattgat gatgatttaa atcatatg 4138

<210> SEQ ID NO 17
<211> LENGTH: 4563
<212> TYPE: DNA
<213> ORGANISM: Artificial Sequence
<220> FEATURE:
<223> OTHER INFORMATION: BLY6 vector middle fragment

<400> SEQUENCE: 17
ggatccatac agggcattgg aaagcagttt ggcaatggag cgcatggttt ggtttttttc 60
tttgtctgcg cgctctttgg cggctatgtt gagttggaca tattcgcggg ccagacattt 120
ccattgtgga aatatggtag ttaattcatc tgggacgatt ctgactttcc agcctctgtt 180
atgcagggta atcagatcca cactggttgc cacttctcct ctaagtggtt cattagtcca 240
gcatagtcgc ccccctttc gagaacagaa agggggtagg ggatctagca tgagttcgtc 300
tggggggtct gcatctatgg tgaaaatccc aggaaggaga tcttcgtcaa aatagctgat 360
ggtggcgggg tcatccagag acatttgcca ttctcgagca gccagagcgc gctcgtaggg 420
gttaagggga gtcccccatg gcatgggatg ggtgagtgca gaagcataca tgccacagat 480
gtcatagaca tagagcggct cttccagaat ccctatgtaa gtgggataac atcgcccccc 540
tctgatgctg gctcgcacat aatcatagag ttcatgtgag ggcgctagaa gacccgagcc 600
caggttggtg cggttgggtt tttctgctct gtagaggatc tggcgaaaga tggcatggga 660
gtttgatgag atggtgggtc tttggaagat gttgaaatgg gcatgaggca gtcccacaga 720
gtcccttatg aagtgagcat aggagtcttg cagtttggcc accagctcgg cggtgaccag 780
cacatccaaa gcacagtagt cgagggtctc tttgatgatg tcatagttag gttccccttt 840
cttttcccac agctcgcggt tgagaaggta ttcttcgcga tccttccagt actcttcgag 900
ggggaacccg tccttgtctg aacggtaaga acccagcatg taaaattgat tgacagcttt 960
gtaggcacaa cacccttct ccacggggag tgagtatgct tgcgcggctt tgcgcagaga 1020
ggtgtgagta agggcgaaag tgtccctgac catgactttg aggaactgat gcttaaagtc 1080
tatgtcatcg caggcccccct gctcccacag ttggaagtcc actcgctttt tgtaggcggg 1140
attgggcaaa gcgaaagtaa catcgttgaa taggatcttt ccagccctgg gcatgaagtt 1200
gcgagtaatg cgaaaaggct gaggcacttc tgccctgttg ttgataactt gggcagccaa 1260
gacgatctcg tcaaagccgt tgatgttgtg acccacaatg taaagttcta cgaagcgtgg 1320
gcgtcccttg atgtggggca gtttttaag ctcttcgtag gtcaagtcgt cagggtcagc 1380
gattccatat tgctccaaag cccagtcagg caggtgagga ttagcatgaa ggaaagaggt 1440
ccaaagatcc acggccagag ctgtttgtaa gcggtctctg tactgacgga aatgtcggcc 1500
taccgccatt ttttcaggag taacacagta aaaggtgcgc gggtcctttt cccagcgatc 1560
ccattgaagt tgcaaggcta ggtcgtgggc gaggttgacg agctgttcgt cccccgaaag 1620
tttcatgacc agcatgaaag ggacaagctg cttgccaaag gaccccatcc aggtgtaggt 1680
ttccacatcg taggtgagga agagcctttc tgtgcgagga tgagaaccga tcgggaagaa 1740
ctggatttcc tgccaccagt tggaggaatg gctgttgata tgatggaagt agaactccct 1800
acggcgcgcc gagcattcgt gcttgtgctt gtacagacgg ccacagtact cgcagcgctg 1860
cacgggatgc acctgatgaa tgagctgtac ctggcttcct ttgacaagaa atttcagtgg 1920

-continued

```
gaagttgagg cgtggcgtct gcatctcgtg ttaacccccg taattggccc gccgccctgg   1980
tgtaccagga aactcctgct cccactacag tactacttcc tcgtgacgcc caggccgaag   2040
ttcagatgac taactcaggt gtacagctgg cgggtggtgc caccctgtgt cgtcaccggc   2100
caagaccggg tataaagggc ctggtgatca gaggccgagg tattcagctc aacgacgagt   2160
cggtgaactc ttcgcttggt ctgcgaccag acggcatctt ccaaatagct ggttgtggga   2220
gatcttcctt cactcctcgt caggctgtcc tgactttgga gagttcgtcc tcgcagcccc   2280
gctcgggcgg catcgggact ctccagttcg tggaggagtt tactccctcg gtctacttca   2340
acccccttctc cggttctcct gggctttacc cggacgagtt catcccgaac tacgacgcca   2400
tcagtgaagc ggtcgacggc tacgattaat gtctaatggt ggcgcggctg agctagctcg   2460
actgcgacac ctagaccact gccggcgctt tcgctgcttt gctcgggatc tctgcgagtt   2520
catctacttc gagtaccctg acgaacatcc tcagggacct gcccacggag ttcggattac   2580
cattgaaggg gctatcgatt ctcacctgct tcggatcttc accgctcggc cagtgctagt   2640
tgagcgcaac cagggcgaca ccaccatctc cctctgctgc atttgtgaca accccggatt   2700
gcatgaaagc ttttgttgtc ttctttgtac tgagtataat aaaagctgaa attagagact   2760
actccggact ctcttgtcgt ctgaacaaca ccaaccagac ccttcacttc agcgggaacc   2820
agactactct tcactgtaag gcttataact ataagtatct tacttggata tacaaaggaa   2880
caccgtttgc tgtggtaaac aggtgctcca acgacggtgt tctcctcacc ttcctaggca   2940
acttctccaa ctttaccttt tctgttcgca gaaacaagct taccctcctt cagccctact   3000
ttcctgggat ctatacctgc ctcagtggac cttgcaacca cacttttcac ctgattgaaa   3060
actctaccct taccttccca gcgccaatcc ctactaacag ctcggagtcc aactcttcca   3120
ttaccgctga tactaacact cctaaaaccg gaggtgagct ccgcagcctt cccccggctg   3180
cagataaccc ttgggtggta gcgggatttg tagcgctagg aatagttgcg ggtgggctcg   3240
cgttcgtcct ctgctaccta taccttacct gctgctcata tttagtagta ctgtgctgtt   3300
ggtttagaaa atgggggcgc tactaatcac acttgcttta ctttcgcttt tgggtctgag   3360
ctcggctaat agcgagaaac caagctgtct agaaacaaac tctccagact gtgtggttcc   3420
tcatgggctc tcagacccag ctgatgatcc atgcttaact tttgacccag aaaaaaactg   3480
ctcggtgact atgcagccct atgcttacat gtgcacatct gttataaagt gcggatgggg   3540
ctgtaaaccg attgaaatta cccacaaagg caaaacctgg aataatagtt tgtttaacac   3600
atggcagcct ggagacgagc agtggtatac ggccggccac tggtggagat gactgacccc   3660
atggaaaact cctctgccaa cgacctggac atggacggcc gttcatctga gcagcgactg   3720
gtccagatgc gcattcgcca gaagcaggaa cgcgccgcca gagagctcaa ggatgccatt   3780
gaaattcacc tgtgcaagaa gggcatcttt tgcttggtta agcaagcaaa gatttcttat   3840
gaaatcactg acaacgacca ccgcctgtat tatgagctcg gtccacagcg gcagaaattc   3900
acctgcatgg ttggagtcaa ccccatagtc atcactcagc aggctgcaga aattaaaggg   3960
tgcatccact gttcctgtga ttcccaagaa tgcgtccaca ccatagtcaa gaccctctgc   4020
ggccttcgag atcttcttcc aatgaactaa ccccttcccc caacccaata aaacattggt   4080
tttaatcata ataaaaaatc acttacttta aatctgaaac agtgtctccg tccaagtttt   4140
cttgtagcac cacttcactc ccctcttccc agctctggta ctgcaagccc cggtgggctg   4200
caaactttct ccacacctta aaagggatgt caaattcctc ttgtccaaca atcttcattg   4260
```

tctcttccta gatgtccaca aagcgcgcgc gggtggaaga tgactttgac cctgtctacc 4320
catacgatgc tgagctggca ccgtctgtac ccttcatcgc ccctcccttc gtttcgtcag 4380
acggatttca agaaaaaccc ctgggagttc tgtccctaag actagccaac ccagtcacta 4440
ctaaaaatgg ggaactcaca cttaaactgg gagatggggt gggcatagac tcagatggaa 4500
acctcacagc acagacagtt actaaagcaa catccccccct tactgtttcc aataacgcaa 4560
ttg 4563

<210> SEQ ID NO 18
<211> LENGTH: 14287
<212> TYPE: DNA
<213> ORGANISM: Artificial Sequence
<220> FEATURE:
<223> OTHER INFORMATION: BLY6 intermediate plasmid 3

<400> SEQUENCE: 18
catcatcaat aatatacctt atatgggcag tgtgccaata tgcaaattag acgagtttga 60
attttgcggg atgtgcggtg attggcccgg ggtcaacggt cgcggggcgg ggcggcgtga 120
cgcggacgat gacgttttgg ggaggaggag ctatgttgca agtaatcgtg ggaaatgcga 180
cgtaaaacga ggtggagttt aaacacggaa gtagacaatt ttcccgcgct gtttgacagg 240
aaatgatgtg tttttgggcg gatgcaagtg aaaattctcc attttcgcgc gaaaactaaa 300
tgaggaagtg aaattctgag taattctgag gttatcacag ggcggagtat ttaccgaggg 360
ccgagtagac tttgacccat tacgtggagg tttcgattac tctatttttc acctaaattt 420
ccgcgtactg tgtcaaagtc cgtgttttta cgcgatcgcg atggcctgtg tttgagcata 480
atgtactgac caggtgtaac gttcatctgg gtggtcgtag aggaatgttc atgccatacc 540
aatgcaattt taatcatgtg aggatcttga tggagccgca agcgttttcc agagtcagct 600
tgactggaat ctttgacatg tgtgtggaag catggaagat cttaagatat gatgatacca 660
aatccagatg ccgcgcatgc gagtgcgggg gcaggcatgc caggttccaa cctgtatgtg 720
tggaggtgac cgaggagctg agaccagatc atttggtgct gacctgcact ggtgcggagt 780
tcggttccag tggtgaagaa actgattaaa gtgagtagtg ggatgttata aaagtgacca 840
taaggtgatg tgagatggac aaatttggta atttttatgt atttttgtct tgcagccatg 900
agtgggagcg cttcctttga agggggcgtc tttagccctt atctgacggg gcgtctgcct 960
cattgggctg gagtgcgtca gaatgtgatg ggtctacag tggatggaag acctgttcag 1020
cctgctaatt cttctactct gacttatgct actatgactt cctcgccttt ggatgcagct 1080
gcagctgctg ccgcttctgc tgccgccaac actgttcggg ggatggcctt ggagatgggg 1140
tattatggaa ctgtagtggc caacaccact accccaaata accccacagc cttgaatgag 1200
gacaagctgc tagttctcat gtcccagctg gagtctttga cccaacgcct gggcgatcta 1260
gctcagcagg tgtcccagct gaaggagcag actcaagctg caattaccac tgcgagggga 1320
aattaaaaaa attcaaagaa tcaataaata aaccgagact ttgttgattt taaagtgtgt 1380
cattctttat ttaatttttc gcgcgcgata tgccctggac caccggtctc tatcattgag 1440
gacacggtgg atcttttcta gaacccgata gaggtgggat tggatgttga ggtacatggg 1500
cataagacca tctttggggt gtagatagct ccactgcaga gcctcatgct ccggggtggt 1560
gttgtatata acccagtcat agcatgggcg ttgggcatga tgttgcacaa tatctttaag 1620
gaggagacta atggccactg ggagaccctt ggtgtaagtg tttacaaatc tattaagctg 1680
ggacgggtgc atccgaggtg agataatgtg cattttggat tggattttta gattggcaat 1740

-continued gtttcccccct agatctctcc tgggattcat gttatgcaag accactagaa cagtgtatcc 1800
ggtgcactta gggaatttgt catgaagttt ggaggggaaa gcatgaaaaa atttagacac 1860
acccttgtgt cctcccaagt tctccatgca ctcatccata ataatggcaa tgggcccatg 1920
ggcggcggca cgggcgaaca cgttcctggg atctgacaca tcatagttgt ggtcttgggt 1980
caggtcatca taagccattt taataaactt ggggcggagg gtgccagatt gggggatgaa 2040
tgttccctcg ggccccggaa catagtttcc ttcacatatt tgcatttccc aggcttttag 2100
ttcagagggg gggatcatgt ccacctgtgg agcgatgaag aagacggtct cgggggcggg 2160
ggtgattaag tgggaggaca gcaagttcct aagcagctgt gacttgccac acccagtggg 2220
accgtagatg acccctataa caggttgcag atggtagttt agggaaagac agctgccgtc 2280
ctctcgcagg aggggggcga cctcgttcat catttccctc acatgcatgt tttcccgcac 2340
aagttccgat aggaggcgct ctccacccag ggaaaggagt tcttgaagag atgagaaatt 2400
tttcaagggt tttaagccat cagccatggg catttttggag agggtttgtt gcaagagttc 2460
aaggcggtcc cagagttcgg tgatgtgttc tatggcatct cgatccagca tacttcctcg 2520
tttctggggt tgggacggct gcgggagtat ggaaccaggc gatgggcgtc cagcgctgcc 2580
agtgtccggt ccttccacgg tcgcagcgtc cgagtcaggg tcgtttccgt cacggtgaag 2640
gggtgcgcgc ctggctgggc gcttgcgagg gtgcgcttca ggctcatcct gctcgtggag 2700
aaccgctgcc gttctgcgcc ctgtgcatcg gccaggtagc aattaaccat gagttcgtag 2760
ttgagcgcct ctgccgcgtg gcctttggcg cgcagcttac ctttggaagt cttctgacag 2820
gtgggacagt agagacactt gagagcatag agttttgggg ctagaaagac cgattctggg 2880
gagtatgcat cggccccaca ggaggcgcag acggtttcgc attccaccag ccatgtaaga 2940
tcgggctcgt tggggtcaaa aacaagtttt ccgccatgtt ttttgatgcg tttcttacct 3000
ttgctttcca tgagttcgtg cccccgttgg gtgacaaaga ggctgtccgt gtccccgtag 3060
actgacttta tgggcctgtc ctcgagcggc gtgccgcggt cctcttcgta gaggaactcg 3120
gaccactctg agacgaaagc acgtgtccag gccagcacaa aggaggctat atgggagggg 3180
tagcgatcgt tgtcaaccaa ggggtctact tttccaaggg tgtgtaaaca catgtcccct 3240
tcttccacat ccaggaaggt gattggcttg taagtgtatg ccacgtgacc tggggtccca 3300 gacgggggggg tataaaaggg ggcgggtctc tgctcgtcct cactgtcttc cggatcgctg 3360
tccaggagcg ccagctgttg aggtaggtat tccctctcga aggcgggcat aacctccgca 3420
ctcaggttgt cagtttctag gaacgaggag gatttgatat tgacagtgcc tgccgagatg 3480
cctttcatga gactgtcgtc catttggtca gaaaagacaa tctttttgtt atcaagtttg 3540
gtggcgaagg atccatacag ggcattggaa agcagtttgg caatggagcg catggtttgg 3600
tttttttctt tgtctgcgcg ctctttggcg gctatgttga gttggacata ttcgcgggcc 3660
agacatttcc attgtggaaa tatggtagtt aattcatctg ggacgattct gactttccag 3720
cctctgttat gcagggtaat cagatccaca ctggttgcca cttctcctct aagtggttca 3780
ttagtccagc atagtcgccc ccctttcga gaacagaaag gggtagggg atctagcatg 3840 agttcgtctg gggggtctgc atctatggtg aaaatcccag gaaggagatc ttcgtcaaaa 3900
tagctgatgg tggcggggtc atccagagac atttgccatt ctcgagcagc cagagcgcgc 3960
tcgtaggggt taaggggagt cccccatggc atgggatggg tgagtgcaga agcatacatg 4020
ccacagatgt catagacata gagcggctct tccagaatcc ctatgtaagt gggataacat 4080

-continued cgcccccctc tgatgctggc tcgcacataa tcatagagtt catgtgaggg cgctagaaga 4140
cccgagccca ggttggtgcg gttgggtttt tctgctctgt agaggatctg gcgaaagatg 4200
gcatgggagt ttgatgagat ggtgggtctt tggaagatgt tgaaatgggc atgaggcagt 4260
cccacagagt cccttatgaa gtgagcatag gagtcttgca gtttggccac cagctcggcg 4320
gtgaccagca catccaaagc acagtagtcg agggtctctt tgatgatgtc atagttaggt 4380
tcccctttct tttcccacag ctcgcggttg agaaggtatt cttcgcgatc cttccagtac 4440
tcttcgaggg ggaacccgtc cttgtctgaa cggtaagaac ccagcatgta aaattgattg 4500
acagctttgt aggcacaaca ccccttctcc acggggagtg agtatgcttg cgcggctttg 4560
cgcagagagg tgtgagtaag ggcgaaagtg tccctgacca tgactttgag gaactgatgc 4620
ttaaagtcta tgtcatcgca ggcccccctgc tcccacagtt ggaagtccac tcgctttttg 4680
taggcgggat tgggcaaagc gaaagtaaca tcgttgaata ggatctttcc agccctgggc 4740
atgaagttgc gagtaatgcg aaaaggctga ggcacttctg ccctgttgtt gataacttgg 4800
gcagccaaga cgatctcgtc aaagccgttg atgttgtgac ccacaatgta aagttctacg 4860
aagcgtgggc gtcccttgat gtggggcagt tttttaagct cttcgtaggt caagtcgtca 4920
gggtcagcga ttccatattg ctccaaagcc cagtcaggca ggtgaggatt agcatgaagg 4980
aaagaggtcc aaagatccac ggccagagct gtttgtaagc ggtctctgta ctgacggaaa 5040
tgtcggccta ccgccatttt ttcaggagta acacagtaaa aggtgcgcgg gtccttttcc 5100
cagcgatccc attgaagttg caaggctagg tcgtgggcga ggttgacgag ctgttcgtcc 5160
cccgaaagtt tcatgaccag catgaaaggg acaagctgct tgccaaagga ccccatccag 5220
gtgtaggttt ccacatcgta ggtgaggaag agcctttctg tgcgaggatg agaaccgatc 5280
gggaagaact ggatttcctg ccaccagttg gaggaatggc tgttgatatg atggaagtag 5340
aactccctac ggcgcgccga gcattcgtgc ttgtgcttgt acagacggcc acagtactcg 5400
cagcgctgca cgggatgcac ctgatgaatg agctgtacct ggcttccttt gacaagaaat 5460
ttcagtggga agttgaggcg tggcgtctgc atctcgtgtt aacccccgta attggcccgc 5520
cgccctggtg taccaggaaa ctcctgctcc cactacagta ctacttcctc gtgacgccca 5580
ggccgaagtt cagatgacta actcaggtgt acagctggcg ggtggtgcca ccctgtgtcg 5640
tcaccggcca agaccgggta taaagggcct ggtgatcaga ggccgaggta ttcagctcaa 5700
cgacgagtcg gtgaactctt cgcttggtct gcgaccagac ggcatcttcc aaatagctgg 5760
ttgtgggaga tcttccttca ctcctcgtca ggctgtcctg actttggaga gttcgtcctc 5820
gcagccccgc tcgggcggca tcgggactct ccagttcgtg gaggagttta ctccctcggt 5880
ctacttcaac cccttctccg gttctcctgg gctttacccg gacgagttca tcccgaacta 5940
cgacgccatc agtgaagcgg tcgacggcta cgattaatgt ctaatggtgg cgcggctgag 6000
ctagctcgac tgcgacacct agaccactgc cggcgctttc gctgctttgc tcgggatctc 6060
tgcgagttca tctacttcga gtaccctgac gaacatcctc agggacctgc ccacggagtt 6120
cggattacca ttgaaggggc tatcgattct cacctgcttc ggatcttcac cgctcggcca 6180
gtgctagttg agcgcaacca gggcgacacc accatctccc tctgctgcat ttgtgacaac 6240
cccggattgc atgaaagctt ttgttgtctt ctttgtactg agtataataa aagctgaaat 6300
tagagactac tccggactct cttgtcgtct gaacaacacc aaccagaccc ttcacttcag 6360
cgggaaccag actactcttc actgtaaggc ttataactat aagtatctta cttggatata 6420
caaaggaaca ccgtttgctg tggtaaacag gtgctccaac gacggtgttc tcctcacctt 6480

-continued cctaggcaac ttctccaact ttaccttttc tgttcgcaga aacaagctta ccctccttca 6540
gccctacttt cctgggatct atacctgcct cagtggacct tgcaaccaca cttttcacct 6600
gattgaaaac tctaccctta ccttcccagc gccaatccct actaacagct cggagtccaa 6660
ctcttccatt accgctgata ctaacactcc taaaaccgga ggtgagctcc gcagccttcc 6720
cccggctgca gataaccctt gggtggtagc gggatttgta gcgctaggaa tagttgcggg 6780
tgggctcgcg ttcgtcctct gctacctata ccttacctgc tgctcatatt tagtagtact 6840
gtgctgttgg tttagaaaat gggggcgcta ctaatcacac ttgctttact ttcgcttttg 6900
ggtctgagct cggctaatag cgagaaacca agctgtctag aaacaaactc tccagactgt 6960
gtggttcctc atgggctctc agacccagct gatgatccat gcttaacttt tgacccagaa 7020
aaaaactgct cggtgactat gcagccctat gcttacatgt gcacatctgt tataaagtgc 7080
ggatggggct gtaaaccgat tgaaattacc cacaaaggca aaacctggaa taatagtttg 7140
tttaacacat ggcagcctgg agacgagcag tggtatacgg ccggccactg gtggagatga 7200
ctgaccccat ggaaaactcc tctgccaacg acctggacat ggacggccgt tcatctgagc 7260
agcgactggt ccagatgcgc attcgccaga agcaggaacg cgccgccaga gagctcaagg 7320
atgccattga aattcacctg tgcaagaagg gcatcttttg cttggttaag caagcaaaga 7380
tttcttatga aatcactgac aacgaccacc gcctgtatta tgagctcggt ccacagcggc 7440
agaaattcac ctgcatggtt ggagtcaacc ccatagtcat cactcagcag gctgcagaaa 7500
ttaaagggtg catccactgt tcctgtgatt cccaagaatg cgtccacacc atagtcaaga 7560
ccctctgcgg ccttcgagat cttcttccaa tgaactaacc ccttccccca acccaataaa 7620
acattggttt taatcataat aaaaaatcac ttactttaaa tctgaaacag tgtctccgtc 7680
caagttttct tgtagcacca cttcactccc ctcttcccag ctctggtact gcaagccccg 7740
gtgggctgca aactttctcc acaccttaaa agggatgtca aattcctctt gtccaacaat 7800
cttcattgtc tcttcctaga tgtccacaaa gcgcgcgcgg gtggaagatg actttgaccc 7860
tgtctaccca tacgatgctg agctggcacc gtctgtaccc ttcatcgccc ctcccttcgt 7920
ttcgtcagac ggatttcaag aaaaacccct gggagttctg tccctaagac tagccaaccc 7980
agtcactact aaaaatgggg aactcacact taaactggga gatggggtgg gcatagactc 8040
agatggaaac ctcacagcac agacagttac taaagcaaca tcccccctta ctgtttccaa 8100
taacgcaatt gcacttaaca tggacaaacc tttttacagt agcaatggaa aactatcctt 8160
acaagttaca tcaccattaa agatagtcga ctctttaaat acattggcta ttggctatgg 8220
gcaaggctta ggactaaaca atagtgctct tgctgtgcaa ttagcatctc cccttacatt 8280
tgacagcaac agcaaaatta aaataaattt gggaagcggg ccattaaaaa ttaatgcgaa 8340
taaactgtca attaactgcc taaggggtgt atatgtaaca actgacggaa cttccattga 8400
aacaaatata agctgggcaa aaggaatgag gtttgaaggt aatgccatgg ctgtaaacgt 8460
tgacagcacc aaaggtctac aatttggcac taccagcaca gaatcaggag tcactaacgc 8520
tttccctatc cagttaaaga ttggatctgg tcttagtttt gacagcacag gagcacttgt 8580
agcttgggat aaggataatg acaagcttac actgtggaca accgctgacc catcacctaa 8640
ttgtaccata tatacagaca aggatgctaa acttacactt tgtcttacaa aatgtggcag 8700
tcaaatacta ggcagtgttt cagtactggc tgttaaagct ggaaccctac agccaatcag 8760
tgaaaaaata ggtactgctt tggtttcact aaaatttaat aacaacggtg tattgttaag 8820

```
caactccaca ttaagtaatg aatactggaa ctacaggaag ggagatgtca caccagccga   8880
agcctatact aatgctgtgg gttttatgcc aaacatcaag gcatatccta aaaacacaaa   8940
ctctgcctca aaaagccaca ttgtaggaca agtgtacctt aatggagatg aaactaaacc   9000
aatgcattta atcattacat ttaatgaaac cagtgatgaa acatgcacat attccataac   9060
gttccaatgg aaatggaaca ttggaacata caccagcgac acccttgcaa caagctcctt   9120
taccttttct tacattgccc aagaataaaa actgcagaca acaataaagt ttaaatgttt   9180
tatttaaaca gtttcacaga accctagtat tcaacctgcc acctccctcc caacacacag   9240
agtacacagt cctttctccc cggctggcct taaaaagcat catatcatgg gtaacagaca   9300
tattcttagg tgttatattc cacacggttt cctgtcgagc caaacgctca tcagtgatat   9360
taataaactc cccgggcagc tcacttaagt tcatgtcgct gtccagctgc tgagccacag   9420
gctgctgtcc aacttgcggt tgcttaacgg gcggcgaagg agaagtccac gcctacatgg   9480
gggtagagtc ataatcgtgc atcaggatag ggcggtggtg ctgcagcagc gcgcgaataa   9540
actgctgccg ccgccgctcc gtcctgcagg aatacaacat ggcagtggtc tcctcagcga   9600
tgattcgcac cgcccgcagc ataaggcgcc ttgtcctccg ggcacagcag cgcaccctga   9660
tctcacttaa atcagcacag taactgcagc acagcaccac aatattgttc aaaatcccac   9720
agtgcaaggc gctgtatcca aagctcatgg cggggaccac agaacccacg tggccatcat   9780
accacaagcg caggtagatt aagtggcgac ccctcataaa cacgctggac ataaacatta   9840
cctcttttgg catgttgtaa ttcaccacct cccggtacca tataaacctc tgattaaaca   9900
tggcgccatc caccaccatc ctaaaccagc tggccaaaac ctgcccgccg gctatacact   9960
gcagggaacc gggactggaa caatgacagt ggagagccca ggactcgtaa ccatggatca  10020
tcatgctcgt catgatatca atgttggcac aacacaggca cacgtgcata cacttcctca  10080
ggattacaag ctcctcccgc gttagaacca tatcccaggg aacaacccat tcctgaatca  10140
gcgtaaatcc cacactgcag ggaagacctc gcacgtaact cacgttgtgc attgtcaaag  10200
tgttacattc gggcagcagc ggatgatcct ccagtatggt agcgcgggtt tctgtctcaa  10260
aaggaggtag acgatcccta ctgtacggag tgcgccgaga caaccgagat cgtgttggtc  10320
gtagtgtcat gccaaatgga acgccggacg tagtcattct cgtactttga gtggcaaaac  10380
cttgctctcg aacagcacac gtctcgtcgc ctcctgtccc ttctcttcgc cttttcagtg  10440
tgatagttgt aatacagcca ttcacgaagc tcagtcagaa gatcttcagc gtctgttgtc  10500
aaaaacaatc catccaatct gattgctttc aaaacatcac aaacagtcga ataagccaaa  10560
cccatccagg caatgcaatt attttggtta tccacaatgg gagggggcgg aagacatgga  10620
agaggcataa ttaatttttt aatccaatcg atcacgcagc acttcaaaat gaagatcgcg  10680
aaggtgacac ctttcacccc cactgtgttg atgaaaaata acagccaagt caaaattgat  10740
gcggttttca aggtgctcga ctgtagcatc aagcagagct tccacacgca cgtccacaaa  10800
taacagaata gcaaaagcgg gaggaggaag taaatcctca atcatcatag tacagtccat  10860
caccatccct aaataatttt catccttcca gccttggact atatttttaa actgctcttg  10920
taaatccaaa ccacacatgt ggaaaagttc ccaaagagct ccctcaacta ccattcttaa  10980
gcacaccttc atagtgacaa aatatcttgt tcctctgtca cctgcagcaa attacaaagt  11040
ccaatattag gatctatgcc cagagatcta agctcatccc tcaattccaa ctgtaaaaag  11100
gcttccagat ctgccctaac ttgttcagcc agtgggctcc ctggaataag cgtgggagaa  11160
gccaaactgc aaaacagacg catgccgcca taattaccac cagaaaacac tacgttacag  11220
```

-continued

```
tatgcatgct gattcattcc agtaatttca tccagtgtat tggatacaaa aaaaggcaag  11280
cactctctca ctaattgtat tatggagaca ttatcacaca ggtaacaatt taaaggttgt  11340
ggaacaataa tgcagtaagt aaccacggtg cgctccaaca tggttagtaa tttttagttc  11400
tgaaaaacaa aacatacaaa aaattatatc atactcattt ggcgaactgg tggaaaaatg  11460
accctatcta gcacaaggca agccactgga tcaccaatgc gcccctcata aaacctgtca  11520
tcatgattaa aaagcaacac cgaaagctct tccctatgtc ctgcatgaat gattctagct  11580
gaggaatata agccagcgca attagtatct gttaaagaaa aaaaacggcc aacatagcct  11640
ctaggaatta gcacacttaa tcttaaagac attactgcca tccccttgg atttaaggta  11700
aaatttacag gagcatagaa aatatactga tttccctcct gcacaggcag catagcacca  11760
ggtccctcta aaaacacaca caaagcttct gcagccatag cttaccgcgc aaaccaggca  11820
cagcagtgag ctaaaaggac aaagctctaa ctcactagcc aacctggcgc acaatatata  11880
gttagtcctt acactgacgt aaccgaccaa agtctaaaaa ccccgccaaa aatacacaca  11940
cgcccaaaaa acgccccgtg agtcaaaaaa cagtttcact tcctcgttac acccaaaacg  12000
tcgtcacttc cggattccca cggttcgtca cttccggagc tccttgctta attaaccccg  12060
cccaaaacgt catcgtccgc gtcacgccgc cccgccccgc gaccgttgac cccgggccaa  12120
tcaccgcaca tcccgcaaaa ttcaaactcg tctaatttgc atattggcac actgcccata  12180
taaggtatat tattgatgat gatttaaatc atatgcggtg tgaaataccg cacagatgcg  12240
taaggagaaa ataccgcatc aggcgctctt ccgcttcctc gctcactgac tcgctgcgct  12300
cggtcgttcg gctgcggcga gcggtatcag ctcactcaaa ggcggtaata cggttatcca  12360
cagaatcagg ggataacgca ggaaagaaca tgtgagcaaa aggccagcaa aaggccagga  12420
accgtaaaaa ggccgcgttg ctggcgtttt tccataggct ccgcccccct gacgagcatc  12480
acaaaaatcg acgctcaagt cagaggtggc gaaacccgac aggactataa agataccagg  12540
cgtttccccc tggaagctcc ctcgtgcgct ctcctgttcc gaccctgccg cttaccggat  12600
acctgtccgc ctttctccct tcgggaagcg tggcgctttc tcatagctca cgctgtaggt  12660
atctcagttc ggtgtaggtc gttcgctcca agctgggctg tgtgcacgaa ccccccgttc  12720
agcccgaccg ctgcgcctta tccggtaact atcgtcttga gtccaacccg gtaagacacg  12780
acttatcgcc actggcagca gccactggta acaggattag cagagcgagg tatgtaggcg  12840
gtgctacaga gttcttgaag tggtggccta actacggcta cactagaagg acagtatttg  12900
gtatctgcgc tctgctgaag ccagttacct tcggaaaaag agttggtagc tcttgatccg  12960
gcaaacaaac caccgctggt agcggtggtt tttttgtttg caagcagcag attacgcgca  13020
gaaaaaaagg atctcaagaa gatcctttga tcttttctac ggggtctgac gctcagtgga  13080
acgaaaactc acgttaaggg attttggtca tgagattatc aaaaaggatc ttcacctaga  13140
tccttttaaa ttaaaaatga agttttaaat caatctaaag tatatatgag taaacttggt  13200
ctgacagtta ccaatgctta atcagtgagg cacctatctc agcgatctgt ctatttcgtt  13260
catccatagt tgcctgactc cccgtcgtgt agataactac gatacgggag ggcttaccat  13320
ctggccccag tgctgcaatg ataccgcgag acccacgctc accggctcca gatttatcag  13380
caataaacca gccagccgga agggccgagc gcagaagtgg tcctgcaact ttatccgcct  13440
ccatccagtc tattaattgt tgccgggaag ctagagtaag tagttcgcca gttaatagtt  13500
tgcgcaacgt tgttgccatt gctgcaggca tcgtggtgtc acgctcgtcg tttggtatgg  13560
```

cttcattcag ctccggttcc caacgatcaa ggcgagttac atgatccccc atgttgtgca 13620
aaaaagcggt tagctccttc ggtcctccga tcgttgtcag aagtaagttg gccgcagtgt 13680
tatcactcat ggttatggca gcactgcata attctcttac tgtcatgcca tccgtaagat 13740
gcttttctgt gactggtgag tactcaacca agtcattctg agaatagtgt atgcggcgac 13800
cgagttgctc ttgcccggcg tcaacacggg ataataccgc gccacatagc agaactttaa 13860
aagtgctcat cattggaaaa cgttcttcgg ggcgaaaact ctcaaggatc ttaccgctgt 13920
tgagatccag ttcgatgtaa cccactcgtg cacccaactg atcttcagca tcttttactt 13980
tcaccagcgt ttctgggtga gcaaaaacag gaaggcaaaa tgccgcaaaa aagggaataa 14040
gggcgacacg gaaatgttga atactcatac tcttcctttt tcaatattat tgaagcattt 14100
atcagggtta ttgtctcatg agcggataca tatttgaatg tatttagaaa aataaacaaa 14160
taggggttcc gcgcacattt ccccgaaaag tgccacctga cgtctaagaa accattatta 14220
tcatgacatt aacctataaa aataggcgta tcacgaggcc ctttcgtctt caagaattga 14280
tttaaat 14287

<210> SEQ ID NO 19
<211> LENGTH: 638
<212> TYPE: DNA
<213> ORGANISM: Artificial Sequence
<220> FEATURE:
<223> OTHER INFORMATION: Ad5 pIX promoter insertion

<400> SEQUENCE: 19
cgcgatcgcg gtactgaaat gtgtgggcgt ggcttaaggg tgggaaagaa tatataaggt 60
gggggtctta tgtagttttg tatctgtttt gcagcagccg ccgccgccat gagtgggagc 120
gcttcctttg aagggggcgt ctttagccct tatctgacgg ggcgtctgcc tcattgggct 180
ggagtgcgtc agaatgtgat ggggtctaca gtggatggaa gacctgttca gcctgctaat 240
tcttctactc tgacttatgc tactatgact tcctcgcctt tggatgcagc tgcagctgct 300
gccgcttctg ctgccgccaa cactgttcgg gggatggcct tggagatggg gtattatgga 360
actgtagtgg ccaacaccac taccccaaat aaccccacag ccttgaatga ggacaagctg 420
ctagttctca tgtcccagct ggagtctttg acccaacgcc tgggcgatct agctcagcag 480
gtgtcccagc tgaaggagca gactcaagct gcaattacca ctgcgagggg aaattaaaaa 540
aattcaaaga atcaataaat aaaccgagac tttgttgatt ttaaagtgtg tcattcttta 600
tttaattttt cgcgcgcgat atgccctgga ccaccggt 638

<210> SEQ ID NO 20
<211> LENGTH: 35711
<212> TYPE: DNA
<213> ORGANISM: Artificial Sequence
<220> FEATURE:
<223> OTHER INFORMATION: pBLY6.FLuc

<400> SEQUENCE: 20
catcatcaat aatatacctt atatgggcag tgtgccaata tgcaaattag acgagtttga 60
attttgcggg atgtgcggtg attggcccgg ggtcaacggt cgcggggcgg ggcggcgtga 120
cgcggacgat gacgttttgg ggaggaggag ctatgttgca agtaatcgtg ggaaatgcga 180
cgtaaaacga ggtggagttt aaacacggaa gtagacaatt ttcccgcgct gtttgacagg 240
aaatgatgtg tttttgggcg gatgcaagtg aaaattctcc attttcgcgc gaaaactaaa 300
tgaggaagtg aaattctgag taattctgag gttatcacag ggcggagtat ttaccgaggg 360

-continued ccgagtagac tttgacccat tacgtggagg tttcgattac tctatttttc acctaaattt 420
ccgcgtactg tgtcaaagtc cgtgttttta cggcgatcgc tcaatattgg ccattagcca 480
tattattcat tggttatata gcataaatca atattggcta ttggccattg catacgttgt 540
atccatatca taatatgtac atttatattg gctcatgtcc aacattaccg ccatgttgac 600
attgattatt gactagttat taatagtaat caattacggg gtcattagtt catagcccat 660
atatggagtt ccgcgttaca taacttacgg taaatggccc gcctggctga ccgcccaacg 720
acccccgccc attgacgtca ataatgacgt atgttcccat agtaacgcca atagggactt 780
tccattgacg tcaatgggtg gagtatttac ggtaaactgc ccacttggca gtacatcaag 840
tgtatcatat gccaagtacg ccccctattg acgtcaatga cggtaaatgg cccgcctggc 900
attatgccca gtacatgacc ttatgggact ttcctacttg gcagtacatc tacgtattag 960
tcatcgctat taccatggtg atgcggtttt ggcagtacat caatgggcgt ggatagcggt 1020
ttgactcacg gggatttcca agtctccacc ccattgacgt caatgggagt ttgttttggc 1080
accaaaatca acgggacttt ccaaaatgtc gtaacaactc cgccccattg acgcaaatgg 1140
gcggtaggcg tgtacggtgg gaggtctata taagcagagc tcgtttagtg aaccgtcaga 1200
tcgcctggag acgccatcca cgctgttttg acctccatag aagacaccgg gaccgatcca 1260
gcctccgcgg ccgggaacgg tgcattggaa gcttggcatt ccggtactgt tggtaaagcc 1320
accatggaag acgccaaaaa cataaagaaa ggcccggcgc cattctatcc gctggaagat 1380
ggaaccgctg gagagcaact gcataaggct atgaagagat acgccctggt tcctggaaca 1440
attgctttta cagatgcaca tatcgaggtg gacatcactt acgctgagta cttcgaaatg 1500
tccgttcggt tggcagaagc tatgaaacga tatgggctga atacaaatca cagaatcgtc 1560
gtatgcagtg aaaactctct tcaattcttt atgccggtgt tgggcgcgtt atttatcgga 1620
gttgcagttg cgcccgcgaa cgacatttat aatgaacgtg aattgctcaa cagtatgggc 1680
atttcgcagc ctaccgtggt gttcgtttcc aaaaaggggt tgcaaaaaat tttgaacgtg 1740
caaaaaaagc tcccaatcat ccaaaaaatt attatcatgg attctaaaac ggattaccag 1800
ggatttcagt cgatgtacac gttcgtcaca tctcatctac ctcccggttt taatgaatac 1860
gattttgtgc cagagtcctt cgatagggac aagacaattg cactgatcat gaactcctct 1920
ggatctactg gtctgcctaa aggtgtcgct ctgcctcata gaactgcctg cgtgagattc 1980
tcgcatgcca gagatcctat ttttggcaat caaatcattc cggatactgc gattttaagt 2040
gttgttccat tccatcacgg ttttggaatg tttactacac tcggatattt gatatgtgga 2100
tttcgagtcg tcttaatgta tagatttgaa gaagagctgt ttctgaggag ccttcaggat 2160
tacaagattc aaagtgcgct gctggtgcca accctattct ccttcttcgc caaaagcact 2220
ctgattgaca aatacgattt atctaattta cacgaaattg cttctggtgg cgctcccctc 2280
tctaaggaag tcggggaagc ggttgccaag aggttccatc tgccaggtat caggcaagga 2340
tatgggctca ctgagactac atcagctatt ctgattacac ccgaggggga tgataaaccg 2400
ggcgcggtcg gtaaagttgt tccatttttt gaagcgaagg ttgtggatct ggataccggg 2460
aaaacgctgg gcgttaatca aagaggcgaa ctgtgtgtga gaggtcctat gattatgtcc 2520
ggttatgtaa acaatccgga agcgaccaac gccttgattg acaaggatgg atggctacat 2580
tctggagaca tagcttactg ggacgaagac gaacacttct tcatcgttga ccgcctgaag 2640
tctctgatta agtacaaagg ctatcaggtg gctcccgctg aattggaatc catcttgctc 2700

-continued caacacccca acatcttcga cgcaggtgtc gcaggtcttc ccgacgatga cgccggtgaa 2760
cttcccgccg ccgttgttgt tttggagcac ggaaagacga tgacggaaaa agagatcgtg 2820
gattacgtcg ccagtcaagt aacaaccgcg aaaaagttgc gcggaggagt tgtgtttgtg 2880
gacgaagtac cgaaaggtct taccggaaaa ctcgacgcaa gaaaaatcag agagatcctc 2940
ataaaggcca agaagggcgg aaagatcgcc gtgtaattct agacgagatc cgaacttgtt 3000
tattgcagct tataatggtt acaaataaag caatagcatc acaaatttca caaataaagc 3060
atttttttca ctgcattcta gttgtggttt gtccaaactc atcaatgtat cttatcatgt 3120
ctgcgatcgc gatggcctgt gtttgagcat aatgtactga ccaggtgtaa cgttcatctg 3180
ggtggtcgta gaggaatgtt catgccatac caatgcaatt ttaatcatgt gaggatcttg 3240
atggagccgc aagcgttttc cagagtcagc ttgactggaa tctttgacat gtgtgtggaa 3300
gcatggaaga tcttaagata tgatgatacc aaatccagat gccgcgcatg cgagtgcggg 3360
ggcaggcatg ccaggttcca acctgtatgt gtggaggtga ccgaggagct gagaccagat 3420
catttggtgc tgacctgcac tggtgcggag ttcggttcca gtggtgaaga aactgattaa 3480
agtgagtagt gggatgttat aaaagtgacc ataaggtgat gtgagatgga caaatttggt 3540
aatttttatg tatttttgtc ttgcagccat gagtgggagc gcttcctttg aagggggcgt 3600
ctttagccct tatctgacgg ggcgtctgcc tcattgggct ggagtgcgtc agaatgtgat 3660
ggggtctaca gtggatggaa gacctgttca gcctgctaat tcttctactc tgacttatgc 3720
tactatgact tcctcgcctt tggatgcagc tgcagctgct gccgcttctg ctgccgccaa 3780
cactgttcgg gggatggcct tggagatggg gtattatgga actgtagtgg ccaacaccac 3840
taccccaaat aaccccacag ccttgaatga ggacaagctg ctagttctca tgtcccagct 3900
ggagtctttg acccaacgcc tgggcgatct agctcagcag gtgtcccagc tgaaggagca 3960
gactcaagct gcaattacca ctgcgagggg aaattaaaaa aattcaaaga atcaataaat 4020
aaaccgagac tttgttgatt ttaaagtgtg tcattcttta tttaattttt cgcgcgcgat 4080
atgccctgga ccaccggtct ctatcattga ggacacggtg gatcttttct agaacccgat 4140
agaggtggga ttggatgttg aggtacatgg gcataagacc atctttgggg tgtagatagc 4200
tccactgcag agcctcatgc tccggggtgg tgttgtatat aacccagtca tagcatgggc 4260
gttgggcatg atgttgcaca atatctttaa ggaggagact aatggccact gggagaccct 4320
tggtgtaagt gtttacaaat ctattaagct gggacgggtg catccgaggt gagataatgt 4380
gcattttgga ttggattttt agattggcaa tgtttccccc tagatctctc ctgggattca 4440
tgttatgcaa gaccactaga acagtgtatc cggtgcactt agggaatttg tcatgaagtt 4500
tggaggggaa agcatgaaaa aatttagaca cacccttgtg tcctcccaag ttctccatgc 4560
actcatccat aataatggca atgggcccat gggcggcggc acgggcgaac acgttcctgg 4620
gatctgacac atcatagttg tggtcttggg tcaggtcatc ataagccatt ttaataaact 4680
tggggcggag ggtgccagat tgggggatga atgttccctc gggccccgga acatagtttc 4740
cttcacatat ttgcatttcc caggctttta gttcagaggg ggggatcatg tccacctgtg 4800
gagcgatgaa gaagacggtc tcgggggcgg gggtgattaa gtgggaggac agcaagttcc 4860
taagcagctg tgacttgcca cacccagtgg gaccgtagat gacccctata acaggttgca 4920
gatggtagtt tagggaaaga cagctgccgt cctctcgcag gaggggggcg acctcgttca 4980
tcatttccct cacatgcatg ttttcccgca caagttccga taggaggcgc tctccaccca 5040
gggaaaggag ttcttgaaga gatgagaaat ttttcaaggg ttttaagcca tcagccatgg 5100

```
gcattttgga gagggtttgt tgcaagagtt caaggcggtc ccagagttcg gtgatgtgtt   5160
ctatggcatc tcgatccagc atacttcctc gtttctgggg ttgggacggc tgcgggagta   5220
tggaaccagg cgatgggcgt ccagcgctgc cagtgtccgg tccttccacg gtcgcagcgt   5280
ccgagtcagg gtcgtttccg tcacggtgaa ggggtgcgcg cctggctggg cgcttgcgag   5340
ggtgcgcttc aggctcatcc tgctcgtgga gaaccgctgc cgttctgcgc cctgtgcatc   5400
ggccaggtag caattaacca tgagttcgta gttgagcgcc tctgccgcgt ggcctttggc   5460
gcgcagctta cctttggaag tcttctgaca ggtgggacag tagagacact tgagagcata   5520
gagttttggg gctagaaaga ccgattctgg ggagtatgca tcggccccac aggaggcgca   5580
gacggtttcg cattccacca gccatgtaag atcgggctcg ttggggtcaa aaacaagttt   5640
tccgccatgt tttttgatgc gtttcttacc tttgctttcc atgagttcgt gcccccgttg   5700
ggtgacaaag aggctgtccg tgtccccgta gactgacttt atgggcctgt cctcgagcgg   5760
cgtgccgcgg tcctcttcgt agaggaactc ggaccactct gagacgaaag cacgtgtcca   5820
ggccagcaca aaggaggcta tatgggaggg gtagcgatcg ttgtcaacca aggggtctac   5880
tttttccaag gtgtgtaaac acatgtcccc ttcttccaca tccaggaagg tgattggctt   5940
gtaagtgtat gccacgtgac ctggggtccc agacgggggg gtataaaagg gggcgggtct   6000
ctgctcgtcc tcactgtctt ccggatcgct gtccaggagc gccagctgtt gaggtaggta   6060
ttccctctcg aaggcgggca taacctccgc actcaggttg tcagtttcta ggaacgagga   6120
ggatttgata ttgacagtgc ctgccgagat gcctttcatg agactgtcgt ccatttggtc   6180
agaaaagaca atctttttgt tatcaagttt ggtggcgaag gatccataca gggcattgga   6240
aagcagtttg gcaatggagc gcatggtttg gttttttct ttgtctgcgc gctctttggc   6300
ggctatgttg agttggacat attcgcgggc cagacatttc cattgtggaa atatggtagt   6360
taattcatct gggacgattc tgactttcca gcctctgtta tgcagggtaa tcagatccac   6420
actggttgcc acttctcctc taagtggttc attagtccag catagtcgcc cccttttcg    6480
agaacagaaa gggggtaggg gatctagcat gagttcgtct ggggggtctg catctatggt   6540
gaaaatccca ggaaggagat cttcgtcaaa atagctgatg gtggcggggt catccagaga   6600
catttgccat tctcgagcag ccagagcgcg ctcgtagggg ttaaggggag tcccccatgg   6660
catgggatgg gtgagtgcag aagcatacat gccacagatg tcatagacat agagcggctc   6720
ttccagaatc cctatgtaag tggataaca tcgccccct ctgatgctgg ctcgcacata    6780
atcatagagt tcatgtgagg gcgctagaag acccgagccc aggttggtgc ggttgggttt   6840
ttctgctctg tagaggatct ggcgaaagat ggcatgggag tttgatgaga tggtgggtct   6900
ttggaagatg ttgaaatggg catgaggcag tcccacagag tcccttatga agtgagcata   6960
ggagtcttgc agtttggcca ccagctcggc ggtgaccagc acatccaaag cacagtagtc   7020
gagggtctct ttgatgatgt catagttagg ttcccctttc ttttcccaca gctcgcggtt   7080
gagaaggtat tcttcgcgat ccttccagta ctcttcgagg gggaacccgt ccttgtctga   7140
acggtaagaa cccagcatgt aaaattgatt gacagctttg taggcacaac accccttctc   7200
cacggggagt gagtatgctt gcgcggcttt gcgcagagag gtgtgagtaa gggcgaaagt   7260
gtccctgacc atgactttga ggaactgatg cttaaagtct atgtcatcgc aggccccctg   7320
ctcccacagt tggaagtcca ctcgcttttt gtaggcggga ttgggcaaag cgaaagtaac   7380
atcgttgaat aggatctttc cagccctggg catgaagttg cgagtaatgc gaaaaggctg   7440
```

aggcacttct gccctgttgt tgataacttg ggcagccaag acgatctcgt caaagccgtt 7500
gatgttgtga cccacaatgt aaagttctac gaagcgtggg cgtcccttga tgtggggcag 7560
ttttttaagc tcttcgtagg tcaagtcgtc agggtcagcg attccatatt gctccaaagc 7620
ccagtcaggc aggtgaggat tagcatgaag gaaagaggtc caaagatcca cggccagagc 7680
tgtttgtaag cggtctctgt actgacggaa atgtcggcct accgccattt tttcaggagt 7740
aacacagtaa aaggtgcgcg ggtccttttc ccagcgatcc cattgaagtt gcaaggctag 7800
gtcgtgggcg aggttgacga gctgttcgtc ccccgaaagt ttcatgacca gcatgaaagg 7860
gacaagctgc ttgccaaagg accccatcca ggtgtaggtt tccacatcgt aggtgaggaa 7920
gagcctttct gtgcgaggat gagaaccgat cgggaagaac tggatttcct gccaccagtt 7980
ggaggaatgg ctgttgatat gatggaagta gaactcccta cggcgcgccg agcattcgtg 8040
cttgtgcttg tacagacggc cacagtactc gcagcgctgc acgggatgca cctgatgaat 8100
gagctgtacc tggcttcctt tgacaagaaa tttcagtggg aagttgaggc gtggcgtctg 8160
catctcgtgt tgtattacgt cctggctatt ggtctggcca tcttctgtct cgatggtggt 8220
catgctgacg agcccgcgcg ggaggcaggt ccagacctcc gcgcggacgg gtctgagagc 8280
gaggacgaga gcgcgcaggc cggaactgtc cagggtcctg agacgctgcg gagtcaggtc 8340
agtagggaga gtacataggt ttacttgcat aagtttttcc agggcatgtg ggaggtcaag 8400
atgatatttg atttctactg gcgagttggt ggagacatcg atggcttgca gggtcccgtg 8460
cccctggggt gctaccaccg tcccttttt tttcttgatc gggggcggtg ttgcttcttg 8520
catggtaagg tcgtcttcta gaagcggcgg cgaggtcgcg cgccgggtgg cagtggcggt 8580
tctggacctg gaggtagagg cggtagaggt acgtcggcgc cgcgcgcggg taggttctgg 8640
tactgcgccc tgagaagact tgcgtgagcg acgacgcggc ggttgacgtc ctggatctga 8700
cgcctctggg tgaatgctac cggacccgtg agcttgaacc tgaaagagag ttcaacagaa 8760
tcaatttcgg tatcgttgac ggctgcctgc cgcaggattt cttgtacgtc gcccgagttg 8820
tcttggtagg cgatctcggc catgaactgc tcgatctctt cttcttggag atctccgcgg 8880
cccgctcgtt ctacggtggc agcaaggtcg ttggagatgc gccccatgag ctgtgagaat 8940
gcattcatgc ccgcctcgtt ccagacgcga ctgtagacca cggctccctc gggatctctg 9000
gcgcgcatga ccacttgggc gaggtttagt tccacgtgtc tggtgaagac cgcatagttg 9060
cagagacgct ggaagaggta gttgagcgtg gtggcgatgt gctcggtgac aaagaaatac 9120
atgatccagc gacgaagcgg catctcgctg atatcgccca gggcttccaa ccgttccatg 9180
gcttcgtaaa agtccacggc gaagttgaaa aactgggagt tgcgagcgga cacggtcaac 9240
tcctcctcca gaagacggat gagctcggcg atggtggcgc gcacttcgcg ctcaaaggct 9300
cccgggatct cttcctcctc ttcttcttcc aactcttcct ccactaacat ctcttctact 9360
tcctcctcag gcggcggggg tggaggaggg ggcgcgcggc gacgccggcg acgcacgggc 9420
agacgatcga tgaagcgttc gatcacttct ccgcggcggc gacgcatggt ctcggtgacg 9480
gcgcgcccgt cctccctggg tcgcagagtg aagacgccgc cgcgcagctc cctgaaatgg 9540
tgactgggag ggtccccgtt tggtagggac agggcactga tgatgcatct tattaattgc 9600
cctgtaggga ctccgcgcaa ggacctgagc gtctcgagat ccacgggatc tgaaaatctc 9660
tgaacgaagg cttcgagcca gtcgcagtcg caaggtaggc tgagcactgt ttcttcgggg 9720
cgggctgctg agctagaggg ttgtacgatg ctgctggtga tgaagttaaa ataggcagtt 9780
ctgagacggc ggatggtggc gaggagcacc aggtctttgg gtccggcttg ctggatgcgc 9840

-continued

```
aggcggtcgg ccattcccca tgcattatct tggcacctgg ccagatcttt atagtagtct   9900
tgcatgagtc gctccacggg cacttcttct tcgcccgctc tgccgtgcat gcgtgtgagt   9960
ccgtaccctc tctgtggttg gacgagcgcc aggtcggcaa cgacccttc ggctagaatg  10020
gcttgctgca cctgggtgag ggtgttctgg aaatcatcaa agtccacaaa gcggtggtag  10080
gcccccgtgt tgatggtgta ggagcagttg gacatgaccg accagttgac tgtctggtgt  10140
cctggtcgta cgagttccgt gtacctgagc cgcgagtatg cgcgggagtc gaagatgtaa  10200
tcgttgcagg ttcgcaccag gtactggtag ccgatgagga agtgaggcgg cggctggcgg  10260
tagagaggcc atcgttcggt ggcgggcgcg ccgggcgcta ggtcttctag catgagacgg  10320
tggtatccgt agacgtacct ggacatccag gtaataccgg cggcggtggt ggaggcgcgc  10380
ggaaactctc gcacgcggtt ccagatgttg cgcagcggca tgaagtagtt catggtgggc  10440
acggtctggc ccgtgaggcg cgcgcagtca ttgatgctct agatacgggc aaaaacgaaa  10500
gcgttgagcg gttcccttcc gtggcctgga ggaacgcgaa cgggttaggt cgcagcgtac  10560
cctggttcga gactaaagaa agcgagcaac tcgaaccggc agagtcgcgg ctaacgggta  10620
ttggcaatcc cgtctcgacc caagccagca aatccaggat acggatgggg gccccttttg  10680
tttttcaggg catgagtcac cggttaaggt ttacaacggc tgtttcatgc ctttagaagt  10740
ggctcgcgcc cgtagtctgg agaatcaatc gccagggttg cgttgcggcg tgccccggtt  10800
cgagcctgca gcttgagtcg gccggtgacc gcggcaaacg agggcgtggc ggccccgtcg  10860
tttctaagac cttgctagcc gacctctcca gtttacggga acgagccccc ttttattttt  10920
tttgtttttg ccagatgcat cccgtactgc ggcagatgcg cccacagccc ccacagcagc  10980
agcagcaggc tggcctacct tctctacctc agccgctacc tgcaactacc gcggtggccg  11040
ctgtaagcgg ggccggacag caggcggctc ctcaatatga attggacttg gaagagggcg  11100
agggattggc aagattgggg gcgccctcgc ccgagcgcca cccgcgggtg cagatgaaaa  11160
aggacgttcg cgaatcttac gtgcccaagc agaatctgtt cagagacaga agcggcgagg  11220
agcccgagga gatgcgcgcg tcccgtttta acgcgggtcg cgagctgcga caaggactgg  11280
atcgaaaacg ggtgttgagg gatgatgatt ttgaggtgga tgaaatgaca gggatcagcc  11340
ccgctcgcgc tcacgtggct gcagctaatc tggtgacagc ttatgagcag accgtgaagg  11400
aggaaagcaa cttccagaaa tcattcaata accacgtgcg caccctgatc gcacgcgagg  11460
aggtgaccct gggcctgatg cacctgtggg atctgctgga agccatagtg cagaacccca  11520
ctagcaaacc cctgactgct caactgtttc tggtggtgca gcacagcagg gataatgagg  11580
cattcagaga ggcgctgctg aatatcactg aacctgaggg gagatggctg ctggatctgg  11640
tgaatatcct gcagagcatt gtagtgcagg aacgcagctt gcctttgtcc gagaaggtgg  11700
cggcgatcaa ttactctgtg ctgagtctgg gcaaatacta tgccaggaag atctacaaaa  11760
ccccttacgt gcccatagac aaggaagtga aaatagatgg gttttacatg cgcatgaccc  11820
tgaaagtgct aaccctgagc gatgacttgg gagtgtaccg caacgacagg atgcaccgcg  11880
cggtgagcgc cagcaggagg cgcgagctga gcgacaaaga attaatgcac agcttgcaac  11940
gagccctgac gggagccggg acggaggggg agaactactt tgacatgggt gcagacttgc  12000
attggctgcc tagtcgcagg gcattggaag cggcaggcga tgggccctat gtagaggaag  12060
tagtagacga ggacgatgag gagggcgagt acctggaaga ctgatggcgc gacccgtatt  12120
tttgctagat ggaacaggcg ccggaccctg cgatgcgggc ggcgctgcag agccagccgt  12180
```

-continued ccggcattaa ttcctcggac gattggaccc aggccatgca acgcatcatg gcgctgacga 12240
cccgcaaccc cgaagccttt agacagcagc ctcaggccaa ccgcctttcg gccatcctgg 12300
aggccgtggt gccctctcgc tccaacccca cccacgagaa ggttctggcc atcgtgaatg 12360
ccctggtgga gaacaaggcc atccgctccg atgaagccgg gctggtatac aacgccttgc 12420
tcgagcgcgt ggctcgctac aacagcagca atgtccagac taacctggac aggatggtga 12480
ccgacgtgcg cgaggccgtg tcccagcgcg aacggttcca tcgcgagtct aacctgggtt 12540
ccatggtagc gctgaacgct ttcctcagtt cccagcctgc caatgtgccc cggggacagg 12600
aagactatac caactttatt agcgccctga gactcatggt agccgaggtt cctcagagcg 12660
aggtgtacca gtccggtcca gactactttt tccagacaag caggaacggt atgcagacag 12720
tgaacttaag ccaggctttc aagaacctgc aagggctgtg gggagtccaa gctccagtgg 12780
gcgacagggc gaccgtgtcg agcctgttga ctccaaattc ccgtttgctg ctgctgctgg 12840
tgtccccctt cactgacagc ggcagcataa acagaaactc ctacttgggc tacctgataa 12900
acttgtatcg cgaagctata ggtcaggccc acgtggacga acagacctat caggagatca 12960
ctaatgtgag tcgcgctctg ggccaggacg accctggaaa cctggaagct actctaaact 13020
ttctgctgac caaccgctcg caaaaaatcc ctcctcagta tacattaact gcggaggagg 13080
aacggatctt gagatacgtg cagcagagcg tgggtctgtt cctgatgcaa gagggtgcga 13140
cccctagcgc cgcgcttgat atgacagcgc gcaacatgga gcccagcatg tatgccagca 13200
acagaccatt cattaataaa ttgatggatt acttccatcg cgcggccgct atgaactctg 13260
attacttcac caatgctatt ctgaaccccc attggctgcc tccgcctggt ttttatactg 13320
gcgagtatga catgcctgac cccaacgatg ggttcttgtg ggacgatgtg gacagcgtgg 13380
cgttctcgcc taccgctcct cgtacttttt ggaagaagga aggtagtgac agaagaccct 13440
cctccgtgct gtcaggacgt gagggtgctg ccgcggcggt ccccgatgct gcaagcccct 13500
ttcccagtct gccattttca ctaaacagcg tgcgcagtag cgagctgggg agaataaccc 13560
gccctcgctt gctgggcgag gacgagtatt tgaatgactc cctactgaga cccgagcggg 13620
aaaagaactt ccctaataat gggattgaaa gcctggtgga taagatgagc agatggaaga 13680
cctatgccca ggagcacaga gatgagccta gaatcttggg tcctacagta ggcacccgca 13740
gacgccagcg ccatgataga cagcggggtc tggtgtggga cgatgaggat tctgcagatg 13800
acagcagcgt gttggacttg ggcgggaggg gaggtgtggg caacccgttc gcacacttgc 13860
gtccccgtat tggacgcatg atgtaaaagt gaaaataaaa aaggaactca ccaaggccat 13920
ggcgaccagc gtgcgttcgt tctttctgtt gttgtatcta gtatgatgag gcgcaccgtg 13980
ctaggcggat cggtggcgta tccggagggt cctcctcctt cgtacgaaag cgtgatgcag 14040
caggtggcgg cggcggcgat gcaacccccc ttggaggctc cttacgtgcc cccgcggtac 14100
ctggcaccta ccgaggggag aaacagcatt cgttattcgg aactcacacc cttgtatgac 14160
accacccggt tgtacctggt ggacaacaaa tcggcggaca ttgcctcgtt gaactatcag 14220
aacgaccaca gcaacttctt gacaacggtg gtgcagaaca atgactttac ccccacggag 14280
gccagcaccc agaccatcaa ctttgacgag cgctcccggt ggggcggtca gctgaagacc 14340
atcatgcaca ccaacatgcc caacgtgaac gagttcatgt ttagcaacaa gttcagggct 14400
agggtgatgg tgtccagaac cacacctaaa gaggtgacag tcacaacaga ctatgatggt 14460
agtcaggaca tcttggaata cgagtgggtt gactttgagt taccagaagg caacttctct 14520
gccaccatga ccatagacct gatgaataat gcaattgttg ataattacct aaaagtgggt 14580
agacagaatg gggtactgga gagtgacata ggtgttaagt ttgacactag gaactttagg 14640
cttggttggg acccagtgac agagttggtc atgcctgggg tctacaccaa tgaagctttc 14700
catcctgaca tagtcctact acctggctgc ggagtggact tcactgagag ccgcctcagt 14760
aatctgctag gcattagaaa gaaacagcca ttccaggaag ggttccagat catgtatgag 14820
gatctggagg gtggtaacat ccccgccctg cttgatgtaa atgcatatga gaagagcaag 14880
gaagataata caaccaccac aaatgaagct gtggccgcgg cttcatctac tgaagccaaa 14940
gctgtggtag atgcttccac ttcaacagaa aacaccactg atgaaaaagt caccagggga 15000
gatacatttg ccacccctga acaagagaag gcagctgagg cagagtctga tattatgctt 15060
ctgtccaccg atgaaaacga aactaaaaaa caactggtta ttcgagcggt gaccaaggat 15120
agtaaggaca ggagttataa tgtattgtca gatggaaaga acacagctta ccgtagttgg 15180
tacctggcat acaattatgg cgaccgtgag aaaggggtgc gttcttggac actgcttacc 15240
acctcggatg tcacctgcgg cgtggagcaa gtctattggt cgctaccaga tatgatgcaa 15300
gatccagtca cctttcgctc cacacgccaa gttagcaact acccagtggt gggcgcagag 15360
ctgctcccag tgcattccag aagcttctac aacgagcaag ccgtctactc gcaacagctc 15420
cgccagtaca cctcgctcac gcacgtcttc aaccgcttcc ccgagaatca gatcctcgtc 15480
cgcccgcccg cgccaaccat taccaccgtc agtgaaaacg ttcctgctct cacagatcac 15540
gggaccctgc cgctgcgcag cagtatccgg ggagtccagc gcgtgaccgt tactgacgcc 15600
agacgccgca cctgtccata cgtatacaag gccctgggca tagtcgcgcc gcgcgtcctt 15660
tcaagccgca ctttctaaaa aaatgtccat tctcatctcg cccagtaata acaccggttg 15720
gggcctgcgc acacctagca agatgtatgg aggcgctcgc agacgctcca ctcagcaccc 15780
tgtgcgcgtg cgcgggcatt tccgcgctcc ctggggcgcc ctcaagggac gctctcgtac 15840
taggaccacc gttgacgatg tgatcgacca ggtggtcgcc gatgcacgta actatacccc 15900
cgcagccgca cctgcatcca ccgtggatgc ggtcattgac agcgtggtag ccgatgcgcg 15960
cgcctatgct cgcgccaaga gcaggaggcg gcgtattgcc aggcgtcacc gagctactcc 16020
agccatgcga gctgcaagag ctttattgcg gagagccaga cgtgtggggc gaagagccat 16080
gcgtagagcg gccagacgcg cggcttcagg tgccagcgca ggcagggtcc gcaggcgcgc 16140
ggctacggcg gcagcggcgg ccatcgctag catgaccaaa ccacgaagag gcaatgtgta 16200
ttgggtgcgc gacgccgcca ccggccagcg cgtgcccgtg cgcacacgcc cccctcgcac 16260
ttagaagata ctgagcagtc tccgatgttg tgtcccagcg gcgagatgtc caagcgcaaa 16320
ttcaaggaag agatgctcca ggtcatcgcg cctgagatct acggtcctgc ggtgaaggat 16380
gaaaaaaagc cccgcaagat caagcgggtc aaaaaggaca aaaaggaaga agatggtgat 16440
gatgggctgg tggagtttgt gcgcgagttt gccccaagga ggcgcgtgca gtggcgcggg 16500
cgcaaagtgt ggccggtgtt gagaccgggg accacagtgg tctttacgcc aggcgagcgc 16560
tccagcaccg tttccaaacg ctcttatgat gaggtgtacg gggacgatga tattctcgag 16620
caggcggctg atcgccttgg cgagtttgca tatggcaaac gcagccgctc gggagccaag 16680
gaagaggcat tgaccatccc cttggatcat ggaaatccca ccccaagcct caaacccgtg 16740
accctgcaac aagtgctgcc cacgccgcca cgcaagggca tcaagcgcga gggcgaggat 16800
ctgtatccca ccatgcagct gatggtgccc aagcgccaga agctggaaga cgtgctggag 16860
aaaatgaaag tggatcctga aatccagcct gaagtcaaag tgaggccaat caagcaggtg 16920

-continued gcgcccggtt tgggggtaca aaccgtggat atcaagatcc ccaccgagtc catggaaatt 16980
caaaccgaac ccatgaagcc cacctccagc accattgagg tgcagacgga tccttggatg 17040
cccgcgcctg ctcctgttac cactactact cgaagaccta gaagaaagta tggttcagcc 17100
aacctgataa tgccaaacta tgctctgcat ccatcaatca tacccactcc tggctaccgc 17160
ggcactcgct actaccgcag tcacagcacc cgccgacgta aagcacctgc cacccgccgc 17220
cgtcgccgcc gccgtgccac tagcaaactt accccctcgg ctatggtgcg gagagtgtac 17280
cgtgatgggc gcgcagctcc tctgacactg ccgcgcgcgc gctaccatcc tagcattgcc 17340
atttaacaac tctgcctcct tgcagatatg gccctcactt gccgccttcg tattcctatt 17400
gctggctacc gcggaagaaa gtcgcgccgt agaagagcag ggttgtctgg gagcgggatg 17460
cgtcgccacc ggcggcggcg cgccatcagc aaacggttgg ggggtggatt tcttcccgct 17520
ttgattccca tcatcgccgc ggcgatcggc gcgataccag gcatagcttc cgtggcggtg 17580
caggcctcgc agcgccactg acattggaaa aagatatctt ataaataaaa atagaatgga 17640
ctctgacgct cctggtcctg tgatatgttt ttgtagacga gatggaagac atcaattttt 17700
catccctggc tccgcgacac ggcacgcggc cgtatatggg cacctggagc gacatcggca 17760
acagccaact gaacgggggga gccttcaatt ggagcagtct atggagcggg cttaaaaatt 17820
ttgggtccac tataaagact tatgggaaca aagcttggaa cagcagcaca gggcatgcgc 17880
tgagacaaaa gcttaaagat cagaatttcc aacagaaggt ggtcgatggt atcgcctctg 17940
gaatcaatgg ggtggtagat ctggccaacc aggccgtgca gaaacagatt aacagtcgcc 18000
tggacccggc tcccccagct cctattcatg agttaatgca agtggaggaa gagctccctt 18060
cattggaaaa gcggggcgat aagcgacctc gtccagatat ggaggaaacg ctgctgacca 18120
aggtggatga gccgccctcc tatgaagagg ctgtaaaact gggaatgccc actacaaagc 18180
ccattatgcc tctggccact ggagtgatga agccatctca gtctaaacct gcagttgctg 18240
ctacattgga cttgcccgct cccgtggcca cccccaaacc tgtcgccgcc ccgaagccca 18300
ccgccgtgca acccgtggcc gtggccagac cgcgtcccgg tggtcggccg aatgcaaact 18360
ggcagagcac tctgaacagc atcgtgggtt tgggagtgca cagtgtgaag cgccgtcgct 18420
gctattgatt aaatatggag tagcgcttaa cttgcttgtc tgtgtgtgta tatgtcgatg 18480
ccgcccgccg tgctacagca aagagagaag gagaagaggc gccgctgagt tcctttcaag 18540
atggccaccc catcgatgct gccccagtgg gcgtacatgc acatcgccgg acaggacgct 18600
tcggagtacc tgagtccggg tctggtgcag ttcgcccgcg ccacagatac ctacttcaat 18660
ctggggaaca agtttaggaa ccctaccgtg gctcccaccc acgatgtgac caccgaccgt 18720
agccagcgcc tgacgctgcg ctttgtgccc gttgaccggg aggacaatac ctactcctac 18780
aaagtcagat acaccctggc tgtgggagac aacagggtgt tggatatggc cagcacctac 18840
tttgacatca ggggcgtgtt ggacagagga cctagcttca aaccatactc tggcactgcc 18900
tacaactccc tggctccaaa aggagctcca aactccagtc agtggcaaca aaaggaaaac 18960
aatggtcaag gtgatgcaaa gactcacacc tatggtgtag ctgccactgg aggtattgac 19020
attgacaaaa atggtcttca aattggaatc gatgaaacta aagaagataa taacgaaatt 19080
tatgcagaca aaacattcca acctgaacct caaattggag aagaaaactg gcaagatagc 19140
gaaaactatt atggaggcag ggctcttaaa ccggaaacca agatgaagcc ttgctatggt 19200
tccttcgcta gaccaactaa tgcaaaggga ggtcaagcca aaattaaacc agctcaagag 19260
ggtcaacagt ctatagatta tgacatagac ctggctttct ttgatattcc aagcactggc 19320
ggaggcaatg gcacaaatgt aaatgacaag ccagatatgg ttatgtatac tgaaaatgta 19380
aatctggaaa ctccagacac tcatcttgtt tacaagccag gaacttcaga tgacagttcc 19440
gaggccaatt taactcagca agccatggct aacagaccca actatattgg gtttagagat 19500
aactttattg gcgtcatgta ctacaacagc actggcaaca tgggagtgct tgctggtcaa 19560
gcatcccagc taaatgctgt ggtggacctg caagacagaa acaccgagct gtcttatcag 19620
ctattacttg actctctggg cgacagaacc aggtatttta gtatgtggaa tcaggcggtg 19680
gacagctatg atcctgatgt gcgcattatt gaaaaccatg gtgtggaaga tgaattgcca 19740
aactattgct tcccattgga cggagctggc actaatgctg tttaccaagg agttaagaca 19800
aaagaggata ataatggcga atgggaaaca gacacaaatg ttgcatcgca gaatcagata 19860
tgcaagggca acatatatgc tatggagatc aacctgcaag ccaacctgtg gaaaagtttc 19920
ctttactcca acgtggctct gtacctacca gactcctaca agtacactcc atccaacgtg 19980
acactcccta ccaacactaa cacctatgac tacatgaatg gcagggtggt gtctccatcc 20040
ctggtggatg cctacattaa cattggcgcc aggtggtctc tggatgccat ggacaatgtc 20100 aacccctttca accaccaccg caatgccggc ctgcgctacc ggtccatgct tctgggcaac 20160
ggccgatacg tgcccttcca catccaagtg ccccagaaat tcttcgctat caagaacctg 20220
ctgcttctcc caggctcata cacctacgag tggaacttcc gcaaggatgt caacatgatc 20280
ctgcagagtt cccttggcaa tgacctcaga accgatgggg ccaccatcca gtacaccagc 20340
atcaatctct atgccacctt cttccccatg gctcacaaca ctgcctccac cctggaagcc 20400
atgctgcgca atgacaccaa tgaccagtcc ttcaatgact acctctcagc tgccaacatg 20460
ctttacccca tccctgccaa tgccaccaac gtgcccatct ccatcccatc tcgtaactgg 20520
gctgccttca ggggctggtc tttcacccgc ctcaagacca aggagacccc atctctggga 20580
tcagggttcg atccctactt cgtctactca ggctccattc catacctgga tggaactttc 20640
taccttaacc acactttcaa gaaagtctcc atcatgtttg actcttctgt cagctggcca 20700
ggcaatgaca ggctgctgac tcccaatgag ttcgaaatca agcgcactgt tgatggggaa 20760
gggtacaatg tggcacaatg caacatgacc aaagactggt tcctggttca gatgctctcc 20820
cactacaaca ttggctacca gggcttctac atcccagaag gatacaagga ccgcatgtac 20880
tccttcttca gaaacttcca gcccatgagc cgccaggtgg tcgatcaggt caactacaaa 20940
gactacatgg cagtcaccct tgcctatcag cacaacaact ctggctttgt gggctacctc 21000
gcgcccacca tgcgacaggg ccaaccctac cctgctaact acccataccc gctcattggc 21060
aagactgcag tcaacagtgt cacccagaaa aagttcctct gcgacagggt catgtggcgc 21120
atccccttct ccagcaactt catgtccatg gggggccctta ccgacctggg gcaaaacatg 21180
ctttatgcca actccgccca cgcgctagac atgaatttcg aagtagaccc catggatgag 21240
tccacccttc tctatgttgt cttcgaagtc ttcgacgtgg tcagagtgca ccagccccac 21300
cgcggcgtca tcgaagctgt ctacctgcgc acccccttct cagctggtaa cgccaccaca 21360
taagcgcctt gcttcttgca agtggctgca gcagcatggc ctgtggatcc tccactggat 21420
ccaatgagca agagctcagg gccatcgcca tagacctggg ctgtggaccc tatttcctgg 21480
gaacctttga caagcggttt ccaggcttca tggctcctga caagctcgcc tgtgccattg 21540
tcaacacggc agggcgcgag actggtggtg agcactggct ggcttttgga tggaaccccc 21600
gctccaatac ctgctatctc tttgacccgt ttgggttttc agacgagcgc ctcaagcaga 21660

-continued

```
tctatcaatt cgagtacgag gggctcctgc gccgcagtgc cctggctact aaggaccgat  21720
gcatcactct ggaaaagtct acccagaccg tgcagggtcc gcgctcggct gcctgcgggc  21780
tcttctgctg catgttcctc catgcttttg tgcactggcc cgaccgcccc atggacaaca  21840
accccaccat gaatttgctg acgggggtac ccaacaacat gctccaatcg ccccaagtag  21900
agcccaccct gcgccacaac caggaggcac tctatcgctt cctgaactcc cactcatctt  21960
actttcgttc taaccgcgcg cgcattgaga aggccactgc cttcgatcga atgaataata  22020
acatgtaaac caaattgtgt gtggctcaaa taaacagcac tttattgttt acatgcactg  22080
aggctctggg atgatcattt tttaaaaatc gaaggggttc tggcgggaat cagcatggcc  22140
agatggcagg gacacgttgc ggaactggaa cttgttctgc cacttgaact cgggaatcac  22200
cagcctggga actggaatct ctggaaaggt atcttgccat agctttctgg tcagttgcag  22260
agcgccaagc aggtcaggag cagatatctt gaaatcacag ttggggccag aattctgggc  22320
gcgggagttg cggtacactg ggttgcagca ctggaacacc ataagggcag ggtgtctcac  22380
gctcgccagc acggtctcgt cactgatgca agacacatcc aggtcttcag cattggccat  22440
tccaaagggg gtcatcttgc aggtctgtct gcccatcacg ggagcgcagc caggtttgtg  22500
gttgcaatca caatgaaggg ggatcagcat catcttggcc tggtcggggg taatccctgg  22560
gtaaacagcc ttcatgaagg cttcatactg cttgaaagct tcctgggctt tggttccctc  22620
ggtgtagaac actccacaag acttgctgga aaactgatta gtagcgcagt tggcatcatt  22680
cacacagcag cgggcgtcgt tattagccag ctggaccaca ttcctgcccc agcggttctg  22740
ggtgatcttg gctcgatctg ggttctcctt caacgcgcgc tggccgttct cgctcgccac  22800
atccatctca atgacatgtt ccttctggat catgatgttg ccatgcaggc atctaatctt  22860
gccttcataa tcagtgcagc catgaggcca cagcgcgcac ccggtgcact cccaattgtt  22920
atgggggatc tgggaatggc tatgaaccag cccttgcagg aatcttccca tcatcacagc  22980
cagggtcttt atgctggtaa aggtcagcgg gataccgcgg tgctcctcgt tcacatactg  23040
ctggcagatg cgtctgtagt gctcggcctg ctcgggcatc agcttgaaag aggttttcaa  23100
ctcattatcc agcctgtatc tctccatcat gatggacatt acttccatgc ccttctccca  23160
ggcagaaaca atagggagac tcaggggatt cttgacagta gagacaacct tacttaaggg  23220
gtcatcactg ccaatctttt cgatgcttct cttgccatcc ttctcggtga tgcgcaccgg  23280
cgggtagctg aatcccacag ccaccaactg agcctcttcc ctttcgtctt cgctgtcttg  23340
actgatgtct tgcagaggaa catgtttggt tttcctgggt ttcttcttgg gcggcagctc  23400
tggaggactc tggctccgtt ccggagaccc catggatgag cgagagttgt cgctcaccac  23460
ttggatctgg ctgcctgtag aagaactgga ccccacgcgg cggtaggtgt tcctcttggt  23520
aggcagaggt ggaggcgacg ggctccggtc cggtctgggt ggcggatggc tggcggagcc  23580
ccttccgcgt tcgggggtgc gctccagatg gcggtcgtct gactgacctc cgcggctggc  23640
cattgtgttc tcctaggtag agaaacaaga catggagact cagccatcgc tgccatcgcc  23700
atccaccacc acaagcaccg ccgaggagga ggagtgttta accaccccac catgcagccc  23760
cgctaccacc accagcaccc ttgaaagcga ggtcgacacg gtcgtggagg atttacaggc  23820
tatggaagat attgaggcag ctgtcgagca agaccccggc tatgtgacac cggcggagca  23880
tgatgaggat ctagcgcgct ttctcgacgg tgtggagaaa gcgaaacaag atgaggacga  23940
ggaagaggca gaagcacaac catcggtggc cgactacctc accggcctag ggctagaaga  24000
cgtgctgctt aagcatcttg caaggcagac agtcatagtc aaagacgccc tgctagagcg  24060
```

ctccgaggtg ccactcagtg tggaagacct cagtcgcgcc tatgagctaa acctcttctc 24120
gcctcgcaag ccccccaagc gtcagcccaa cgggacctgt gagcccaatc cgcgcctcaa 24180
cttctatcca gccttcactg tgcccgaagt actagctacc taccacatct tttcaagaa 24240
ccaaaagatc cccatctcct gccgcgccaa tcgcacccgc gcagatgccc tactcaactt 24300
ggggcccggc gctcgcatac ctgatatcgc ttccttggaa gaggttccta agatctttga 24360
gggtctgggc aatgaggaaa ctcgggcagc aaacgctctg caaagagaaa cagatgatgg 24420
tgaacaccac agcgctctgg tggagctcca gggcgacaac gctcgtcttg cagtcctcaa 24480
acgcagcatc gaggtcaccc atttcgccta ccccgcactt aatctcccac ccaaagtcat 24540
gagctcggtc atggacacgt tgctcatgaa gcgcgcgagc cccatctccg aggatcagaa 24600
catgcaggac cccgatgcct cagatgaagg caagcctgta gtcagcgacg agcaactggc 24660
tcgctggcta ggctctgact ccccccagtc tttggaggag cggcgcaagc ttatgatggc 24720
agtggtcctg atcacagcgg agctggagtg tctccgccgc ttcttcactg acccagagac 24780
cctgcgcaag cttgaggaga acctgcatta cacattcagt catgggttcg tgcgccaggc 24840
gtgcaagatc tccaacgttc aactcaccaa cctggtctcc tacctgggca tcttgcatga 24900
aaaccggctg gggcagaacg tgctccacac caccctgaag ggggaggccc gccgcgacta 24960
tatccgcgac tgtatctacc tctacctatg ctacacctgg caaagcggga tgggtgtgtg 25020
gcaacagtgc ttggaagagc aaaatctaaa agagctggaa aagctgcttc agaaatctct 25080
taaatctctg tggaccgggt tcgatgagcg gaccaccgct tcggacatgg ccgatattat 25140
cttccccgag cggctcagac acactctgcg cgacgggctg cctgactttg ccagccagag 25200
catgctacaa aactttaggt cattcatctt ggaacgctcc gggatcctgc ccgccacttg 25260
ctgcgcactg ccctccgatt ttgtgcccat cacctaccgg gagtgccccc cgccgctatg 25320
gagccactgc tacctgttcc gcctggccaa ctacttggcc taccactctg atgtgataga 25380
agatgttagt ggcgaagggc tcctggagtg ccactgccgc tgcaacctct gcacccccca 25440
ccgctccctc gcctgcaatc cccagctgct gagcgaaacc cagatcatcg gcaccttcga 25500
gttgcaaggt cccagcggcg aaggcgaggg gtcctctccg gggcaaagtc tgaaactgac 25560
tccggggcta tggacctccg cttaccttcg caagttcgcc cccaaagact accaccccta 25620
tgagatcagg ttttatgaag accaatcaca gccccccaag gccgaactga cggcctgcgt 25680
catcacccag ggggcaatct tggcccaatt gcaagccatc caaaaatccc gccaagaatt 25740
tttgctgaaa aagggacacg ggatctatct agacccccag accggtgagg agctgaatac 25800
acgcttccct caggatgccc cgaggaggca agagaatgaa agttcagatg ccgcccgagg 25860
aggagctgga agactgggac agtcaggcag aggaggaaga ctgggacagc caggcagaag 25920
aggaggacag cctggaggag gacagtctgg aggaaggcga ggagcccaag gaagaggcag 25980
ccgccgccag accatcgtcc tcggcggtgg agacaagcaa ggtcccagac agcacggcta 26040
ccacctccgc tccagctcaa ggggccgctc ggcgacccaa cagtagatgg gacgagacgg 26100
gtcgcttcca gaaccccacc accgtcaaga ccggtaagca ggagcggcag ggatacaagt 26160
cctggcgggg gcataaaagt gccatcatcg cttgcttgca ggagtgtggg ggcaatatat 26220
cctttgccag acgctacctg ctattccatc acggggtgaa tttcccccgc aacatcttgc 26280
attactaccg tcacctccac agcccctact accagcagca agagacagca gaggaaacca 26340
gcggcaactc cgagagttag aaaaccagca gctaaaaaat ccacagcggc ggcagcaggt 26400
gcaggcggac tgaggatcac cgcgaacgag ccagctcaga ccagggagtt gaggaatcgg 26460
atctttccca ccctctatgc catattccaa caaagtcggg gtcaggaaca agaactgaaa 26520
gtaaaaaaca gatctcttcg ctcgctcacc cgcagttgtt tgtatcacaa gagcgaagac 26580
caacttcagc gcactctcga ggacgccgag gctctcttca acaagtactg cgcgctgact 26640
cttaaagagt agactgcgcg cgcttggcga gaaaaggcgg gaattacgtc acctcttggc 26700
cacacctgtg cttcattatg agtaaagaaa ttcccacgcc ttacatgtgg agctatcagc 26760
cccagatggg attggccgct ggcgccgccc aggactactc cacccgcatg aattggctca 26820
gcgccggtcc cgcgatgatc tcacgggtta atggtgtgag agagcaccga aaccagatac 26880
tcctagaaca gtccgccctc accgccactc cccgcaatca cctcaacccc cgtaattggc 26940
ccgccgccct ggtgtaccag gaaactcctg ctcccactac agtactactt cctcgtgacg 27000
cccaggccga agttcagatg actaactcag gtgtacagct ggcgggtggt gccaccctgt 27060
gtcgtcaccg gccaagaccg ggtataaagg gcctggtgat cagaggccga ggtattcagc 27120
tcaacgacga gtcggtgaac tcttcgcttg gtctgcgacc agacggcatc ttccaaatag 27180
ctggttgtgg gagatcttcc ttcactcctc gtcaggctgt cctgactttg gagagttcgt 27240
cctcgcagcc ccgctcgggc ggcatcggga ctctccagtt cgtggaggag tttactccct 27300
cggtctactt caaccccttc tccggttctc ctgggcttta cccggacgag ttcatcccga 27360
actacgacgc catcagtgaa gcggtcgacg gctacgatta atgtctaatg gtggcgcggc 27420
tgagctagct cgactgcgac acctagacca ctgccggcgc tttcgctgct ttgctcggga 27480
tctctgcgag ttcatctact tcgagtaccc tgacgaacat cctcagggac ctgcccacgg 27540
agttcggatt accattgaag gggctatcga ttctcacctg cttcggatct tcaccgctcg 27600
gccagtgcta gttgagcgca accagggcga caccaccatc tccctctgct gcatttgtga 27660
caaccccgga ttgcatgaaa gcttttgttg tcttctttgt actgagtata ataaaagctg 27720
aaattagaga ctactccgga ctctcttgtc gtctgaacaa caccaaccag acccttcact 27780
tcagcgggaa ccagactact cttcactgta aggcttataa ctataagtat cttacttgga 27840
tatacaaagg aacaccgttt gctgtggtaa acaggtgctc caacgacggt gttctcctca 27900
ccttcctagg caacttctcc aactttacct tttctgttcg cagaaacaag cttaccctcc 27960
ttcagcccta ctttcctggg atctatacct gcctcagtgg accttgcaac cacacttttc 28020
acctgattga aaactctacc cttaccttcc cagcgccaat ccctactaac agctcggagt 28080
ccaactcttc cattaccgct gatactaaca ctcctaaaac cggaggtgag ctccgcagcc 28140
ttcccccggc tgcagataac ccttgggtgg tagcgggatt tgtagcgcta ggaatagttg 28200
cgggtgggct cgcgttcgtc ctctgctacc tataccttac ctgctgctca tatttagtag 28260
tactgtgctg ttggtttaga aaatgggggc gctactaatc acacttgctt tactttcgct 28320
tttgggtctg agctcggcta atagcgagaa accaagctgt ctagaaacaa actctccaga 28380
ctgtgtggtt cctcatgggc tctcagaccc agctgatgat ccatgcttaa cttttgaccc 28440
agaaaaaaac tgctcggtga ctatgcagcc ctatgcttac atgtgcacat ctgttataaa 28500
gtgcggatgg ggctgtaaac cgattgaaat tacccacaaa ggcaaaacct ggaataatag 28560
tttgtttaac acatggcagc ctggagacga gcagtggtat acggccggcc actggtggag 28620
atgactgacc ccatggaaaa ctcctctgcc aacgacctgg acatggacgg ccgttcatct 28680
gagcagcgac tggtccagat gcgcattcgc cagaagcagg aacgcgccgc cagagagctc 28740
aaggatgcca ttgaaattca cctgtgcaag aagggcatct tttgcttggt taagcaagca 28800

```
aagatttctt atgaaatcac tgacaacgac caccgcctgt attatgagct cggtccacag  28860
cggcagaaat tcacctgcat ggttggagtc aaccccatag tcatcactca gcaggctgca  28920
gaaattaaag ggtgcatcca ctgttcctgt gattcccaag aatgcgtcca caccatagtc  28980
aagaccctct gcggccttcg agatcttctt ccaatgaact aaccccttcc cccaacccaa  29040
taaaacattg gttttaatca taataaaaaa tcacttactt taaatctgaa acagtgtctc  29100
cgtccaagtt ttcttgtagc accacttcac tcccctcttc ccagctctgg tactgcaagc  29160
cccggtgggc tgcaaacttt ctccacacct taaaagggat gtcaaattcc tcttgtccaa  29220
caatcttcat tgtctcttcc tagatgtcca caaagcgcgc gcgggtggaa gatgactttg  29280
accctgtcta cccatacgat gctgagctgg caccgtctgt acccttcatc gcccctccct  29340
tcgtttcgtc agacggattt caagaaaaac ccctgggagt tctgtcccta agactagcca  29400
acccagtcac tactaaaaat ggggaactca cacttaaact gggagatggg gtgggcatag  29460
actcagatgg aaacctcaca gcacagacag ttactaaagc aacatccccc cttactgttt  29520
ccaataacgc aattgcactt aacatggaca aacctttttta cagtagcaat ggaaaactat  29580
ccttacaagt tacatcacca ttaaagatag tcgactcttt aaatacattg gctattggct  29640
atgggcaagg cttaggacta aacaatagtg ctcttgctgt gcaattagca tctcccctta  29700
catttgacag caacagcaaa attaaaataa atttgggaag cgggccatta aaaattaatg  29760
cgaataaact gtcaattaac tgcctaaggg gtgtatatgt aacaactgac ggaacttcca  29820
ttgaaacaaa tataagctgg gcaaaaggaa tgaggtttga aggtaatgcc atggctgtaa  29880
acgttgacag caccaaaggt ctacaatttg gcactaccag cacagaatca ggagtcacta  29940
acgctttccc tatccagtta aagattggat ctggtcttag ttttgacagc acaggagcac  30000
ttgtagcttg ggataaggat aatgacaagc ttacactgtg gacaaccgct gacccatcac  30060
ctaattgtac catatataca gacaaggatg ctaaacttac actttgtctt acaaaatgtg  30120
gcagtcaaat actaggcagt gtttcagtac tggctgttaa agctggaacc ctacagccaa  30180
tcagtgaaaa aataggtact gctttggttt cactaaaatt taataacaac ggtgtattgt  30240
taagcaactc cacattaagt aatgaatact ggaactacag gaagggagat gtcacaccag  30300
ccgaagccta tactaatgct gtgggtttta tgccaaacat caaggcatat cctaaaaaca  30360
caaactctgc ctcaaaaagc cacattgtag gacaagtgta ccttaatgga gatgaaacta  30420
aaccaatgca tttaatcatt acatttaatg aaaccagtga tgaaacatgc acatattcca  30480
taacgttcca atggaaatgg aacattggaa catacaccag cgacaccctt gcaacaagct  30540
cctttacctt ttcttacatt gcccaagaat aaaaactgca gacaacaata aagtttaaat  30600
gttttattta aacagtttca cagaacccta gtattcaacc tgccacctcc ctcccaacac  30660
acagagtaca cagtcctttc tccccggctg gccttaaaaa gcatcatatc atgggtaaca  30720
gacatattct taggtgttat attccacacg gtttcctgtc gagccaaacg ctcatcagtg  30780
atattaataa actccccggg cagctcactt aagttcatgt cgctgtccag ctgctgagcc  30840
acaggctgct gtccaacttg cggttgctta acgggcggcg aaggagaagt ccacgcctac  30900
atgggggtag agtcataatc gtgcatcagg atagggcggt ggtgctgcag cagcgcgcga  30960
ataaactgct gccgccgccg ctccgtcctg caggaataca acatggcagt ggtctcctca  31020
gcgatgattc gcaccgcccg cagcataagg cgccttgtcc tccgggcaca gcagcgcacc  31080
ctgatctcac ttaaatcagc acagtaactg cagcacagca ccacaatatt gttcaaaatc  31140
```

```
ccacagtgca aggcgctgta tccaaagctc atggcgggga ccacagaacc cacgtggcca  31200
tcataccaca agcgcaggta gattaagtgg cgacccctca taaacacgct ggacataaac  31260
attacctctt ttggcatgtt gtaattcacc acctcccggt accatataaa cctctgatta  31320
aacatggcgc catccaccac catcctaaac cagctggcca aaacctgccc gccggctata  31380
cactgcaggg aaccgggact ggaacaatga cagtggagag cccaggactc gtaaccatgg  31440
atcatcatgc tcgtcatgat atcaatgttg gcacaacaca ggcacacgtg catacacttc  31500
ctcaggatta caagctcctc ccgcgttaga accatatccc agggaacaac ccattcctga  31560
atcagcgtaa atcccacact gcagggaaga cctcgcacgt aactcacgtt gtgcattgtc  31620
aaagtgttac attcgggcag cagcggatga tcctccagta tggtagcgcg ggtttctgtc  31680
tcaaaaggag gtagacgatc cctactgtac ggagtgcgcc gagacaaccg agatcgtgtt  31740
ggtcgtagtg tcatgccaaa tggaacgccg gacgtagtca ttctcgtact ttgagtggca  31800
aaaccttgct ctcgaacagc acacgtctcg tcgcctcctg tcccttctct tcgccttttc  31860
agtgtgatag ttgtaataca gccattcacg aagctcagtc agaagatctt cagcgtctgt  31920
tgtcaaaaac aatccatcca atctgattgc tttcaaaaca tcacaaacag tcgaataagc  31980
caaacccatc caggcaatgc aattattttg gttatccaca atgggagggg gcggaagaca  32040
tggaagaggc ataattaatt ttttaatcca atcgatcacg cagcacttca aaatgaagat  32100
cgcgaaggtg acacctttca cccccactgt gttgatgaaa aataacagcc aagtcaaaat  32160
tgatgcggtt ttcaaggtgc tcgactgtag catcaagcag agcttccaca cgcacgtcca  32220
caaataacag aatagcaaaa gcgggaggag gaagtaaatc ctcaatcatc atagtacagt  32280
ccatcaccat ccctaaataa ttttcatcct tccagccttg gactatattt ttaaactgct  32340
cttgtaaatc caaaccacac atgtggaaaa gttcccaaag agctccctca actaccattc  32400
ttaagcacac cttcatagtg acaaaatatc ttgttcctct gtcacctgca gcaaattaca  32460
aagtccaata ttaggatcta tgcccagaga tctaagctca tccctcaatt ccaactgtaa  32520
aaaggcttcc agatctgccc taacttgttc agccagtggg ctccctggaa taagcgtggg  32580
agaagccaaa ctgcaaaaca gacgcatgcc gccataatta ccaccagaaa acactacgtt  32640
acagtatgca tgctgattca ttccagtaat ttcatccagt gtattggata caaaaaaagg  32700
caagcactct ctcactaatt gtattatgga gacattatca cacaggtaac aatttaaagg  32760
ttgtggaaca ataatgcagt aagtaaccac ggtgcgctcc aacatggtta gtaattttta  32820
gttctgaaaa acaaaacata caaaaaatta tatcatactc atttggcgaa ctggtggaaa  32880
aatgacccta tctagcacaa ggcaagccac tggatcacca atgcgcccct cataaaacct  32940
gtcatcatga ttaaaaagca acaccgaaag ctcttcccta tgtcctgcat gaatgattct  33000
agctgaggaa tataagccag cgcaattagt atctgttaaa gaaaaaaaac ggccaacata  33060
gcctctagga attagcacac ttaatcttaa agacattact gccatccccc ttggatttaa  33120
ggtaaaattt acaggagcat agaaaatata ctgatttccc tcctgcacag gcagcatagc  33180
accaggtccc tctaaaaaca cacacaaagc ttctgcagcc atagcttacc gcgcaaacca  33240
ggcacagcag tgagctaaaa ggacaaagct ctaactcact agccaacctg gcgcacaata  33300
tatagttagt ccttacactg acgtaaccga ccaaagtcta aaaaccccgc caaaaataca  33360
cacacgccca aaaaacgccc cgtgagtcaa aaaacagttt cacttcctcg ttacacccaa  33420
aacgtcgtca cttccggatt cccacggttc gtcacttccg gagctccttg cttaattaac  33480
cccgcccaaa acgtcatcgt ccgcgtcacg ccgccccgcc ccgcgaccgt tgaccccggg  33540
```

```
ccaatcaccg cacatcccgc aaaattcaaa ctcgtctaat ttgcatattg gcacactgcc  33600
catataaggt atattattga tgatgattta aatcatatgc ggtgtgaaat accgcacaga  33660
tgcgtaagga gaaaataccg catcaggcgc tcttccgctt cctcgctcac tgactcgctg  33720
cgctcggtcg ttcggctgcg gcgagcggta tcagctcact caaaggcggt aatacggtta  33780
tccacagaat caggggataa cgcaggaaag aacatgtgag caaaaggcca gcaaaaggcc  33840
aggaaccgta aaaaggccgc gttgctggcg tttttccata ggctccgccc ccctgacgag  33900
catcacaaaa atcgacgctc aagtcagagg tggcgaaacc cgacaggact ataaagatac  33960
caggcgtttc cccctggaag ctccctcgtg cgctctcctg ttccgaccct gccgcttacc  34020
ggatacctgt ccgcctttct cccttcggga agcgtggcgc tttctcatag ctcacgctgt  34080
aggtatctca gttcggtgta ggtcgttcgc tccaagctgg gctgtgtgca cgaacccccc  34140
gttcagcccg accgctgcgc cttatccggt aactatcgtc ttgagtccaa cccggtaaga  34200
cacgacttat cgccactggc agcagccact ggtaacagga ttagcagagc gaggtatgta  34260
ggcggtgcta cagagttctt gaagtggtgg cctaactacg gctacactag aaggacagta  34320
tttggtatct gcgctctgct gaagccagtt accttcggaa aaagagttgg tagctcttga  34380
tccggcaaac aaaccaccgc tggtagcggt ggtttttttg tttgcaagca gcagattacg  34440
cgcagaaaaa aaggatctca agaagatcct ttgatctttt ctacggggtc tgacgctcag  34500
tggaacgaaa actcacgtta agggattttg gtcatgagat tatcaaaaag gatcttcacc  34560
tagatccttt taaattaaaa atgaagtttt aaatcaatct aaagtatata tgagtaaact  34620
tggtctgaca gttaccaatg cttaatcagt gaggcaccta tctcagcgat ctgtctattt  34680
cgttcatcca tagttgcctg actccccgtc gtgtagataa ctacgatacg ggagggctta  34740
ccatctggcc ccagtgctgc aatgataccg cgagacccac gctcaccggc tccagattta  34800
tcagcaataa accagccagc cggaagggcc gagcgcagaa gtggtcctgc aactttatcc  34860
gcctccatcc agtctattaa ttgttgccgg gaagctagag taagtagttc gccagttaat  34920
agtttgcgca acgttgttgc cattgctgca ggcatcgtgg tgtcacgctc gtcgtttggt  34980
atggcttcat tcagctccgg ttcccaacga tcaaggcgag ttacatgatc ccccatgttg  35040
tgcaaaaaag cggttagctc cttcggtcct ccgatcgttg tcagaagtaa gttggccgca  35100
gtgttatcac tcatggttat ggcagcactg cataattctc ttactgtcat gccatccgta  35160
agatgctttt ctgtgactgg tgagtactca accaagtcat tctgagaata gtgtatgcgg  35220
cgaccgagtt gctcttgccc ggcgtcaaca cgggataata ccgcgccaca tagcagaact  35280
ttaaaagtgc tcatcattgg aaaacgttct tcggggcgaa aactctcaag gatcttaccg  35340
ctgttgagat ccagttcgat gtaacccact cgtgcaccca actgatcttc agcatctttt  35400
actttcacca gcgtttctgg gtgagcaaaa acaggaaggc aaaatgccgc aaaaaaggga  35460
ataagggcga cacggaaatg ttgaatactc atactcttcc tttttcaata ttattgaagc  35520
atttatcagg gttattgtct catgagcgga tacatatttg aatgtattta gaaaaataaa  35580
caaatagggg ttccgcgcac atttccccga aaagtgccac ctgacgtcta agaaaccatt  35640
attatcatga cattaaccta taaaaatagg cgtatcacga ggccctttcg tcttcaagaa  35700
ttgatttaaa t                                                       35711
```

<210> SEQ ID NO 21
<211> LENGTH: 36702
<212> TYPE: DNA

<213> ORGANISM: Artificial Sequence
<220> FEATURE:
<223> OTHER INFORMATION: pBLY6.RSVF-2A-GLuc

<400> SEQUENCE: 21
catcatcaat aatatacctt atatgggcag tgtgccaata tgcaaattag acgagtttga 60
attttgcggg atgtgcggtg attggcccgg ggtcaacggt cgcggggcgg ggcggcgtga 120
cgcggacgat gacgttttgg ggaggaggag ctatgttgca agtaatcgtg ggaaatgcga 180
cgtaaaacga ggtggagttt aaacacggaa gtagacaatt ttcccgcgct gtttgacagg 240
aaatgatgtg tttttgggcg gatgcaagtg aaaattctcc attttcgcgc gaaaactaaa 300
tgaggaagtg aaattctgag taattctgag gttatcacag ggcggagtat ttaccgaggg 360
ccgagtagac tttgacccat tacgtggagg tttcgattac tctatttttc acctaaattt 420
ccgcgtactg tgtcaaagtc cgtgttttta cgcgatcgct caatattggc cattagccat 480
attattcatt ggttatatag cataaatcaa tattggctat tggccattgc atacgttgta 540
tccatatcat aatatgtaca tttatattgg ctcatgtcca acattaccgc catgttgaca 600
ttgattattg actagttatt aatagtaatc aattacgggg tcattagttc atagcccata 660
tatggagttc cgcgttacat aacttacggt aaatggcccg cctggctgac cgcccaacga 720
cccccgccca ttgacgtcaa taatgacgta tgttcccata gtaacgccaa tagggacttt 780
ccattgacgt caatgggtgg agtatttacg gtaaactgcc cacttggcag tacatcaagt 840
gtatcatatg ccaagtacgc cccctattga cgtcaatgac ggtaaatggc ccgcctggca 900
ttatgcccag tacatgacct tatgggactt tcctacttgg cagtacatct acgtattagt 960
catcgctatt accatggtga tgcggttttg gcagtacatc aatgggcgtg gatagcggtt 1020
tgactcacgg ggatttccaa gtctccaccc cattgacgtc aatgggagtt tgttttggca 1080
ccaaaatcaa cgggactttc caaaatgtcg taacaactcc gccccattga cgcaaatggg 1140
cggtaggcgt gtacggtggg aggtctatat aagcagagct cgtttagtga accgtcagat 1200
cgcctggaga cgccatccac gctgttttga cctccataga agacaccggg accgatccag 1260
cctccgcggt tggccgtgct cttcctgacg ggtaggtgtc ccctaaccta gggagccaac 1320
catcgggggg ccttctccct aaatccccgt ggcccaccct cctgggcaga ggcagcaggt 1380
ttctcactgg ccccctctcc cccacctcca agcttggcct ttcggctcag atctcagccc 1440
acagctggcc tgatctgggt ctcccctccc accctcaggg agccaggctc ggcatttcgt 1500
cgacatggaa ctgctgatcc tgaaggccaa cgccatcacc accatcctga ccgccgtgac 1560
cttctgcttc gccagcggcc agaacatcac cgaggaattc taccagagca cctgtagcgc 1620
cgtgtccaag ggctacctga gcgccctgcg gaccggctgg tacaccagcg tgatcaccat 1680
cgagctgagc aacatcaaaa agaacaagtg caacggcacc gacgccaaaa tcaagctgat 1740
caagcaggaa ctggacaagt acaagaacgc cgtgaccgag ctgcagctgc tgatgcagag 1800
cacccccgcc accaacaacc gggccagacg ggagctgccc cggttcatga actacaccct 1860
gaacaacgcc aaaaagacca acgtgaccct gagcaagaag cggaagcggc ggttcctggg 1920
cttcctgctg ggcgtgggca gcgccattgc tagcggagtg gctgtgtcta aggtgctgca 1980
cctggaaggc gaagtgaaca agatcaagtc cgccctgctg agcaccaaca aggccgtggt 2040
gtccctgagc aacggcgtgt ccgtgctgac cagcaaggtg ctggatctga agaactacat 2100
cgacaagcag ctgctgccca tcgtgaacaa gcagagctgc agcatcagca acatcgagac 2160
agtgatcgag ttccagcaga agaacaaccg gctgctggaa atcacccgcg agttcagcgt 2220
gaacgccggc gtgaccaccc ccgtgtccac ctacatgctg accaacagcg agctgctgag 2280
cctgatcaac gacatgccca tcaccaacga ccagaaaaag ctgatgagca acaacgtgca 2340
gatcgtgcgg cagcagagct actccatcat gtccatcatc aaagaagagg tgctggccta 2400
cgtggtgcag ctgcccctgt acggcgtgat cgacaccccc tgctggaagc tgcacaccag 2460
ccccctgtgc accaccaaca ccaaagaggg cagcaacatc tgcctgaccc ggaccgaccg 2520
gggctggtac tgcgataatg ccggcagcgt gtcattcttt ccacaagccg agacatgcaa 2580
ggtgcagagc aaccgggtgt tctgcgacac catgaacagc ctgaccctgc ccagcgaggt 2640
gaacctgtgc aacgtggaca tcttcaaccc taagtacgac tgcaagatca tgacctccaa 2700
gaccgacgtg tccagctccg tgatcacctc cctgggcgcc atcgtgtcct gctacggcaa 2760
gaccaagtgc accgccagca acaagaaccg gggcatcatc aagaccttca gcaacggctg 2820
cgactacgtg tccaacaagg gcgtggacac cgtgtccgtg ggcaacaccc tgtactacgt 2880
gaacaaacag gaaggcaaga gcctgtacgt gaagggcgag cccatcatca acttctacga 2940
cccccctggtg ttccccagcg acgagttcga cgccagcatc agccaggtca acgagaagat 3000
caaccagagc ctggccttca tcagaaagag cgacgagctg ctgcacaatg tgaatgccgt 3060
gaagtccacc accaatatca tgatcaccac aatcatcatc gtgatcatcg tcatcctgct 3120
gtccctgatc gccgtgggcc tgctgctgta ctgcaaggcc cggtccaccc ctgtgaccct 3180
gtccaaggac cagctgagcg gcatcaacaa tatcgccttc tccaacggac gcgtgaccga 3240
gctgctttac cggatgaagc gggctgagac atattgcccg agacccctgt tggcaatcca 3300
tcctactgag gctcgccaca aacagaaaat cgtggccccc gtcaaacaga cactcaattt 3360
tgacttgttg aaacttgcag gagatgttga gtcaaacccc gggcctatgg gcgtcaaggt 3420
cctgttcgct ctgatttgta tcgctgtcgc tgaagctaag ccaaccgaga ataatgaaga 3480
ctttaatatc gtggccgtgg cttctaactt cgctaccaca gacctggatg cagacagggg 3540
aaagctgcca ggcaagaaac tgcccctgga ggtcctgaag gagatggaag caaatgcccg 3600
gaaagccggg tgcacaagag gatgcctgat ttgtctgagc cacatcaagt gcactcctaa 3660
gatgaagaag ttcatccccg gccggtgcca tacctacgag ggcgataagg aatccgccca 3720
gggaggaatc ggagaggcta tcgtggatat tcccgaaatc cctggcttca aagacctgga 3780
gcccatggaa cagtttattg cacaggtgga tctgtgcgtc gactgtacta ccggatgcct 3840
gaagggactg gcaaacgtcc agtgtagcga cctgctgaag aaatggctgc ctcagcgatg 3900
tgctacattt gccagcaaga ttcagggcca ggtggacaag attaagggag caggaggcga 3960
ctgataattc tagacgagat ccgaacttgt ttattgcagc ttataatggt tacaaataaa 4020
gcaatagcat cacaaatttc acaaataaag catttttttc actgcattct agttgtggtt 4080
tgtccaaact catcaatgta tcttatcatg tctgcgatcg cgatggcctg tgtttgagca 4140
taatgtactg accaggtgta acgttcatct gggtggtcgt agaggaatgt tcatgccata 4200
ccaatgcaat tttaatcatg tgaggatctt gatggagccg caagcgtttt ccagagtcag 4260
cttgactgga atctttgaca tgtgtgtgga agcatggaag atcttaagat atgatgatac 4320
caaatccaga tgccgcgcat gcgagtgcgg gggcaggcat gccaggttcc aacctgtatg 4380
tgtggaggtg accgaggagc tgagaccaga tcatttggtg ctgacctgca ctggtgcgga 4440
gttcggttcc agtggtgaag aaactgatta aagtgagtag tgggatgtta taaaagtgac 4500
cataaggtga tgtgagatgg acaaatttgg taatttttat gtatttttgt cttgcagcca 4560
tgagtgggag cgcttccttt gaagggggcg tctttagccc ttatctgacg gggcgtctgc 4620
ctcattgggc tggagtgcgt cagaatgtga tggggtctac agtggatgga agacctgttc 4680
agcctgctaa ttcttctact ctgacttatg ctactatgac ttcctcgcct ttggatgcag 4740
ctgcagctgc tgccgcttct gctgccgcca acactgttcg gggatggcc ttggagatgg 4800 ggtattatgg aactgtagtg gccaacacca ctaccccaaa taaccccaca gccttgaatg 4860
aggacaagct gctagttctc atgtcccagc tggagtcttt gacccaacgc ctgggcgatc 4920
tagctcagca ggtgtcccag ctgaaggagc agactcaagc tgcaattacc actgcgaggg 4980
gaaattaaaa aaattcaaag aatcaataaa taaaccgaga ctttgttgat tttaaagtgt 5040
gtcattcttt atttaatttt tcgcgcgcga tatgccctgg accaccggtc tctatcattg 5100
aggacacggt ggatcttttc tagaacccga tagaggtggg attggatgtt gaggtacatg 5160
ggcataagac catctttggg gtgtagatag ctccactgca gagcctcatg ctccggggtg 5220
gtgttgtata taacccagtc atagcatggg cgttgggcat gatgttgcac aatatcttta 5280
aggaggagac taatggccac tgggagaccc ttggtgtaag tgtttacaaa tctattaagc 5340
tgggacgggt gcatccgagg tgagataatg tgcattttgg attggatttt tagattggca 5400
atgtttcccc ctagatctct cctgggattc atgttatgca agaccactag aacagtgtat 5460
ccggtgcact tagggaattt gtcatgaagt ttggagggga aagcatgaaa aaatttagac 5520
acacccttgt gtcctcccaa gttctccatg cactcatcca taataatggc aatgggccca 5580
tgggcggcgg cacgggcgaa cacgttcctg ggatctgaca catcatagtt gtggtcttgg 5640
gtcaggtcat cataagccat tttaataaac ttggggcgga gggtgccaga ttgggggatg 5700
aatgttccct cgggccccgg aacatagttt ccttcacata tttgcatttc ccaggctttt 5760
agttcagagg gggggatcat gtccacctgt ggagcgatga agaagacggt ctcgggggcg 5820
ggggtgatta agtgggagga cagcaagttc ctaagcagct gtgacttgcc acacccagtg 5880
ggaccgtaga tgacccctat aacaggttgc agatggtagt ttagggaaag acagctgccg 5940
tcctctcgca ggaggggggc gacctcgttc atcatttccc tcacatgcat gttttcccgc 6000
acaagttccg ataggaggcg ctctccaccc agggaaagga gttcttgaag agatgagaaa 6060
tttttcaagg gttttaagcc atcagccatg ggcattttgg agagggtttg ttgcaagagt 6120
tcaaggcggt cccagagttc ggtgatgtgt tctatggcat ctcgatccag catacttcct 6180
cgtttctggg gttgggacgg ctgcgggagt atggaaccag gcgatgggcg tccagcgctg 6240
ccagtgtccg gtccttccac ggtcgcagcg tccgagtcag ggtcgtttcc gtcacggtga 6300
aggggtgcgc gcctggctgg gcgcttgcga gggtgcgctt caggctcatc ctgctcgtgg 6360
agaaccgctg ccgttctgcg ccctgtgcat cggccaggta gcaattaacc atgagttcgt 6420
agttgagcgc ctctgccgcg tggcctttgg cgcgcagctt acctttggaa gtcttctgac 6480
aggtgggaca gtagagacac ttgagagcat agagttttgg ggctagaaag accgattctg 6540
gggagtatgc atcggcccca caggaggcgc agacggtttc gcattccacc agccatgtaa 6600
gatcgggctc gttggggtca aaaacaagtt ttccgccatg ttttttgatg cgtttcttac 6660
ctttgctttc catgagttcg tgcccccgtt gggtgacaaa gaggctgtcc gtgtccccgt 6720
agactgactt tatgggcctg tcctcgagcg gcgtgccgcg gtcctcttcg tagaggaact 6780
cggaccactc tgagacgaaa gcacgtgtcc aggccagcac aaaggaggct atatgggagg 6840
ggtagcgatc gttgtcaacc aaggggtcta ctttttccaa ggtgtgtaaa cacatgtccc 6900
cttcttccac atccaggaag gtgattggct tgtaagtgta tgccacgtga cctggggtcc 6960
cagacggggg ggtataaaag ggggcgggtc tctgctcgtc ctcactgtct tccggatcgc 7020
tgtccaggag cgccagctgt tgaggtaggt attccctctc gaaggcgggc ataacctccg 7080
cactcaggtt gtcagtttct aggaacgagg aggatttgat attgacagtg cctgccgaga 7140
tgcctttcat gagactgtcg tccatttggt cagaaaagac aatctttttg ttatcaagtt 7200
tggtggcgaa ggatccatac agggcattgg aaagcagttt ggcaatggag cgcatggttt 7260
ggttttttc tttgtctgcg cgctctttgg cggctatgtt gagttggaca tattcgcggg 7320
ccagacattt ccattgtgga aatatggtag ttaattcatc tgggacgatt ctgactttcc 7380
agcctctgtt atgcagggta atcagatcca cactggttgc cacttctcct ctaagtggtt 7440
cattagtcca gcatagtcgc cccccttttc gagaacagaa agggggtagg ggatctagca 7500
tgagttcgtc tggggggtct gcatctatgg tgaaaatccc aggaaggaga tcttcgtcaa 7560
aatagctgat ggtggcgggg tcatccagag acatttgcca ttctcgagca gccagagcgc 7620
gctcgtaggg gttaagggga gtcccccatg gcatgggatg ggtgagtgca gaagcataca 7680
tgccacagat gtcatagaca tagagcggct cttccagaat ccctatgtaa gtgggataac 7740
atcgcccccc tctgatgctg gctcgcacat aatcatagag ttcatgtgag ggcgctagaa 7800
gacccgagcc caggttggtg cggttgggtt tttctgctct gtagaggatc tggcgaaaga 7860
tggcatggga gtttgatgag atggtgggtc tttggaagat gttgaaatgg gcatgaggca 7920
gtcccacaga gtcccttatg aagtgagcat aggagtcttg cagtttggcc accagctcgg 7980
cggtgaccag cacatccaaa gcacagtagt cgagggtctc tttgatgatg tcatagttag 8040
gttccccttt cttttcccac agctcgcggt tgagaaggta ttcttcgcga tccttccagt 8100
actcttcgag gggggaacccg tccttgtctg aacggtaaga acccagcatg taaaattgat 8160
tgacagcttt gtaggcacaa cacccccttct ccacggggag tgagtatgct tgcgcggctt 8220
tgcgcagaga ggtgtgagta agggcgaaag tgtccctgac catgactttg aggaactgat 8280
gcttaaagtc tatgtcatcg caggcccccct gctcccacag ttggaagtcc actcgctttt 8340
tgtaggcggg attgggcaaa gcgaaagtaa catcgttgaa taggatcttt ccagccctgg 8400
gcatgaagtt gcgagtaatg cgaaaaggct gaggcacttc tgccctgttg ttgataactt 8460
gggcagccaa gacgatctcg tcaaagccgt tgatgttgtg acccacaatg taaagttcta 8520
cgaagcgtgg gcgtcccttg atgtggggca gttttttaag ctcttcgtag gtcaagtcgt 8580
cagggtcagc gattccatat tgctccaaag cccagtcagg caggtgagga ttagcatgaa 8640
ggaaagaggt ccaaagatcc acggccagag ctgtttgtaa gcggtctctg tactgacgga 8700
aatgtcggcc taccgccatt ttttcaggag taacacagta aaaggtgcgc gggtcctttt 8760
cccagcgatc ccattgaagt tgcaaggcta ggtcgtgggc gaggttgacg agctgttcgt 8820
cccccgaaag tttcatgacc agcatgaaag ggacaagctg cttgccaaag gaccccatcc 8880
aggtgtaggt ttccacatcg taggtgagga agagcctttc tgtgcgagga tgagaaccga 8940
tcgggaagaa ctggatttcc tgccaccagt tggaggaatg gctgttgata tgatggaagt 9000
agaactccct acggcgcgcc gagcattcgt gcttgtgctt gtacagacgg ccacagtact 9060
cgcagcgctg cacgggatgc acctgatgaa tgagctgtac ctggcttcct ttgacaagaa 9120
atttcagtgg gaagttgagg cgtggcgtct gcatctcgtg ttgtattacg tcctggctat 9180
tggtctggcc atcttctgtc tcgatggtgg tcatgctgac gagcccgcgc gggaggcagg 9240
tccagacctc cgcgcggacg ggtctgagag cgaggacgag agcgcgcagg ccggaactgt 9300

```
ccagggtcct gagacgctgc ggagtcaggt cagtagggag agtacatagg tttacttgca   9360
taagtttttc cagggcatgt gggaggtcaa gatgatattt gatttctact ggcgagttgg   9420
tggagacatc gatggcttgc agggtcccgt gcccctgggg tgctaccacc gtcccttttt   9480
ttttcttgat cgggggcggt gttgcttctt gcatggtaag gtcgtcttct agaagcggcg   9540
gcgaggtcgc gcgccgggtg gcagtggcgg ttctggacct ggaggtagag gcggtagagg   9600
tacgtcggcg ccgcgcgcgg gtaggttctg gtactgcgcc ctgagaagac ttgcgtgagc   9660
gacgacgcgg cggttgacgt cctggatctg acgcctctgg gtgaatgcta ccggacccgt   9720
gagcttgaac ctgaaagaga gttcaacaga atcaatttcg gtatcgttga cggctgcctg   9780
ccgcaggatt tcttgtacgt cgcccgagtt gtcttggtag gcgatctcgg ccatgaactg   9840
ctcgatctct tcttcttgga gatctccgcg gcccgctcgt tctacggtgg cagcaaggtc   9900
gttggagatg cgccccatga gctgtgagaa tgcattcatg cccgcctcgt tccagacgcg   9960
actgtagacc acggctccct cgggatctct ggcgcgcatg accacttggg cgaggtttag  10020
ttccacgtgt ctggtgaaga ccgcatagtt gcagagacgc tggaagaggt agttgagcgt  10080
ggtggcgatg tgctcggtga caaagaaata catgatccag cgacgaagcg gcatctcgct  10140
gatatcgccc agggcttcca accgttccat ggcttcgtaa aagtccacgg cgaagttgaa  10200
aaactgggag ttgcgagcgg acacggtcaa ctcctcctcc agaagacgga tgagctcggc  10260
gatggtggcg cgcacttcgc gctcaaaggc tcccgggatc tcttcctcct cttcttcttc  10320
caactcttcc tccactaaca tctcttctac ttcctcctca ggcggcgggg gtggaggagg  10380
gggcgcgcgg cgacgccggc gacgcacggg cagacgatcg atgaagcgtt cgatcacttc  10440
tccgcggcgg cgacgcatgg tctcggtgac ggcgcgcccg tcctccctgg gtcgcagagt  10500
gaagacgccg ccgcgcagct ccctgaaatg gtgactggga gggtccccgt ttggtaggga  10560
cagggcactg atgatgcatc ttattaattg ccctgtaggg actccgcgca aggacctgag  10620
cgtctcgaga tccacgggat ctgaaaatct ctgaacgaag gcttcgagcc agtcgcagtc  10680
gcaaggtagg ctgagcactg tttcttcggg gcgggctgct gagctagagg gttgtacgat  10740
gctgctggtg atgaagttaa aataggcagt tctgagacgg cggatggtgg cgaggagcac  10800
caggtctttg ggtccggctt gctggatgcg caggcggtcg gccattcccc atgcattatc  10860
ttggcacctg gccagatctt tatagtagtc ttgcatgagt cgctccacgg gcacttcttc  10920
ttcgcccgct ctgccgtgca tgcgtgtgag tccgtaccct ctctgtggtt ggacgagcgc  10980
caggtcggca acgacccttt cggctagaat ggcttgctgc acctgggtga gggtgttctg  11040
gaaatcatca aagtccacaa agcggtggta ggcccccgtg ttgatggtgt aggagcagtt  11100
ggacatgacc gaccagttga ctgtctggtg tcctggtcgt acgagttccg tgtacctgag  11160
ccgcgagtat gcgcgggagt cgaagatgta atcgttgcag gttcgcacca ggtactggta  11220
gccgatgagg aagtgaggcg gcggctggcg gtagagaggc catcgttcgg tggcgggcgc  11280
gccgggcgct aggtcttcta gcatgagacg gtggtatccg tagacgtacc tggacatcca  11340
ggtaataccg gcggcggtgg tggaggcgcg cggaaactct cgcacgcggt tccagatgtt  11400
gcgcagcggc atgaagtagt tcatggtggg cacggtctgg cccgtgaggc gcgcgcagtc  11460
attgatgctc tagatacggg caaaaacgaa agcgttgagc ggttcccttc cgtggcctgg  11520
aggaacgcga acgggttagg tcgcagcgta ccctggttcg agactaaaga aagcgagcaa  11580
ctcgaaccgg cagagtcgcg gctaacgggt attggcaatc ccgtctcgac ccaagccagc  11640
aaatccagga tacggatggg ggcccctttt gtttttcagg gcatgagtca ccggttaagg  11700
```

tttacaacgg ctgtttcatg cctttagaag tggctcgcgc ccgtagtctg gagaatcaat 11760
cgccagggtt gcgttgcggc gtgccccggt tcgagcctgc agcttgagtc ggccggtgac 11820
cgcggcaaac gagggcgtgg cggccccgtc gtttctaaga ccttgctagc cgacctctcc 11880
agtttacggg aacgagcccc cttttatttt ttttgttttt gccagatgca tcccgtactg 11940
cggcagatgc gcccacagcc cccacagcag cagcagcagg ctggcctacc ttctctacct 12000
cagccgctac ctgcaactac cgcggtggcc gctgtaagcg gggccggaca gcaggcggct 12060
cctcaatatg aattggactt ggaagagggc gagggattgg caagattggg ggcgccctcg 12120
cccgagcgcc acccgcgggt gcagatgaaa aaggacgttc gcgaatctta cgtgcccaag 12180
cagaatctgt tcagagacag aagcggcgag gagcccgagg agatgcgcgc gtcccgtttt 12240
aacgcgggtc gcgagctgcg acaaggactg gatcgaaaac gggtgttgag ggatgatgat 12300
tttgaggtgg atgaaatgac agggatcagc cccgctcgcg ctcacgtggc tgcagctaat 12360
ctggtgacag cttatgagca gaccgtgaag gaggaaagca acttccagaa atcattcaat 12420
aaccacgtgc gcaccctgat cgcacgcgag gaggtgaccc tgggcctgat gcacctgtgg 12480
gatctgctgg aagccatagt gcagaacccc actagcaaac ccctgactgc tcaactgttt 12540
ctggtggtgc agcacagcag ggataatgag gcattcagag aggcgctgct gaatatcact 12600
gaacctgagg ggagatggct gctggatctg gtgaatatcc tgcagagcat tgtagtgcag 12660
gaacgcagct tgcctttgtc cgagaaggtg gcggcgatca attactctgt gctgagtctg 12720
ggcaaatact atgccaggaa gatctacaaa accccttacg tgcccataga caaggaagtg 12780
aaaatagatg ggttttacat gcgcatgacc ctgaaagtgc taaccctgag cgatgacttg 12840
ggagtgtacc gcaacgacag gatgcaccgc gcggtgagcg ccagcaggag gcgcgagctg 12900
agcgacaaag aattaatgca cagcttgcaa cgagccctga cgggagccgg gacggagggg 12960
gagaactact ttgacatggg tgcagacttg cattggctgc ctagtcgcag ggcattggaa 13020
gcggcaggcg atgggcccta tgtagaggaa gtagtagacg aggacgatga ggagggcgag 13080
tacctggaag actgatggcg cgacccgtat ttttgctaga tggaacaggc gccggaccct 13140
gcgatgcggg cggcgctgca gagccagccg tccggcatta attcctcgga cgattggacc 13200
caggccatgc aacgcatcat ggcgctgacg acccgcaacc ccgaagcctt tagacagcag 13260
cctcaggcca accgcctttc ggccatcctg gaggccgtgg tgccctctcg ctccaacccc 13320
acccacgaga aggttctggc catcgtgaat gccctggtgg agaacaaggc catccgctcc 13380
gatgaagccg ggctggtata caacgccttg ctcgagcgcg tggctcgcta caacagcagc 13440
aatgtccaga ctaacctgga caggatggtg accgacgtgc gcgaggccgt gtcccagcgc 13500
gaacggttcc atcgcgagtc taacctgggt tccatggtag cgctgaacgc tttcctcagt 13560
tcccagcctg ccaatgtgcc ccggggacag gaagactata ccaactttat tagcgccctg 13620
agactcatgg tagccgaggt tcctcagagc gaggtgtacc agtccggtcc agactacttt 13680
ttccagacaa gcaggaacgg tatgcagaca gtgaacttaa gccaggcttt caagaacctg 13740
caagggctgt ggggagtcca agctccagtg ggcgacaggg cgaccgtgtc gagcctgttg 13800
actccaaatt cccgtttgct gctgctgctg gtgtcccccct tcactgacag cggcagcata 13860
aacagaaact cctacttggg ctacctgata aacttgtatc gcgaagctat aggtcaggcc 13920
cacgtggacg aacagaccta tcaggagatc actaatgtga gtcgcgctct gggccaggac 13980
gaccctggaa acctggaagc tactctaaac tttctgctga ccaaccgctc gcaaaaaatc 14040

-continued

```
cctcctcagt atacattaac tgcggaggag gaacggatct tgagatacgt gcagcagagc  14100
gtgggtctgt tcctgatgca agagggtgcg accccctagcg ccgcgcttga tatgacagcg  14160
cgcaacatgg agcccagcat gtatgccagc aacagaccat tcattaataa attgatggat  14220
tacttccatc gcgcggccgc tatgaactct gattacttca ccaatgctat tctgaacccc  14280
cattggctgc ctccgcctgg tttttatact ggcgagtatg acatgcctga ccccaacgat  14340
gggttcttgt gggacgatgt ggacagcgtg gcgttctcgc ctaccgctcc tcgtactttt  14400
tggaagaagg aaggtagtga cagaagaccc tcctccgtgc tgtcaggacg tgagggtgct  14460
gccgcggcgg tccccgatgc tgcaagcccc tttcccagtc tgccattttc actaaacagc  14520
gtgcgcagta gcgagctggg gagaataacc cgccctcgct tgctgggcga ggacgagtat  14580
ttgaatgact ccctactgag acccgagcgg gaaaagaact tccctaataa tgggattgaa  14640
agcctggtgg ataagatgag cagatggaag acctatgccc aggagcacag agatgagcct  14700
agaatcttgg gtcctacagt aggcacccgc agacgccagc gccatgatag acagcggggt  14760
ctggtgtggg acgatgagga ttctgcagat gacagcagcg tgttggactt gggcgggagg  14820
ggaggtgtgg gcaacccgtt cgcacacttg cgtccccgta ttggacgcat gatgtaaaag  14880
tgaaaataaa aaaggaactc accaaggcca tggcgaccag cgtgcgttcg ttctttctgt  14940
tgttgtatct agtatgatga ggcgcaccgt gctaggcgga tcggtggcgt atccggaggg  15000
tcctcctcct tcgtacgaaa gcgtgatgca gcaggtggcg gcggcggcga tgcaaccccc  15060
cttggaggct ccttacgtgc ccccgcggta cctggcacct accgaggggga gaaacagcat  15120
tcgttattcg gaactcacac ccttgtatga caccacccgg ttgtacctgg tggacaacaa  15180
atcggcggac attgcctcgt tgaactatca gaacgaccac agcaacttct tgacaacggt  15240
ggtgcagaac aatgacttta cccccacgga ggccagcacc cagaccatca actttgacga  15300
gcgctcccgg tggggcggtc agctgaagac catcatgcac accaacatgc ccaacgtgaa  15360
cgagttcatg tttagcaaca agttcagggc tagggtgatg gtgtccagaa ccacacctaa  15420
agaggtgaca gtcacaacag actatgatgg tagtcaggac atcttggaat acgagtgggt  15480
tgactttgag ttaccagaag gcaacttctc tgccaccatg accatagacc tgatgaataa  15540
tgcaattgtt gataattacc taaaagtggg tagacagaat ggggtactgg agagtgacat  15600
aggtgttaag tttgacacta ggaactttag gcttggttgg gacccagtga cagagttggt  15660
catgcctggg gtctacacca atgaagcttt ccatcctgac atagtcctac tacctggctg  15720
cggagtggac ttcactgaga gccgcctcag taatctgcta ggcattagaa agaaacagcc  15780
attccaggaa gggttccaga tcatgtatga ggatctggag ggtggtaaca tccccgccct  15840
gcttgatgta aatgcatatg agaagagcaa ggaagataat acaaccacca caaatgaagc  15900
tgtggccgcg gcttcatcta ctgaagccaa agctgtggta gatgcttcca cttcaacaga  15960
aaacaccact gatgaaaaag tcaccagggg agatacattt gccacccctg aacaagagaa  16020
ggcagctgag gcagagtctg atattatgct tctgtccacc gatgaaaacg aaactaaaaa  16080
acaactggtt attcgagcgg tgaccaagga tagtaaggac aggagttata atgtattgtc  16140
agatggaaag aacacagctt accgtagttg gtacctggca tacaattatg gcgaccgtga  16200
gaaaggggtg cgttcttgga cactgcttac cacctcggat gtcacctgcg gcgtggagca  16260
agtctattgg tcgctaccag atatgatgca agatccagtc acctttcgct ccacacgcca  16320
agttagcaac tacccagtgg tgggcgcaga gctgctccca gtgcattcca gaagcttcta  16380
caacgagcaa gccgtctact cgcaacagct ccgccagtac acctcgctca cgcacgtctt  16440
```

caaccgcttc cccgagaatc agatcctcgt ccgcccgccc gcgccaacca ttaccaccgt 16500
cagtgaaaac gttcctgctc tcacagatca cgggaccctg ccgctgcgca gcagtatccg 16560
gggagtccag cgcgtgaccg ttactgacgc cagacgccgc acctgtccat acgtatacaa 16620
ggccctgggc atagtcgcgc cgcgcgtcct ttcaagccgc actttctaaa aaaatgtcca 16680
ttctcatctc gcccagtaat aacaccggtt ggggcctgcg cacacctagc aagatgtatg 16740
gaggcgctcg cagacgctcc actcagcacc ctgtgcgcgt gcgcgggcat ttccgcgctc 16800
cctggggcgc cctcaaggga cgctctcgta ctaggaccac cgttgacgat gtgatcgacc 16860
aggtggtcgc cgatgcacgt aactataccc ccgcagccgc acctgcatcc accgtggatg 16920
cggtcattga cagcgtggta gccgatgcgc gcgcctatgc tcgcgccaag agcaggaggc 16980
ggcgtattgc caggcgtcac cgagctactc cagccatgcg agctgcaaga gctttattgc 17040
ggagagccag acgtgtgggg cgaagagcca tgcgtagagc ggccagacgc gcggcttcag 17100
gtgccagcgc aggcagggtc cgcaggcgcg cggctacggc ggcagcggcg gccatcgcta 17160
gcatgaccaa accacgaaga ggcaatgtgt attgggtgcg cgacgccgcc accggccagc 17220
gcgtgcccgt gcgcacacgc ccccctcgca cttagaagat actgagcagt ctccgatgtt 17280
gtgtcccagc ggcgagatgt ccaagcgcaa attcaaggaa gagatgctcc aggtcatcgc 17340
gcctgagatc tacggtcctg cggtgaagga tgaaaaaaag ccccgcaaga tcaagcgggt 17400
caaaaaggac aaaaaggaag aagatggtga tgatgggctg gtggagtttg tgcgcgagtt 17460
tgccccaagg aggcgcgtgc agtggcgcgg gcgcaaagtg tggccggtgt tgagaccggg 17520
gaccacagtg gtctttacgc caggcgagcg ctccagcacc gtttccaaac gctcttatga 17580
tgaggtgtac ggggacgatg atattctcga gcaggcggct gatcgccttg gcgagtttgc 17640
atatggcaaa cgcagccgct cgggagccaa ggaagaggca ttgaccatcc ccttggatca 17700
tggaaatccc accccaagcc tcaaacccgt gaccctgcaa caagtgctgc ccacgccgcc 17760
acgcaagggc atcaagcgcg agggcgagga tctgtatccc accatgcagc tgatggtgcc 17820
caagcgccag aagctggaag acgtgctgga gaaaatgaaa gtggatcctg aaatccagcc 17880
tgaagtcaaa gtgaggccaa tcaagcaggt ggcgcccggt ttgggggtac aaaccgtgga 17940
tatcaagatc cccaccgagt ccatggaaat tcaaaccgaa cccatgaagc ccacctccag 18000
caccattgag gtgcagacgg atccttggat gcccgcgcct gctcctgtta ccactactac 18060
tcgaagacct agaagaaagt atggttcagc caacctgata atgccaaact atgctctgca 18120
tccatcaatc atacccactc ctggctaccg cggcactcgc tactaccgca gtcacagcac 18180
ccgccgacgt aaagcacctg ccacccgccg ccgtcgccgc cgccgtgcca ctagcaaact 18240 tacccccctcg gctatggtgc ggagagtgta ccgtgatggg cgcgcagctc ctctgacact 18300
gccgcgcgcg cgctaccatc ctagcattgc catttaacaa ctctgcctcc ttgcagatat 18360
ggccctcact tgccgccttc gtattcctat tgctggctac cgcggaagaa agtcgcgccg 18420
tagaagagca gggttgtctg ggagcgggat gcgtcgccac cggcggcggc gcgccatcag 18480
caaacggttg gggggtggat ttcttcccgc tttgattccc atcatcgccg cggcgatcgg 18540
cgcgatacca ggcatagctt ccgtggcggt gcaggcctcg cagcgccact gacattggaa 18600
aaagatatct tataaataaa aatagaatgg actctgacgc tcctggtcct gtgatatgtt 18660
tttgtagacg agatggaaga catcaatttt tcatccctgg ctccgcgaca cggcacgcgg 18720
ccgtatatgg gcacctggag cgacatcggc aacagccaac tgaacggggg agccttcaat 18780

-continued

```
tggagcagtc tatggagcgg gcttaaaaat tttgggtcca ctataaagac ttatgggaac  18840
aaagcttgga acagcagcac agggcatgcg ctgagacaaa agcttaaaga tcagaatttc  18900
caacagaagg tggtcgatgg tatcgcctct ggaatcaatg gggtggtaga tctggccaac  18960
caggccgtgc agaaacagat taacagtcgc ctggacccgg ctcccccagc tcctattcat  19020
gagttaatgc aagtggagga agagctccct tcattggaaa agcggggcga taagcgacct  19080
cgtccagata tggaggaaac gctgctgacc aaggtggatg agccgccctc ctatgaagag  19140
gctgtaaaac tgggaatgcc cactacaaag cccattatgc ctctggccac tggagtgatg  19200
aagccatctc agtctaaacc tgcagttgct gctacattgg acttgcccgc tcccgtggcc  19260
acccccaaac ctgtcgccgc cccgaagccc accgccgtgc aacccgtggc cgtggccaga  19320
ccgcgtcccg gtggtcggcc gaatgcaaac tggcagagca ctctgaacag catcgtgggt  19380
ttgggagtgc acagtgtgaa gcgccgtcgc tgctattgat taaatatgga gtagcgctta  19440
acttgcttgt ctgtgtgtgt atatgtcgat gccgcccgcc gtgctacagc aaagagagaa  19500
ggagaagagg cgccgctgag ttcctttcaa gatggccacc ccatcgatgc tgccccagtg  19560
ggcgtacatg cacatcgccg gacaggacgc ttcggagtac ctgagtccgg gtctggtgca  19620
gttcgcccgc gccacagata cctacttcaa tctggggaac aagtttagga accctaccgt  19680
ggctcccacc cacgatgtga ccaccgaccg tagccagcgc ctgacgctgc gctttgtgcc  19740
cgttgaccgg gaggacaata cctactccta caaagtcaga tacaccctgg ctgtgggaga  19800
caacagggtg ttggatatgg ccagcaccta ctttgacatc aggggcgtgt tggacagagg  19860
acctagcttc aaaccatact ctggcactgc ctacaactcc ctggctccaa aaggagctcc  19920
aaactccagt cagtggcaac aaaaggaaaa caatggtcaa ggtgatgcaa agactcacac  19980
ctatggtgta gctgccactg gaggtattga cattgacaaa aatggtcttc aaattggaat  20040
cgatgaaact aaagaagata ataacgaaat ttatgcagac aaaacattcc aacctgaacc  20100
tcaaattgga gaagaaaact ggcaagatag cgaaaactat tatggaggca gggctcttaa  20160
accggaaacc aagatgaagc cttgctatgg ttccttcgct agaccaacta atgcaaaggg  20220
aggtcaagcc aaaattaaac cagctcaaga gggtcaacag tctatagatt atgacataga  20280
cctggctttc tttgatattc caagcactgg cggaggcaat ggcacaaatg taaatgacaa  20340
gccagatatg gttatgtata ctgaaaatgt aaatctggaa actccagaca ctcatcttgt  20400
ttacaagcca ggaacttcag atgacagttc cgaggccaat ttaactcagc aagccatggc  20460
taacagaccc aactatattg ggtttagaga taactttatt ggcgtcatgt actacaacag  20520
cactggcaac atgggagtgc ttgctggtca agcatcccag ctaaatgctg tggtggacct  20580
gcaagacaga aacaccgagc tgtcttatca gctattactt gactctctgg gcgacagaac  20640
caggtatttt agtatgtgga atcaggcggt ggacagctat gatcctgatg tgcgcattat  20700
tgaaaaccat ggtgtggaag atgaattgcc aaactattgc ttcccattgg acggagctgg  20760
cactaatgct gtttaccaag gagttaagac aaaagaggat aataatggcg aatgggaaac  20820
agacacaaat gttgcatcgc agaatcagat atgcaagggc aacatatatg ctatggagat  20880
caacctgcaa gccaacctgt ggaaaagttt cctttactcc aacgtggctc tgtacctacc  20940
agactcctac aagtacactc catccaacgt gacactccct accaacacta acacctatga  21000
ctacatgaat ggcagggtgg tgtctccatc cctggtggat gcctacatta acattggcgc  21060
caggtggtct ctggatgcca tggacaatgt caaccctttc aaccaccacc gcaatgccgg  21120
cctgcgctac cggtccatgc ttctgggcaa cggccgatac gtgcccttcc acatccaagt  21180
```

```
gccccagaaa ttcttcgcta tcaagaacct gctgcttctc ccaggctcat acacctacga  21240
gtggaacttc cgcaaggatg tcaacatgat cctgcagagt tcccttggca atgacctcag  21300
aaccgatggg gccaccatcc agtacaccag catcaatctc tatgccacct tcttccccat  21360
ggctcacaac actgcctcca ccctggaagc catgctgcgc aatgacacca atgaccagtc  21420
cttcaatgac tacctctcag ctgccaacat gctttacccc atccctgcca atgccaccaa  21480
cgtgcccatc tccatcccat ctcgtaactg ggctgccttc aggggctggt ctttcacccg  21540
cctcaagacc aaggagaccc catctctggg atcagggttc gatccctact tcgtctactc  21600
aggctccatt ccatacctgg atggaacttt ctaccttaac cacactttca agaaagtctc  21660
catcatgttt gactcttctg tcagctggcc aggcaatgac aggctgctga ctcccaatga  21720
gttcgaaatc aagcgcactg ttgatgggga agggtacaat gtggcacaat gcaacatgac  21780
caaagactgg ttcctggttc agatgctctc ccactacaac attggctacc agggcttcta  21840
catcccagaa ggatacaagg accgcatgta ctccttcttc agaaacttcc agcccatgag  21900
ccgccaggtg gtcgatcagg tcaactacaa agactacatg gcagtcaccc ttgcctatca  21960
gcacaacaac tctggctttg tgggctacct cgcgcccacc atgcgacagg gccaacccta  22020
ccctgctaac tacccatacc cgctcattgg caagactgca gtcaacagtg tcacccagaa  22080
aaagttcctc tgcgacaggg tcatgtggcg catccccttc tccagcaact tcatgtccat  22140
gggggccctt accgacctgg ggcaaaacat gctttatgcc aactccgccc acgcgctaga  22200
catgaatttc gaagtagacc ccatggatga gtccaccctt ctctatgttg tcttcgaagt  22260
cttcgacgtg gtcagagtgc accagcccca ccgcggcgtc atcgaagctg tctacctgcg  22320
cacccccttc tcagctggta acgccaccac ataagcgcct tgcttcttgc aagtggctgc  22380
agcagcatgg cctgtggatc ctccactgga tccaatgagc aagagctcag ggccatcgcc  22440
atagacctgg gctgtggacc ctatttcctg ggaacctttg acaagcggtt tccaggcttc  22500
atggctcctg acaagctcgc ctgtgccatt gtcaacacgg cagggcgcga gactggtggt  22560
gagcactggc tggcttttgg atggaacccc cgctccaata cctgctatct ctttgacccg  22620
tttgggtttt cagacgagcg cctcaagcag atctatcaat tcgagtacga ggggctcctg  22680
cgccgcagtg ccctggctac taaggaccga tgcatcactc tggaaaagtc tacccagacc  22740
gtgcagggtc cgcgctcggc tgcctgcggg ctcttctgct gcatgttcct ccatgctttt  22800
gtgcactggc ccgaccgccc catggacaac aaccccacca tgaatttgct gacgggggta  22860
cccaacaaca tgctccaatc gccccaagta gagcccaccc tgcgccacaa ccaggaggca  22920
ctctatcgct tcctgaactc ccactcatct tactttcgtt ctaaccgcgc gcgcattgag  22980
aaggccactg ccttcgatcg aatgaataat aacatgtaaa ccaaattgtg tgtggctcaa  23040
ataaacagca ctttattgtt tacatgcact gaggctctgg gatgatcatt ttttaaaaat  23100
cgaaggggtt ctggcgggaa tcagcatggc cagatggcag ggacacgttg cggaactgga  23160
acttgttctg ccacttgaac tcgggaatca ccagcctggg aactggaatc tctggaaagg  23220
tatcttgcca tagctttctg gtcagttgca gagcgccaag caggtcagga gcagatatct  23280
tgaaatcaca gttggggcca gaattctggg cgcgggagtt gcggtacact gggttgcagc  23340
actggaacac cataagggca gggtgtctca cgctcgccag cacggtctcg tcactgatgc  23400
aagacacatc caggtcttca gcattggcca ttccaaaggg ggtcatcttg caggtctgtc  23460
tgcccatcac gggagcgcag ccaggtttgt ggttgcaatc acaatgaagg gggatcagca  23520
```

tcatcttggc ctggtcgggg gtaatccctg ggtaaacagc cttcatgaag gcttcatact 23580
gcttgaaagc ttcctgggct ttggttccct cggtgtagaa cactccacaa gacttgctgg 23640
aaaactgatt agtagcgcag ttggcatcat tcacacagca gcgggcgtcg ttattagcca 23700
gctggaccac attcctgccc cagcggttct gggtgatctt ggctcgatct gggttctcct 23760
tcaacgcgcg ctggccgttc tcgctcgcca catccatctc aatgacatgt tccttctgga 23820
tcatgatgtt gccatgcagg catctaatct tgccttcata atcagtgcag ccatgaggcc 23880
acagcgcgca cccggtgcac tcccaattgt tatgggggat ctgggaatgg ctatgaacca 23940
gcccttgcag gaatcttccc atcatcacag ccagggtctt tatgctggta aaggtcagcg 24000
ggataccgcg gtgctcctcg ttcacatact gctggcagat gcgtctgtag tgctcggcct 24060
gctcgggcat cagcttgaaa gaggttttca actcattatc cagcctgtat ctctccatca 24120
tgatggacat tacttccatg cccttctccc aggcagaaac aatagggaga ctcaggggat 24180
tcttgacagt agagacaacc ttacttaagg ggtcatcact gccaatcttt tcgatgcttc 24240
tcttgccatc cttctcggtg atgcgcaccg gcgggtagct gaatcccaca gccaccaact 24300
gagcctcttc cctttcgtct tcgctgtctt gactgatgtc ttgcagagga acatgtttgg 24360
ttttcctggg tttcttcttg ggcggcagct ctggaggact ctggctccgt tccggagacc 24420
ccatggatga gcgagagttg tcgctcacca cttggatctg gctgcctgta gaagaactgg 24480
accccacgcg gcggtaggtg ttcctcttgg taggcagagg tggaggcgac gggctccggt 24540
ccggtctggg tggcggatgg ctggcggagc cccttccgcg ttcgggggtg cgctccagat 24600
ggcggtcgtc tgactgacct ccgcggctgg ccattgtgtt ctcctaggta gagaaacaag 24660
acatggagac tcagccatcg ctgccatcgc catccaccac cacaagcacc gccgaggagg 24720
aggagtgttt aaccacccca ccatgcagcc ccgctaccac caccagcacc cttgaaagcg 24780
aggtcgacac ggtcgtggag gatttacagg ctatggaaga tattgaggca gctgtcgagc 24840
aagaccccgg ctatgtgaca ccggcggagc atgatgagga tctagcgcgc tttctcgacg 24900
gtgtggagaa agcgaaacaa gatgaggacg aggaagaggc agaagcacaa ccatcggtgg 24960
ccgactacct caccggccta gggctagaag acgtgctgct taagcatctt gcaaggcaga 25020
cagtcatagt caaagacgcc ctgctagagc gctccgaggt gccactcagt gtggaagacc 25080
tcagtcgcgc ctatgagcta aacctcttct cgcctcgcaa gccccccaag cgtcagccca 25140
acgggacctg tgagcccaat ccgcgcctca acttctatcc agccttcact gtgcccgaag 25200
tactagctac ctaccacatc tttttcaaga accaaaagat ccccatctcc tgccgcgcca 25260
atcgcacccg cgcagatgcc ctactcaact tggggcccgg cgctcgcata cctgatatcg 25320
cttccttgga agaggttcct aagatctttg agggtctggg caatgaggaa actcgggcag 25380
caaacgctct gcaaagagaa acagatgatg gtgaacacca cagcgctctg gtggagctcc 25440
agggcgacaa cgctcgtctt gcagtcctca aacgcagcat cgaggtcacc catttcgcct 25500
accccgcact taatctccca cccaaagtca tgagctcggt catggacacg ttgctcatga 25560
agcgcgcgag ccccatctcc gaggatcaga acatgcagga ccccgatgcc tcagatgaag 25620
gcaagcctgt agtcagcgac gagcaactgg ctcgctggct aggctctgac tccccccagt 25680
ctttggagga gcggcgcaag cttatgatgg cagtggtcct gatcacagcg gagctggagt 25740
gtctccgccg cttcttcact gacccagaga ccctgcgcaa gcttgaggag aacctgcatt 25800
acacattcag tcatgggttc gtgcgccagg cgtgcaagat ctccaacgtt caactcacca 25860
acctggtctc ctacctgggc atcttgcatg aaaaccggct ggggcagaac gtgctccaca 25920

-continued

```
ccaccctgaa gggggaggcc cgccgcgact atatccgcga ctgtatctac ctctacctat  25980
gctacacctg gcaaagcggg atgggtgtgt ggcaacagtg cttggaagag caaaatctaa  26040
aagagctgga aaagctgctt cagaaatctc ttaaatctct gtggaccggg ttcgatgagc  26100
ggaccaccgc ttcggacatg gccgatatta tcttccccga gcggctcaga cacactctgc  26160
gcgacgggct gcctgacttt gccagccaga gcatgctaca aaactttagg tcattcatct  26220
tggaacgctc cgggatcctg cccgccactt gctgcgcact gccctccgat tttgtgccca  26280
tcacctaccg ggagtgcccc ccgccgctat ggagccactg ctacctgttc cgcctggcca  26340
actacttggc ctaccactct gatgtgatag aagatgttag tggcgaaggg ctcctggagt  26400
gccactgccg ctgcaacctc tgcacccccc accgctccct cgcctgcaat ccccagctgc  26460
tgagcgaaac ccagatcatc ggcaccttcg agttgcaagg tcccagcggc gaaggcgagg  26520
ggtcctctcc ggggcaaagt ctgaaactga ctccggggct atggacctcc gcttaccttc  26580
gcaagttcgc ccccaaagac taccacccct atgagatcag gttttatgaa gaccaatcac  26640
agccccccaa ggccgaactg acggcctgcg tcatcaccca gggggcaatc ttggcccaat  26700
tgcaagccat ccaaaaatcc cgccaagaat tttgctgaa aaagggacac gggatctatc  26760
tagaccccca gaccggtgag gagctgaata cacgcttccc tcaggatgcc ccgaggaggc  26820
aagagaatga aagttcagat gccgcccgag gaggagctgg aagactggga cagtcaggca  26880
gaggaggaag actgggacag ccaggcagaa gaggaggaca gcctggagga ggacagtctg  26940
gaggaaggcg aggagcccaa ggaagaggca gccgccgcca gaccatcgtc ctcggcggtg  27000
gagacaagca aggtcccaga cagcacggct accacctccg ctccagctca aggggccgct  27060
cggcgaccca acagtagatg ggacgagacg ggtcgcttcc agaaccccac caccgtcaag  27120
accggtaagc aggagcggca gggatacaag tcctggcggg ggcataaaag tgccatcatc  27180
gcttgcttgc aggagtgtgg gggcaatata tcctttgcca gacgctacct gctattccat  27240
cacggggtga atttcccccg caacatcttg cattactacc gtcacctcca cagcccctac  27300
taccagcagc aagagacagc agaggaaacc agcggcaact ccgagagtta gaaaaccagc  27360
agctaaaaaa tccacagcgg cggcagcagg tgcaggcgga ctgaggatca ccgcgaacga  27420
gccagctcag accagggagt tgaggaatcg gatctttccc accctctatg ccatattcca  27480
acaaagtcgg ggtcaggaac aagaactgaa agtaaaaaac agatctcttc gctcgctcac  27540
ccgcagttgt ttgtatcaca agagcgaaga ccaacttcag cgcactctcg aggacgccga  27600
ggctctcttc aacaagtact gcgcgctgac tcttaaagag tagactgcgc gcgcttggcg  27660
agaaaaggcg ggaattacgt cacctcttgg ccacacctgt gcttcattat gagtaaagaa  27720
attcccacgc cttacatgtg gagctatcag ccccagatgg gattggccgc tggcgccgcc  27780
caggactact ccacccgcat gaattggctc agcgccggtc ccgcgatgat ctcacgggtt  27840
aatggtgtga gagagcaccg aaaccagata ctcctagaac agtccgccct caccgccact  27900
ccccgcaatc acctcaaccc ccgtaattgg cccgccgccc tggtgtacca ggaaactcct  27960
gctcccacta cagtactact tcctcgtgac gcccaggccg aagttcagat gactaactca  28020
ggtgtacagc tggcgggtgg tgccaccctg tgtcgtcacc ggccaagacc gggtataaag  28080
ggcctggtga tcagaggccg aggtattcag ctcaacgacg agtcggtgaa ctcttcgctt  28140
ggtctgcgac cagacggcat cttccaaata gctggttgtg ggagatcttc cttcactcct  28200
cgtcaggctg tcctgacttt ggagagttcg tcctcgcagc cccgctcggg cggcatcggg  28260
```

```
actctccagt tcgtggagga gtttactccc tcggtctact tcaaccccctt ctccggttct    28320
cctgggcttt acccggacga gttcatcccg aactacgacg ccatcagtga agcggtcgac    28380
ggctacgatt aatgtctaat ggtggcgcgg ctgagctagc tcgactgcga cacctagacc    28440
actgccggcg ctttcgctgc tttgctcggg atctctgcga gttcatctac ttcgagtacc    28500
ctgacgaaca tcctcaggga cctgcccacg gagttcggat taccattgaa ggggctatcg    28560
attctcacct gcttcggatc ttcaccgctc ggccagtgct agttgagcgc aaccagggcg    28620
acaccaccat ctccctctgc tgcatttgtg acaaccccgg attgcatgaa agcttttgtt    28680
gtcttctttg tactgagtat aataaaagct gaaattagag actactccgg actctcttgt    28740
cgtctgaaca acaccaacca gacccttcac ttcagcggga accagactac tcttcactgt    28800
aaggcttata actataagta tcttacttgg atatacaaag gaacaccgtt tgctgtggta    28860
aacaggtgct ccaacgacgg tgttctcctc accttcctag gcaacttctc caactttacc    28920
ttttctgttc gcagaaacaa gcttaccctc cttcagccct actttcctgg gatctatacc    28980
tgcctcagtg gaccttgcaa ccacactttt cacctgattg aaaactctac ccttaccttc    29040
ccagcgccaa tccctactaa cagctcggag tccaactctt ccattaccgc tgatactaac    29100
actcctaaaa ccggaggtga gctccgcagc cttcccccgg ctgcagataa cccttgggtg    29160
gtagcgggat ttgtagcgct aggaatagtt gcgggtgggc tcgcgttcgt cctctgctac    29220
ctataccta cctgctgctc atatttagta gtactgtgct gttggtttag aaaatggggg    29280
cgctactaat cacacttgct ttactttcgc ttttgggtct gagctcggct aatagcgaga    29340
aaccaagctg tctagaaaca aactctccag actgtgtggt tcctcatggg ctctcagacc    29400
cagctgatga tccatgctta acttttgacc cagaaaaaaa ctgctcggtg actatgcagc    29460
cctatgctta catgtgcaca tctgttataa agtgcggatg gggctgtaaa ccgattgaaa    29520
ttacccacaa aggcaaaacc tggaataata gtttgtttaa cacatggcag cctggagacg    29580
agcagtggta tacggccggc cactggtgga gatgactgac cccatggaaa actcctctgc    29640
caacgacctg gacatggacg gccgttcatc tgagcagcga ctggtccaga tgcgcattcg    29700
ccagaagcag gaacgcgccg ccagagagct caaggatgcc attgaaattc acctgtgcaa    29760
gaagggcatc ttttgcttgg ttaagcaagc aaagatttct tatgaaatca ctgacaacga    29820
ccaccgcctg tattatgagc tcggtccaca gcggcagaaa ttcacctgca tggttggagt    29880
caaccccata gtcatcactc agcaggctgc agaaattaaa gggtgcatcc actgttcctg    29940
tgattcccaa gaatgcgtcc acaccatagt caagaccctc tgcggccttc gagatcttct    30000
tccaatgaac taaccccttc ccccaaccca ataaaacatt ggttttaatc ataataaaaa    30060
atcacttact ttaaatctga aacagtgtct ccgtccaagt tttcttgtag caccacttca    30120
ctcccctctt cccagctctg gtactgcaag ccccggtggg ctgcaaactt tctccacacc    30180
ttaaaaggga tgtcaaattc ctcttgtcca acaatcttca ttgtctcttc ctagatgtcc    30240
acaaagcgcg cgcgggtgga agatgacttt gaccctgtct acccatacga tgctgagctg    30300
gcaccgtctg tacccttcat cgcccctccc ttcgtttcgt cagacggatt tcaagaaaaa    30360
cccctgggag ttctgtccct aagactagcc aacccagtca ctactaaaaa tggggaactc    30420
acacttaaac tgggagatgg ggtgggcata gactcagatg gaaacctcac agcacagaca    30480
gttactaaag caacatcccc ccttactgtt tccaataacg caattgcact taacatggac    30540
aaaccttttt acagtagcaa tggaaaacta tccttacaag ttcatcacc attaaagata    30600
gtcgactctt taaatacatt ggctattggc tatgggcaag gcttaggact aaacaatagt    30660
```

gctcttgctg tgcaattagc atctcccctt acatttgaca gcaacagcaa aattaaaata 30720
aatttgggaa gcgggccatt aaaaattaat gcgaataaac tgtcaattaa ctgcctaagg 30780
ggtgtatatg taacaactga cggaacttcc attgaaacaa atataagctg ggcaaaagga 30840
atgaggtttg aaggtaatgc catggctgta aacgttgaca gcaccaaagg tctacaattt 30900
ggcactacca gcacagaatc aggagtcact aacgctttcc ctatccagtt aaagattgga 30960
tctggtctta gttttgacag cacaggagca cttgtagctt gggataagga taatgacaag 31020
cttacactgt ggacaaccgc tgacccatca cctaattgta ccatatatac agacaaggat 31080
gctaaactta cactttgtct tacaaaatgt ggcagtcaaa tactaggcag tgtttcagta 31140
ctggctgtta aagctggaac cctacagcca atcagtgaaa aaataggtac tgctttggtt 31200
tcactaaaat ttaataacaa cggtgtattg ttaagcaact ccacattaag taatgaatac 31260
tggaactaca ggaagggaga tgtcacacca gccgaagcct atactaatgc tgtgggtttt 31320
atgccaaaca tcaaggcata tcctaaaaac acaaactctg cctcaaaaag ccacattgta 31380
ggacaagtgt accttaatgg agatgaaact aaaccaatgc atttaatcat tacatttaat 31440
gaaaccagtg atgaaacatg cacatattcc ataacgttcc aatggaaatg gaacattgga 31500
acatacacca gcgacaccct tgcaacaagc tcctttacct tttcttacat tgcccaagaa 31560
taaaaactgc agacaacaat aaagtttaaa tgttttattt aaacagtttc acagaaccct 31620
agtattcaac ctgccacctc cctcccaaca cacagagtac acagtccttt ctccccggct 31680
ggccttaaaa agcatcatat catgggtaac agacatattc ttaggtgtta tattccacac 31740
ggtttcctgt cgagccaaac gctcatcagt gatattaata aactccccgg gcagctcact 31800
taagttcatg tcgctgtcca gctgctgagc cacaggctgc tgtccaactt gcggttgctt 31860
aacgggcggc gaaggagaag tccacgccta catgggggta gagtcataat cgtgcatcag 31920
gatagggcgg tggtgctgca gcagcgcgcg aataaactgc tgccgccgcc gctccgtcct 31980
gcaggaatac aacatggcag tggtctcctc agcgatgatt cgcaccgccc gcagcataag 32040
gcgccttgtc ctccgggcac agcagcgcac cctgatctca cttaaatcag cacagtaact 32100
gcagcacagc accacaatat tgttcaaaat cccacagtgc aaggcgctgt atccaaagct 32160
catggcgggg accacagaac ccacgtggcc atcataccac aagcgcaggt agattaagtg 32220
gcgacccctc ataaacacgc tggacataaa cattacctct tttggcatgt tgtaattcac 32280
cacctcccgg taccatataa acctctgatt aaacatggcg ccatccacca ccatcctaaa 32340
ccagctggcc aaaacctgcc cgccggctat acactgcagg gaaccgggac tggaacaatg 32400
acagtggaga gcccaggact cgtaaccatg gatcatcatg ctcgtcatga tatcaatgtt 32460
ggcacaacac aggcacacgt gcatacactt cctcaggatt acaagctcct cccgcgttag 32520
aaccatatcc cagggaacaa cccattcctg aatcagcgta aatcccacac tgcagggaag 32580
acctcgcacg taactcacgt tgtgcattgt caaagtgtta cattcgggca gcagcggatg 32640
atcctccagt atggtagcgc gggtttctgt ctcaaaagga ggtagacgat ccctactgta 32700
cggagtgcgc cgagacaacc gagatcgtgt tggtcgtagt gtcatgccaa atggaacgcc 32760
ggacgtagtc attctcgtac tttgagtggc aaaaccttgc tctcgaacag cacacgtctc 32820
gtcgcctcct gtcccttctc ttcgcctttt cagtgtgata gttgtaatac agccattcac 32880
gaagctcagt cagaagatct tcagcgtctg ttgtcaaaaa caatccatcc aatctgattg 32940
ctttcaaaac atcacaaaca gtcgaataag ccaaacccat ccaggcaatg caattatttt 33000

```
ggttatccac aatgggaggg ggcggaagac atggaagagg cataattaat tttttaatcc  33060
aatcgatcac gcagcacttc aaaatgaaga tcgcgaaggt gacacctttc acccccactg  33120
tgttgatgaa aaataacagc caagtcaaaa ttgatgcggt tttcaaggtg ctcgactgta  33180
gcatcaagca gagcttccac acgcacgtcc acaaataaca gaatagcaaa agcgggagga  33240
ggaagtaaat cctcaatcat catagtacag tccatcacca tccctaaata attttcatcc  33300
ttccagcctt ggactatatt tttaaactgc tcttgtaaat ccaaaccaca catgtggaaa  33360
agttcccaaa gagctccctc aactaccatt cttaagcaca ccttcatagt gacaaaatat  33420
cttgttcctc tgtcacctgc agcaaattac aaagtccaat attaggatct atgcccagag  33480
atctaagctc atccctcaat tccaactgta aaaaggcttc cagatctgcc ctaacttgtt  33540
cagccagtgg gctccctgga ataagcgtgg gagaagccaa actgcaaaac agacgcatgc  33600
cgccataatt accaccagaa aacactacgt tacagtatgc atgctgattc attccagtaa  33660
tttcatccag tgtattggat acaaaaaaag gcaagcactc tctcactaat tgtattatgg  33720
agacattatc acacaggtaa caatttaaag gttgtggaac aataatgcag taagtaacca  33780
cggtgcgctc caacatggtt agtaattttt agttctgaaa aacaaaacat acaaaaaatt  33840
atatcatact catttggcga actggtggaa aaatgaccct atctagcaca aggcaagcca  33900
ctggatcacc aatgcgcccc tcataaaacc tgtcatcatg attaaaaagc aacaccgaaa  33960
gctcttccct atgtcctgca tgaatgattc tagctgagga atataagcca gcgcaattag  34020
tatctgttaa agaaaaaaaa cggccaacat agcctctagg aattagcaca cttaatctta  34080
aagacattac tgccatcccc cttggattta aggtaaaatt tacaggagca tagaaaatat  34140
actgatttcc ctcctgcaca ggcagcatag caccaggtcc ctctaaaaac acacacaaag  34200
cttctgcagc catagcttac cgcgcaaacc aggcacagca gtgagctaaa aggacaaagc  34260
tctaactcac tagccaacct ggcgcacaat atatagttag tccttacact gacgtaaccg  34320
accaaagtct aaaaaccccg ccaaaaatac acacacgccc aaaaaacgcc ccgtgagtca  34380
aaaaacagtt tcacttcctc gttacaccca aaacgtcgtc acttccggat tcccacggtt  34440
cgtcacttcc ggagctcctt gcttaattaa ccccgcccaa aacgtcatcg tccgcgtcac  34500
gccgccccgc cccgcgaccg ttgaccccgg gccaatcacc gcacatcccg caaaattcaa  34560
actcgtctaa tttgcatatt ggcacactgc ccatataagg tatattattg atgatgattt  34620
aaatcatatg cggtgtgaaa taccgcacag atgcgtaagg agaaaatacc gcatcaggcg  34680
ctcttccgct tcctcgctca ctgactcgct gcgctcggtc gttcggctgc ggcgagcggt  34740
atcagctcac tcaaaggcgg taatacggtt atccacagaa tcaggggata acgcaggaaa  34800
gaacatgtga gcaaaaggcc agcaaaaggc caggaaccgt aaaaaggccg cgttgctggc  34860
gtttttccat aggctccgcc cccctgacga gcatcacaaa aatcgacgct caagtcagag  34920
gtggcgaaac ccgacaggac tataaagata ccaggcgttt ccccctggaa gctccctcgt  34980
gcgctctcct gttccgaccc tgccgcttac cggatacctg tccgcctttc tcccttcggg  35040
aagcgtggcg ctttctcata gctcacgctg taggtatctc agttcggtgt aggtcgttcg  35100
ctccaagctg ggctgtgtgc acgaaccccc cgttcagccc gaccgctgcg ccttatccgg  35160
taactatcgt cttgagtcca acccggtaag acacgactta tcgccactgg cagcagccac  35220
tggtaacagg attagcagag cgaggtatgt aggcggtgct acagagttct tgaagtggtg  35280
gcctaactac ggctacacta gaaggacagt atttggtatc tgcgctctgc tgaagccagt  35340
taccttcgga aaaagagttg gtagctcttg atccggcaaa caaaccaccg ctggtagcgg  35400
```

```
tggttttttt gtttgcaagc agcagattac gcgcagaaaa aaaggatctc aagaagatcc  35460

tttgatcttt tctacggggt ctgacgctca gtggaacgaa aactcacgtt aagggatttt  35520

ggtcatgaga ttatcaaaaa ggatcttcac ctagatcctt ttaaattaaa aatgaagttt  35580

taaatcaatc taaagtatat atgagtaaac ttggtctgac agttaccaat gcttaatcag  35640

tgaggcacct atctcagcga tctgtctatt tcgttcatcc atagttgcct gactccccgt  35700

cgtgtagata actacgatac gggagggctt accatctggc cccagtgctg caatgatacc  35760

gcgagaccca cgctcaccgg ctccagattt atcagcaata aaccagccag ccggaagggc  35820

cgagcgcaga agtggtcctg caactttatc cgcctccatc cagtctatta attgttgccg  35880

ggaagctaga gtaagtagtt cgccagttaa tagtttgcgc aacgttgttg ccattgctgc  35940

aggcatcgtg gtgtcacgct cgtcgtttgg tatggcttca ttcagctccg gttcccaacg  36000

atcaaggcga gttacatgat cccccatgtt gtgcaaaaaa gcggttagct ccttcggtcc  36060

tccgatcgtt gtcagaagta agttggccgc agtgttatca ctcatggtta tggcagcact  36120

gcataattct cttactgtca tgccatccgt aagatgcttt tctgtgactg gtgagtactc  36180

aaccaagtca ttctgagaat agtgtatgcg gcgaccgagt tgctcttgcc cggcgtcaac  36240

acgggataat accgcgccac atagcagaac tttaaaagtg ctcatcattg gaaaacgttc  36300

ttcggggcga aaactctcaa ggatcttacc gctgttgaga tccagttcga tgtaacccac  36360

tcgtgcaccc aactgatctt cagcatcttt tactttcacc agcgtttctg ggtgagcaaa  36420

aacaggaagg caaaatgccg caaaaaaggg aataagggcg acacggaaat gttgaatact  36480

catactcttc ctttttcaat attattgaag catttatcag ggttattgtc tcatgagcgg  36540

atacatattt gaatgtattt agaaaaataa acaaataggg gttccgcgca catttccccg  36600

aaaagtgcca cctgacgtct aagaaaccat tattatcatg acattaacct ataaaaatag  36660

gcgtatcacg aggccctttc gtcttcaaga attgatttaa at                     36702
```

<210> SEQ ID NO 22
<211> LENGTH: 33625
<212> TYPE: DNA
<213> ORGANISM: Artificial Sequence
<220> FEATURE:
<223> OTHER INFORMATION: BLY6.FLuc Ad vector

<400> SEQUENCE: 22

```
catcatcaat aatatacctt atatgggcag tgtgccaata tgcaaattag acgagtttga     60

attttgcggg atgtgcggtg attggcccgg ggtcaacggt cgcggggcgg ggcggcgtga    120

cgcggacgat gacgttttgg ggaggaggag ctatgttgca agtaatcgtg ggaaatgcga    180

cgtaaaacga ggtggagttt aaacacggaa gtagacaatt ttcccgcgct gtttgacagg    240

aaatgatgtg tttttgggcg gatgcaagtg aaaattctcc attttcgcgc gaaaactaaa    300

tgaggaagtg aaattctgag taattctgag gttatcacag ggcggagtat ttaccgaggg    360

ccgagtagac tttgacccat tacgtggagg tttcgattac tctatttttc acctaaattt    420

ccgcgtactg tgtcaaagtc cgtgttttta cggcgatcgc tcaatattgg ccattagcca    480

tattattcat tggttatata gcataaatca atattggcta ttggccattg catacgttgt    540

atccatatca taatatgtac atttatattg gctcatgtcc aacattaccg ccatgttgac    600

attgattatt gactagttat taatagtaat caattacggg gtcattagtt catagcccat    660

atatggagtt ccgcgttaca taacttacgg taaatggccc gcctggctga ccgcccaacg    720
```

-continued

```
acccccgccc attgacgtca ataatgacgt atgttcccat agtaacgcca atagggactt    780
tccattgacg tcaatgggtg gagtatttac ggtaaactgc ccacttggca gtacatcaag    840
tgtatcatat gccaagtacg ccccctattg acgtcaatga cggtaaatgg cccgcctggc    900
attatgccca gtacatgacc ttatgggact ttcctacttg gcagtacatc tacgtattag    960
tcatcgctat taccatggtg atgcggtttt ggcagtacat caatgggcgt ggatagcggt   1020
ttgactcacg gggatttcca agtctccacc ccattgacgt caatgggagt ttgttttggc   1080
accaaaatca acgggacttt ccaaaatgtc gtaacaactc cgccccattg acgcaaatgg   1140
gcggtaggcg tgtacggtgg gaggtctata taagcagagc tcgtttagtg aaccgtcaga   1200
tcgcctggag acgccatcca cgctgttttg acctccatag aagacaccgg gaccgatcca   1260
gcctccgcgg ccgggaacgg tgcattggaa gcttggcatt ccggtactgt tggtaaagcc   1320
accatggaag acgccaaaaa cataaagaaa ggcccggcgc cattctatcc gctggaagat   1380
ggaaccgctg gagagcaact gcataaggct atgaagagat acgccctggt tcctggaaca   1440
attgctttta cagatgcaca tatcgaggtg gacatcactt acgctgagta cttcgaaatg   1500
tccgttcggt tggcagaagc tatgaaacga tatgggctga atacaaatca cagaatcgtc   1560
gtatgcagtg aaaactctct tcaattcttt atgccggtgt tgggcgcgtt atttatcgga   1620
gttgcagttg cgcccgcgaa cgacatttat aatgaacgtg aattgctcaa cagtatgggc   1680
atttcgcagc ctaccgtggt gttcgtttcc aaaaaggggt tgcaaaaaat tttgaacgtg   1740
caaaaaaagc tcccaatcat ccaaaaaatt attatcatgg attctaaaac ggattaccag   1800
ggatttcagt cgatgtacac gttcgtcaca tctcatctac ctcccggttt taatgaatac   1860
gattttgtgc cagagtcctt cgatagggac aagacaattg cactgatcat gaactcctct   1920
ggatctactg gtctgcctaa aggtgtcgct ctgcctcata gaactgcctg cgtgagattc   1980
tcgcatgcca gagatcctat ttttggcaat caaatcattc cggatactgc gattttaagt   2040
gttgttccat tccatcacgg ttttggaatg tttactacac tcggatattt gatatgtgga   2100
tttcgagtcg tcttaatgta tagatttgaa gaagagctgt ttctgaggag ccttcaggat   2160
tacaagattc aaagtgcgct gctggtgcca accctattct ccttcttcgc caaaagcact   2220
ctgattgaca aatacgattt atctaattta cacgaaattg cttctggtgg cgctcccctc   2280
tctaaggaag tcggggaagc ggttgccaag aggttccatc tgccaggtat caggcaagga   2340
tatgggctca ctgagactac atcagctatt ctgattacac ccgaggggga tgataaaccg   2400
ggcgcggtcg gtaaagttgt tccatttttt gaagcgaagg ttgtggatct ggataccggg   2460
aaaacgctgg gcgttaatca aagaggcgaa ctgtgtgtga gaggtcctat gattatgtcc   2520
ggttatgtaa acaatccgga agcgaccaac gccttgattg acaaggatgg atggctacat   2580
tctggagaca tagcttactg ggacgaagac gaacacttct tcatcgttga ccgcctgaag   2640
tctctgatta agtacaaagg ctatcaggtg gctcccgctg aattggaatc catcttgctc   2700
caacacccca acatcttcga cgcaggtgtc gcaggtcttc ccgacgatga cgccggtgaa   2760
cttcccgccg ccgttgttgt tttggagcac ggaaagacga tgacggaaaa agagatcgtg   2820
gattacgtcg ccagtcaagt aacaaccgcg aaaaagttgc gcggaggagt tgtgtttgtg   2880
gacgaagtac cgaaaggtct taccggaaaa ctcgacgcaa gaaaaatcag agagatcctc   2940
ataaaggcca agaagggcgg aaagatcgcc gtgtaattct agacgagatc cgaacttgtt   3000
tattgcagct tataatggtt acaaataaag caatagcatc acaaatttca caaataaagc   3060
atttttttca ctgcattcta gttgtggttt gtccaaactc atcaatgtat cttatcatgt   3120
```

ctgcgatcgc gatggcctgt gtttgagcat aatgtactga ccaggtgtaa cgttcatctg 3180
ggtggtcgta gaggaatgtt catgccatac caatgcaatt ttaatcatgt gaggatcttg 3240
atggagccgc aagcgttttc cagagtcagc ttgactggaa tctttgacat gtgtgtggaa 3300
gcatggaaga tcttaagata tgatgatacc aaatccagat gccgcgcatg cgagtgcggg 3360
ggcaggcatg ccaggttcca acctgtatgt gtggaggtga ccgaggagct gagaccagat 3420
catttggtgc tgacctgcac tggtgcggag ttcggttcca gtggtgaaga aactgattaa 3480
agtgagtagt gggatgttat aaaagtgacc ataaggtgat gtgagatgga caaatttggt 3540
aatttttatg tatttttgtc ttgcagccat gagtgggagc gcttcctttg aagggggcgt 3600
ctttagccct tatctgacgg ggcgtctgcc tcattgggct ggagtgcgtc agaatgtgat 3660
ggggtctaca gtggatggaa gacctgttca gcctgctaat tcttctactc tgacttatgc 3720
tactatgact tcctcgcctt tggatgcagc tgcagctgct gccgcttctg ctgccgccaa 3780
cactgttcgg gggatggcct tggagatggg gtattatgga actgtagtgg ccaacaccac 3840
taccccaaat aaccccacag ccttgaatga ggacaagctg ctagttctca tgtcccagct 3900
ggagtctttg acccaacgcc tggcgatct agctcagcag gtgtcccagc tgaaggagca 3960
gactcaagct gcaattacca ctgcgagggg aaattaaaaa aattcaaaga atcaataaat 4020
aaaccgagac tttgttgatt ttaaagtgtg tcattcttta tttaattttt cgcgcgcgat 4080
atgccctgga ccaccggtct ctatcattga ggacacggtg gatcttttct agaacccgat 4140
agaggtggga ttggatgttg aggtacatgg gcataagacc atctttgggg tgtagatagc 4200
tccactgcag agcctcatgc tccggggtgg tgttgtatat aacccagtca tagcatgggc 4260
gttgggcatg atgttgcaca atatctttaa ggaggagact aatggccact gggagaccct 4320
tggtgtaagt gtttacaaat ctattaagct gggacgggtg catccgaggt gagataatgt 4380
gcattttgga ttggattttt agattggcaa tgtttccccc tagatctctc ctgggattca 4440
tgttatgcaa gaccactaga acagtgtatc cggtgcactt agggaatttg tcatgaagtt 4500
tggaggggaa agcatgaaaa aatttagaca caccettgtg tcctcccaag ttctccatgc 4560
actcatccat aataatggca atgggcccat gggcggcggc acgggcgaac acgttcctgg 4620
gatctgacac atcatagttg tggtcttggg tcaggtcatc ataagccatt ttaataaact 4680
tggggcggag ggtgccagat tgggggatga atgttccctc gggccccgga acatagtttc 4740
cttcacatat ttgcatttcc caggctttta gttcagaggg ggggatcatg tccacctgtg 4800
gagcgatgaa gaagacggtc tcgggggcgg gggtgattaa gtgggaggac agcaagttcc 4860
taagcagctg tgacttgcca cacccagtgg gaccgtagat gaccccctata acaggttgca 4920 gatggtagtt tagggaaaga cagctgccgt cctctcgcag gaggggggcg acctcgttca 4980
tcatttccct cacatgcatg ttttcccgca caagttccga taggaggcgc tctccaccca 5040
gggaaaggag ttcttgaaga gatgagaaat ttttcaaggg ttttaagcca tcagccatgg 5100
gcattttgga gagggtttgt tgcaagagtt caaggcggtc ccagagttcg gtgatgtgtt 5160
ctatggcatc tcgatccagc atacttcctc gtttctgggg ttgggacggc tgcgggagta 5220
tggaaccagg cgatgggcgt ccagcgctgc cagtgtccgg tccttccacg gtcgcagcgt 5280
ccgagtcagg gtcgtttccg tcacggtgaa ggggtgcgcg cctggctggg cgcttgcgag 5340
ggtgcgcttc aggctcatcc tgctcgtgga gaaccgctgc cgttctgcgc cctgtgcatc 5400
ggccaggtag caattaacca tgagttcgta gttgagcgcc tctgccgcgt ggcctttggc 5460

-continued

```
gcgcagctta cctttggaag tcttctgaca ggtgggacag tagagacact tgagagcata   5520
gagttttggg gctagaaaga ccgattctgg ggagtatgca tcggccccac aggaggcgca   5580
gacggtttcg cattccacca gccatgtaag atcgggctcg ttggggtcaa aaacaagttt   5640
tccgccatgt tttttgatgc gtttcttacc tttgctttcc atgagttcgt gcccccgttg   5700
ggtgacaaag aggctgtccg tgtccccgta gactgacttt atgggcctgt cctcgagcgg   5760
cgtgccgcgg tcctcttcgt agaggaactc ggaccactct gagacgaaag cacgtgtcca   5820
ggccagcaca aaggaggcta tatgggaggg gtagcgatcg ttgtcaacca aggggtctac   5880
tttttccaag gtgtgtaaac acatgtcccc ttcttccaca tccaggaagg tgattggctt   5940
gtaagtgtat gccacgtgac ctggggtccc agacgggggg gtataaaagg gggcgggtct   6000
ctgctcgtcc tcactgtctt ccggatcgct gtccaggagc gccagctgtt gaggtaggta   6060
ttccctctcg aaggcgggca taacctccgc actcaggttg tcagtttcta ggaacgagga   6120
ggatttgata ttgacagtgc ctgccgagat gcctttcatg agactgtcgt ccatttggtc   6180
agaaaagaca atctttttgt tatcaagttt ggtggcgaag gatccataca gggcattgga   6240
aagcagtttg gcaatggagc gcatggtttg gttttttttct ttgtctgcgc gctctttggc   6300
ggctatgttg agttggacat attcgcgggc cagacatttc cattgtggaa atatggtagt   6360
taattcatct gggacgattc tgactttcca gcctctgtta tgcagggtaa tcagatccac   6420
actggttgcc acttctcctc taagtggttc attagtccag catagtcgcc cccttttcg   6480
agaacagaaa gggggtaggg gatctagcat gagttcgtct gggggggtctg catctatggt   6540
gaaaatccca ggaaggagat cttcgtcaaa atagctgatg gtggcggggt catccagaga   6600
catttgccat tctcgagcag ccagagcgcg ctcgtagggg ttaaggggag tcccccatgg   6660
catgggatgg gtgagtgcag aagcatacat gccacagatg tcatagacat agagcggctc   6720
ttccagaatc cctatgtaag tgggataaca tcgcccccct ctgatgctgg ctcgcacata   6780
atcatagagt tcatgtgagg gcgctagaag acccgagccc aggttggtgc ggttgggttt   6840
ttctgctctg tagaggatct ggcgaaagat ggcatgggag tttgatgaga tggtgggtct   6900
ttggaagatg ttgaaatggg catgaggcag tcccacagag tcccttatga agtgagcata   6960
ggagtcttgc agtttggcca ccagctcggc ggtgaccagc acatccaaag cacagtagtc   7020
gagggtctct ttgatgatgt catagttagg ttcccctttc ttttcccaca gctcgcggtt   7080
gagaaggtat tcttcgcgat ccttccagta ctcttcgagg gggaacccgt ccttgtctga   7140
acggtaagaa cccagcatgt aaaattgatt gacagctttg taggcacaac accccttctc   7200
cacggggagt gagtatgctt gcgcggcttt gcgcagagag gtgtgagtaa gggcgaaagt   7260
gtccctgacc atgactttga ggaactgatg cttaaagtct atgtcatcgc aggccccctg   7320
ctcccacagt tggaagtcca ctcgcttttt gtaggcggga ttgggcaaag cgaaagtaac   7380
atcgttgaat aggatctttc cagccctggg catgaagttg cgagtaatgc gaaaaggctg   7440
aggcacttct gccctgttgt tgataacttg ggcagccaag acgatctcgt caaagccgtt   7500
gatgttgtga cccacaatgt aaagttctac gaagcgtggg cgtcccttga tgtggggcag   7560
ttttttaagc tcttcgtagg tcaagtcgtc agggtcagcg attccatatt gctccaaagc   7620
ccagtcaggc aggtgaggat tagcatgaag gaaagaggtc caaagatcca cggccagagc   7680
tgtttgtaag cggtctctgt actgacggaa atgtcggcct accgccattt tttcaggagt   7740
aacacagtaa aaggtgcgcg ggtccttttc ccagcgatcc cattgaagtt gcaaggctag   7800
gtcgtgggcg aggttgacga gctgttcgtc ccccgaaagt ttcatgacca gcatgaaagg   7860
```

-continued gacaagctgc ttgccaaagg accccatcca ggtgtaggtt tccacatcgt aggtgaggaa 7920
gagcctttct gtgcgaggat gagaaccgat cgggaagaac tggatttcct gccaccagtt 7980
ggaggaatgg ctgttgatat gatggaagta gaactcccta cggcgcgccg agcattcgtg 8040
cttgtgcttg tacagacggc cacagtactc gcagcgctgc acgggatgca cctgatgaat 8100
gagctgtacc tggcttcctt tgacaagaaa tttcagtggg aagttgaggc gtggcgtctg 8160
catctcgtgt tgtattacgt cctggctatt ggtctggcca tcttctgtct cgatggtggt 8220
catgctgacg agcccgcgcg ggaggcaggt ccagacctcc gcgcggacgg gtctgagagc 8280
gaggacgaga gcgcgcaggc cggaactgtc cagggtcctg agacgctgcg gagtcaggtc 8340
agtagggaga gtacataggt ttacttgcat aagtttttcc agggcatgtg ggaggtcaag 8400
atgatatttg atttctactg gcgagttggt ggagacatcg atggcttgca gggtcccgtg 8460
cccctggggt gctaccaccg tcccttttt tttcttgatc gggggcggtg ttgcttcttg 8520
catggtaagg tcgtcttcta gaagcggcgg cgaggtcgcg cgccgggtgg cagtggcggt 8580
tctggacctg gaggtagagg cggtagaggt acgtcggcgc cgcgcgcggg taggttctgg 8640
tactgcgccc tgagaagact tgcgtgagcg acgacgcggc ggttgacgtc ctggatctga 8700
cgcctctggg tgaatgctac cggacccgtg agcttgaacc tgaaagagag ttcaacagaa 8760
tcaatttcgg tatcgttgac ggctgcctgc cgcaggattt cttgtacgtc gcccgagttg 8820
tcttggtagg cgatctcggc catgaactgc tcgatctctt cttcttggag atctccgcgg 8880
cccgctcgtt ctacggtggc agcaaggtcg ttggagatgc gccccatgag ctgtgagaat 8940
gcattcatgc ccgcctcgtt ccagacgcga ctgtagacca cggctccctc gggatctctg 9000
gcgcgcatga ccacttgggc gaggtttagt tccacgtgtc tggtgaagac cgcatagttg 9060
cagagacgct ggaagaggta gttgagcgtg gtggcgatgt gctcggtgac aaagaaatac 9120
atgatccagc gacgaagcgg catctcgctg atatcgccca gggcttccaa ccgttccatg 9180
gcttcgtaaa agtccacggc gaagttgaaa aactgggagt tgcgagcgga cacggtcaac 9240
tcctcctcca gaagacggat gagctcggcg atggtggcgc gcacttcgcg ctcaaaggct 9300
cccgggatct cttcctcctc ttcttcttcc aactcttcct ccactaacat ctcttctact 9360
tcctcctcag gcggcggggg tggaggaggg ggcgcgcggc gacgccggcg acgcacgggc 9420
agacgatcga tgaagcgttc gatcacttct ccgcggcggc gacgcatggt ctcggtgacg 9480
gcgcgcccgt cctccctggg tcgcagagtg aagacgccgc cgcgcagctc cctgaaatgg 9540
tgactgggag ggtccccgtt tggtagggac agggcactga tgatgcatct tattaattgc 9600
cctgtaggga ctccgcgcaa ggacctgagc gtctcgagat ccacgggatc tgaaaatctc 9660
tgaacgaagg cttcgagcca gtcgcagtcg caaggtaggc tgagcactgt ttcttcgggg 9720
cgggctgctg agctagaggg ttgtacgatg ctgctggtga tgaagttaaa ataggcagtt 9780
ctgagacggc ggatggtggc gaggagcacc aggtctttgg gtccggcttg ctggatgcgc 9840
aggcggtcgg ccattcccca tgcattatct tggcacctgg ccagatcttt atagtagtct 9900
tgcatgagtc gctccacggg cacttcttct tcgcccgctc tgccgtgcat gcgtgtgagt 9960
ccgtaccctc tctgtggttg gacgagcgcc aggtcggcaa cgaccctttc ggctagaatg 10020
gcttgctgca cctgggtgag ggtgttctgg aaatcatcaa agtccacaaa gcggtggtag 10080
gcccccgtgt tgatggtgta ggagcagttg gacatgaccg accagttgac tgtctggtgt 10140
cctggtcgta cgagttccgt gtacctgagc cgcgagtatg cgcgggagtc gaagatgtaa 10200

-continued

```
tcgttgcagg ttcgcaccag gtactggtag ccgatgagga agtgaggcgg cggctggcgg  10260
tagagaggcc atcgttcggt ggcgggcgcg ccgggcgcta ggtcttctag catgagacgg  10320
tggtatccgt agacgtacct ggacatccag gtaataccgg cggcggtggt ggaggcgcgc  10380
ggaaactctc gcacgcggtt ccagatgttg cgcagcggca tgaagtagtt catggtgggc  10440
acggtctggc ccgtgaggcg cgcgcagtca ttgatgctct agatacgggc aaaaacgaaa  10500
gcgttgagcg gttcccttcc gtggcctgga ggaacgcgaa cgggttaggt cgcagcgtac  10560
cctggttcga gactaaagaa agcgagcaac tcgaaccggc agagtcgcgg ctaacgggta  10620
ttggcaatcc cgtctcgacc caagccagca aatccaggat acggatgggg gccccttttg  10680
tttttcaggg catgagtcac cggttaaggt ttacaacggc tgtttcatgc ctttagaagt  10740
ggctcgcgcc cgtagtctgg agaatcaatc gccagggttg cgttgcggcg tgccccggtt  10800
cgagcctgca gcttgagtcg gccggtgacc gcggcaaacg agggcgtggc ggccccgtcg  10860
tttctaagac cttgctagcc gacctctcca gtttacggga acgagccccc ttttattttt  10920
tttgtttttg ccagatgcat cccgtactgc ggcagatgcg cccacagccc ccacagcagc  10980
agcagcaggc tggcctacct tctctacctc agccgctacc tgcaactacc gcggtggccg  11040
ctgtaagcgg ggccggacag caggcggctc ctcaatatga attggacttg gaagagggcg  11100
agggattggc aagattgggg gcgccctcgc ccgagcgcca cccgcgggtg cagatgaaaa  11160
aggacgttcg cgaatcttac gtgcccaagc agaatctgtt cagagacaga agcggcgagg  11220
agcccgagga gatgcgcgcg tcccgtttta acgcgggtcg cgagctgcga caaggactgg  11280
atcgaaaacg ggtgttgagg gatgatgatt ttgaggtgga tgaaatgaca gggatcagcc  11340
ccgctcgcgc tcacgtggct gcagctaatc tggtgacagc ttatgagcag accgtgaagg  11400
aggaaagcaa cttccagaaa tcattcaata accacgtgcg caccctgatc gcacgcgagg  11460
aggtgaccct gggcctgatg cacctgtggg atctgctgga agccatagtg cagaacccca  11520
ctagcaaacc cctgactgct caactgtttc tggtggtgca gcacagcagg gataatgagg  11580
cattcagaga ggcgctgctg aatatcactg aacctgaggg gagatggctg ctggatctgg  11640
tgaatatcct gcagagcatt gtagtgcagg aacgcagctt gcctttgtcc gagaaggtgg  11700
cggcgatcaa ttactctgtg ctgagtctgg gcaaatacta tgccaggaag atctacaaaa  11760
ccccttacgt gcccatagac aaggaagtga aaatagatgg gttttacatg cgcatgaccc  11820
tgaaagtgct aaccctgagc gatgacttgg gagtgtaccg caacgacagg atgcaccgcg  11880
cggtgagcgc cagcaggagg cgcgagctga gcgacaaaga attaatgcac agcttgcaac  11940
gagccctgac gggagccggg acggaggggg agaactactt tgacatgggt gcagacttgc  12000
attggctgcc tagtcgcagg gcattggaag cggcaggcga tgggccctat gtagaggaag  12060
tagtagacga ggacgatgag gagggcgagt acctggaaga ctgatggcgc gacccgtatt  12120
tttgctagat ggaacaggcg ccggaccctg cgatgcgggc ggcgctgcag agccagccgt  12180
ccggcattaa ttcctcggac gattggaccc aggccatgca acgcatcatg gcgctgacga  12240
cccgcaaccc cgaagccttt agacagcagc ctcaggccaa ccgcctttcg gccatcctgg  12300
aggccgtggt gccctctcgc tccaacccca cccacgagaa ggttctggcc atcgtgaatg  12360
ccctggtgga gaacaaggcc atccgctccg atgaagccgg gctggtatac aacgccttgc  12420
tcgagcgcgt ggctcgctac aacagcagca atgtccagac taacctggac aggatggtga  12480
ccgacgtgcg cgaggccgtg tcccagcgcg aacggttcca tcgcgagtct aacctgggtt  12540
ccatggtagc gctgaacgct ttcctcagtt cccagcctgc caatgtgccc cggggacagg  12600
```

```
aagactatac caactttatt agcgccctga gactcatggt agccgaggtt cctcagagcg  12660
aggtgtacca gtccggtcca gactactttt tccagacaag caggaacggt atgcagacag  12720
tgaacttaag ccaggctttc aagaacctgc aagggctgtg gggagtccaa gctccagtgg  12780
gcgacagggc gaccgtgtcg agcctgttga ctccaaattc ccgtttgctg ctgctgctgg  12840
tgtcccccctt cactgacagc ggcagcataa acagaaactc ctacttgggc tacctgataa  12900
acttgtatcg cgaagctata ggtcaggccc acgtggacga acagacctat caggagatca  12960
ctaatgtgag tcgcgctctg ggccaggacg accctggaaa cctggaagct actctaaact  13020
ttctgctgac caaccgctcg caaaaaatcc ctcctcagta tacattaact gcggaggagg  13080
aacggatctt gagatacgtg cagcagagcg tgggtctgtt cctgatgcaa gagggtgcga  13140
cccctagcgc cgcgcttgat atgacagcgc gcaacatgga gcccagcatg tatgccagca  13200
acagaccatt cattaataaa ttgatggatt acttccatcg cgcggccgct atgaactctg  13260
attacttcac caatgctatt ctgaaccccc attggctgcc tccgcctggt ttttatactg  13320
gcgagtatga catgcctgac cccaacgatg ggttcttgtg ggacgatgtg gacagcgtgg  13380
cgttctcgcc taccgctcct cgtacttttt ggaagaagga aggtagtgac agaagaccct  13440
cctccgtgct gtcaggacgt gagggtgctg ccgcggcggt ccccgatgct gcaagcccct  13500
ttcccagtct gccattttca ctaaacagcg tgcgcagtag cgagctgggg agaataaccc  13560
gccctcgctt gctgggcgag gacgagtatt tgaatgactc cctactgaga cccgagcggg  13620
aaaagaactt ccctaataat gggattgaaa gcctggtgga taagatgagc agatggaaga  13680
cctatgccca ggagcacaga gatgagccta gaatcttggg tcctacagta ggcacccgca  13740
gacgccagcg ccatgataga cagcggggtc tggtgtggga cgatgaggat tctgcagatg  13800
acagcagcgt gttggacttg ggcgggaggg gaggtgtggg caacccgttc gcacacttgc  13860
gtccccgtat tggacgcatg atgtaaaagt gaaaataaaa aaggaactca ccaaggccat  13920
ggcgaccagc gtgcgttcgt tctttctgtt gttgtatcta gtatgatgag gcgcaccgtg  13980
ctaggcggat cggtggcgta tccggagggt cctcctcctt cgtacgaaag cgtgatgcag  14040
caggtggcgg cggcggcgat gcaacccccc ttggaggctc cttacgtgcc cccgcggtac  14100
ctggcaccta ccgaggggag aaacagcatt cgttattcgg aactcacacc cttgtatgac  14160
accacccggt tgtacctggt ggacaacaaa tcggcggaca ttgcctcgtt gaactatcag  14220
aacgaccaca gcaacttctt gacaacggtg gtgcagaaca atgactttac ccccacggag  14280
gccagcaccc agaccatcaa ctttgacgag cgctcccggt ggggcggtca gctgaagacc  14340
atcatgcaca ccaacatgcc caacgtgaac gagttcatgt ttagcaacaa gttcagggct  14400
agggtgatgg tgtccagaac cacacctaaa gaggtgacag tcacaacaga ctatgatggt  14460
agtcaggaca tcttggaata cgagtgggtt gactttgagt taccagaagg caacttctct  14520
gccaccatga ccatagacct gatgaataat gcaattgttg ataattacct aaaagtgggt  14580
agacagaatg gggtactgga gagtgacata ggtgttaagt ttgacactag gaactttagg  14640
cttggttggg acccagtgac agagttggtc atgcctgggg tctacaccaa tgaagctttc  14700
catcctgaca tagtcctact acctggctgc ggagtggact tcactgagag ccgcctcagt  14760
aatctgctag gcattagaaa gaaacagcca ttccaggaag ggttccagat catgtatgag  14820
gatctggagg gtggtaacat ccccgccctg cttgatgtaa atgcatatga gaagagcaag  14880
gaagataata caaccaccac aaatgaagct gtggccgcgg cttcatctac tgaagccaaa  14940
```

-continued

```
gctgtggtag atgcttccac ttcaacagaa aacaccactg atgaaaaagt caccagggga  15000
gatacatttg ccacccctga acaagagaag gcagctgagg cagagtctga tattatgctt  15060
ctgtccaccg atgaaaacga aactaaaaaa caactggtta ttcgagcggt gaccaaggat  15120
agtaaggaca ggagttataa tgtattgtca gatggaaaga acacagctta ccgtagttgg  15180
tacctggcat acaattatgg cgaccgtgag aaaggggtgc gttcttggac actgcttacc  15240
acctcggatg tcacctgcgg cgtggagcaa gtctattggt cgctaccaga tatgatgcaa  15300
gatccagtca cctttcgctc cacacgccaa gttagcaact acccagtggt gggcgcagag  15360
ctgctcccag tgcattccag aagcttctac aacgagcaag ccgtctactc gcaacagctc  15420
cgccagtaca cctcgctcac gcacgtcttc aaccgcttcc ccgagaatca gatcctcgtc  15480
cgcccgcccg cgccaaccat taccaccgtc agtgaaaacg ttcctgctct cacagatcac  15540
gggaccctgc cgctgcgcag cagtatccgg ggagtccagc gcgtgaccgt tactgacgcc  15600
agacgccgca cctgtccata cgtatacaag gccctgggca tagtcgcgcc gcgcgtcctt  15660
tcaagccgca ctttctaaaa aaatgtccat tctcatctcg cccagtaata acaccggttg  15720
gggcctgcgc acacctagca agatgtatgg aggcgctcgc agacgctcca ctcagcaccc  15780
tgtgcgcgtg cgcgggcatt tccgcgctcc ctggggcgcc ctcaagggac gctctcgtac  15840
taggaccacc gttgacgatg tgatcgacca ggtggtcgcc gatgcacgta actatacccc  15900
cgcagccgca cctgcatcca ccgtggatgc ggtcattgac agcgtggtag ccgatgcgcg  15960
cgcctatgct cgcgccaaga gcaggaggcg gcgtattgcc aggcgtcacc gagctactcc  16020
agccatgcga gctgcaagag ctttattgcg gagagccaga cgtgtggggc gaagagccat  16080
gcgtagagcg gccagacgcg cggcttcagg tgccagcgca ggcagggtcc gcaggcgcgc  16140
ggctacggcg gcagcggcgg ccatcgctag catgaccaaa ccacgaagag gcaatgtgta  16200
ttgggtgcgc gacgccgcca ccggccagcg cgtgcccgtg cgcacacgcc cccctcgcac  16260
ttagaagata ctgagcagtc tccgatgttg tgtcccagcg gcgagatgtc caagcgcaaa  16320
ttcaaggaag agatgctcca ggtcatcgcg cctgagatct acggtcctgc ggtgaaggat  16380
gaaaaaaagc cccgcaagat caagcgggtc aaaaaggaca aaaaggaaga agatggtgat  16440
gatgggctgg tggagtttgt gcgcgagttt gccccaagga ggcgcgtgca gtggcgcggg  16500
cgcaaagtgt ggccggtgtt gagaccgggg accacagtgg tctttacgcc aggcgagcgc  16560
tccagcaccg tttccaaacg ctcttatgat gaggtgtacg gggacgatga tattctcgag  16620
caggcggctg atcgccttgg cgagtttgca tatggcaaac gcagccgctc gggagccaag  16680
gaagaggcat tgaccatccc cttggatcat ggaaatccca ccccaagcct caaacccgtg  16740
accctgcaac aagtgctgcc cacgccgcca cgcaagggca tcaagcgcga gggcgaggat  16800
ctgtatccca ccatgcagct gatggtgccc aagcgccaga agctggaaga cgtgctggag  16860
aaaatgaaag tggatcctga aatccagcct gaagtcaaag tgaggccaat caagcaggtg  16920
gcgcccggtt tgggggtaca aaccgtggat atcaagatcc ccaccgagtc catggaaatt  16980
caaaccgaac ccatgaagcc cacctccagc accattgagg tgcagacgga tccttggatg  17040
cccgcgcctg ctcctgttac cactactact cgaagaccta gaagaaagta tggttcagcc  17100
aacctgataa tgccaaacta tgctctgcat ccatcaatca tacccactcc tggctaccgc  17160
ggcactcgct actaccgcag tcacagcacc cgccgacgta aagcacctgc cacccgccgc  17220
cgtcgccgcc gccgtgccac tagcaaactt accccctcgg ctatggtgcg gagagtgtac  17280
cgtgatgggc gcgcagctcc tctgacactg ccgcgcgcgc gctaccatcc tagcattgcc  17340
```

atttaacaac tctgcctcct tgcagatatg gccctcactt gccgccttcg tattcctatt 17400
gctggctacc gcggaagaaa gtcgcgccgt agaagagcag ggttgtctgg gagcgggatg 17460
cgtcgccacc ggcggcggcg cgccatcagc aaacggttgg ggggtggatt tcttcccgct 17520
ttgattccca tcatcgccgc ggcgatcggc gcgataccag gcatagcttc cgtggcggtg 17580
caggcctcgc agcgccactg acattggaaa aagatatctt ataaataaaa atagaatgga 17640
ctctgacgct cctggtcctg tgatatgttt ttgtagacga gatggaagac atcaattttt 17700
catccctggc tccgcgacac ggcacgcggc cgtatatggg cacctggagc gacatcggca 17760
acagccaact gaacgggggga gccttcaatt ggagcagtct atggagcggg cttaaaaatt 17820
ttgggtccac tataaagact tatgggaaca aagcttggaa cagcagcaca gggcatgcgc 17880
tgagacaaaa gcttaaagat cagaatttcc aacagaaggt ggtcgatggt atcgcctctg 17940
gaatcaatgg ggtggtagat ctggccaacc aggccgtgca gaaacagatt aacagtcgcc 18000
tggacccggc tcccccagct cctattcatg agttaatgca agtggaggaa gagctccctt 18060
cattggaaaa gcggggcgat aagcgacctc gtccagatat ggaggaaacg ctgctgacca 18120
aggtggatga gccgccctcc tatgaagagg ctgtaaaact gggaatgccc actacaaagc 18180
ccattatgcc tctggccact ggagtgatga agccatctca gtctaaacct gcagttgctg 18240
ctacattgga cttgcccgct cccgtggcca cccccaaacc tgtcgccgcc ccgaagccca 18300
ccgccgtgca acccgtggcc gtggccagac cgcgtcccgg tggtcggccg aatgcaaact 18360
ggcagagcac tctgaacagc atcgtgggtt tgggagtgca cagtgtgaag cgccgtcgct 18420
gctattgatt aaatatggag tagcgcttaa cttgcttgtc tgtgtgtgta tatgtcgatg 18480
ccgcccgccg tgctacagca aagagagaag gagaagaggc gccgctgagt tcctttcaag 18540
atggccaccc catcgatgct gccccagtgg gcgtacatgc acatcgccgg acaggacgct 18600
tcggagtacc tgagtccggg tctggtgcag ttcgcccgcg ccacagatac ctacttcaat 18660
ctggggaaca agtttaggaa ccctaccgtg gctcccaccc acgatgtgac caccgaccgt 18720
agccagcgcc tgacgctgcg ctttgtgccc gttgaccggg aggacaatac ctactcctac 18780
aaagtcagat acaccctggc tgtgggagac aacagggtgt tggatatggc cagcacctac 18840
tttgacatca ggggcgtgtt ggacagagga cctagcttca aaccatactc tggcactgcc 18900
tacaactccc tggctccaaa aggagctcca aactccagtc agtggcaaca aaaggaaaac 18960
aatggtcaag gtgatgcaaa gactcacacc tatggtgtag ctgccactgg aggtattgac 19020
attgacaaaa atggtcttca aattggaatc gatgaaacta aagaagataa taacgaaatt 19080
tatgcagaca aaacattcca acctgaacct caaattggag aagaaaactg gcaagatagc 19140
gaaaactatt atggaggcag ggctcttaaa ccggaaacca agatgaagcc ttgctatggt 19200
tccttcgcta gaccaactaa tgcaaaggga ggtcaagcca aaattaaacc agctcaagag 19260
ggtcaacagt ctatagatta tgacatagac ctggctttct ttgatattcc aagcactggc 19320
ggaggcaatg gcacaaatgt aaatgacaag ccagatatgg ttatgtatac tgaaaatgta 19380
aatctggaaa ctccagacac tcatcttgtt tacaagccag gaacttcaga tgacagttcc 19440
gaggccaatt taactcagca agccatggct aacagaccca actatattgg gtttagagat 19500
aactttattg gcgtcatgta ctacaacagc actggcaaca tgggagtgct tgctggtcaa 19560
gcatcccagc taaatgctgt ggtggacctg caagacagaa acaccgagct gtcttatcag 19620
ctattacttg actctctggg cgacagaacc aggtatttta gtatgtggaa tcaggcggtg 19680

-continued

```
gacagctatg atcctgatgt gcgcattatt gaaaaccatg gtgtggaaga tgaattgcca  19740
aactattgct tcccattgga cggagctggc actaatgctg tttaccaagg agttaagaca  19800
aaagaggata ataatggcga atgggaaaca gacacaaatg ttgcatcgca gaatcagata  19860
tgcaagggca acatatatgc tatggagatc aacctgcaag ccaacctgtg gaaaagtttc  19920
ctttactcca acgtggctct gtacctacca gactcctaca agtacactcc atccaacgtg  19980
acactcccta ccaacactaa cacctatgac tacatgaatg gcagggtggt gtctccatcc  20040
ctggtggatg cctacattaa cattggcgcc aggtggtctc tggatgccat ggacaatgtc  20100
aaccctttca accaccaccg caatgccggc ctgcgctacc ggtccatgct tctgggcaac  20160
ggccgatacg tgcccttcca catccaagtg ccccagaaat tcttcgctat caagaacctg  20220
ctgcttctcc caggctcata cacctacgag tggaacttcc gcaaggatgt caacatgatc  20280
ctgcagagtt cccttggcaa tgacctcaga accgatgggg ccaccatcca gtacaccagc  20340
atcaatctct atgccacctt cttccccatg gctcacaaca ctgcctccac cctggaagcc  20400
atgctgcgca atgacaccaa tgaccagtcc ttcaatgact acctctcagc tgccaacatg  20460
ctttacccca tccctgccaa tgccaccaac gtgcccatct ccatcccatc tcgtaactgg  20520
gctgccttca ggggctggtc tttcacccgc ctcaagacca aggagacccc atctctggga  20580
tcagggttcg atccctactt cgtctactca ggctccattc catacctgga tggaactttc  20640
taccttaacc acactttcaa gaaagtctcc atcatgtttg actcttctgt cagctggcca  20700
ggcaatgaca ggctgctgac tcccaatgag ttcgaaatca agcgcactgt tgatggggaa  20760
gggtacaatg tggcacaatg caacatgacc aaagactggt tcctggttca gatgctctcc  20820
cactacaaca ttggctacca gggcttctac atcccagaag gatacaagga ccgcatgtac  20880
tccttcttca gaaacttcca gcccatgagc cgccaggtgg tcgatcaggt caactacaaa  20940
gactacatgg cagtcaccct tgcctatcag cacaacaact ctggctttgt gggctacctc  21000
gcgcccacca tgcgacaggg ccaaccctac cctgctaact acccataccc gctcattggc  21060
aagactgcag tcaacagtgt cacccagaaa aagttcctct gcgacagggt catgtggcgc  21120
atccccttct ccagcaactt catgtccatg gggggccctta ccgacctggg gcaaaacatg  21180
ctttatgcca actccgccca cgcgctagac atgaatttcg aagtagaccc catggatgag  21240
tccacccttc tctatgttgt cttcgaagtc ttcgacgtgg tcagagtgca ccagccccac  21300
cgcggcgtca tcgaagctgt ctacctgcgc accccccttct cagctggtaa cgccaccaca  21360
taagcgcctt gcttcttgca agtggctgca gcagcatggc ctgtggatcc tccactggat  21420
ccaatgagca agagctcagg gccatcgcca tagacctggg ctgtggaccc tatttcctgg  21480
gaacctttga caagcggttt ccaggcttca tggctcctga caagctcgcc tgtgccattg  21540
tcaacacggc agggcgcgag actggtggtg agcactggct ggcttttgga tggaaccccc  21600
gctccaatac ctgctatctc tttgacccgt ttgggttttc agacgagcgc ctcaagcaga  21660
tctatcaatt cgagtacgag gggctcctgc gccgcagtgc cctggctact aaggaccgat  21720
gcatcactct ggaaaagtct acccagaccg tgcagggtcc gcgctcggct gcctgcgggc  21780
tcttctgctg catgttcctc catgcttttg tgcactggcc cgaccgcccc atggacaaca  21840
accccaccat gaatttgctg acgggggtac ccaacaacat gctccaatcg ccccaagtag  21900
agcccaccct gcgccacaac caggaggcac tctatcgctt cctgaactcc cactcatctt  21960
actttcgttc taaccgcgcg cgcattgaga aggccactgc cttcgatcga atgaataata  22020
acatgtaaac caaattgtgt gtggctcaaa taaacagcac tttattgttt acatgcactg  22080
```

-continued

```
aggctctggg atgatcattt tttaaaaatc gaaggggttc tggcgggaat cagcatggcc  22140
agatggcagg gacacgttgc ggaactggaa cttgttctgc cacttgaact cgggaatcac  22200
cagcctggga actggaatct ctggaaaggt atcttgccat agctttctgg tcagttgcag  22260
agcgccaagc aggtcaggag cagatatctt gaaatcacag ttggggccag aattctgggc  22320
gcgggagttg cggtacactg ggttgcagca ctggaacacc ataagggcag ggtgtctcac  22380
gctcgccagc acggtctcgt cactgatgca agacacatcc aggtcttcag cattggccat  22440
tccaaagggg gtcatcttgc aggtctgtct gcccatcacg ggagcgcagc caggtttgtg  22500
gttgcaatca caatgaaggg ggatcagcat catcttggcc tggtcggggg taatccctgg  22560
gtaaacagcc ttcatgaagg cttcatactg cttgaaagct tcctgggctt tggttccctc  22620
ggtgtagaac actccacaag acttgctgga aaactgatta gtagcgcagt tggcatcatt  22680
cacacagcag cgggcgtcgt tattagccag ctggaccaca ttcctgcccc agcggttctg  22740
ggtgatcttg gctcgatctg ggttctcctt caacgcgcgc tggccgttct cgctcgccac  22800
atccatctca atgacatgtt ccttctggat catgatgttg ccatgcaggc atctaatctt  22860
gccttcataa tcagtgcagc catgaggcca cagcgcgcac ccggtgcact cccaattgtt  22920
atgggggatc tgggaatggc tatgaaccag cccttgcagg aatcttccca tcatcacagc  22980
cagggtcttt atgctggtaa aggtcagcgg gataccgcgg tgctcctcgt tcacatactg  23040
ctggcagatg cgtctgtagt gctcggcctg ctcgggcatc agcttgaaag aggttttcaa  23100
ctcattatcc agcctgtatc tctccatcat gatggacatt acttccatgc ccttctccca  23160
ggcagaaaca atagggagac tcaggggatt cttgacagta gagacaacct tacttaaggg  23220
gtcatcactg ccaatctttt cgatgcttct cttgccatcc ttctcggtga tgcgcaccgg  23280
cgggtagctg aatcccacag ccaccaactg agcctcttcc ctttcgtctt cgctgtcttg  23340
actgatgtct tgcagaggaa catgtttggt tttcctgggt ttcttcttgg gcggcagctc  23400
tggaggactc tggctccgtt ccggagaccc catggatgag cgagagttgt cgctcaccac  23460
ttggatctgg ctgcctgtag aagaactgga ccccacgcgg cggtaggtgt tcctcttggt  23520
aggcagaggt ggaggcgacg ggctccggtc cggtctgggt ggcggatggc tggcggagcc  23580
ccttccgcgt tcgggggtgc gctccagatg gcggtcgtct gactgacctc cgcggctggc  23640
cattgtgttc tcctaggtag agaaacaaga catggagact cagccatcgc tgccatcgcc  23700
atccaccacc acaagcaccg ccgaggagga ggagtgttta accaccccac catgcagccc  23760
cgctaccacc accagcaccc ttgaaagcga ggtcgacacg gtcgtggagg atttacaggc  23820
tatggaagat attgaggcag ctgtcgagca agaccccggc tatgtgacac cggcggagca  23880
tgatgaggat ctagcgcgct ttctcgacgg tgtggagaaa gcgaaacaag atgaggacga  23940
ggaagaggca gaagcacaac catcggtggc cgactacctc accggcctag ggctagaaga  24000
cgtgctgctt aagcatcttg caaggcagac agtcatagtc aaagacgccc tgctagagcg  24060
ctccgaggtg ccactcagtg tggaagacct cagtcgcgcc tatgagctaa acctcttctc  24120
gcctcgcaag ccccccaagc gtcagcccaa cgggacctgt gagcccaatc cgcgcctcaa  24180
cttctatcca gccttcactg tgcccgaagt actagctacc taccacatct tttcaagaa  24240
ccaaaagatc cccatctcct gccgcgccaa tcgcacccgc gcagatgccc tactcaactt  24300
ggggcccggc gctcgcatac ctgatatcgc ttccttggaa gaggttccta agatctttga  24360
gggtctgggc aatgaggaaa ctcgggcagc aaacgctctg caaagagaaa cagatgatgg  24420
```

-continued

```
tgaacaccac agcgctctgg tggagctcca gggcgacaac gctcgtcttg cagtcctcaa  24480
acgcagcatc gaggtcaccc atttcgccta ccccgcactt aatctcccac ccaaagtcat  24540
gagctcggtc atggacacgt tgctcatgaa gcgcgcgagc cccatctccg aggatcagaa  24600
catgcaggac cccgatgcct cagatgaagg caagcctgta gtcagcgacg agcaactggc  24660
tcgctggcta ggctctgact ccccccagtc tttggaggag cggcgcaagc ttatgatggc  24720
agtggtcctg atcacagcgg agctggagtg tctccgccgc ttcttcactg acccagagac  24780
cctgcgcaag cttgaggaga acctgcatta cacattcagt catgggttcg tgcgccaggc  24840
gtgcaagatc tccaacgttc aactcaccaa cctggtctcc tacctgggca tcttgcatga  24900
aaaccggctg gggcagaacg tgctccacac caccctgaag ggggaggccc gccgcgacta  24960
tatccgcgac tgtatctacc tctacctatg ctacacctgg caaagcggga tgggtgtgtg  25020
gcaacagtgc ttggaagagc aaaatctaaa agagctggaa aagctgcttc agaaatctct  25080
taaatctctg tggaccgggt tcgatgagcg gaccaccgct tcggacatgg ccgatattat  25140
cttccccgag cggctcagac acactctgcg cgacgggctg cctgactttg ccagccagag  25200
catgctacaa aactttaggt cattcatctt ggaacgctcc gggatcctgc ccgccacttg  25260
ctgcgcactg ccctccgatt ttgtgcccat cacctaccgg gagtgccccc cgccgctatg  25320
gagccactgc tacctgttcc gcctggccaa ctacttggcc taccactctg atgtgataga  25380
agatgttagt ggcgaagggc tcctggagtg ccactgccgc tgcaacctct gcacccccca  25440
ccgctccctc gcctgcaatc cccagctgct gagcgaaacc cagatcatcg gcaccttcga  25500
gttgcaaggt cccagcggcg aaggcgaggg gtcctctccg gggcaaagtc tgaaactgac  25560
tccgggggcta tggacctccg cttaccttcg caagttcgcc cccaaagact accaccccta  25620
tgagatcagg ttttatgaag accaatcaca gccccccaag gccgaactga cggcctgcgt  25680
catcacccag gggggcaatct tggcccaatt gcaagccatc caaaaatccc gccaagaatt  25740
tttgctgaaa aagggacacg ggatctatct agacccccag accggtgagg agctgaatac  25800
acgcttccct caggatgccc cgaggaggca agagaatgaa agttcagatg ccgcccgagg  25860
aggagctgga agactgggac agtcaggcag aggaggaaga ctgggacagc caggcagaag  25920
aggaggacag cctggaggag gacagtctgg aggaaggcga ggagcccaag gaagaggcag  25980
ccgccgccag accatcgtcc tcggcggtgg agacaagcaa ggtcccagac agcacggcta  26040
ccacctccgc tccagctcaa ggggccgctc ggcgacccaa cagtagatgg gacgagacgg  26100
gtcgcttcca gaaccccacc accgtcaaga ccggtaagca ggagcggcag ggatacaagt  26160
cctggcgggg gcataaaagt gccatcatcg cttgcttgca ggagtgtggg ggcaatatat  26220
cctttgccag acgctacctg ctattccatc acggggtgaa tttcccccgc aacatcttgc  26280
attactaccg tcacctccac agcccctact accagcagca agagacagca gaggaaacca  26340
gcggcaactc cgagagttag aaaaccagca gctaaaaaat ccacagcggc ggcagcaggt  26400
gcaggcggac tgaggatcac cgcgaacgag ccagctcaga ccagggagtt gaggaatcgg  26460
atctttccca ccctctatgc catattccaa caaagtcggg gtcaggaaca agaactgaaa  26520
gtaaaaaaca gatctcttcg ctcgctcacc cgcagttgtt tgtatcacaa gagcgaagac  26580
caacttcagc gcactctcga ggacgccgag gctctcttca acaagtactg cgcgctgact  26640
cttaaagagt agactgcgcg cgcttggcga gaaaaggcgg gaattacgtc acctcttggc  26700
cacacctgtg cttcattatg agtaaagaaa ttcccacgcc ttacatgtgg agctatcagc  26760
cccagatggg attggccgct ggcgccgccc aggactactc cacccgcatg aattggctca  26820
```

```
gcgccggtcc cgcgatgatc tcacgggtta atggtgtgag agagcaccga aaccagatac  26880
tcctagaaca gtccgccctc accgccactc cccgcaatca cctcaacccc cgtaattggc  26940
ccgccgccct ggtgtaccag gaaactcctg ctcccactac agtactactt cctcgtgacg  27000
cccaggccga agttcagatg actaactcag gtgtacagct ggcgggtggt gccaccctgt  27060
gtcgtcaccg gccaagaccg ggtataaagg gcctggtgat cagaggccga ggtattcagc  27120
tcaacgacga gtcggtgaac tcttcgcttg gtctgcgacc agacggcatc ttccaaatag  27180
ctggttgtgg gagatcttcc ttcactcctc gtcaggctgt cctgactttg gagagttcgt  27240
cctcgcagcc ccgctcgggc ggcatcggga ctctccagtt cgtggaggag tttactccct  27300
cggtctactt caaccccttc tccggttctc ctgggcttta cccggacgag ttcatcccga  27360
actacgacgc catcagtgaa gcggtcgacg gctacgatta atgtctaatg gtggcgcggc  27420
tgagctagct cgactgcgac acctagacca ctgccggcgc tttcgctgct ttgctcggga  27480
tctctgcgag ttcatctact tcgagtaccc tgacgaacat cctcagggac ctgcccacgg  27540
agttcggatt accattgaag gggctatcga ttctcacctg cttcggatct tcaccgctcg  27600
gccagtgcta gttgagcgca accagggcga caccaccatc tccctctgct gcatttgtga  27660
caaccccgga ttgcatgaaa gcttttgttg tcttctttgt actgagtata ataaaagctg  27720
aaattagaga ctactccgga ctctcttgtc gtctgaacaa caccaaccag acccttcact  27780
tcagcgggaa ccagactact cttcactgta aggcttataa ctataagtat cttacttgga  27840
tatacaaagg aacaccgttt gctgtggtaa acaggtgctc caacgacggt gttctcctca  27900
ccttcctagg caacttctcc aactttacct tttctgttcg cagaaacaag cttaccctcc  27960
ttcagcccta ctttcctggg atctatacct gcctcagtgg accttgcaac cacacttttc  28020
acctgattga aaactctacc cttaccttcc cagcgccaat ccctactaac agctcggagt  28080
ccaactcttc cattaccgct gatactaaca ctcctaaaac cggaggtgag ctccgcagcc  28140
ttcccccggc tgcagataac ccttgggtgg tagcgggatt tgtagcgcta ggaatagttg  28200
cgggtgggct cgcgttcgtc ctctgctacc tataccttac ctgctgctca tatttagtag  28260
tactgtgctg ttggtttaga aaatgggggc gctactaatc acacttgctt tactttcgct  28320
tttgggtctg agctcggcta atagcgagaa accaagctgt ctagaaacaa actctccaga  28380
ctgtgtggtt cctcatgggc tctcagaccc agctgatgat ccatgcttaa cttttgaccc  28440
agaaaaaaac tgctcggtga ctatgcagcc ctatgcttac atgtgcacat ctgttataaa  28500
gtgcggatgg ggctgtaaac cgattgaaat tacccacaaa ggcaaaacct ggaataatag  28560
tttgtttaac acatggcagc ctggagacga gcagtggtat acggccggcc actggtggag  28620
atgactgacc ccatggaaaa ctcctctgcc aacgacctgg acatggacgg ccgttcatct  28680
gagcagcgac tggtccagat gcgcattcgc cagaagcagg aacgcgccgc cagagagctc  28740
aaggatgcca ttgaaattca cctgtgcaag aagggcatct tttgcttggt taagcaagca  28800
aagatttctt atgaaatcac tgacaacgac caccgcctgt attatgagct cggtccacag  28860
cggcagaaat tcacctgcat ggttggagtc aaccccatag tcatcactca gcaggctgca  28920
gaaattaaag ggtgcatcca ctgttcctgt gattcccaag aatgcgtcca caccatagtc  28980
aagaccctct gcggccttcg agatcttctt ccaatgaact aacccccttcc cccaacccaa  29040
taaaacattg gttttaatca taataaaaaa tcacttactt taaatctgaa acagtgtctc  29100
cgtccaagtt ttcttgtagc accacttcac tcccctcttc ccagctctgg tactgcaagc  29160
```

cccggtgggc tgcaaacttt ctccacacct taaaagggat gtcaaattcc tcttgtccaa 29220
caatcttcat tgtctcttcc tagatgtcca caaagcgcgc gcgggtggaa gatgactttg 29280
accctgtcta cccatacgat gctgagctgg caccgtctgt acccttcatc gcccctccct 29340
tcgtttcgtc agacggattt caagaaaaac ccctgggagt tctgtcccta agactagcca 29400
acccagtcac tactaaaaat ggggaactca cacttaaact gggagatggg gtgggcatag 29460
actcagatgg aaacctcaca gcacagacag ttactaaagc aacatccccc cttactgttt 29520
ccaataacgc aattgcactt aacatggaca aacctttta cagtagcaat ggaaaactat 29580
ccttacaagt tacatcacca ttaaagatag tcgactcttt aaatacattg gctattggct 29640
atgggcaagg cttaggacta aacaatagtg ctcttgctgt gcaattagca tctcccctta 29700
catttgacag caacagcaaa attaaaataa atttgggaag cgggccatta aaaattaatg 29760
cgaataaact gtcaattaac tgcctaaggg gtgtatatgt aacaactgac ggaacttcca 29820
ttgaaacaaa tataagctgg gcaaaaggaa tgaggtttga aggtaatgcc atggctgtaa 29880
acgttgacag caccaaaggt ctacaatttg gcactaccag cacagaatca ggagtcacta 29940
acgctttccc tatccagtta aagattggat ctggtcttag ttttgacagc acaggagcac 30000
ttgtagcttg ggataaggat aatgacaagc ttacactgtg gacaaccgct gacccatcac 30060
ctaattgtac catatataca gacaaggatg ctaaacttac actttgtctt acaaaatgtg 30120
gcagtcaaat actaggcagt gtttcagtac tggctgttaa agctggaacc ctacagccaa 30180
tcagtgaaaa aataggtact gctttggttt cactaaaatt taataacaac ggtgtattgt 30240
taagcaactc cacattaagt aatgaatact ggaactacag gaagggagat gtcacaccag 30300
ccgaagccta tactaatgct gtgggtttta tgccaaacat caaggcatat cctaaaaaca 30360
caaactctgc ctcaaaaagc cacattgtag gacaagtgta ccttaatgga gatgaaacta 30420
aaccaatgca tttaatcatt acatttaatg aaaccagtga tgaaacatgc acatattcca 30480
taacgttcca atggaaatgg aacattggaa catacaccag cgacaccctt gcaacaagct 30540
cctttacctt ttcttacatt gcccaagaat aaaaactgca gacaacaata aagtttaaat 30600
gttttattta aacagtttca cagaacccta gtattcaacc tgccacctcc ctcccaacac 30660
acagagtaca cagtcctttc tccccggctg gccttaaaaa gcatcatatc atgggtaaca 30720
gacatattct taggtgttat attccacacg gtttcctgtc gagccaaacg ctcatcagtg 30780
atattaataa actccccggg cagctcactt aagttcatgt cgctgtccag ctgctgagcc 30840
acaggctgct gtccaacttg cggttgctta acgggcggcg aaggagaagt ccacgcctac 30900
atgggggtag agtcataatc gtgcatcagg atagggcggt ggtgctgcag cagcgcgcga 30960
ataaactgct gccgccgccg ctccgtcctg caggaataca acatggcagt ggtctcctca 31020
gcgatgattc gcaccgcccg cagcataagg cgccttgtcc tccgggcaca gcagcgcacc 31080
ctgatctcac ttaaatcagc acagtaactg cagcacagca ccacaatatt gttcaaaatc 31140
ccacagtgca aggcgctgta tccaaagctc atggcgggga ccacagaacc cacgtggcca 31200
tcataccaca agcgcaggta gattaagtgg cgacccctca taaacacgct ggacataaac 31260
attacctctt ttggcatgtt gtaattcacc acctcccggt accatataaa cctctgatta 31320
aacatggcgc catccaccac catcctaaac cagctggcca aaacctgccc gccggctata 31380
cactgcaggg aaccgggact ggaacaatga cagtggagag cccaggactc gtaaccatgg 31440
atcatcatgc tcgtcatgat atcaatgttg gcacaacaca ggcacacgtg catacacttc 31500
ctcaggatta caagctcctc ccgcgttaga accatatccc agggaacaac ccattcctga 31560

```
atcagcgtaa atcccacact gcagggaaga cctcgcacgt aactcacgtt gtgcattgtc  31620
aaagtgttac attcgggcag cagcggatga tcctccagta tggtagcgcg ggtttctgtc  31680
tcaaaaggag gtagacgatc cctactgtac ggagtgcgcc gagacaaccg agatcgtgtt  31740
ggtcgtagtg tcatgccaaa tggaacgccg gacgtagtca ttctcgtact ttgagtggca  31800
aaaccttgct ctcgaacagc acacgtctcg tcgcctcctg tcccttctct tcgccttttc  31860
agtgtgatag ttgtaataca gccattcacg aagctcagtc agaagatctt cagcgtctgt  31920
tgtcaaaaac aatccatcca atctgattgc tttcaaaaca tcacaaacag tcgaataagc  31980
caaacccatc caggcaatgc aattattttg gttatccaca atgggagggg gcggaagaca  32040
tggaagaggc ataattaatt ttttaatcca atcgatcacg cagcacttca aaatgaagat  32100
cgcgaaggtg acacctttca cccccactgt gttgatgaaa aataacagcc aagtcaaaat  32160
tgatgcggtt ttcaaggtgc tcgactgtag catcaagcag agcttccaca cgcacgtcca  32220
caaataacag aatagcaaaa gcgggaggag gaagtaaatc ctcaatcatc atagtacagt  32280
ccatcaccat ccctaaataa ttttcatcct tccagccttg gactatattt ttaaactgct  32340
cttgtaaatc caaaccacac atgtggaaaa gttcccaaag agctccctca actaccattc  32400
ttaagcacac cttcatagtg acaaaatatc ttgttcctct gtcacctgca gcaaattaca  32460
aagtccaata ttaggatcta tgcccagaga tctaagctca tccctcaatt ccaactgtaa  32520
aaaggcttcc agatctgccc taacttgttc agccagtggg ctccctggaa taagcgtggg  32580
agaagccaaa ctgcaaaaca gacgcatgcc gccataatta ccaccagaaa acactacgtt  32640
acagtatgca tgctgattca ttccagtaat ttcatccagt gtattggata caaaaaaagg  32700
caagcactct ctcactaatt gtattatgga gacattatca cacaggtaac aatttaaagg  32760
ttgtggaaca ataatgcagt aagtaaccac ggtgcgctcc aacatggtta gtaattttta  32820
gttctgaaaa acaaaacata caaaaaatta tatcatactc atttggcgaa ctggtggaaa  32880
aatgacccta tctagcacaa ggcaagccac tggatcacca atgcgcccct cataaaacct  32940
gtcatcatga ttaaaaagca acaccgaaag ctcttcccta tgtcctgcat gaatgattct  33000
agctgaggaa tataagccag cgcaattagt atctgttaaa gaaaaaaaac ggccaacata  33060
gcctctagga attagcacac ttaatcttaa agacattact gccatccccc ttggatttaa  33120
ggtaaaattt acaggagcat agaaaatata ctgatttccc tcctgcacag gcagcatagc  33180
accaggtccc tctaaaaaca cacacaaagc ttctgcagcc atagcttacc gcgcaaacca  33240
ggcacagcag tgagctaaaa ggacaaagct ctaactcact agccaacctg gcgcacaata  33300
tatagttagt ccttacactg acgtaaccga ccaaagtcta aaaccccgc caaaaataca  33360
cacacgccca aaaaacgccc cgtgagtcaa aaaacagttt cacttcctcg ttacacccaa  33420
aacgtcgtca cttccggatt cccacggttc gtcacttccg gagctccttg cttaattaac  33480
cccgcccaaa acgtcatcgt ccgcgtcacg ccgccccgcc ccgcgaccgt tgaccccggg  33540
ccaatcaccg cacatcccgc aaaattcaaa ctcgtctaat ttgcatattg gcacactgcc  33600
catataaggt atattattga tgatg                                        33625
```

<210> SEQ ID NO 23
<211> LENGTH: 34616
<212> TYPE: DNA
<213> ORGANISM: Artificial Sequence
<220> FEATURE:
<223> OTHER INFORMATION: BLY6.RSVF-2A-GLuc Ad vector

<400> SEQUENCE: 23

```
catcatcaat aatatacctt atatgggcag tgtgccaata tgcaaattag acgagtttga     60
attttgcggg atgtgcggtg attggcccgg ggtcaacggt cgcggggcgg ggcggcgtga    120
cgcggacgat gacgttttgg ggaggaggag ctatgttgca agtaatcgtg ggaaatgcga    180
cgtaaaacga ggtggagttt aaacacggaa gtagacaatt ttcccgcgct gtttgacagg    240
aaatgatgtg tttttgggcg gatgcaagtg aaaattctcc attttcgcgc gaaaactaaa    300
tgaggaagtg aaattctgag taattctgag gttatcacag ggcggagtat ttaccgaggg    360
ccgagtagac tttgacccat tacgtggagg tttcgattac tctatttttc acctaaattt    420
ccgcgtactg tgtcaaagtc cgtgttttta cgcgatcgct caatattggc cattagccat    480
attattcatt ggttatatag cataaatcaa tattggctat tggccattgc atacgttgta    540
tccatatcat aatatgtaca tttatattgg ctcatgtcca acattaccgc catgttgaca    600
ttgattattg actagttatt aatagtaatc aattacgggg tcattagttc atagcccata    660
tatggagttc cgcgttacat aacttacggt aaatggcccg cctggctgac cgcccaacga    720
cccccgccca ttgacgtcaa taatgacgta tgttcccata gtaacgccaa tagggacttt    780
ccattgacgt caatgggtgg agtatttacg gtaaactgcc cacttggcag tacatcaagt    840
gtatcatatg ccaagtacgc cccctattga cgtcaatgac ggtaaatggc ccgcctggca    900
ttatgcccag tacatgacct tatgggactt tcctacttgg cagtacatct acgtattagt    960
catcgctatt accatggtga tgcggttttg gcagtacatc aatgggcgtg gatagcggtt   1020
tgactcacgg ggatttccaa gtctccaccc cattgacgtc aatgggagtt tgttttggca   1080
ccaaaatcaa cgggactttc caaaatgtcg taacaactcc gccccattga cgcaaatggg   1140
cggtaggcgt gtacggtggg aggtctatat aagcagagct cgtttagtga accgtcagat   1200
cgcctggaga cgccatccac gctgttttga cctccataga agacaccggg accgatccag   1260
cctccgcggt tggccgtgct cttcctgacg ggtaggtgtc ccctaaccta gggagccaac   1320
catcgggggg ccttctccct aaatccccgt ggcccaccct cctgggcaga ggcagcaggt   1380
ttctcactgg ccccctctcc cccacctcca agcttggcct ttcggctcag atctcagccc   1440
acagctggcc tgatctgggt ctcccctccc accctcaggg agccaggctc ggcatttcgt   1500
cgacatggaa ctgctgatcc tgaaggccaa cgccatcacc accatcctga ccgccgtgac   1560
cttctgcttc gccagcggcc agaacatcac cgaggaattc taccagagca cctgtagcgc   1620
cgtgtccaag ggctacctga gcgccctgcg gaccggctgg tacaccagcg tgatcaccat   1680
cgagctgagc aacatcaaaa agaacaagtg caacggcacc gacgccaaaa tcaagctgat   1740
caagcaggaa ctggacaagt acaagaacgc cgtgaccgag ctgcagctgc tgatgcagag   1800
cacccccgcc accaacaacc gggccagacg ggagctgccc cggttcatga actacaccct   1860
gaacaacgcc aaaaagacca acgtgaccct gagcaagaag cggaagcggc ggttcctggg   1920
cttcctgctg ggcgtgggca gcgccattgc tagcggagtg gctgtgtcta aggtgctgca   1980
cctggaaggc gaagtgaaca agatcaagtc cgccctgctg agcaccaaca aggccgtggt   2040
gtccctgagc aacggcgtgt ccgtgctgac cagcaaggtg ctggatctga agaactacat   2100
cgacaagcag ctgctgccca tcgtgaacaa gcagagctgc agcatcagca acatcgagac   2160
agtgatcgag ttccagcaga agaacaaccg gctgctggaa atcacccgcg agttcagcgt   2220
gaacgccggc gtgaccaccc ccgtgtccac ctacatgctg accaacagcg agctgctgag   2280
cctgatcaac gacatgccca tcaccaacga ccagaaaaag ctgatgagca acaacgtgca   2340
```

gatcgtgcgg cagcagagct actccatcat gtccatcatc aaagaagagg tgctggccta 2400
cgtggtgcag ctgcccctgt acggcgtgat cgacaccccc tgctggaagc tgcacaccag 2460
ccccctgtgc accaccaaca ccaaagaggg cagcaacatc tgcctgaccc ggaccgaccg 2520
gggctggtac tgcgataatg ccggcagcgt gtcattcttt ccacaagccg agacatgcaa 2580
ggtgcagagc aaccgggtgt tctgcgacac catgaacagc ctgaccctgc ccagcgaggt 2640
gaacctgtgc aacgtggaca tcttcaaccc taagtacgac tgcaagatca tgacctccaa 2700
gaccgacgtg tccagctccg tgatcacctc cctgggcgcc atcgtgtcct gctacggcaa 2760
gaccaagtgc accgccagca acaagaaccg gggcatcatc aagaccttca gcaacggctg 2820
cgactacgtg tccaacaagg gcgtggacac cgtgtccgtg ggcaacaccc tgtactacgt 2880
gaacaaacag gaaggcaaga gcctgtacgt gaagggcgag cccatcatca acttctacga 2940
cccccctggtg ttccccagcg acgagttcga cgccagcatc agccaggtca acgagaagat 3000
caaccagagc ctggccttca tcagaaagag cgacgagctg ctgcacaatg tgaatgccgt 3060
gaagtccacc accaatatca tgatcaccac aatcatcatc gtgatcatcg tcatcctgct 3120
gtccctgatc gccgtgggcc tgctgctgta ctgcaaggcc cggtccaccc ctgtgaccct 3180
gtccaaggac cagctgagcg gcatcaacaa tatcgccttc tccaacggac gcgtgaccga 3240
gctgctttac cggatgaagc gggctgagac atattgcccg agacccctgt tggcaatcca 3300
tcctactgag gctcgccaca aacagaaaat cgtggccccc gtcaaacaga cactcaattt 3360
tgacttgttg aaacttgcag gagatgttga gtcaaacccc gggcctatgg gcgtcaaggt 3420
cctgttcgct ctgatttgta tcgctgtcgc tgaagctaag ccaaccgaga ataatgaaga 3480
ctttaatatc gtggccgtgg cttctaactt cgctaccaca gacctggatg cagacagggg 3540
aaagctgcca ggcaagaaac tgcccctgga ggtcctgaag gagatggaag caaatgcccg 3600
gaaagccggg tgcacaagag gatgcctgat ttgtctgagc cacatcaagt gcactcctaa 3660
gatgaagaag ttcatccccg gccggtgcca tacctacgag ggcgataagg aatccgccca 3720
gggaggaatc ggagaggcta tcgtggatat tcccgaaatc cctggcttca aagacctgga 3780
gcccatggaa cagtttattg cacaggtgga tctgtgcgtc gactgtacta ccggatgcct 3840
gaagggactg gcaaacgtcc agtgtagcga cctgctgaag aaatggctgc ctcagcgatg 3900
tgctacattt gccagcaaga ttcagggcca ggtggacaag attaagggag caggaggcga 3960
ctgataattc tagacgagat ccgaacttgt ttattgcagc ttataatggt tacaaataaa 4020
gcaatagcat cacaaatttc acaaataaag catttttttc actgcattct agttgtggtt 4080
tgtccaaact catcaatgta tcttatcatg tctgcgatcg cgatggcctg tgtttgagca 4140
taatgtactg accaggtgta acgttcatct gggtggtcgt agaggaatgt tcatgccata 4200
ccaatgcaat tttaatcatg tgaggatctt gatggagccg caagcgtttt ccagagtcag 4260
cttgactgga atctttgaca tgtgtgtgga agcatggaag atcttaagat atgatgatac 4320
caaatccaga tgccgcgcat gcgagtgcgg gggcaggcat gccaggttcc aacctgtatg 4380
tgtggaggtg accgaggagc tgagaccaga tcatttggtg ctgacctgca ctggtgcgga 4440
gttcggttcc agtggtgaag aaactgatta aagtgagtag tgggatgtta taaaagtgac 4500
cataaggtga tgtgagatgg acaaatttgg taatttttat gtatttttgt cttgcagcca 4560
tgagtgggag cgcttccttt gaagggggcg tctttagccc ttatctgacg gggcgtctgc 4620
ctcattgggc tggagtgcgt cagaatgtga tggggtctac agtggatgga agacctgttc 4680
agcctgctaa ttcttctact ctgacttatg ctactatgac ttcctcgcct ttggatgcag 4740
ctgcagctgc tgccgcttct gctgccgcca acactgttcg ggggatggcc ttggagatgg 4800
ggtattatgg aactgtagtg gccaacacca ctaccccaaa taaccccaca gccttgaatg 4860
aggacaagct gctagttctc atgtcccagc tggagtcttt gacccaacgc ctgggcgatc 4920
tagctcagca ggtgtcccag ctgaaggagc agactcaagc tgcaattacc actgcgaggg 4980
gaaattaaaa aaattcaaag aatcaataaa taaaccgaga ctttgttgat tttaaagtgt 5040
gtcattcttt atttaatttt tcgcgcgcga tatgccctgg accaccggtc tctatcattg 5100
aggacacggt ggatcttttc tagaacccga tagaggtggg attggatgtt gaggtacatg 5160
ggcataagac catctttggg gtgtagatag ctccactgca gagcctcatg ctccggggtg 5220
gtgttgtata taacccagtc atagcatggg cgttgggcat gatgttgcac aatatcttta 5280
aggaggagac taatggccac tgggagaccc ttggtgtaag tgtttacaaa tctattaagc 5340
tgggacgggt gcatccgagg tgagataatg tgcattttgg attggatttt tagattggca 5400
atgtttcccc ctagatctct cctgggattc atgttatgca agaccactag aacagtgtat 5460
ccggtgcact tagggaattt gtcatgaagt ttggagggga aagcatgaaa aaatttagac 5520
acacccttgt gtcctcccaa gttctccatg cactcatcca taataatggc aatgggccca 5580
tgggcggcgg cacgggcgaa cacgttcctg ggatctgaca catcatagtt gtggtcttgg 5640
gtcaggtcat cataagccat tttaataaac ttggggcgga gggtgccaga ttgggggatg 5700
aatgttccct cgggccccgg aacatagttt ccttcacata tttgcatttc ccaggctttt 5760
agttcagagg gggggatcat gtccacctgt ggagcgatga agaagacggt ctcgggggcg 5820
ggggtgatta agtgggagga cagcaagttc ctaagcagct gtgacttgcc acacccagtg 5880
ggaccgtaga tgacccctat aacaggttgc agatggtagt ttagggaaag acagctgccg 5940
tcctctcgca ggaggggggc gacctcgttc atcatttccc tcacatgcat gttttcccgc 6000
acaagttccg ataggaggcg ctctccaccc agggaaagga gttcttgaag agatgagaaa 6060
tttttcaagg gttttaagcc atcagccatg ggcattttgg agagggtttg ttgcaagagt 6120
tcaaggcggt cccagagttc ggtgatgtgt tctatggcat ctcgatccag catacttcct 6180
cgtttctggg gttgggacgg ctgcgggagt atggaaccag gcgatgggcg tccagcgctg 6240
ccagtgtccg gtccttccac ggtcgcagcg tccgagtcag ggtcgtttcc gtcacggtga 6300
aggggtgcgc gcctggctgg gcgcttgcga gggtgcgctt caggctcatc ctgctcgtgg 6360
agaaccgctg ccgttctgcg ccctgtgcat cggccaggta gcaattaacc atgagttcgt 6420
agttgagcgc ctctgccgcg tggcctttgg cgcgcagctt acctttggaa gtcttctgac 6480
aggtgggaca gtagagacac ttgagagcat agagttttgg ggctagaaag accgattctg 6540
gggagtatgc atcggcccca caggaggcgc agacggtttc gcattccacc agccatgtaa 6600
gatcgggctc gttggggtca aaaacaagtt ttccgccatg ttttttgatg cgtttcttac 6660
ctttgctttc catgagttcg tgcccccgtt gggtgacaaa gaggctgtcc gtgtccccgt 6720
agactgactt tatgggcctg tcctcgagcg gcgtgccgcg gtcctcttcg tagaggaact 6780
cggaccactc tgagacgaaa gcacgtgtcc aggccagcac aaaggaggct atatgggagg 6840
ggtagcgatc gttgtcaacc aaggggtcta ctttttccaa ggtgtgtaaa cacatgtccc 6900
cttcttccac atccaggaag gtgattggct tgtaagtgta tgccacgtga cctggggtcc 6960
cagacggggg ggtataaaag gggcgggtc tctgctcgtc ctcactgtct tccggatcgc 7020
tgtccaggag cgccagctgt tgaggtaggt attccctctc gaaggcgggc ataacctccg 7080

-continued

```
cactcaggtt gtcagtttct aggaacgagg aggatttgat attgacagtg cctgccgaga   7140
tgcctttcat gagactgtcg tccatttggt cagaaaagac aatctttttg ttatcaagtt   7200
tggtggcgaa ggatccatac agggcattgg aaagcagttt ggcaatggag cgcatggttt   7260
ggtttttttc tttgtctgcg cgctctttgg cggctatgtt gagttggaca tattcgcggg   7320
ccagacattt ccattgtgga aatatggtag ttaattcatc tgggacgatt ctgactttcc   7380
agcctctgtt atgcagggta atcagatcca cactggttgc cacttctcct ctaagtggtt   7440
cattagtcca gcatagtcgc ccccttttc gagaacagaa agggggtagg ggatctagca   7500
tgagttcgtc tggggggtct gcatctatgg tgaaaatccc aggaaggaga tcttcgtcaa   7560
aatagctgat ggtggcgggg tcatccagag acatttgcca ttctcgagca gccagagcgc   7620
gctcgtaggg gttaagggga gtcccccatg gcatgggatg ggtgagtgca gaagcataca   7680
tgccacagat gtcatagaca tagagcggct cttccagaat ccctatgtaa gtgggataac   7740
atcgcccccc tctgatgctg gctcgcacat aatcatagag ttcatgtgag ggcgctagaa   7800
gacccgagcc caggttggtg cggttgggtt tttctgctct gtagaggatc tggcgaaaga   7860
tggcatggga gtttgatgag atggtgggtc tttggaagat gttgaaatgg gcatgaggca   7920
gtcccacaga gtcccttatg aagtgagcat aggagtcttg cagtttggcc accagctcgg   7980
cggtgaccag cacatccaaa gcacagtagt cgagggtctc tttgatgatg tcatagttag   8040
gttccccttt cttttcccac agctcgcggt tgagaaggta ttcttcgcga tccttccagt   8100
actcttcgag gggggaacccg tccttgtctg aacggtaaga acccagcatg taaaattgat   8160
tgacagcttt gtaggcacaa cacccctct ccacggggag tgagtatgct tgcgcggctt   8220
tgcgcagaga ggtgtgagta agggcgaaag tgtccctgac catgactttg aggaactgat   8280
gcttaaagtc tatgtcatcg caggcccccct gctcccacag ttggaagtcc actcgctttt   8340
tgtaggcggg attgggcaaa gcgaaagtaa catcgttgaa taggatcttt ccagccctgg   8400
gcatgaagtt gcgagtaatg cgaaaaggct gaggcacttc tgccctgttg ttgataactt   8460
gggcagccaa gacgatctcg tcaaagccgt tgatgttgtg acccacaatg taaagttcta   8520
cgaagcgtgg gcgtcccttg atgtggggca gtttttttaag ctcttcgtag gtcaagtcgt   8580
cagggtcagc gattccatat tgctccaaag cccagtcagg caggtgagga ttagcatgaa   8640
ggaaagaggt ccaaagatcc acggccagag ctgtttgtaa gcggtctctg tactgacgga   8700
aatgtcggcc taccgccatt ttttcaggag taacacagta aaaggtgcgc gggtcctttt   8760
cccagcgatc ccattgaagt tgcaaggcta ggtcgtgggc gaggttgacg agctgttcgt   8820
cccccgaaag tttcatgacc agcatgaaag ggacaagctg cttgccaaag gaccccatcc   8880
aggtgtaggt ttccacatcg taggtgagga agagcctttc tgtgcgagga tgagaaccga   8940
tcgggaagaa ctggatttcc tgccaccagt tggaggaatg gctgttgata tgatggaagt   9000
agaactccct acggcgcgcc gagcattcgt gcttgtgctt gtacagacgg ccacagtact   9060
cgcagcgctg cacgggatgc acctgatgaa tgagctgtac ctggcttcct ttgacaagaa   9120
atttcagtgg gaagttgagg cgtggcgtct gcatctcgtg ttgtattacg tcctggctat   9180
tggtctggcc atcttctgtc tcgatggtgg tcatgctgac gagcccgcgc gggaggcagg   9240
tccagacctc cgcgcggacg ggtctgagag cgaggacgag agcgcgcagg ccggaactgt   9300
ccagggtcct gagacgctgc ggagtcaggt cagtagggag agtacatagg tttacttgca   9360
taagtttttc cagggcatgt gggaggtcaa gatgatattt gatttctact ggcgagttgg   9420
```

-continued

```
tggagacatc gatggcttgc agggtcccgt gcccctgggg tgctaccacc gtccctttt   9480
ttttcttgat cgggggcggt gttgcttctt gcatggtaag gtcgtcttct agaagcggcg   9540
gcgaggtcgc gcgccgggtg gcagtggcgg ttctggacct ggaggtagag gcggtagagg   9600
tacgtcggcg ccgcgcgcgg gtaggttctg gtactgcgcc ctgagaagac ttgcgtgagc   9660
gacgacgcgg cggttgacgt cctggatctg acgcctctgg gtgaatgcta ccggacccgt   9720
gagcttgaac ctgaaagaga gttcaacaga atcaatttcg gtatcgttga cggctgcctg   9780
ccgcaggatt tcttgtacgt cgcccgagtt gtcttggtag gcgatctcgg ccatgaactg   9840
ctcgatctct tcttcttgga gatctccgcg gcccgctcgt tctacggtgg cagcaaggtc   9900
gttggagatg cgccccatga gctgtgagaa tgcattcatg cccgcctcgt tccagacgcg   9960
actgtagacc acggctccct cgggatctct ggcgcgcatg accacttggg cgaggtttag  10020
ttccacgtgt ctggtgaaga ccgcatagtt gcagagacgc tggaagaggt agttgagcgt  10080
ggtggcgatg tgctcggtga caaagaaata catgatccag cgacgaagcg gcatctcgct  10140
gatatcgccc agggcttcca accgttccat ggcttcgtaa aagtccacgg cgaagttgaa  10200
aaactgggag ttgcgagcgg acacggtcaa ctcctcctcc agaagacgga tgagctcggc  10260
gatggtggcg cgcacttcgc gctcaaaggc tcccgggatc tcttcctcct cttcttcttc  10320
caactcttcc tccactaaca tctcttctac ttcctcctca ggcggcgggg gtggaggagg  10380
gggcgcgcgg cgacgccggc gacgcacggg cagacgatcg atgaagcgtt cgatcacttc  10440
tccgcggcgg cgacgcatgg tctcggtgac ggcgcgcccg tcctccctgg gtcgcagagt  10500
gaagacgccg ccgcgcagct ccctgaaatg gtgactggga gggtccccgt ttggtaggga  10560
cagggcactg atgatgcatc ttattaattg ccctgtaggg actccgcgca aggacctgag  10620
cgtctcgaga tccacgggat ctgaaaatct ctgaacgaag gcttcgagcc agtcgcagtc  10680
gcaaggtagg ctgagcactg tttcttcggg gcgggctgct gagctagagg gttgtacgat  10740
gctgctggtg atgaagttaa aataggcagt tctgagacgg cggatggtgg cgaggagcac  10800
caggtctttg ggtccggctt gctggatgcg caggcggtcg gccattcccc atgcattatc  10860
ttggcacctg gccagatctt tatagtagtc ttgcatgagt cgctccacgg gcacttcttc  10920
ttcgcccgct ctgccgtgca tgcgtgtgag tccgtaccct ctctgtggtt ggacgagcgc  10980
caggtcggca acgacccttt cggctagaat ggcttgctgc acctgggtga gggtgttctg  11040
gaaatcatca aagtccacaa agcggtggta ggcccccgtg ttgatggtgt aggagcagtt  11100
ggacatgacc gaccagttga ctgtctggtg tcctggtcgt acgagttccg tgtacctgag  11160
ccgcgagtat gcgcgggagt cgaagatgta atcgttgcag gttcgcacca ggtactggta  11220
gccgatgagg aagtgaggcg gcggctggcg gtagagaggc catcgttcgg tggcgggcgc  11280
gccgggcgct aggtcttcta gcatgagacg gtggtatccg tagacgtacc tggacatcca  11340
ggtaataccg gcggcggtgg tggaggcgcg cggaaactct cgcacgcggt tccagatgtt  11400
gcgcagcggc atgaagtagt tcatggtggg cacggtctgg cccgtgaggc gcgcgcagtc  11460
attgatgctc tagatacggg caaaaacgaa agcgttgagc ggttcccttc cgtggcctgg  11520
aggaacgcga acgggttagg tcgcagcgta ccctggttcg agactaaaga aagcgagcaa  11580
ctcgaaccgg cagagtcgcg gctaacgggt attggcaatc ccgtctcgac ccaagccagc  11640
aaatccagga tacggatggg ggcccctttt gtttttcagg gcatgagtca ccggttaagg  11700
tttacaacgg ctgtttcatg cctttagaag tggctcgcgc ccgtagtctg gagaatcaat  11760
cgccagggtt gcgttgcggc gtgccccggt tcgagcctgc agcttgagtc ggccggtgac  11820
```

cgcggcaaac gagggcgtgg cggccccgtc gtttctaaga ccttgctagc cgacctctcc 11880
agtttacggg aacgagcccc cttttatttt ttttgttttt gccagatgca tcccgtactg 11940
cggcagatgc gcccacagcc cccacagcag cagcagcagg ctggcctacc ttctctacct 12000
cagccgctac ctgcaactac cgcggtggcc gctgtaagcg gggccggaca gcaggcggct 12060
cctcaatatg aattggactt ggaagagggc gagggattgg caagattggg ggcgccctcg 12120
cccgagcgcc acccgcgggt gcagatgaaa aaggacgttc gcgaatctta cgtgcccaag 12180
cagaatctgt tcagagacag aagcggcgag gagcccgagg agatgcgcgc gtcccgtttt 12240
aacgcgggtc gcgagctgcg acaaggactg gatcgaaaac gggtgttgag ggatgatgat 12300
tttgaggtgg atgaaatgac agggatcagc cccgctcgcg ctcacgtggc tgcagctaat 12360
ctggtgacag cttatgagca gaccgtgaag gaggaaagca acttccagaa atcattcaat 12420
aaccacgtgc gcaccctgat cgcacgcgag gaggtgaccc tgggcctgat gcacctgtgg 12480
gatctgctgg aagccatagt gcagaacccc actagcaaac ccctgactgc tcaactgttt 12540
ctggtggtgc agcacagcag ggataatgag gcattcagag aggcgctgct gaatatcact 12600
gaacctgagg ggagatggct gctggatctg gtgaatatcc tgcagagcat tgtagtgcag 12660
gaacgcagct tgcctttgtc cgagaaggtg gcggcgatca attactctgt gctgagtctg 12720
ggcaaatact atgccaggaa gatctacaaa accccttacg tgcccataga caaggaagtg 12780
aaaatagatg ggttttacat gcgcatgacc ctgaaagtgc taaccctgag cgatgacttg 12840
ggagtgtacc gcaacgacag gatgcaccgc gcggtgagcg ccagcaggag gcgcgagctg 12900
agcgacaaag aattaatgca cagcttgcaa cgagccctga cgggagccgg gacggagggg 12960
gagaactact ttgacatggg tgcagacttg cattggctgc ctagtcgcag ggcattggaa 13020
gcggcaggcg atgggcccta tgtagaggaa gtagtagacg aggacgatga ggagggcgag 13080
tacctggaag actgatggcg cgacccgtat ttttgctaga tggaacaggc gccggaccct 13140
gcgatgcggg cggcgctgca gagccagccg tccggcatta attcctcgga cgattggacc 13200
caggccatgc aacgcatcat ggcgctgacg acccgcaacc ccgaagcctt tagacagcag 13260
cctcaggcca accgcctttc ggccatcctg gaggccgtgg tgccctctcg ctccaacccc 13320
acccacgaga aggttctggc catcgtgaat gccctggtgg agaacaaggc catccgctcc 13380
gatgaagccg ggctggtata caacgccttg ctcgagcgcg tggctcgcta caacagcagc 13440
aatgtccaga ctaacctgga caggatggtg accgacgtgc gcgaggccgt gtcccagcgc 13500
gaacggttcc atcgcgagtc taacctgggt tccatggtag cgctgaacgc tttcctcagt 13560
tcccagcctg ccaatgtgcc ccggggacag gaagactata ccaactttat tagcgccctg 13620
agactcatgg tagccgaggt tcctcagagc gaggtgtacc agtccggtcc agactacttt 13680
ttccagacaa gcaggaacgg tatgcagaca gtgaacttaa gccaggcttt caagaacctg 13740
caagggctgt ggggagtcca agctccagtg ggcgacaggg cgaccgtgtc gagcctgttg 13800
actccaaatt cccgtttgct gctgctgctg gtgtccccct tcactgacag cggcagcata 13860
aacagaaact cctacttggg ctacctgata aacttgtatc gcgaagctat aggtcaggcc 13920
cacgtggacg aacagaccta tcaggagatc actaatgtga gtcgcgctct gggccaggac 13980
gaccctggaa acctggaagc tactctaaac tttctgctga ccaaccgctc gcaaaaaatc 14040
cctcctcagt atacattaac tgcggaggag gaacggatct tgagatacgt gcagcagagc 14100
gtgggtctgt tcctgatgca agagggtgcg acccctagcg ccgcgcttga tatgacagcg 14160

-continued

```
cgcaacatgg agcccagcat gtatgccagc aacagaccat tcattaataa attgatggat  14220
tacttccatc gcgcggccgc tatgaactct gattacttca ccaatgctat tctgaacccc  14280
cattggctgc ctccgcctgg tttttatact ggcgagtatg acatgcctga ccccaacgat  14340
gggttcttgt gggacgatgt ggacagcgtg gcgttctcgc ctaccgctcc tcgtactttt  14400
tggaagaagg aaggtagtga cagaagaccc tcctccgtgc tgtcaggacg tgagggtgct  14460
gccgcggcgg tccccgatgc tgcaagcccc tttcccagtc tgccattttc actaaacagc  14520
gtgcgcagta gcgagctggg gagaataacc cgccctcgct tgctgggcga ggacgagtat  14580
ttgaatgact ccctactgag acccgagcgg gaaaagaact tccctaataa tgggattgaa  14640
agcctggtgg ataagatgag cagatggaag acctatgccc aggagcacag agatgagcct  14700
agaatcttgg gtcctacagt aggcacccgc agacgccagc gccatgatag acagcggggt  14760
ctggtgtggg acgatgagga ttctgcagat gacagcagcg tgttggactt gggcgggagg  14820
ggaggtgtgg gcaacccgtt cgcacacttg cgtccccgta ttggacgcat gatgtaaaag  14880
tgaaaataaa aaaggaactc accaaggcca tggcgaccag cgtgcgttcg ttctttctgt  14940
tgttgtatct agtatgatga ggcgcaccgt gctaggcgga tcggtggcgt atccggaggg  15000
tcctcctcct tcgtacgaaa gcgtgatgca gcaggtggcg gcggcggcga tgcaaccccc  15060
cttggaggct ccttacgtgc cccgcggta cctggcacct accgagggga gaaacagcat  15120
tcgttattcg gaactcacac ccttgtatga caccacccgg ttgtacctgg tggacaacaa  15180
atcggcggac attgcctcgt tgaactatca gaacgaccac agcaacttct tgacaacggt  15240
ggtgcagaac aatgacttta cccccacgga ggccagcacc cagaccatca actttgacga  15300
gcgctcccgg tggggcggtc agctgaagac catcatgcac accaacatgc ccaacgtgaa  15360
cgagttcatg tttagcaaca agttcagggc tagggtgatg gtgtccagaa ccacacctaa  15420
agaggtgaca gtcacaacag actatgatgg tagtcaggac atcttggaat acgagtgggt  15480
tgactttgag ttaccagaag gcaacttctc tgccaccatg accatagacc tgatgaataa  15540
tgcaattgtt gataattacc taaaagtggg tagacagaat ggggtactgg agagtgacat  15600
aggtgttaag tttgacacta ggaactttag gcttggttgg gacccagtga cagagttggt  15660
catgcctggg gtctacacca atgaagcttt ccatcctgac atagtcctac tacctggctg  15720
cggagtggac ttcactgaga gccgcctcag taatctgcta ggcattagaa agaaacagcc  15780
attccaggaa gggttccaga tcatgtatga ggatctggag ggtggtaaca tccccgccct  15840
gcttgatgta aatgcatatg agaagagcaa ggaagataat acaaccacca caaatgaagc  15900
tgtggccgcg gcttcatcta ctgaagccaa agctgtggta gatgcttcca cttcaacaga  15960
aaacaccact gatgaaaaag tcaccagggg agatacattt gccacccctg aacaagagaa  16020
ggcagctgag gcagagtctg atattatgct tctgtccacc gatgaaaacg aaactaaaaa  16080
acaactggtt attcgagcgg tgaccaagga tagtaaggac aggagttata atgtattgtc  16140
agatggaaag aacacagctt accgtagttg gtacctggca tacaattatg gcgaccgtga  16200
gaaaggggtg cgttcttgga cactgcttac cacctcggat gtcacctgcg gcgtggagca  16260
agtctattgg tcgctaccag atatgatgca agatccagtc acctttcgct ccacacgcca  16320
agttagcaac tacccagtgg tgggcgcaga gctgctccca gtgcattcca gaagcttcta  16380
caacgagcaa gccgtctact cgcaacagct ccgccagtac acctcgctca cgcacgtctt  16440
caaccgcttc cccgagaatc agatcctcgt ccgcccgccc gcgccaacca ttaccaccgt  16500
cagtgaaaac gttcctgctc tcacagatca cgggaccctg ccgctgcgca gcagtatccg  16560
```

gggagtccag cgcgtgaccg ttactgacgc cagacgccgc acctgtccat acgtatacaa 16620
ggccctgggc atagtcgcgc cgcgcgtcct ttcaagccgc actttctaaa aaaatgtcca 16680
ttctcatctc gcccagtaat aacaccggtt ggggcctgcg cacacctagc aagatgtatg 16740
gaggcgctcg cagacgctcc actcagcacc ctgtgcgcgt gcgcgggcat ttccgcgctc 16800
cctggggcgc cctcaaggga cgctctcgta ctaggaccac cgttgacgat gtgatcgacc 16860
aggtggtcgc cgatgcacgt aactataccc ccgcagccgc acctgcatcc accgtggatg 16920
cggtcattga cagcgtggta gccgatgcgc gcgcctatgc tcgcgccaag agcaggaggc 16980
ggcgtattgc caggcgtcac cgagctactc cagccatgcg agctgcaaga gctttattgc 17040
ggagagccag acgtgtgggg cgaagagcca tgcgtagagc ggccagacgc gcggcttcag 17100
gtgccagcgc aggcagggtc cgcaggcgcg cggctacggc ggcagcggcg gccatcgcta 17160
gcatgaccaa accacgaaga ggcaatgtgt attgggtgcg cgacgccgcc accggccagc 17220
gcgtgcccgt gcgcacacgc cccccctcgca cttagaagat actgagcagt ctccgatgtt 17280
gtgtcccagc ggcgagatgt ccaagcgcaa attcaaggaa gagatgctcc aggtcatcgc 17340
gcctgagatc tacggtcctg cggtgaagga tgaaaaaaag ccccgcaaga tcaagcgggt 17400
caaaaaggac aaaaaggaag aagatggtga tgatgggctg gtggagtttg tgcgcgagtt 17460
tgccccaagg aggcgcgtgc agtggcgcgg gcgcaaagtg tggccggtgt tgagaccggg 17520
gaccacagtg gtctttacgc caggcgagcg ctccagcacc gtttccaaac gctcttatga 17580
tgaggtgtac ggggacgatg atattctcga gcaggcggct gatcgccttg gcgagtttgc 17640
atatggcaaa cgcagccgct cgggagccaa ggaagaggca ttgaccatcc ccttggatca 17700
tggaaatccc accccaagcc tcaaacccgt gaccctgcaa caagtgctgc ccacgccgcc 17760
acgcaagggc atcaagcgcg agggcgagga tctgtatccc accatgcagc tgatggtgcc 17820
caagcgccag aagctggaag acgtgctgga gaaaatgaaa gtggatcctg aaatccagcc 17880
tgaagtcaaa gtgaggccaa tcaagcaggt ggcgcccggt ttgggggtac aaaccgtgga 17940
tatcaagatc cccaccgagt ccatggaaat tcaaaccgaa cccatgaagc ccacctccag 18000
caccattgag gtgcagacgg atccttggat gcccgcgcct gctcctgtta ccactactac 18060
tcgaagacct agaagaaagt atggttcagc caacctgata atgccaaact atgctctgca 18120
tccatcaatc atacccactc ctggctaccg cggcactcgc tactaccgca gtcacagcac 18180
ccgccgacgt aaagcacctg ccacccgccg ccgtcgccgc cgccgtgcca ctagcaaact 18240
taccccctcg gctatggtgc ggagagtgta ccgtgatggg cgcgcagctc ctctgacact 18300
gccgcgcgcg cgctaccatc ctagcattgc catttaacaa ctctgcctcc ttgcagatat 18360
ggccctcact tgccgccttc gtattcctat tgctggctac cgcggaagaa agtcgcgccg 18420
tagaagagca gggttgtctg ggagcgggat gcgtcgccac cggcggcggc gcgccatcag 18480
caaacggttg gggggtggat ttcttcccgc tttgattccc atcatcgccg cggcgatcgg 18540
cgcgatacca ggcatagctt ccgtggcggt gcaggcctcg cagcgccact gacattggaa 18600
aaagatatct tataaataaa aatagaatgg actctgacgc tcctggtcct gtgatatgtt 18660
tttgtagacg agatggaaga catcaatttt tcatccctgg ctccgcgaca cggcacgcgg 18720
ccgtatatgg gcacctggag cgacatcggc aacagccaac tgaacggggg agccttcaat 18780
tggagcagtc tatggagcgg gcttaaaaat tttgggtcca ctataaagac ttatgggaac 18840
aaagcttgga acagcagcac agggcatgcg ctgagacaaa agcttaaaga tcagaatttc 18900

-continued

```
caacagaagg tggtcgatgg tatcgcctct ggaatcaatg gggtggtaga tctggccaac  18960
caggccgtgc agaaacagat taacagtcgc ctggacccgg ctcccccagc tcctattcat  19020
gagttaatgc aagtggagga agagctccct tcattggaaa agcggggcga taagcgacct  19080
cgtccagata tggaggaaac gctgctgacc aaggtggatg agccgccctc ctatgaagag  19140
gctgtaaaac tgggaatgcc cactacaaag cccattatgc ctctggccac tggagtgatg  19200
aagccatctc agtctaaacc tgcagttgct gctacattgg acttgcccgc tcccgtggcc  19260
acccccaaac ctgtcgccgc cccgaagccc accgccgtgc aacccgtggc cgtggccaga  19320
ccgcgtcccg gtggtcggcc gaatgcaaac tggcagagca ctctgaacag catcgtgggt  19380
ttgggagtgc acagtgtgaa gcgccgtcgc tgctattgat taaatatgga gtagcgctta  19440
acttgcttgt ctgtgtgtgt atatgtcgat gccgcccgcc gtgctacagc aaagagagaa  19500
ggagaagagg cgccgctgag ttcctttcaa gatggccacc ccatcgatgc tgccccagtg  19560
ggcgtacatg cacatcgccg gacaggacgc ttcggagtac ctgagtccgg gtctggtgca  19620
gttcgcccgc gccacagata cctacttcaa tctggggaac aagtttagga accctaccgt  19680
ggctcccacc cacgatgtga ccaccgaccg tagccagcgc ctgacgctgc gctttgtgcc  19740
cgttgaccgg gaggacaata cctactccta caaagtcaga tacaccctgg ctgtgggaga  19800
caacagggtg ttggatatgg ccagcaccta ctttgacatc aggggcgtgt tggacagagg  19860
acctagcttc aaaccatact ctggcactgc ctacaactcc ctggctccaa aaggagctcc  19920
aaactccagt cagtggcaac aaaaggaaaa caatggtcaa ggtgatgcaa agactcacac  19980
ctatggtgta gctgccactg gaggtattga cattgacaaa aatggtcttc aaattggaat  20040
cgatgaaact aaagaagata ataacgaaat ttatgcagac aaaacattcc aacctgaacc  20100
tcaaattgga gaagaaaact ggcaagatag cgaaaactat tatggaggca gggctcttaa  20160
accggaaacc aagatgaagc cttgctatgg ttccttcgct agaccaacta atgcaaaggg  20220
aggtcaagcc aaaattaaac cagctcaaga gggtcaacag tctatagatt atgacataga  20280
cctggctttc tttgatattc caagcactgg cggaggcaat ggcacaaatg taaatgacaa  20340
gccagatatg gttatgtata ctgaaaatgt aaatctggaa actccagaca ctcatcttgt  20400
ttacaagcca ggaacttcag atgacagttc cgaggccaat ttaactcagc aagccatggc  20460
taacagaccc aactatattg ggtttagaga taactttatt ggcgtcatgt actacaacag  20520
cactggcaac atgggagtgc ttgctggtca agcatcccag ctaaatgctg tggtggacct  20580
gcaagacaga aacaccgagc tgtcttatca gctattactt gactctctgg gcgacagaac  20640
caggtatttt agtatgtgga atcaggcggt ggacagctat gatcctgatg tgcgcattat  20700
tgaaaaccat ggtgtggaag atgaattgcc aaactattgc ttcccattgg acggagctgg  20760
cactaatgct gtttaccaag gagttaagac aaaagaggat aataatggcg aatgggaaac  20820
agacacaaat gttgcatcgc agaatcagat atgcaagggc aacatatatg ctatggagat  20880
caacctgcaa gccaacctgt ggaaaagttt cctttactcc aacgtggctc tgtacctacc  20940
agactcctac aagtacactc catccaacgt gacactccct accaacacta acacctatga  21000
ctacatgaat ggcagggtgg tgtctccatc cctggtggat gcctacatta acattggcgc  21060
caggtggtct ctggatgcca tggacaatgt caaccccttc aaccaccacc gcaatgccgg  21120
cctgcgctac cggtccatgc ttctgggcaa cggccgatac gtgcccttcc acatccaagt  21180
gccccagaaa ttcttcgcta tcaagaacct gctgcttctc ccaggctcat acacctacga  21240
gtggaacttc cgcaaggatg tcaacatgat cctgcagagt tcccttggca atgacctcag  21300
```

-continued

```
aaccgatggg gccaccatcc agtacaccag catcaatctc tatgccacct tcttccccat  21360
ggctcacaac actgcctcca ccctggaagc catgctgcgc aatgacacca atgaccagtc  21420
cttcaatgac tacctctcag ctgccaacat gctttacccc atccctgcca atgccaccaa  21480
cgtgcccatc tccatcccat ctcgtaactg ggctgccttc aggggctggt ctttcacccg  21540
cctcaagacc aaggagaccc catctctggg atcagggttc gatccctact tcgtctactc  21600
aggctccatt ccatacctgg atggaacttt ctaccttaac cacactttca agaaagtctc  21660
catcatgttt gactcttctg tcagctggcc aggcaatgac aggctgctga ctcccaatga  21720
gttcgaaatc aagcgcactg ttgatgggga agggtacaat gtggcacaat gcaacatgac  21780
caaagactgg ttcctggttc agatgctctc ccactacaac attggctacc agggcttcta  21840
catcccagaa ggatacaagg accgcatgta ctccttcttc agaaacttcc agcccatgag  21900
ccgccaggtg gtcgatcagg tcaactacaa agactacatg gcagtcaccc ttgcctatca  21960
gcacaacaac tctggctttg tgggctacct cgcgcccacc atgcgacagg gccaacccta  22020
ccctgctaac tacccatacc cgctcattgg caagactgca gtcaacagtg tcacccagaa  22080
aaagttcctc tgcgacaggg tcatgtggcg catccccttc tccagcaact tcatgtccat  22140
gggggccctt accgacctgg ggcaaaacat gctttatgcc aactccgccc acgcgctaga  22200
catgaatttc gaagtagacc ccatggatga gtccaccctt ctctatgttg tcttcgaagt  22260
cttcgacgtg gtcagagtgc accagcccca ccgcggcgtc atcgaagctg tctacctgcg  22320
cacccccttc tcagctggta acgccaccac ataagcgcct tgcttcttgc aagtggctgc  22380
agcagcatgg cctgtggatc ctccactgga tccaatgagc aagagctcag ggccatcgcc  22440
atagacctgg gctgtggacc ctatttcctg ggaacctttg acaagcggtt tccaggcttc  22500
atggctcctg acaagctcgc ctgtgccatt gtcaacacgg cagggcgcga gactggtggt  22560
gagcactggc tggcttttgg atggaacccc cgctccaata cctgctatct ctttgacccg  22620
tttgggtttt cagacgagcg cctcaagcag atctatcaat tcgagtacga ggggctcctg  22680
cgccgcagtg ccctggctac taaggaccga tgcatcactc tggaaaagtc tacccagacc  22740
gtgcagggtc cgcgctcggc tgcctgcggg ctcttctgct gcatgttcct ccatgctttt  22800
gtgcactggc ccgaccgccc catggacaac aaccccacca tgaatttgct gacgggggta  22860
cccaacaaca tgctccaatc gccccaagta gagcccaccc tgcgccacaa ccaggaggca  22920
ctctatcgct tcctgaactc ccactcatct tactttcgtt ctaaccgcgc gcgcattgag  22980
aaggccactg ccttcgatcg aatgaataat aacatgtaaa ccaaattgtg tgtggctcaa  23040
ataaacagca ctttattgtt tacatgcact gaggctctgg gatgatcatt ttttaaaaat  23100
cgaaggggtt ctggcgggaa tcagcatggc cagatggcag ggacacgttg cggaactgga  23160
acttgttctg ccacttgaac tcgggaatca ccagcctggg aactggaatc tctggaaagg  23220
tatcttgcca tagctttctg gtcagttgca gagcgccaag caggtcagga gcagatatct  23280
tgaaatcaca gttggggcca gaattctggg cgcgggagtt gcggtacact gggttgcagc  23340
actggaacac cataagggca gggtgtctca cgctcgccag cacggtctcg tcactgatgc  23400
aagacacatc caggtcttca gcattggcca ttccaaaggg ggtcatcttg caggtctgtc  23460
tgcccatcac gggagcgcag ccaggtttgt ggttgcaatc acaatgaagg gggatcagca  23520
tcatcttggc ctggtcgggg gtaatccctg ggtaaacagc cttcatgaag gcttcatact  23580
gcttgaaagc ttcctgggct ttggttccct cggtgtagaa cactccacaa gacttgctgg  23640
```

-continued

```
aaaactgatt agtagcgcag ttggcatcat tcacacagca gcgggcgtcg ttattagcca  23700
gctggaccac attcctgccc cagcggttct gggtgatctt ggctcgatct gggttctcct  23760
tcaacgcgcg ctggccgttc tcgctcgcca catccatctc aatgacatgt tccttctgga  23820
tcatgatgtt gccatgcagg catctaatct tgccttcata atcagtgcag ccatgaggcc  23880
acagcgcgca cccggtgcac tcccaattgt tatgggggat ctgggaatgg ctatgaacca  23940
gcccttgcag gaatcttccc atcatcacag ccagggtctt tatgctggta aaggtcagcg  24000
ggataccgcg gtgctcctcg ttcacatact gctggcagat gcgtctgtag tgctcggcct  24060
gctcgggcat cagcttgaaa gaggttttca actcattatc cagcctgtat ctctccatca  24120
tgatggacat tacttccatg cccttctccc aggcagaaac aatagggaga ctcaggggat  24180
tcttgacagt agagacaacc ttacttaagg ggtcatcact gccaatcttt tcgatgcttc  24240
tcttgccatc cttctcggtg atgcgcaccg gcgggtagct gaatcccaca gccaccaact  24300
gagcctcttc cctttcgtct tcgctgtctt gactgatgtc ttgcagagga acatgtttgg  24360
ttttcctggg tttcttcttg ggcggcagct ctggaggact ctggctccgt tccggagacc  24420
ccatggatga gcgagagttg tcgctcacca cttggatctg gctgcctgta gaagaactgg  24480
accccacgcg gcggtaggtg ttcctcttgg taggcagagg tggaggcgac gggctccggt  24540
ccggtctggg tggcggatgg ctggcggagc cccttccgcg ttcgggggtg cgctccagat  24600
ggcggtcgtc tgactgacct ccgcggctgg ccattgtgtt ctcctaggta gagaaacaag  24660
acatggagac tcagccatcg ctgccatcgc catccaccac cacaagcacc gccgaggagg  24720
aggagtgttt aaccacccca ccatgcagcc ccgctaccac caccagcacc cttgaaagcg  24780
aggtcgacac ggtcgtggag gatttacagg ctatggaaga tattgaggca gctgtcgagc  24840
aagaccccgg ctatgtgaca ccggcggagc atgatgagga tctagcgcgc tttctcgacg  24900
gtgtggagaa agcgaaacaa gatgaggacg aggaagaggc agaagcacaa ccatcggtgg  24960
ccgactacct caccggccta gggctagaag acgtgctgct taagcatctt gcaaggcaga  25020
cagtcatagt caaagacgcc ctgctagagc gctccgaggt gccactcagt gtggaagacc  25080
tcagtcgcgc ctatgagcta aacctcttct cgcctcgcaa gcccccccaag cgtcagccca  25140
acgggacctg tgagcccaat ccgcgcctca acttctatcc agccttcact gtgcccgaag  25200
tactagctac ctaccacatc tttttcaaga accaaaagat ccccatctcc tgccgcgcca  25260
atcgcacccg cgcagatgcc ctactcaact tggggcccgg cgctcgcata cctgatatcg  25320
cttccttgga agaggttcct aagatctttg agggtctggg caatgaggaa actcgggcag  25380
caaacgctct gcaaagagaa acagatgatg gtgaacacca cagcgctctg gtggagctcc  25440
agggcgacaa cgctcgtctt gcagtcctca aacgcagcat cgaggtcacc catttcgcct  25500
accccgcact taatctccca cccaaagtca tgagctcggt catggacacg ttgctcatga  25560
agcgcgcgag ccccatctcc gaggatcaga acatgcagga ccccgatgcc tcagatgaag  25620
gcaagcctgt agtcagcgac gagcaactgg ctcgctggct aggctctgac tccccccagt  25680
ctttggagga gcggcgcaag cttatgatgg cagtggtcct gatcacagcg gagctggagt  25740
gtctccgccg cttcttcact gacccagaga ccctgcgcaa gcttgaggag aacctgcatt  25800
acacattcag tcatgggttc gtgcgccagg cgtgcaagat ctccaacgtt caactcacca  25860
acctggtctc ctacctgggc atcttgcatg aaaaccggct ggggcagaac gtgctccaca  25920
ccaccctgaa gggggaggcc cgccgcgact atatccgcga ctgtatctac ctctacctat  25980
gctacacctg gcaaagcggg atgggtgtgt ggcaacagtg cttggaagag caaaatctaa  26040
```

aagagctgga aaagctgctt cagaaatctc ttaaatctct gtggaccggg ttcgatgagc 26100
ggaccaccgc ttcggacatg gccgatatta tcttccccga gcggctcaga cacactctgc 26160
gcgacgggct gcctgacttt gccagccaga gcatgctaca aaactttagg tcattcatct 26220
tggaacgctc cgggatcctg cccgccactt gctgcgcact gccctccgat tttgtgccca 26280
tcacctaccg ggagtgcccc ccgccgctat ggagccactg ctacctgttc cgcctggcca 26340
actacttggc ctaccactct gatgtgatag aagatgttag tggcgaaggg ctcctggagt 26400
gccactgccg ctgcaacctc tgcacccccc accgctccct cgcctgcaat ccccagctgc 26460
tgagcgaaac ccagatcatc ggcaccttcg agttgcaagg tcccagcggc gaaggcgagg 26520
ggtcctctcc ggggcaaagt ctgaaactga ctccggggct atggacctcc gcttaccttc 26580
gcaagttcgc ccccaaagac taccacccct atgagatcag gttttatgaa gaccaatcac 26640
agccccccaa ggccgaactg acggcctgcg tcatcaccca gggggcaatc ttggcccaat 26700
tgcaagccat ccaaaaatcc cgccaagaat ttttgctgaa aaagggacac gggatctatc 26760
tagaccccca gaccggtgag gagctgaata cacgcttccc tcaggatgcc ccgaggaggc 26820
aagagaatga aagttcagat gccgcccgag gaggagctgg aagactggga cagtcaggca 26880
gaggaggaag actgggacag ccaggcagaa gaggaggaca gcctggagga ggacagtctg 26940
gaggaaggcg aggagcccaa ggaagaggca gccgccgcca gaccatcgtc ctcggcggtg 27000
gagacaagca aggtcccaga cagcacggct accacctccg ctccagctca aggggccgct 27060
cggcgaccca acagtagatg ggacgagacg ggtcgcttcc agaaccccac caccgtcaag 27120
accggtaagc aggagcggca gggatacaag tcctggcggg ggcataaaag tgccatcatc 27180
gcttgcttgc aggagtgtgg gggcaatata tcctttgcca gacgctacct gctattccat 27240
cacggggtga atttcccccg caacatcttg cattactacc gtcacctcca cagcccctac 27300
taccagcagc aagagacagc agaggaaacc agcggcaact ccgagagtta gaaaaccagc 27360
agctaaaaaa tccacagcgg cggcagcagg tgcaggcgga ctgaggatca ccgcgaacga 27420
gccagctcag accagggagt tgaggaatcg gatctttccc accctctatg ccatattcca 27480
acaaagtcgg ggtcaggaac aagaactgaa agtaaaaaac agatctcttc gctcgctcac 27540
ccgcagttgt ttgtatcaca agagcgaaga ccaacttcag cgcactctcg aggacgccga 27600
ggctctcttc aacaagtact gcgcgctgac tcttaaagag tagactgcgc gcgcttggcg 27660
agaaaaggcg ggaattacgt cacctcttgg ccacacctgt gcttcattat gagtaaagaa 27720
attcccacgc cttacatgtg gagctatcag ccccagatgg gattggccgc tggcgccgcc 27780
caggactact ccacccgcat gaattggctc agcgccggtc ccgcgatgat ctcacgggtt 27840
aatggtgtga gagagcaccg aaaccagata ctcctagaac agtccgccct caccgccact 27900
ccccgcaatc acctcaaccc ccgtaattgg cccgccgccc tggtgtacca ggaaactcct 27960
gctcccacta cagtactact tcctcgtgac gcccaggccg aagttcagat gactaactca 28020
ggtgtacagc tggcgggtgg tgccaccctg tgtcgtcacc ggccaagacc gggtataaag 28080
ggcctggtga tcagaggccg aggtattcag ctcaacgacg agtcggtgaa ctcttcgctt 28140
ggtctgcgac cagacggcat cttccaaata gctggttgtg ggagatcttc cttcactcct 28200
cgtcaggctg tcctgacttt ggagagttcg tcctcgcagc cccgctcggg cggcatcggg 28260
actctccagt tcgtggagga gtttactccc tcggtctact tcaacccctt ctccggttct 28320
cctgggcttt acccggacga gttcatcccg aactacgacg ccatcagtga agcggtcgac 28380
ggctacgatt aatgtctaat ggtggcgcgg ctgagctagc tcgactgcga cacctagacc 28440
actgccggcg ctttcgctgc tttgctcggg atctctgcga gttcatctac ttcgagtacc 28500
ctgacgaaca tcctcaggga cctgcccacg gagttcggat taccattgaa ggggctatcg 28560
attctcacct gcttcggatc ttcaccgctc ggccagtgct agttgagcgc aaccagggcg 28620
acaccaccat ctccctctgc tgcatttgtg acaaccccgg attgcatgaa agcttttgtt 28680
gtcttctttg tactgagtat aataaaagct gaaattagag actactccgg actctcttgt 28740
cgtctgaaca acaccaacca gacccttcac ttcagcggga accagactac tcttcactgt 28800
aaggcttata actataagta tcttacttgg atatacaaag gaacaccgtt tgctgtggta 28860
aacaggtgct ccaacgacgg tgttctcctc accttcctag gcaacttctc caactttacc 28920
ttttctgttc gcagaaacaa gcttaccctc cttcagccct actttcctgg gatctatacc 28980
tgcctcagtg gaccttgcaa ccacactttt cacctgattg aaaactctac ccttaccttc 29040
ccagcgccaa tccctactaa cagctcggag tccaactctt ccattaccgc tgatactaac 29100
actcctaaaa ccggaggtga gctccgcagc cttcccccgg ctgcagataa cccttgggtg 29160
gtagcgggat ttgtagcgct aggaatagtt gcgggtgggc tcgcgttcgt cctctgctac 29220
ctataccta cctgctgctc atatttagta gtactgtgct gttggtttag aaaatggggg 29280
cgctactaat cacacttgct ttactttcgc ttttgggtct gagctcggct aatagcgaga 29340
aaccaagctg tctagaaaca aactctccag actgtgtggt tcctcatggg ctctcagacc 29400
cagctgatga tccatgctta acttttgacc cagaaaaaaa ctgctcggtg actatgcagc 29460
cctatgctta catgtgcaca tctgttataa agtgcggatg gggctgtaaa ccgattgaaa 29520
ttacccacaa aggcaaaacc tggaataata gtttgtttaa cacatggcag cctggagacg 29580
agcagtggta tacggccggc cactggtgga gatgactgac cccatggaaa actcctctgc 29640
caacgacctg gacatggacg gccgttcatc tgagcagcga ctggtccaga tgcgcattcg 29700
ccagaagcag gaacgcgccg ccagagagct caaggatgcc attgaaattc acctgtgcaa 29760
gaagggcatc ttttgcttgg ttaagcaagc aaagatttct tatgaaatca ctgacaacga 29820
ccaccgcctg tattatgagc tcggtccaca gcggcagaaa ttcacctgca tggttggagt 29880
caaccccata gtcatcactc agcaggctgc agaaattaaa gggtgcatcc actgttcctg 29940
tgattcccaa gaatgcgtcc acaccatagt caagaccctc tgcggccttc gagatcttct 30000
tccaatgaac taacccctc ccccaaccca ataaaacatt ggttttaatc ataataaaaa 30060
atcacttact ttaaatctga aacagtgtct ccgtccaagt tttcttgtag caccacttca 30120
ctcccctctt cccagctctg gtactgcaag ccccggtggg ctgcaaactt tctccacacc 30180
ttaaaaggga tgtcaaattc ctcttgtcca acaatcttca ttgtctcttc ctagatgtcc 30240
acaaagcgcg cgcgggtgga agatgacttt gaccctgtct acccatacga tgctgagctg 30300
gcaccgtctg taccttcat cgcccctccc ttcgtttcgt cagacggatt tcaagaaaaa 30360
cccctgggag ttctgtccct aagactagcc aacccagtca ctactaaaaa tggggaactc 30420
acacttaaac tgggagatgg ggtgggcata gactcagatg gaaacctcac agcacagaca 30480
gttactaaag caacatcccc ccttactgtt tccaataacg caattgcact taacatggac 30540
aaaccttttt acagtagcaa tggaaaacta tccttacaag ttacatcacc attaaagata 30600
gtcgactctt taaatacatt ggctattggc tatgggcaag gcttaggact aaacaatagt 30660
gctcttgctg tgcaattagc atctccccctt acatttgaca gcaacagcaa aattaaaata 30720
aatttgggaa gcgggccatt aaaaattaat gcgaataaac tgtcaattaa ctgcctaagg 30780
ggtgtatatg taacaactga cggaacttcc attgaaacaa atataagctg ggcaaaagga 30840
atgaggtttg aaggtaatgc catggctgta aacgttgaca gcaccaaagg tctacaattt 30900
ggcactacca gcacagaatc aggagtcact aacgctttcc ctatccagtt aaagattgga 30960
tctggtctta gttttgacag cacaggagca cttgtagctt gggataagga taatgacaag 31020
cttacactgt ggacaaccgc tgacccatca cctaattgta ccatatatac agacaaggat 31080
gctaaactta cactttgtct tacaaaatgt ggcagtcaaa tactaggcag tgtttcagta 31140
ctggctgtta aagctggaac cctacagcca atcagtgaaa aaataggtac tgctttggtt 31200
tcactaaaat ttaataacaa cggtgtattg ttaagcaact ccacattaag taatgaatac 31260
tggaactaca ggaagggaga tgtcacacca gccgaagcct atactaatgc tgtgggtttt 31320
atgccaaaca tcaaggcata tcctaaaaac acaaactctg cctcaaaaag ccacattgta 31380
ggacaagtgt accttaatgg agatgaaact aaaccaatgc atttaatcat tacatttaat 31440
gaaaccagtg atgaaacatg cacatattcc ataacgttcc aatggaaatg gaacattgga 31500
acatacacca gcgacaccct tgcaacaagc tcctttacct tttcttacat tgcccaagaa 31560
taaaaactgc agacaacaat aaagtttaaa tgttttattt aaacagtttc acagaaccct 31620
agtattcaac ctgccacctc cctcccaaca cacagagtac acagtccttt ctccccggct 31680
ggccttaaaa agcatcatat catgggtaac agacatattc ttaggtgtta tattccacac 31740
ggtttcctgt cgagccaaac gctcatcagt gatattaata aactccccgg gcagctcact 31800
taagttcatg tcgctgtcca gctgctgagc cacaggctgc tgtccaactt gcggttgctt 31860
aacgggcggc gaaggagaag tccacgccta catgggggta gagtcataat cgtgcatcag 31920
gatagggcgg tggtgctgca gcagcgcgcg aataaactgc tgccgccgcc gctccgtcct 31980
gcaggaatac aacatggcag tggtctcctc agcgatgatt cgcaccgccc gcagcataag 32040
gcgccttgtc ctccgggcac agcagcgcac cctgatctca cttaaatcag cacagtaact 32100
gcagcacagc accacaatat tgttcaaaat cccacagtgc aaggcgctgt atccaaagct 32160
catggcgggg accacagaac ccacgtggcc atcataccac aagcgcaggt agattaagtg 32220
gcgacccctc ataaacacgc tggacataaa cattacctct tttggcatgt tgtaattcac 32280
cacctcccgg taccatataa acctctgatt aaacatggcg ccatccacca ccatcctaaa 32340
ccagctggcc aaaacctgcc cgccggctat acactgcagg gaaccgggac tggaacaatg 32400
acagtggaga gcccaggact cgtaaccatg gatcatcatg ctcgtcatga tatcaatgtt 32460
ggcacaacac aggcacacgt gcatacactt cctcaggatt acaagctcct cccgcgttag 32520
aaccatatcc cagggaacaa cccattcctg aatcagcgta aatcccacac tgcagggaag 32580
acctcgcacg taactcacgt tgtgcattgt caaagtgtta cattcgggca gcagcggatg 32640
atcctccagt atggtagcgc gggtttctgt ctcaaaagga ggtagacgat ccctactgta 32700
cggagtgcgc cgagacaacc gagatcgtgt tggtcgtagt gtcatgccaa atggaacgcc 32760
ggacgtagtc attctcgtac tttgagtggc aaaaccttgc tctcgaacag cacacgtctc 32820
gtcgcctcct gtcccttctc ttcgcctttt cagtgtgata gttgtaatac agccattcac 32880
gaagctcagt cagaagatct tcagcgtctg ttgtcaaaaa caatccatcc aatctgattg 32940
ctttcaaaac atcacaaaca gtcgaataag ccaaacccat ccaggcaatg caattatttt 33000
ggttatccac aatgggaggg ggcggaagac atggaagagg cataattaat tttttaatcc 33060
aatcgatcac gcagcacttc aaaatgaaga tcgcgaaggt gacacctttc acccccactg 33120

-continued

```
tgttgatgaa aaataacagc caagtcaaaa ttgatgcggt tttcaaggtg ctcgactgta  33180
gcatcaagca gagcttccac acgcacgtcc acaaataaca gaatagcaaa agcgggagga  33240
ggaagtaaat cctcaatcat catagtacag tccatcacca tccctaaata attttcatcc  33300
ttccagcctt ggactatatt tttaaactgc tcttgtaaat ccaaaccaca catgtggaaa  33360
agttcccaaa gagctccctc aactaccatt cttaagcaca ccttcatagt gacaaaatat  33420
cttgttcctc tgtcacctgc agcaaattac aaagtccaat attaggatct atgcccagag  33480
atctaagctc atccctcaat tccaactgta aaaaggcttc cagatctgcc ctaacttgtt  33540
cagccagtgg gctccctgga ataagcgtgg gagaagccaa actgcaaaac agacgcatgc  33600
cgccataatt accaccagaa aacactacgt tacagtatgc atgctgattc attccagtaa  33660
tttcatccag tgtattggat acaaaaaaag gcaagcactc tctcactaat tgtattatgg  33720
agacattatc acacaggtaa caatttaaag gttgtggaac aataatgcag taagtaacca  33780
cggtgcgctc caacatggtt agtaattttt agttctgaaa aacaaaacat acaaaaaatt  33840
atatcatact catttggcga actggtggaa aaatgaccct atctagcaca aggcaagcca  33900
ctggatcacc aatgcgcccc tcataaaacc tgtcatcatg attaaaaagc aacaccgaaa  33960
gctcttccct atgtcctgca tgaatgattc tagctgagga atataagcca gcgcaattag  34020
tatctgttaa agaaaaaaaa cggccaacat agcctctagg aattagcaca cttaatctta  34080
aagacattac tgccatcccc cttggattta aggtaaaatt tacaggagca tagaaaatat  34140
actgatttcc ctcctgcaca ggcagcatag caccaggtcc ctctaaaaac acacacaaag  34200
cttctgcagc catagcttac cgcgcaaacc aggcacagca gtgagctaaa aggacaaagc  34260
tctaactcac tagccaacct ggcgcacaat atatagttag tccttacact gacgtaaccg  34320
accaaagtct aaaaaccccg ccaaaaatac acacacgccc aaaaaacgcc ccgtgagtca  34380
aaaaacagtt tcacttcctc gttacaccca aaacgtcgtc acttccggat tcccacggtt  34440
cgtcacttcc ggagctcctt gcttaattaa ccccgcccaa aacgtcatcg tccgcgtcac  34500
gccgccccgc cccgcgaccg ttgaccccgg gccaatcacc gcacatcccg caaaattcaa  34560
actcgtctaa tttgcatatt ggcacactgc ccatataagg tatattattg atgatg      34616
```